(12) United States Patent
Pruitt et al.

(10) Patent No.: US 6,569,874 B1
(45) Date of Patent: May 27, 2003

(54) THIAZOLES AS FACTOR XA INHIBITORS

(75) Inventors: James Russell Pruitt, Landenberg, PA (US); John Matthew Fevig, Lincoln University, PA (US); Mimi Lifen Quan, Newark, DE (US); Donald Joseph Phillip Pinto, Kennett Square, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/713,002

(22) Filed: Nov. 17, 2000

Related U.S. Application Data

(62) Division of application No. 08/996,378, filed on Dec. 22, 1997, now Pat. No. 6,187,797.
(60) Provisional application No. 60/033,843, filed on Dec. 23, 1996, and provisional application No. 60/050,975, filed on Jun. 20, 1997.

(51) Int. Cl.$^7$ .................. A61K 31/426; A61K 31/4439; C07D 277/30; C07D 401/04
(52) U.S. Cl. .................. 514/342; 514/369; 514/365; 514/370; 514/371; 546/270.4; 546/269.7; 548/200; 548/194; 548/195; 548/188
(58) Field of Search .................. 548/200, 194, 548/195, 188; 546/270.4, 269.7; 514/369, 365, 370, 371, 342

(56) References Cited

U.S. PATENT DOCUMENTS

| | | |
|---|---|---|
| 5,103,014 A * | 4/1992 | Musser et al. .............. 548/204 |
| 5,317,103 A | 5/1994 | Baker et al. |
| 5,463,071 A | 10/1995 | Himmelsbach et al. |
| 5,514,696 A | 5/1996 | Murugesan et al. |
| 5,612,359 A | 3/1997 | Murugesan |
| 5,658,909 A | 8/1997 | DeBernardis et al. |
| 5,668,159 A | 9/1997 | Jin et al. |
| 5,691,329 A | 11/1997 | DeGrado et al. |

FOREIGN PATENT DOCUMENTS

| | | |
|---|---|---|
| EP | 0513387 | 11/1992 |
| EP | 0768305 | 4/1997 |
| WO | WO 9424095 | 10/1994 |
| WO | WO 9514683 | 6/1995 |
| WO | WO 9518111 | 7/1995 |
| WO | WO 9638426 | 12/1996 |
| WO | WO 9747299 | 12/1997 |

\* cited by examiner

*Primary Examiner*—Laura L. Stockton
(74) *Attorney, Agent, or Firm*—David H. Vance; Jing S. Belfield

(57) ABSTRACT

The present application describes oxygen and sulfur containing heteroaromatics and derivatives thereof of formula I:

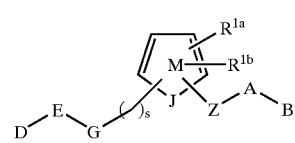

or pharmaceutically acceptable salt or prodrug forms thereof, wherein J is O or S and D may be C(=NH)NH$_2$, which are useful as inhibitors of factor Xa.

45 Claims, No Drawings

THIAZOLES AS FACTOR XA INHIBITORS

This application is a divisional of Ser. No. 08/996,378 filed Dec. 22, 1997, now U.S. Pat. No. 6,187,797, which claims the benefit of U.S. Provisional Nos. 60/033,843 filed Dec. 23, 1996 and 60/050,975 filed Jun. 20, 1997.

FIELD OF THE INVENTION

This invention relates generally to oxygen or sulfur containing 5-membered ring heteroaromatics which are inhibitors of trypsin-like serine protease enzymes, especially factor Xa, pharmaceutical compositions containing the same, and methods of using the same as anticoagulant agents for treatment and prevention of thromboembolic disorders.

BACKGROUND OF THE INVENTION

WO 95/13155 and PCT International Application US 96/07692 describe isoxazoline and isoxazole fibrinogen receptor antagonists of the formula:

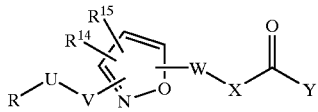

wherein $R^1$ may be a basic group, U-V may be a six-membered aromatic ring, W-X may be a variety of linear or cyclic groups, and Y is an oxy group. Thus, these compounds all contain an acid functionality (i.e., W—X—C(=O)—Y). In contrast, the presently claimed compounds do not contain such an acid functionality.

EP 0,513,387 depicts active oxygen inhibitors which are oxazoles or thiazoles of the formula:

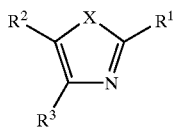

wherein X is O or S, $R^2$ is preferably hydrogen, and both $R^1$ and $R^3$ are substituted cyclic groups, with at least one being phenyl. The presently claimed invention does not relate to these types of oxazoles or thiazoles.

WO 95/18111 addresses fibrinogen receptor antagonists, containing basic and acidic termini, of the formula:

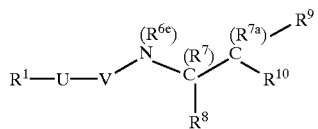

wherein $R^1$ represents the basic termini, U is an alkylene or heteroatom linker, V may be a heterocycle, and the right hand portion of the molecule represents the acidic termini. The presently claimed compounds do not contain the acidic termini of WO 95/18111.

In U.S. Pat. No. 5,463,071, Himmelsbach et al depict cell aggregation inhibitors which are 5-membered heterocycles of the formula:

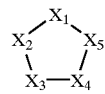

wherein the heterocycle may be aromatic and groups A—B—C— and F—E—D— are attached to the ring system. A—B—C— can be a wide variety of substituents including a basic group attached to an aromatic ring. The F—E—D— group, however, would appear to be an acidic functionality which differs from the present invention. Furthermore, use of these compounds as inhibitors of factor Xa is not discussed.

Baker et al, in U.S. Pat. No. 5,317,103, discuss 5-HT$_1$ agonists which are indole substituted five-membered heteroaromatic compounds of the formula:

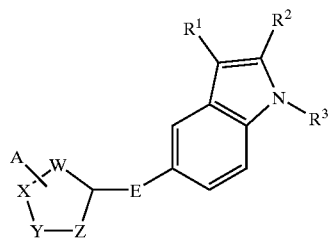

wherein $R^1$ may be pyrrolidine or piperidine and A may be a basic group including amino and amidino. Baker et al, however, do not indicate that A can be a substituted ring system like that contained in the presently claimed heteroaromatics.

Tidwell et al, in J. Med. Chem. 1978, 21(7), 613–623, describe a series of diarylamidine derivatives including 3,5-bis(4-amidinophenyl)isoxazole. This series of compounds was tested against thrombin, trypsin, and pancreatic kallikrein. The presently claimed invention does not include these types of compounds.

Activated factor Xa, whose major practical role is the generation of thrombin by the limited proteolysis of prothrombin, holds a central position that links the intrinsic and extrinsic activation mechanisms in the final common pathway of blood coagulation. The generation of thrombin, the final serine protease in the pathway to generate a fibrin clot, from its precursor is amplified by formation of prothrombinase complex (factor Xa, factor V, Ca$^{2+}$ and phospholipid). Since it is calculated that one molecule of factor Xa can generate 138 molecules of thrombin (Elodi, S., Varadi, K.: Optimization of conditions for the catalytic effect of the factor IXa-factor VIII Complex: Probable role of the complex in the amplification of blood coagulation. Thromb. Res. 1979, 15, 617–629), inhibition of factor Xa may be more efficient than inactivation of thrombin in interrupting the blood coagulation system.

Therefore, efficacious and specific inhibitors of factor Xa are needed as potentially valuable therapeutic agents for the treatment of thromboembolic disorders. It is thus desirable to discover new factor Xa inhibitors.

SUMMARY OF THE INVENTION

Accordingly, one object of the present invention is to provide novel oxygen or sulfur containing aromatic heterocycles which are useful as factor Xa inhibitors or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating thromboembolic disorders comprising administering to a host in need of such treatment a therapeutically effective amount of at least one of the compounds of the present invention or a pharmaceutically acceptable salt or prodrug form thereof.

These and other objects, which will become apparent during the following detailed description, have been achieved by the inventors' discovery that compounds of formula (I):

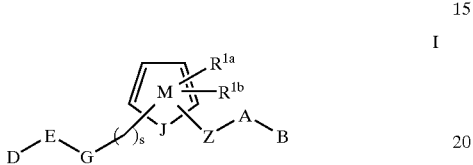

or pharmaceutically acceptable salt or prodrug forms thereof, wherein A, B, D, E, G, J, M, $R^{1a}$, $R^{1b}$, s and Z are defined below, are effective factor Xa inhibitors.

DETAILED DESCRIPTION OF PREFERRED EMBODIMENTS

[1] Thus, in a first embodiment, the present invention provides novel compounds of formula I:

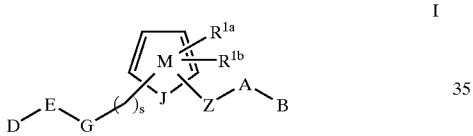

or a stereoisomer or pharmaceutically acceptable salt thereof, wherein;

ring M contains, in addition to J, 0–2 N atoms;

J is O or S;

D is selected from CN, C(=$NR^8$)$NR^7R^9$, NHC(=$NR^8$)$NR^7R^9$, $NR^8$CH(=$NR^7$), C(O)$NR^7R^8$, and (C$R^8R^9$)$_t$$NR^7R^8$, provided that D is substituted meta or para to G on E;

E is selected from phenyl, pyridyl, pyrimidyl, pyrazinyl, pyridazinyl, and piperidinyl substituted with 1 R;

alternatively, D—E—G together represent pyridyl substituted with 1 R;

R is selected from H, halogen, (CH$_2$)$_r$OR$^3$, C$_{1-4}$ alkyl, OCF$_3$, and CF$_3$;

G is absent or is selected from NHCH$_2$, OCH$_2$, and SCH$_2$;

Z is selected from a C$_{1-4}$ alkylene, (CH$_2$)$_r$O(CH$_2$)$_r$, (CH$_2$)$_r$ NR$^3$(CH$_2$)$_r$, (CH$_2$)$_r$C(O)(CH$_2$)$_r$, (CH$_2$)$_r$C(O)O (CH$_2$)$_r$, (CH$_2$)$_r$OC(O)(CH$_2$)$_r$, (CH$_2$)$_r$C(O)NR$^3$(CH$_2$)$_r$, (CH$_2$)$_r$ NR$^3$C(O)(CH$_2$)$_r$, (CH$_2$)$_r$OC(O)O(CH$_2$)$_r$, (CH$_2$)$_r$ OC(O)NR$^3$(CH$_2$)$_r$, (CH$_2$)$_r$NR$^3$C(O)O(CH$_2$)$_r$, (CH$_2$)$_r$ NR$^3$C(O)NR$^3$ (CH$_2$)$_r$, (CH$_2$)$_r$S(O)$_p$(CH$_2$)$_r$, (CH$_2$)$_r$ SO$_2$NR$^3$(CH$_2$)$_r$, (CH$_2$)$_r$NR$^3$SO$_2$(CH$_2$)$_r$, and (CH$_2$)$_r$ NR$^3$SO$_2$NR$^3$(CH$_2$)$_r$, provided that Z does not form a N—N, N—O, N—S, NCH$_2$N, NCH$_2$O, or NCH$_2$S bond with ring M or group A;

$R^{1a}$ and $R^{1b}$ are independently absent or selected from —(CH$_2$)$_r$—R$^{1'}$, NCH$_2$R$^{1''}$, OCH$_2$R$^{1''}$, SCH$_2$R$^{1''}$, N(CH$_2$)$_2$(CH$_2$)$_r$R$^{1'}$, O(CH$_2$)$_2$(CH$_2$)$_r$R$^{1'}$, and S(CH$_2$)$_2$ (CH$_2$)$_r$R$^{1'}$, or combined to form a 5–8 membered saturated, partially saturated or unsaturated ring substituted with 0–2 R$^4$ and which contains from 0–2 heteroatoms selected from the group consisting of N, O, and S;

$R^{1'}$ is selected from H, C$_{1-3}$ alkyl, halo, (CF$_2$)$_r$CF$_3$, OR$^2$, NR$^2$R$^{2a}$, C(O)R$^{2c}$, OC(O)R$^2$, (CF$_2$)$_r$CO$_2$R$^{2c}$, S(O)$_p$R$^{2b}$, NR$^2$(CH$_2$)$_r$OR$^2$, NR$^2$C(O)R$^{2b}$, NR$^2$C(O) NHR$^{2b}$, NR$^2$C(O)$_2$R$^{2a}$, OC(O)NR$^{2b}$, C(O)NR$^2$R$^{2a}$, SO$_2$NR$^2$R$^{2a}$, NR$^2$SO$_2$R$^{2b}$, C$_{3-6}$ carbocyclic residue substituted with 0–2 R$^4$, and 5–10 membered heterocyclic system containing from 1–4 heteroatoms selected from the group consisting of N, O, and S substituted with 0–2 R$^4$;

$R^{1''}$ is selected from H, C(O)R$^{2b}$, C(O)NR$^2$R$^{2a}$, S(O) R$^{2b}$, S(O)$_2$R$^{2b}$, and SO$_2$NR$^2$R$^{2a}$; R$^2$, at each occurrence, is selected from H, CF$_3$, C$_{1-6}$ alkyl, benzyl, C$_{3-6}$ carbocyclic residue substituted with 0–2 R$^{4b}$, and 5–6 membered heterocyclic system containing from 1–4 heteroatoms selected from the group consisting of N, O, and S substituted with 0–2 R$^{4b}$;

R$^{2a}$, at each occurrence, is selected from H, CF$_3$, C$_{1-6}$ alkyl, benzyl, C$_{3-6}$ carbocyclic residue substituted with 0–2 R$^{4b}$, and 5–6 membered heterocyclic system containing from 1–4 heteroatoms selected from the group consisting of N, O, and S substituted with 0–2 R$^{4b}$;

R$^{2b}$, at each occurrence, is selected from CF$_3$, C$_{1-4}$ alkoxy, C$_{1-6}$ alkyl, benzyl, C$_{3-6}$ carbocyclic residue substituted with 0–2 R$^{4b}$, and 5–6 membered heterocyclic system containing from 1–4 heteroatoms selected from the group consisting of N, O, and S substituted with 0–2 R$^{4b}$;

R$^{2c}$, at each occurrence, is selected from CF$_3$, OH, C$_{1-4}$ alkoxy, C$_{1-6}$ alkyl, benzyl, C$_{3-6}$ carbocyclic residue substituted with 0–2 R$^{4b}$, and 5–6 membered heterocyclic system containing from 1–4 heteroatoms selected from the group consisting of N, O, and S substituted with 0–2 R$^{4b}$;

alternatively, R$^2$ and R$^{2a}$ combine to form a 5 or 6 membered saturated, partially saturated or unsaturated ring substituted with 0–2 R$^{4b}$ which contains from 0–1 additional heteroatoms selected from the group consisting of N, O, and S;

R$^3$, at each occurrence, is selected from H, C$_{1-4}$ alkyl, and phenyl;

R$^{3a}$, at each occurrence, is selected from H, C$_{1-4}$ alkyl, and phenyl;

A is selected from:

C$_{3-10}$ carbocyclic residue substituted with 0–2 R$^4$, and 5–10 membered heterocyclic system containing from 1–4 heteroatoms selected from the group consisting of N, O, and S substituted with 0–2 R$^4$;

B is selected from:

X—Y, NR$^2$R$^{2a}$, C(=NR$^2$)NR$^2$R$^{2a}$, NR$^2$C(=NR$^2$) NR$^2$R$^{2a}$,

C$_{3-10}$ carbocyclic residue substituted with 0–2 R$^{4a}$, and 5–10 membered heterocyclic system containing from 1–4 heteroatoms selected from the group consisting of N, O, and S substituted with 0–2 R$^{4a}$;

X is selected from C$_{1-4}$ alkylene, —CR$^2$(CR$^2$R$^{2b}$)(CH$_2$)$_t$—, —C(O)—, —C(=NR)—, —CR$^2$(NR$^{1''}$R$^2$)—, —CR$^2$(OR$^2$)—, —CR$^2$(SR$^2$)—, —C(O)CR$^2$R$^{2a}$—, CR$^2$R$^{2a}$C(O), —S(O)$_p$—, —S(O)$_p$ CR$^2$R$^{2a}$—, —CR$^2$R$^{2a}$S(O)$_p$—, —S(O)$_2$NR$^2$—, —NR$^2$S(O)$_2$—, —NR$^2$S(O)$_2$CR$^2$R$^{2a}$—, —CR$^2$R$^{2a}$S (O)$_2$NR$^2$—, —NR²S(O)₂NR²—, —C(O)NR²—, —NR²C(O)—, —C(O)NR²CR²R²ᵃ—, —NR²C(O)CR²R²ᵃ—, CR²R²ᵃC(O)NR²—, —CR²R²ᵃNR²C(O)—, —NR²C(O)O—, —OC(O)NR²—, —NR²C(O)NR²—, —NR²—, NR²CR²R²ᵃ—, —CR²R²ᵃNR²—, O, —CR²R²ᵃO—, and —OCR²R²ᵃ—;

Y is selected from:
(CH₂)ᵣNR²R²ᵃ, provided that X-Y do not form a N—N, O—N, or S—N bond,
$C_{3-10}$ carbocyclic residue substituted with 0–2 R⁴ᵃ, and 5–10 membered heterocyclic system containing from 1–4 heteroatoms selected from the group consisting of N, O, and S substituted with 0–2 R⁴ᵃ;

R⁴, at each occurrence, is selected from =O, (CH₂)ᵣOR², halo, $C_{1-4}$ alkyl, —CN, NO₂, (CH₂)ᵣNR²R²ᵃ, (CH₂)ᵣC(O)R²ᵇ, NR²C(O)R²ᵇ, C(O)NR²R²ᵃ, NR²C(O)NR²R²ᵃ, CH(=NR²)NR²R²ᵃ, NHC(=NR²)NR²R²ᵃ, SO₂NR²R²ᵃ, NR²SO₂NR²R²ᵃ, NR²SO₂—$C_{1-4}$ alkyl, NR²SO₂R⁵, S(O)ₚR⁵, (CF₂)ᵣCF₃, NCH₂R¹', OCH₂R¹'', SCH₂R¹'', N(CH₂)₂(CH₂)ᵣR¹', O(CH₂)₂(CH₂)ᵣR¹', and S(CH₂)₂(CH₂)ᵣR¹',
alternatively, one R⁴ is a 5–6 membered aromatic heterocycle containing from 1–4 heteroatoms selected from the group consisting of N, O, and S;

R⁴ᵃ, at each occurrence, is selected from =O, (CH₂)ᵣOR², halo, $C_{1-4}$ alkyl, —CN, NO₂, (CH₂)ᵣNR²R²ᵃ, (CH₂)ᵣC(O)R²ᵇ, NR²C(O)R²ᵇ, C(O)NR²R²ᵃ, NR²C(O)NR²R²ᵃ, CH(=NR²)NR²R²ᵃ, NHC(=NR²)NR²R²ᵃ, SO₂NR²R²ᵃ, NR²SO₂NR²R²ᵃ, NR²SO₂—$C_{1-4}$ alkyl, NR²SO₂R⁵, S(O)ₚR⁵, and (CF₂)ᵣCF₃;
alternatively, one R⁴ᵃ is a 5–6 membered aromatic heterocycle containing from 1–4 heteroatoms selected from the group consisting of N, O, and S substituted with 0–1 R⁵;

R⁴ᵇ, at each occurrence, is selected from =O, (CH₂)ᵣOR³, halo, $C_{1-4}$ alkyl, —CN, NO₂, (CH₂)ᵣNR³R³ᵃ, (CH₂)ᵣC(O)R³, NR³C(O)R³ᵃ, C(O)NR³R³ᵃ, NR³C(O)NR³R³ᵃ, CH(=NR³)NR³R³ᵃ, NH³C(=NR³)NR³R³ᵃ, SO₂NR³R³ᵃ, NR³SO₂NR³R³ᵃ, NR³SO₂—$C_{1-4}$ alkyl, NR³SO₂CF₃, NR³SO₂-phenyl, S(O)ₚCF₃, S(O)ₚ—$C_{1-4}$ alkyl, S(O)ₚ-phenyl, and (CF₂)ᵣCF₃;

R⁵, at each occurrence, is selected from CF₃, $C_{1-6}$ alkyl, phenyl substituted with 0–2 R⁶, and benzyl substituted with 0–2 R⁶;

R⁶, at each occurrence, is selected from H, OH, (CH₂)ᵣOR², halo, $C_{1-4}$ alkyl, CN, NO₂, (CH₂)ᵣNR²R²ᵃ, (CH₂)ᵣ C(O)R²ᵇ, NR²C(O)R²ᵇ, NR²C(O)NR²R²ᵃ, CH(=NH)NH₂, NHC(=NH)NH₂, SO₂NR²R²ᵃ, NR²SO₂NR²R²ᵃ, and NR²SO₂$C_{1-4}$ alkyl;

R⁷, at each occurrence, is selected from H, OH, $C_{1-6}$ alkyl, $C_{1-6}$ alkylcarbonyl, $C_{1-6}$ alkoxy, $C_{1-4}$ alkoxycarbonyl, (CH₂)ₙ-phenyl, $C_{6-10}$ aryloxy, $C_{6-10}$ aryloxycarbonyl, $C_{6-10}$ arylmethylcarbonyl, $C_{1-4}$ alkylcarbonyloxy $C_{1-4}$ alkoxycarbonyl, $C_{6-10}$ arylcarbonyloxy $C_{1-4}$ alkoxycarbonyl, $C_{1-6}$ alkylaminocarbonyl, phenylaminocarbonyl, and phenyl $C_{1-4}$ alkoxycarbonyl;

R⁸, at each occurrence, is selected from H, $C_{1-6}$ alkyl and (CH₂)ₙ-phenyl;
alternatively, R⁷ and R⁸ combine to form a 5 or 6 membered saturated, ring which contains from 0–1 additional heteroatoms selected from the group consisting of N, O, and S;

R⁹, at each occurrence, is selected from H, $C_{1-6}$ alkyl and (CH₂)ₙ-phenyl;

n, at each occurrence, is selected from 0, 1, 2, and 3;
m, at each occurrence, is selected from 0, 1, and 2;
p, at each occurrence, is selected from 0, 1, and 2;
r, at each occurrence, is selected from 0, 1, 2, and 3;
s, at each occurrence, is selected from 0, 1, and 2; and,
t, at each occurrence, is selected from 0 and 1;
provided that D—E—G—(CH₂)ₛ— and —Z—A—B are not both benzamidines.

[2] In a preferred embodiment, the present invention provides novel compounds of formulae Ia–If:

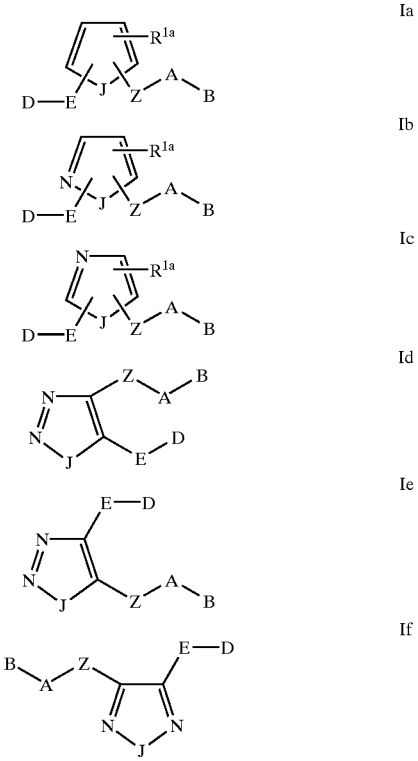

wherein, groups D—E— and —Z—A—B are attached to adjacent atoms on the ring;
Z is selected from a CH₂O, OCH₂, CH₂NH, NHCH₂, C(O), CH₂C(O), C(O)CH₂, NHC(O), C(O)NH, CH₂S(O)₂, S(O)₂(CH₂), SO₂NH, and NHSO₂, provided that Z does not form a N—N, N—O, NCH₂N, or NCH₂O bond with ring M or group A;
A is selected from one of the following carbocyclic and heterocyclic systems which are substituted with 0–2 R⁴;
phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, pxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;
B is selected from: Y, X-Y, NR²R²ᵃ, C(=NR²)NR²R²ᵃ, and NR²C(=NR²)NR²R²ᵃ;
X is selected from $C_{1-4}$ alkylene, —C(O)—, —C(=NR)—, —CR²(NR²R²ᵃ)—, —C(O)CR²R²ᵃ—, —CR$^2$R$^{2a}$C(O), —C(O)NR$^2$—, —NR$^2$C(O)—, —C(O)NR$^2$CR$^2$R$^{2a}$—, —NR$^2$C(O)CR$^2$R$^{2a}$—, —CR$^2$R$^{2a}$C(O)NR$^2$—, —CR$^2$R$^{2a}$NR$^2$C(O)—, —NR$^2$C(O)NR$^2$—, —NR$^2$—, —NR$^2$CR$^2$R$^{2a}$—, —CR$^2$R$^{2a}$NR$^2$—, O, —CR$^2$R$^{2a}$O—, and —OCR$^2$R$^{2a}$—;

Y is NR$^2$R$^{2a}$, provided that X–Y do not form a N—N or O—N bond;

alternatively, Y is selected from one of the following carbocyclic and heterocyclic systems which are substituted with 0–2 R$^{4a}$;

cylcopropyl, cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

alternatively, Y is selected from the following bicyclic heteroaryl ring systems:

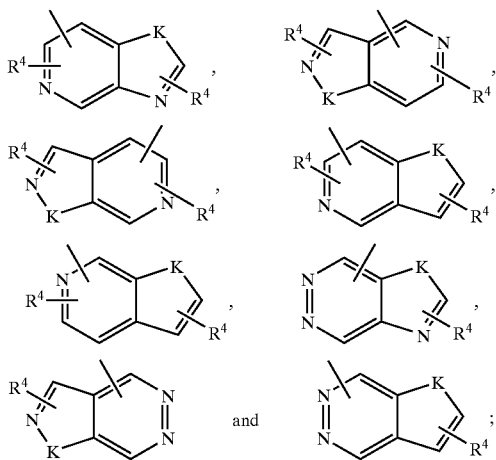

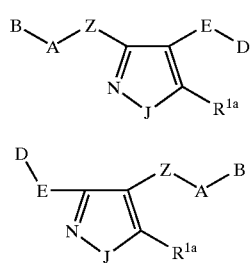

K is selected from O, S, NH, and N.

[3] In a more preferred embodiment, the present invention provides novel compounds of formulae Ib and Ic:

Ib$_1$

Ib$_2$

Ib$_3$

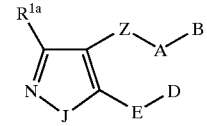

Ib$_4$

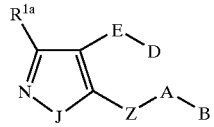

Ic$_1$

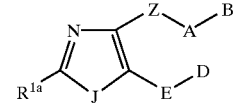

Ic$_2$

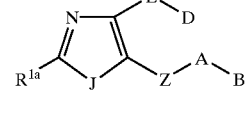

wherein;

J is O or S; and,

Z is selected from a C(O), CH$_2$C(O), C(O)CH$_2$, NHC(O), C(O)NH, C(O)N(CH$_3$), CH$_2$S(O)$_2$, S(O)$_2$(CH$_2$), SO$_2$NH, and NHSO$_2$, provided that Z does not form a N—N or NCH$_2$N bond with ring M or group A.

[4] In an even more preferred embodiment, the present invention provides novel compounds of formulae Ib and Ic, wherein;

E is phenyl substituted with R or 2-pyridyl substituted with R;

D is selected from NH$_2$, C(O)NH$_2$, C(=NH)NH$_2$, CH$_2$NH$_2$, CH$_2$NHCH$_3$, CH(CH$_3$)NH$_2$, and C(CH$_3$)$_2$NH$_2$, provided that D is substituted meta or para to ring M on E; and, R is selected from H, OCH$_3$, Cl, and F.

[5] In a further preferred embodiment, the present invention provides novel compounds of formulae Ib and Ic, wherein; D—E is selected from 3-aminophenyl, 3-amidinophenyl, 3-aminomethylphenyl, 3-aminocarbonylphenyl, 3-(methylaminomethyl)phenyl, 3-(1-aminoethyl)phenyl, 3-(2-amino-2-propyl)phenyl, 4-chloro-3-aminophenyl, 4-chloro-3-amidinophenyl, 4-chloro-3-aminomethylphenyl, 4-chloro-3-(methylaminomethyl)phenyl, 4-fluoro-3-aminophenyl, 4-fluoro-3-amidinophenyl, 4-fluoro-3-aminomethylphenyl, 4-fluoro-3-(methylaminomethyl) phenyl, 6-aminopyrid-2-yl, 6-amidinopyrid-2-yl, 6-aminomethylpyrid-2-yl, 6-aminocarbonylpyrid-2-yl, 6-(methylaminomethyl)pyrid-2-yl, 6-(1-aminoethyl) pyrid-2-yl, and 6-(2-amino-2-propyl)pyrid-2-yl.

[6] In another even more preferred embodiment, the present invention provides novel compounds of formulae Ib and Ic, wherein;

Z is C(O)CH$_2$ and CONH, provided that Z does not form a N—N bond with group A;

A is selected from phenyl, pyridyl, and pyrimidyl, and is substituted with 0–2 R$^4$; and, B is selected from X–Y, phenyl, pyrrolidino, morpholino, 1,2,3-triazolyl, and imidazolyl, and is substituted with 0–1 R$^{4a}$;

R$^4$, at each occurrence, is selected from OH, (CH$_2$)$_r$OR$^2$, halo, C$_{1-4}$ alkyl, (CH$_2$)$_r$NR$^2$R$^{2a}$, and (CF$_2$)$_r$CF$_3$;

$R^{4a}$ is selected from $C_{1-4}$ alkyl, $CF_3$, $S(O)_pR^5$, $SO_2NR^2R^{2a}$, and 1-$CF_3$-tetrazol-2-yl;

$R^5$, at each occurrence, is selected from $CF_3$, $C_{1-6}$ alkyl, phenyl, and benzyl;

X is $CH_2$ or C(O); and,

Y is selected from pyrrolidino and morpholino.

[7] In another further preferred embodiment, the present invention provides novel compounds of formulae Ib and Ic, wherein;

A is selected from the group: phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl; and, B is selected from the group: 2-$CF_3$-phenyl, 2-(aminosulfonyl)phenyl, 2-(methylaminosulfonyl) phenyl, 2-(dimethylaminosulfonyl)phenyl, 1-pyrrolidinocarbonyl, 2-(methylsulfonyl)phenyl, 4-morpholino, 2-(1'-$CF_3$-tetrazol-2-yl)phenyl, 4-morpholinocarbonyl, 2-methyl-1-imidazolyl, 5-methyl-1-imidazolyl, 2-methylsulfonyl-1-imidazolyl and, 5-methyl-1,2,3-triazolyl.

[8] In another even more preferred embodiment, the present invention provides novel compounds of formulae Ib and Ic, wherein;

E is phenyl substituted with R or 2-pyridyl substituted with R;

D is selected from $NH_2$, $C(O)NH_2$, $C(=NH)NH_2$, $CH_2NH_2$, $CH_2NHCH_3$, $CH(CH_3)NH_2$, and $C(CH_3)_2NH_2$, provided that D is substituted meta or para to ring M on E; and, R is selected from H, $OCH_3$, Cl, and F;

Z is $C(O)CH_2$ and CONH, provided that Z does not form a N—N bond with group A;

A is selected from phenyl, pyridyl, and pyrimidyl, and is substituted with 0–2 $R^4$; and, B is selected from X–Y, phenyl, pyrrolidino, morpholino, 1,2,3-triazolyl, and imidazolyl, and is substituted with 0–1 $R^{4a}$;

$R^4$, at each occurrence, is selected from OH, $(CH_2)_rOR^2$, halo, $C_{1-4}$ alkyl, $(CH_2)_rNR^2R^{2a}$, and $(CF_2)_rCF_3$;

$R^{4a}$ is selected from $C_{1-4}$ alkyl, $CF_3$, $S(O)_pR^5$, $SO_2NR^2R^{2a}$, and 1-$CF_3$-tetrazol-2-yl;

$R^5$, at each occurrence, is selected from $CF_3$, $C_{1-6}$ alkyl, phenyl, and benzyl;

X is $CH_2$ or C(O); and,

Y is selected from pyrrolidino and morpholino.

[9] In another further preferred embodiment, the present invention provides novel compounds of formulae Ib and Ic, wherein;

D—E is selected from 3-aminophenyl, 3-amidinophenyl, 3-aminomethylphenyl, 3-aminocarbonylphenyl, 3-(methylaminomethyl)phenyl, 3-(1-aminoethyl) phenyl, 3-(2-amino-2-propyl)phenyl, 4-chloro-3-aminophenyl, 4-chloro-3-amidinophenyl, 4-chloro-3-aminomethylphenyl, 4-chloro-3-(methylaminomethyl) phenyl, 4-fluoro-3-aminophenyl, 4-fluoro-3-amidinophenyl, 4-fluoro-3-aminomethylphenyl, 4-fluoro-3-(methylaminomethyl)phenyl, 6-aminopyrid-2-yl, 6-amidinopyrid-2-yl, 6-aminomethylpyrid-2-yl, 6-aminocarbonylpyrid-2-yl, 6-(methylaminomethyl)pyrid-2-yl, 6-(1-aminoethyl) pyrid-2-yl, 6-(2-amino-2-propyl)pyrid-2-yl;

A is selected from the group: phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl; and, B is selected from the group: 2-$CF_3$-phenyl, 2-(aminosulfonyl)phenyl, 2-(methylaminosulfonyl) phenyl, 2-(dimethylaminosulfonyl)phenyl, 1-pyrrolidinocarbonyl, 2-(methylsulfonyl)phenyl, 4-morpholino, 2-(1'-$CF_3$-tetrazol-2-yl)phenyl, 4-morpholinocarbonyl, 2-methyl-1-imidazolyl, 5-methyl-1-imidazolyl, 2-methylsulfonyl-1-imidazolyl and, 5-methyl-1,2,3-triazolyl.

[10] In a still further preferred embodiment, the present invention provides a novel compound of formula $Ib_1$.

[11] In another still further preferred embodiment, the present invention provides a novel compound of formula $Ib_2$.

[12] In another still further preferred embodiment, the present invention provides a novel compound of formula $Ib_3$.

[13] In another still further preferred embodiment, the present invention provides a novel compound of formula $Ib_4$.

[14] In another still further preferred embodiment, the present invention provides a novel compound of formula $Ic_1$.

[15] In another still further preferred embodiment, the present invention provides a novel compound of formula $Ic_2$.

[16] In another even more preferred embodiment, the present invention provides novel compounds of formulae Ib and Ic, wherein;

D is selected from $C(=NR^8)NR^7R^9$, $C(O)NR^7R^8$, $NR^7R^8$, and $CH_2NR^7R^8$, provided that D is substituted meta or para to ring M on E;

E is phenyl substituted with R or pyridyl substituted with R;

R is selected from H, Cl, F, $OR^3$, $CH_3$, $CH_2CH_3$, $OCF_3$, and $CF_3$;

Z is selected from C(O), $CH_2C(O)$, $C(O)CH_2$, NHC(O), and C(O)NH, provided that Z does not form a N—N bond with ring M or group A;

$R^{1a}$ and $R^{1b}$ are independently absent or selected from $-(CH_2)_r-R^{1'}$, $NCH_2R^{1''}$, $OCH_2R^{1''}$, $SCH_2R^{1''}$, $N(CH_2)_2(CH_2)_rR^{1'}$, $O(CH_2)_2(CH_2)_rR^{1'}$, and $S(CH_2)_2(CH_2)_rR^{1'}$, or combined to form a 5–8 membered saturated, partially saturated or unsaturated ring substituted with 0–2 $R^4$ and which contains from 0–2 heteroatoms selected from the group consisting of N, O, and S;

$R^{1'}$, at each occurrence, is selected from H, $C_{1-3}$ alkyl, halo, $(CF_2)_rCF_3$, $OR^2$, $NR^2R^{2a}$, $C(O)R^{2c}$, $(CF_2)_rCO_2R^{2c}$, $S(O)_pR^{2b}$, $NR^2(CH_2)_rOR^2$, $NR^2C(O)R^{2b}$, $NR^2C(O)_2R^{2b}$, $C(O)NR^2R^{2a}$, $SO_2NR^2R^{2a}$, and $NR^2SO_2R^{2b}$;

A is selected from one of the following carbocyclic and heterocyclic systems which are substituted with 0–2 $R^4$:

phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, and imidazolyl;

B is selected from: Y, X–Y, $NR^2R^{2a}$, $C(=NR^2)NR^2R^{2a}$, and $NR^2C(=NR^2)NR^2R^{2a}$;

X is selected from $CH_2$, $-CR^2(CR^2R^{2b})(CH_2)_r-$, $-C(O)-$, $-C(=NR)-$, $-CH(NR^2R^{2a})-$, $-C(O)NR^2-$, $-NR^2C(O)-$, $-NR^2C(O)NR^2-$, $-NR^2-$, and O;

Y is $NR^2R^{2a}$, provided that X–Y do not form a N—N or O—N bond;

alternatively, Y is selected from one of the following carbocyclic and heterocyclic systems which are substituted with 0–2 $R^{4a}$;

phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, and 1,3,4-triazolyl;

$R^4$, at each occurrence, is selected from =O, OH, Cl, F, $C_{1-4}$ alkyl, $(CH_2)_rNR^2R^{2a}$, $(CH_2)_rC(O)R^{2b}$, $NR^2C(O)R^{2b}$, $C(O)NR^2R^{2a}$, $CH(=NH)NH_2$, $NHC(=NH)NH_2$, $SO_2NR^2R^{2a}$, $NR^2SO_2$—$C_{1-4}$ alkyl, $NR^2SO_2R^5$, $S(O)_pR^5$, and $(CF_2)_rCF_3$;

$R^{4a}$, at each occurrence, is selected from =O, OH, Cl, F, $C_{1-4}$ alkyl, $(CH_2)_rNR^2R^{2a}$, $(CH_2)_rC(O)R^{2b}$, $NR^2C(O)R^{2b}$, $C(O)NR^2R^{2a}$, $CH(=NH)NH_2$, $NHC(=NH)NH_2$, $SO_2NR^2R^{2a}$, $NR^2SO_2$—$C_{1-4}$ alkyl, $NR^2SO_2R^5$, $S(O)_pR^5$, $(CF_2)_rCF_3$, and 1-$CF_3$-tetrazol-2-yl;

$R^5$, at each occurrence, is selected from $CF_3$, $C_{1-6}$ alkyl, phenyl substituted with 0–2 $R^6$, and benzyl substituted with 0–2 $R^6$;

$R^6$, at each occurrence, is selected from H, =O, OH, $OR^2$, Cl, F, $CH_3$, ON, $NO_2$, $(CH_2)_rNR^2R^{2a}$, $(CH_2)_rC(O)R^{2b}$, $NR^2C(O)R^{2b}$, $CH(=NH)NH_2$, $NHC(=NH)NH_2$, and $SO_2NR^2R^{2a}$;

$R^7$, at each occurrence, is selected from H, OH, $C_{1-6}$ alkyl, $C_{1-6}$ alkylcarbonyl, $C_{1-6}$ alkoxy, $C_{1-4}$ alkoxycarbonyl, benzyl, $C_{6-10}$ aryloxy, $C_{6-10}$ aryloxycarbonyl, $C_{6-10}$ arylmethylcarbonyl, $C_{1-4}$ alkylcarbonyloxy $C_{1-4}$ alkoxycarbonyl, $C_{6-10}$ arylcarbonyloxy $C_{1-4}$ alkoxycarbonyl, $C_{1-6}$ alkylaminocarbonyl, phenylaminocarbonyl, and phenyl $C_{1-4}$ alkoxycarbonyl;

$R^8$, at each occurrence, is selected from H, $C_{1-6}$ alkyl and benzyl; and alternatively, $R^7$ and $R^8$ combine to form a morpholino group; and, $R^9$, at each occurrence, is selected from H, $C_{1-6}$ alkyl and benzyl.

[17] In a another further preferred embodiment, the present invention provides novel compounds of formulae Ib and Ic, wherein;

E is phenyl substituted with R or 2-pyridyl substituted with R;

R is selected from H, $C_1$, F, $OCH_3$, $CH_3$, $OCF_3$, and $CF_3$;

Z is selected from a $C(O)CH_2$ and C(O)NH, provided that Z does not form a N—N bond with group A;

$R^{1a}$ is selected from H, $CH_3$, $CH_2CH_3$, Cl, F, $CF_3$, $OCH_3$, $NR^2R^{2a}$, $S(O)_pR^{2b}$, $CH_2S(O)_pR^{2b}$, $CH_2NR^2S(O)_pR^{2b}$, $C(O)R^{2c}$, $CH_2C(O)R^{2c}$, $C(O)NR^2R^{2a}$, and $SO_2NR^2R^{2a}$;

$R^{1b}$ is selected from H, $CH_3$, $CH_2CH_3$, Cl, F, $CF_3$, $OCH_3$, $NR^2R^{2a}$, $S(O)_pR^{2b}$, $CH_2S(O)_pR^{2b}$, $CH_2NR^2S(O)_pR^{2b}$, $C(O)R^{2c}$, $CH_2C(O)R^{2c}$, $C(O)NR^2R^{2a}$, and $SO_2NR^2R^{2a}$;

A is selected from one of the following carbocyclic and heterocyclic systems which are substituted with 0–2 $R^4$;

phenyl, pyridyl, pyrimidyl, furanyl, thiophenyl, pyrrolyl, oxazolyl, isoxazolyl, thiazolyl, isothiazolyl, pyrazolyl, and imidazolyl;

B is selected from: Y and X–Y;

X is selected from $CH_2$, —$CR^2(CR^2R^{2b})$—, —C(O)—, —C(=NR)—, —$CH(NR^2R^{2a})$—, —$C(O)NR^2$—, —$NR^2C(O)$—, —$NR^2C(O)NR^2$—, —$NR^2$—, and O;

Y is $NR^2R^{2a}$, provided that X–Y do not form a N—N or O—N bond;

alternatively, Y is selected from one of the following carbocyclic and heterocyclic systems which are substituted with 0–2 $R^{4a}$;

phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, and 1,3,4-triazolyl;

$R^2$, at each occurrence, is selected from H, $CF_3$, $CH_3$, benzyl, and phenyl;

$R^{2a}$, at each occurrence, is selected from H, $CF_3$, $CH_3$, benzyl, and phenyl;

$R^{2b}$, at each occurrence, is selected from $CF_3$, $OCH_3$, $CH_3$, benzyl, and phenyl;

$R^{2c}$, at each occurrence, is selected from $CF_3$, OH, $OCH_3$, $CH_3$, benzyl, and phenyl;

alternatively, $R^2$ and $R^{2a}$ combine to form a 5 or 6 membered saturated, partially unsaturated, or unsaturated ring which contains from 0–1 additional heteroatoms selected from the group consisting of N, O, and S;

$R^3$, at each occurrence, is selected from H, $CH_3$, $CH_2CH_3$, and phenyl;

$R^{3a}$, at each occurrence, is selected from H, $CH_3$, $CH_2CH_3$, and phenyl;

$R^4$, at each occurrence, is selected from OH, Cl, F, $CH_3$, $CH_2CH_3$, $NR^2R^{2a}$, $CH_2NR^2R^{2a}$, $C(O)$ $R^{2b}$, $NR^2C(O)R^{2b}$, $C(O)NR^2R^{2a}$, and $CF_3$;

$R^{4a}$, at each occurrence, is selected from OH, Cl, F, $CH_3$, $CH_2CH_3$, $NR^2R^{2a}$, $CH_2NR^2R^{2a}$, $C(O)$ $R^{2b}$, $C(O)NR^2R^{2a}$, $SO_2NR^2R^{2a}$, $S(O)_pR^5$, $CF_3$, and 1-$CF_3$-tetrazol-2-yl;

$R^5$, at each occurrence, is selected from $CF_3$, $C_{1-6}$ alkyl, phenyl substituted with 0–2 $R^6$, and benzyl substituted with 1 $R^6$;

$R^6$, at each occurrence, is selected from H, OH, $OCH_3$, Cl, F, $CH_3$, CN, $NO_2$, $NR^2R^{2a}$, $CH_2NR^2R^{2a}$, and $SO_2NR^2R^{2a}$;

$R^7$, at each occurrence, is selected from H, OH, $C_{1-3}$ alkyl, $C_{1-3}$ alkylcarbonyl, $C_{1-3}$ alkoxy, $C_{1-4}$ alkoxycarbonyl, benzyl, phenoxy, phenoxycarbonyl, benzylcarbonyl, $C_{1-4}$ alkylcarbonyloxy $C_{1-4}$ alkoxycarbonyl, phenylcarbonyloxy $C_{1-4}$ alkoxycarbonyl, $C_{1-6}$ alkylaminocarbonyl, phenylaminocarbonyl, and phenyl $C_{1-4}$ alkoxycarbonyl;

$R^8$, at each occurrence, is selected from H, $CH_3$, and benzyl; and, alternatively, $R^7$ and $R^8$ combine to form a morpholino group;

$R^9$, at each occurrence, is selected from H, $CH_3$, and benzyl.

[18] In a another still further preferred embodiment, the present invention provides novel compounds of formulae Ib and Ic, wherein;

$R^{1a}$ is absent or is selected from H, $CH_3$, $CH_2CH_3$, Cl, F, $CF_3$, $OCH_3$, $NR^2R^{2a}$, $S(O)_pR^{2b}$, $C(O)NR^2R^{2a}$, $CH_2S(O)_pR^{2b}$, $CH_2NR^2S(O)_pR^{2b}$, $C(O)R^{2c}$, $CH_2C(O)R^{2c}$, and $SO_2NR^2R^{2a}$;

$R^{1b}$ is absent or is selected from H, $CH_3$, $CH_2CH_3$, Cl, F, $CF_3$, $OCH_3$, $NR^2R^{2a}$, $S(O)_pR^{2b}$, $C(O)NR^2R^{2a}$, $CH_2S(O)_pR^{2b}$, $CH_2NR^2S(O)_pR^{2b}$, $C(O)R^{2b}$, $CH_2C(O)R^{2b}$, and $SO_2NR^2R^{2a}$;

A is selected from one of the following carbocyclic and heterocyclic systems which are substituted with 0–2 $R^4$;
phenyl, pyridyl, and pyrimidyl;

B is selected from: Y and X–Y;

X is selected from —C(O)— and O;

Y is $NR^2R^{2a}$, provided that X–Y do not form a O—N bond;

alternatively, Y is selected from one of the following carbocyclic and heterocyclic systems which are substituted with 0–2 $R^{4a}$;
phenyl piperazinyl, pyridyl, pyrimidyl, morpholinyl, pyrrolidinyl, imidazolyl, and 1,2,3-triazolyl;

$R^2$, at each occurrence, is selected from H, $CF_3$, $CH_3$, benzyl, and phenyl;

$R^{2a}$, at each occurrence, is selected from H, $CF_3$, $CH_3$, benzyl, and phenyl;

$R^{2b}$, at each occurrence, is selected from $CF_3$, $OCH_3$, $CH_3$, benzyl, and phenyl;

$R^{2c}$, at each occurrence, is selected from $CF_3$, OH, $OCH_3$, $CH_3$, benzyl, and phenyl;

alternatively, $R^2$ and $R^{2a}$ combine to form a ring system selected from pyrrolidinyl, piperazinyl and morpholino;

$R^4$, at each occurrence, is selected from Cl, F, $CH_3$, $NR^2R^{2a}$, and $CF_3$;

$R^{4a}$, at each occurrence, is selected from Cl, F, $CH_3$, $SO_2NR^2R^{2a}$, $S(O)_pR^5$, and $CF_3$; and, $R^5$, at each occurrence, is selected from $CF_3$ and $CH_3$.

[19] Specifically preferred compounds of the present invention invention is selected from the group:

3-(3-amidinophenyl)-4-[(2'-aminosulfonyl-[1,1']-biphen-4-yl)aminocarbonyl]-5-(hydroxymethyl)isoxazole;
3-(3-amidinophenyl)-4-[(2'-aminosulfonyl-[1,1']-biphen-4-yl)aminocarbonyl]isoxazole;
3-(3-amidinophenyl)-4-[(2'-methylsulfonyl-[1,1']-biphen-4-yl)aminocarbonyl]isoxazole;
3-(3-amidinophenyl)-4-[5-(2-aminosulfonyl)phenylpyrid-2-yl)aminocarbonyl]-5-(methoxymethyl)isoxazole;
3-(3-amidinophenyl)-4-[(2'-trifluoromethyl-[1,1']-biphen-4-yl)aminocarbonyl]isoxazole;
3-(3-amidinophenyl)-4-[(2'-aminosulfonyl-[1,1']-biphen-4-yl)aminocarbonyl]-5-(trifluoromethyl)isoxazole;
2-acetylamino-4-(3-amidinophenyl)-5-[(2'-aminosulfonyl-[1,1']-biphen-4-yl)aminocarbonyl]thiazole;
2-amino-4-(3-amidinophenyl)-5-[(2'-aminosulfonyl-[1,1']-biphen-4-yl)aminocarbonyl]thiazole;
2-methyl-4-(3-amidinophenyl)-5-[(2'-aminosulfonyl-[1,1']-biphen-4-yl)aminocarbonyl]thiazole;
5-(3-amidinophenyl)-4-[(2'-aminosulfonyl-[1,1']-biphen-4-yl)aminocarbonyl]oxazole;
3-(3-amidinophenyl)-4-[(2'-t-butylaminosulfonyl-[1,1']-biphen-4-yl)aminocarbonyl]isoxazole;
3-(3-amidinophenyl)-4-[(2'-aminosulfonyl-[1,1']-biphen-4-yl)aminocarbonyl]-5-(methoxymethyl)-isoxazole;
3-(3-amidinophenyl)-4-[(2'-t-butylaminosulfonyl-[1,1']-biphen-4-yl)aminocarbonyl]isoxazole;
3-(3-amidinophenyl)-4-[(2'-aminosulfonyl-[1,1']-biphen-4-yl)aminocarbonyl]-5-(methoxymethyl)isoxazole;
2-methyl-4-(3-amidinophenyl)-5-[(2'-trifluoromethyl-[1,1']-biphen-4-yl)aminocarbonyl]thiazole;
2-phenyl-4-(3-amidinophenyl)-5-[(2'-aminosulfonyl-[1,1']-biphen-4-yl)aminocarbonyl]thiazole;
3-(3-amidinophenyl)-4-[(3-fluoro-2'-methylsulfonyl-[1,1']-biphen-4-yl)aminocarbonyl]isoxazole;
3-(3-amidinophenyl)-4-[(2'-trifluoromethylthio-[1,1']-biphen-4-yl)aminocarbonyl]isoxazole;
3-(3-amidinophenyl)-5-amino-4-[(2'-aminosulfonyl-[1,1']-biphen-4-yl)aminocarbonyl]isoxazole;
2-(phenylamino)-4-(3-amidinophenyl)-5-[(2'-aminosulfonyl-[1,1']-biphen-4-yl)aminocarbonyl]thiazole;
2-(benzylamino)-4-(3-amidinophenyl)-5-[(2'-aminosulfonyl-[1,1']-biphen-4-yl)aminocarbonyl]thiazole;
2-(methylamino)-4-(3-amidinophenyl)-5-[(2'-aminosulfonyl-[1,1']-biphen-4-yl)aminocarbonyl]thiazole;
2-(methylamino)-4-(3-carboxamidophenyl)-5-[(2'-aminosulfonyl-[1,1']-biphen-4-yl)aminocarbonyl]thiazole;
2-methyl-4-(3-amidinophenyl)-5-[[5-(2'-aminosulfonylphenyl-1-yl)pyridin-2-yl]aminocarbonyl]thiazole;
2-methyl-4-(3-(carboxamido)phenyl)-5-[[5-(2'-aminosulfonylphenyl-1-yl)pyridin-2-yl]aminocarbonyl]thiazole;
2-(3-pyridyl)-4-(3-amidinophenyl)-5-[(2'-aminosulfonyl-[1,1']-biphen-4-yl)aminocarbonyl]thiazole;
2-(3-pyridyl)-4-(3-carboxamidophenyl)-5-[(2'-aminosulfonyl-[1,1']-biphen-4-yl)aminocarbonyl]thiazole;
2-chloro-4-(3-amidinophenyl)-5-[(2'-aminosulfonyl-[1,1']-biphen-4-yl)aminocarbonyl]thiazole;
2-chloro-4-(3-carboxamidophenyl)-5-[(2'-aminosulfonyl-[1,1']-biphen-4-yl)aminocarbonyl]thiazole;
2-chloro-4-(3-amidinophenyl)-5-[[5-(2'-aminosulfonylphenyl-1-yl)pyridin-2-yl]aminocarbonyl]thiazole;
2-chloro-4-(3-(carboxamido)phenyl)-5-[[5-(2'-aminosulfonylphenyl-1-yl)pyridin-2-yl]aminocarbonyl]thiazole;
2-hydroxy-4-(3-amidinophenyl)-5-[[5-(2'-aminosulfonylphenyl-1-yl)pyridin-2-yl]aminocarbonyl]thiazole;
2-chloro-4-(3-aminophenyl)-5-[(2'-aminosulfonyl-[1,1']-biphen-4-yl)aminocarbonyl]thiazole;
2-amino-4-[(3-amino-4-chloro)phenyl]-5-[(2'-aminosulfonyl-[1,1']-biphen-4-yl)aminocarbonyl]thiazole;
2-chloro-4-[(3-amino-4-chloro)phenyl]-5-[(2'-aminosulfonyl-[1,1']-biphen-4-yl)aminocarbonyl]thiazole; and,
2-amino-4-[(3-aminomethyl)phenyl]-5-[(2'-aminosulfonyl-[1,1']-biphen-4-yl)aminocarbonyl]thiazole;

and a pharmaceutically acceptable salt thereof.

In a second embodiment, the present invention provides novel pharmaceutical compositions, comprising: a pharmaceutically acceptable carrier and a therapeutically effective amount of a compound of formula (I) or a pharmaceutically acceptable salt form thereof.

In a third embodiment, the present invention provides a novel method for treating or preventing a thromboembolic disorder, comprising: administering to a patient in need thereof a therapeutically effective amount of a compound of formula (I) or a pharmaceutically acceptable salt form thereof.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

When any variable (e.g., $R^6$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "$C_{1-6}$ alkyl" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, t-butyl, pentyl, and hexyl; "Alkenyl" is intended to include hydrocarbon chains of either a straight or branched configuration and one or more unsaturated carbon-carbon bonds which may occur in any stable point along the chain, such as ethenyl, propenyl, and the like.

"Halo" or "halogen" as used herein refers to fluoro, chloro, bromo, and iodo; and "counterion" is used to represent a small, negatively charged species such as chloride, bromide, hydroxide, acetate, sulfate, and the like.

As used herein, "carbocycle" or "carbocyclic residue" is intended to mean any stable 3- to 10-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic system" is intended to mean a stable 5- to 7-membered monocyclic or bicyclic or 7- to 10-membered bicyclic heterocyclic ring which is saturated partially unsaturated or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" is intended to mean a stable 5- to 7-membered monocyclic or bicyclic or 7- to 10-membered bicyclic heterocyclic aromatic ring which consists of carbon atoms and from 1 to 4 heterotams independently selected from the group consisting of N, O and S. It is preferred that the total number of S and O atoms in the aromatic heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinoyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is hereby incorporated by reference.

"Prodrugs" are intended to include any covalently bonded carriers which release the active parent drug according to formula (I) in vivo when such prodrug is administered to a mammalian subject. Prodrugs of a compound of formula (I) are prepared by modifying functional groups present in the compound in such a way that the modifications are cleaved, either in routine manipulation or in vivo, to the parent compound. Prodrugs include compounds of formula (I) wherein a hydroxy, amino, or sulfhydryl group is bonded to any group that, when the prodrug or compound of formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of formula (I), and the like. Preferred prodrugs are amidine prodrugs wherein D is C(=NR$^7$)NH$_2$, and R$^7$ is selected from OH, C$_{1-4}$ alkoxy, C$_{6-10}$ aryloxy, C$_{1-4}$ alkoxycarbonyl, C$_{6-10}$ aryloxycarbonyl, C$_{6-10}$ arylmethylcarbonyl, C$_{1-4}$ alkylcarbonyloxy C$_{1-4}$ alkoxycarbonyl, and C$_{6-10}$ arylcarbonyloxy C$_{1-4}$ alkoxycarbonyl. More preferred prodrugs are where R$^7$ is OH, methoxy, ethoxy, benzyloxycarbonyl, methoxycarbonyl, and methylcarbonyloxymethoxycarbonyl.

"Stable compound" and "stable structure" are meant to indicate a compound that is sufficiently robust to survive isolation to a useful degree of purity from a reaction mixture, and formulation into an efficacious therapeutic agent.

SYNTHESIS

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (Protective Groups In Organic Synthesis, Wiley and Sons, 1991). All references cited herein are hereby incorporated in their entirety herein by reference.

Schemes 1–4 describe the synthesis of compounds wherein M is furan and Q is a protected precursor of group D of formula I. Each scheme represents a different substitution pattern for the furan ring. In Scheme 1, an alpha-substituted carboxylic acid, wherein V is a nitro, protected sulfonamide or ester group, can be treated with two equivalents of base to activate it, quenched with an appropriate aldehyde electrophile as described by Wierenga (J. Org. Chem., 44(2), 310, 1979) and then oxidized by pyridinium dichromate to a ketone. Treatment with base and acetic anhydride should give the enol acetate which can react with a vinyl sulfoxide to give a dihydrofuran as shown by Chan (J. Chem. Soc., Perkins Trans. 1 1992, 945). This sulfoxide can then be oxidized and eliminated to give the desired furan.

Scheme 1

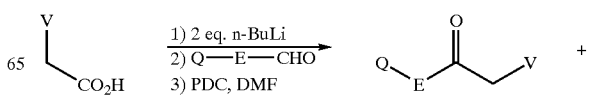

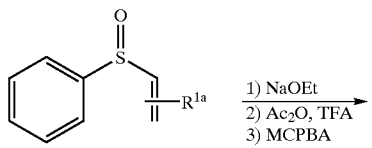
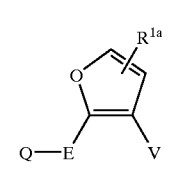

Scheme 3

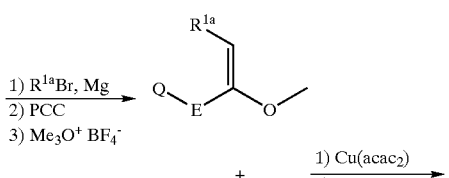

In Scheme 2, the readily available bromides Q—E—Br are coupled to a terminal acetylene, to give a disubstituted alkyne as shown by Padwa (J. Org. Chem. 1991, 56(7), 2523). Also shown in Scheme 2, a carboxylic acid can be homologated into a ketone and then converted into a diazoketone. Rhodium catalyzed cyclization can provide the desired furan as in Davies (Tetrahedron 1988, 44(11), 3343).

Scheme 2

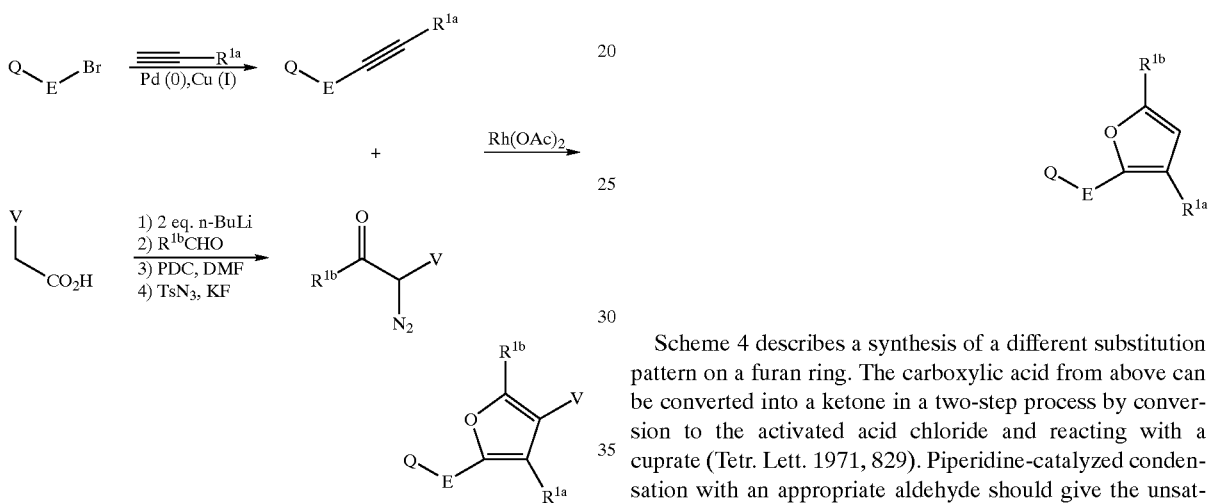

Addition of a grignard reagent to the appropriate aldehyde, oxidation and O-methylation should give the required enol ether as shown in Scheme 3. Diazoketone formation of the acetyl derivative, AcW, and copper catalyzed cyclization can be done like Alonos (J. Org. Chem. 1991, 56(7), 2523) followed by standard deprotection should give the desired furan.

Scheme 4 describes a synthesis of a different substitution pattern on a furan ring. The carboxylic acid from above can be converted into a ketone in a two-step process by conversion to the activated acid chloride and reacting with a cuprate (Tetr. Lett. 1971, 829). Piperidine-catalyzed condensation with an appropriate aldehyde should give the unsaturated ketone as shown by Taylor (J. Het. Chem. 1989, 26, 1353). Conjugate addition of a dithiane to the unsaturated ketone should give the required substitution pattern. N-bromosuccinimide deprotection of the dithiane followed by acid-catalyzed cyclization can provide the furan.

Scheme 4

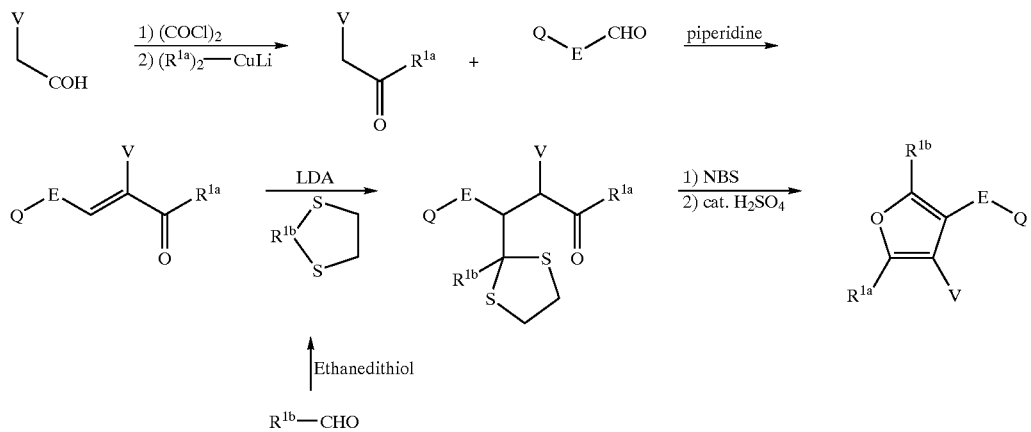

Schemes 5 and 6 describe the synthesis of compounds wherein ring M is thiophene. The appropriate aldehyde in Scheme 5 can be oxidized to a carboxylic acid and converted to an acid chloride. Reaction of this acid chloride with methyl ketone and lithium bis(trimethylsilyl)amide as shown by Cushman (Tetr. Lett. 1990, 45, 6497). Further treatment with diazomethane can provide a mixture of two regioisomers which need not be separated at this time. Treatment of the commercially available bromide with sodium sulfide followed by the unsaturated ketone should give a mixture of thiophene regioisomers which can be separated according to Alberola (Synth. Comm. 1990, 20, 2537).

Alternatively, in Scheme 6, ethyl acetate can be diazotized by tosyl azide and carbene insertion into the E—Br bond as in D'yakonov (J. Gen. Chem. USSR, 1951, 21, 851). Nucleophilic displacement with a thiocarboxylic acid (Org. Syn. Coll. 1963, 4, 924) should give the appropriate carboxylic acid after basic hydrolysis as shown by Masuda (Chem. Pharm. Bull. 1977, 25, 1471). Reaction with a disubstituted alkyne with trifluoroacetic anhydride can give a mixture of regioisomers. By analogy switching the position of V and Q—E in the reagents can give a different set of regioisomers.

Scheme 6

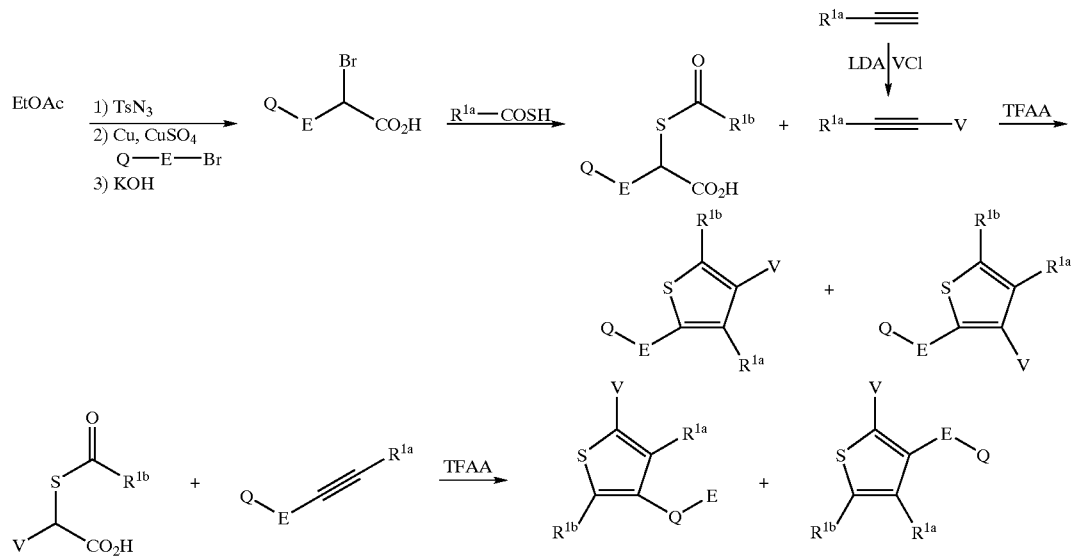

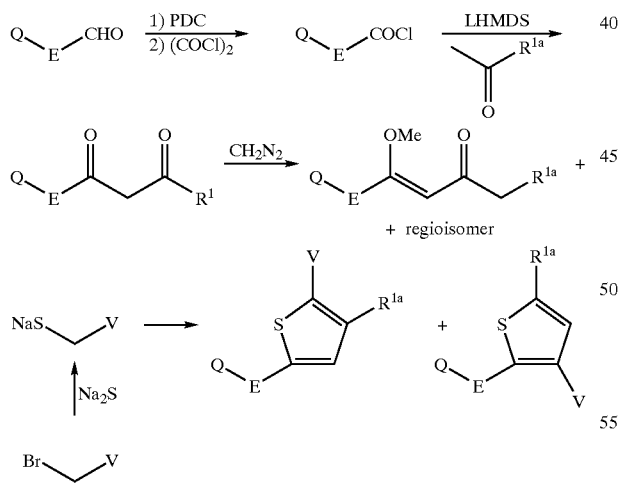

Scheme 5

Schemes 7 and 8 provide routes to compounds of Formula I wherein ring M is isoxazole. Scheme 7 shows one possible synthesis of isoxazoles. Substituted benzaldehydes can be reacted with hydroxyl amine then chlorinated to give the hydroximinoyl chloride (see J. Org. Chem. 1980, 45, 3916). Preparation of the nitrile oxide in situ with triethylamine and cycloaddition with a substituted alkyne can give a mixture of regioisomeric isoxazoles as shown by H. Kawakami (Chem. Lett. 1987, 1, 85). Preparation of the disubstituted alkyne can be achieved by nucleophilic attack of the alkynyl anion on an electrophile as shown by L. N. Jungheim (J. Org. Chem. 1987, 57, 4007). Alternatively, one could make the hydroxyiminoyl chloride of the $R^{1a}$ piece and react it with an appropriately substituted alkyne to give another set of regioisomeric isoxazoles which can be separated chromatographically.

Scheme 7

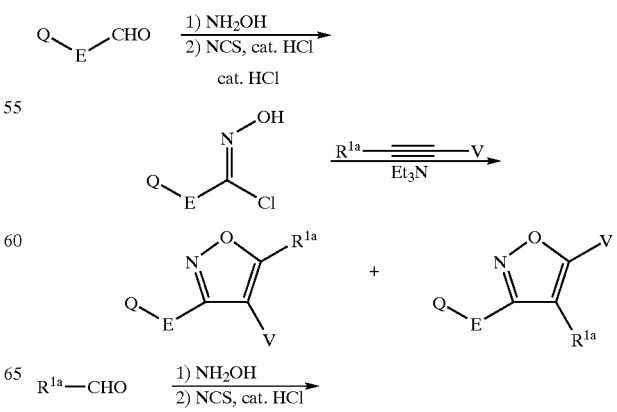

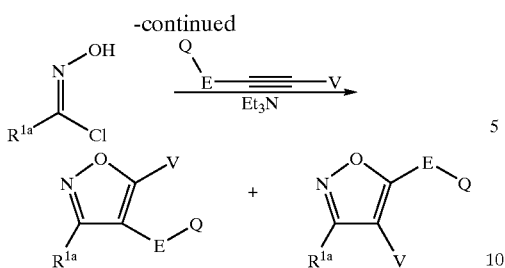

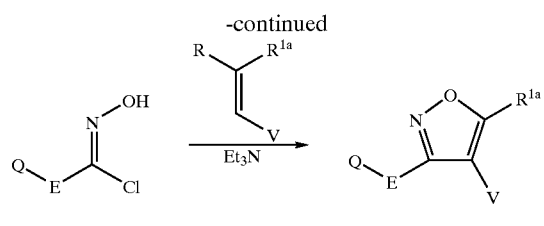

Where R = OMe, Cl or F

An alternate procedure which should produce only one isoxazole regioisomer is described in Scheme 8. The methylated form of substituent V can be deprotonated and silylated. Chlorination with carbon tetrachloride or fluorination with difluorodibromomethane under triethylborane catalysis can give the geminal dihalo compound as shown by Sugimoto (Chem. Lett. 1991, 1319). Cuprate-mediated conjugate addition-elimination give the desired alkene as in Harding (J. Org. Chem. 1978, 43, 3874).

Alternatively, one can acylate with an acid chloride to form a ketone as in Andrews (Tetr. Lett. 1991, 7731) followed by diazomethane to form the enol ether. Each of these compounds can be reacted with a hydroximinoyl chloride in the presence of triethylamine to give one regioisomeric isoxazole as shown by Stevens (Tetr. Lett. 1984, 4587).

Scheme 8

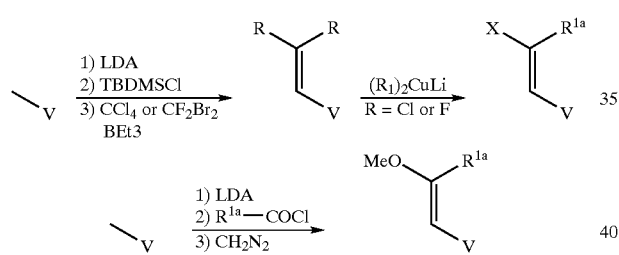

The following is a reaction grid for the synthesis of the Z linkage. The following coupling reaction would be readily known to those skilled in the art of organic synthesis.

When Z=

CONH then use V=$CO_2CH_3$ and W=$NH_2$ under $AlMe_3$ catalysis $SO_2NH$ then make heterocycle after sulfonamide formation $CH_2NH$ then reduce V=$CO_2CH_3$ with DIBAL to $CH_2OH$ and couple with W=$NH_2$ using $PPh_3$ $CH_2S$ then reduce V=$CO_2CH_3$ with DIBAL to $CH_2OH$ and couple with W=SH using MsCl $CH_2O$ then reduce V=$CO_2CH_3$ with DIBAL to $CH_2OH$ and couple with W =OH using $PPh_3$ NHCO then reduce V=$NO_2$ to $NH_2$ using $H_2$/Pd and couple with W=$C_{02}CH_3$ using $AlMe_3$ $NHSO_2$ then reduce V=$NO_2$ to $NH_2$ using $H_2$/Pd and couple with W=$SO_2Cl$ $NHCH_2$ then reduce V=$NO_2$ to $NH_2$ using $H_2$/Pd and couple with W=$CH_2Br$ $OCH_2$ then reduce, then diazotize V=$NO_2$ and couple with W=$CH_2Br$ $SCH_2$ then reduce V=$SO_2NR_2$ with LAH and couple with W=$CH_2Br$.

To complete the final reaction sequence, substituent Q can be deprotected or reacted to give an amine or amide. The amine can converted into an amidine, guanidine or formamidine under standard conditions as outline in Scheme 9. From the nitrile, imididate formation followed by amination with ammonium carbonate can provide the amidine.

Scheme 9

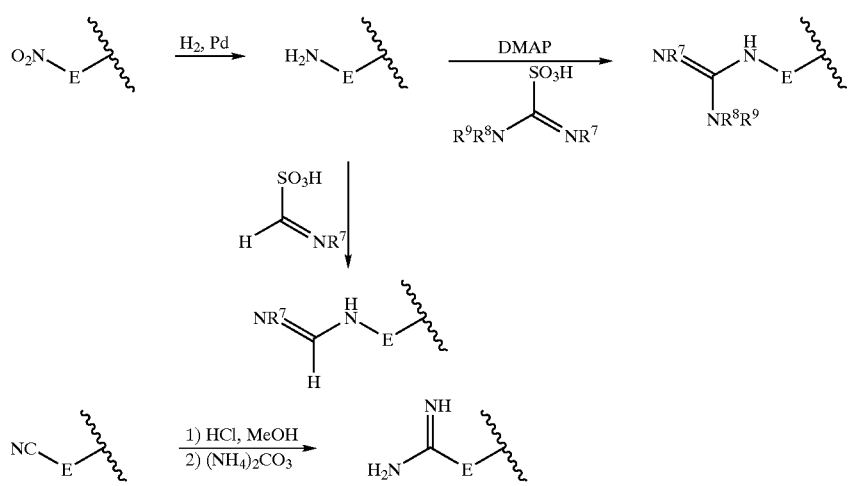

The compounds of Formula I in which ring M is thiazole or oxazole can be prepared as outlined in Schemes 10–16 wherein, $R^e$ and $R^f$ can be Z—A—B or $R^{1a}$ or precursors thereof. There are numerous methods by which to prepare and manipulate substituted thiazole and oxazole rings (for reviews, see Comprehensive Heterocyclic Chemistry, Katritzky and Rees, eds. 1984, 6, 247 and Chem. Het. Cmpds. 1979, 34–2, 1). One particularly useful method for preparing thiazole and oxazole containing compounds of the present invention is the Hantzsch method, which involves condensation of α-haloketones with thioamides, thioureas, amides and ureas.

As shown in Scheme 10, an appropriate ketone can be brominated by a variety of electrophilic brominating reagents such as pyridinium bromide perbromide, NBS, etc. to afford an α-bromoketone. Heating with a wide variety of substituted thioamides and thioureas, and amides and ureas can afford thiazole and oxazole derivatives. Regioisomeric thiazoles and oxazoles can be prepared by a similar reaction sequence beginning with a similar ketone. The ketones in Scheme 10 are readily available by procedures familiar to those skilled in the art of organic synthesis. The functionality Q can later be transformed into the group D found in compounds of Formula I.

The thioamides are either commercially available or can be prepared from the corresponding amides using Lawesson's reagent or phosphorous pentasulfide. They can also be prepared and cyclized in situ by performing the cyclization reaction with the corresponding amide in the presence of phosphorous pentasulfide. The thioureas are either commercially available or are readily prepared from other commercially available thioureas. The amides and ureas are either commercially available or are readily prepared by procedures known to those skilled in the art.

Scheme 10

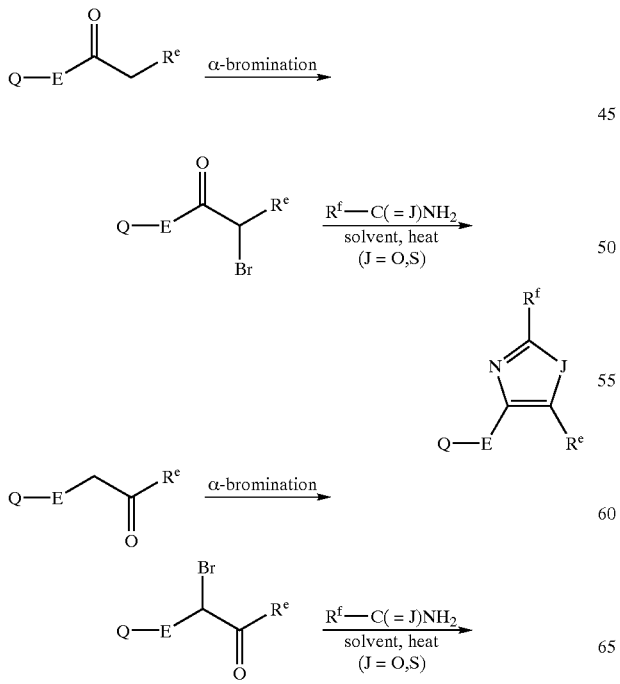

In Scheme 11 is shown how α-acylaminoketones can be converted into oxazoles by dehydration with an acid such as sulfuric acid. Treating with phosphorous pentasulfide can afford thiazoles. The starting materials are prepared by standard methods known to those skilled in the art.

Scheme 11

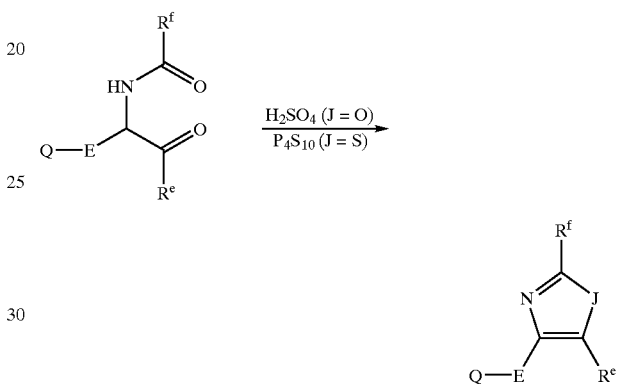

Oxazoles can also be prepared by the cyclization strategy shown in Scheme 12. Ketones can be converted into their oxime derivatives by standard treatment with hydroxylamine. Treating these intermediates with acid chlorides can provide the corresponding oxazoles.

Scheme 12

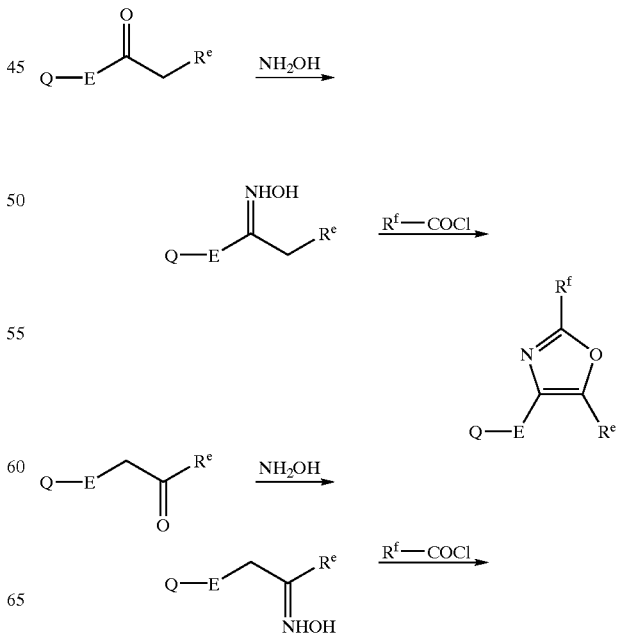

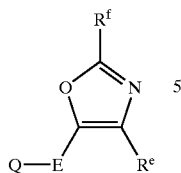

2-Unsubstituted oxazoles can be prepared by the cyclization shown in Scheme 13. Treatment of acid chlorides with an isocyanoacetate (wherein $R^g$ can be A—B or a precursor thereof) in the presence of a base such as triethylamine can afford the oxazoles (Suzuki et. al. Syn. Comm. 1972, 2, 237).

Scheme 13

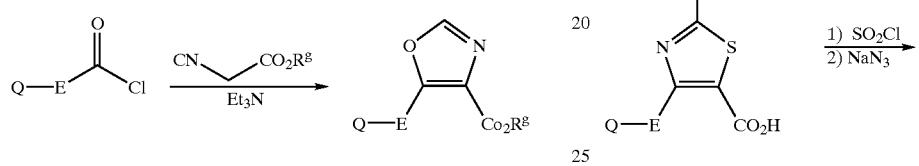

Other cyclization strategies can afford differently substituted thiazoles and oxazoles. In Scheme 14 is shown how cyclizations can be modified to afford 5-aminooxazoles and 4- and 5-aminothiazoles. Treatment of aldehydes with NaCN and ammonium chloride can afford α-aminonitriles (Steiger Org. Syn. Coll. Vol. III 1955, 84). Acylation with acid chlorides followed by acid-catalyzed dehydration can afford 5-aminooxazoles. The bromination of nitrites with bromine can afford α-bromonitriles. These can be treated with a variety of thioamides to afford 4-aminothiazoles. The 5-aminothiazoles can be prepared by elaboration of thiazole carboxylic acids. Formation of the acyl azide by standard methods can be followed by heating to effect a Curtius rearrangement to give the isocyanate (South, J. Het. Chem. 1991, 28, 1003). Addition of water can then afford the 5-aminothiazoles.

Scheme 14

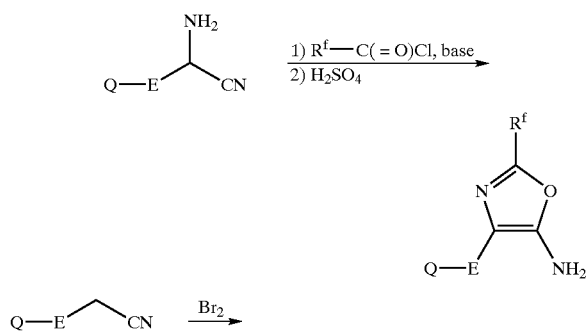

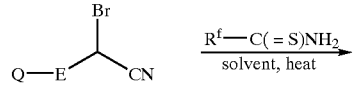

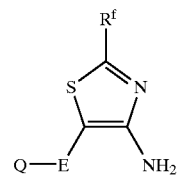

In Scheme 15 is shown how thiazoles and oxazoles with halogen substituents can be prepared. The 2-halo-derivatives can be prepared from the corresponding amino derivatives by diazotization with nitrous acid or isoamyl nitrite followed by displacement with an appropriate halide source such as copper bromide or chloride. The 5-halo-derivatives can be prepared by ring bromination with NBS or $Br_2$, or chlorination with NCS or $Cl_2$. Alternatively, the Hunsdiecker procedure (Ber. 1942, 75, 291) can be applied to the 5-carboxylic acid derivatives to prepare the bromides. The 4-halo derivatives can be prepared in the same manner from the regioisomer in which the group Q—E occupies position 5 on the ring.

Scheme 15

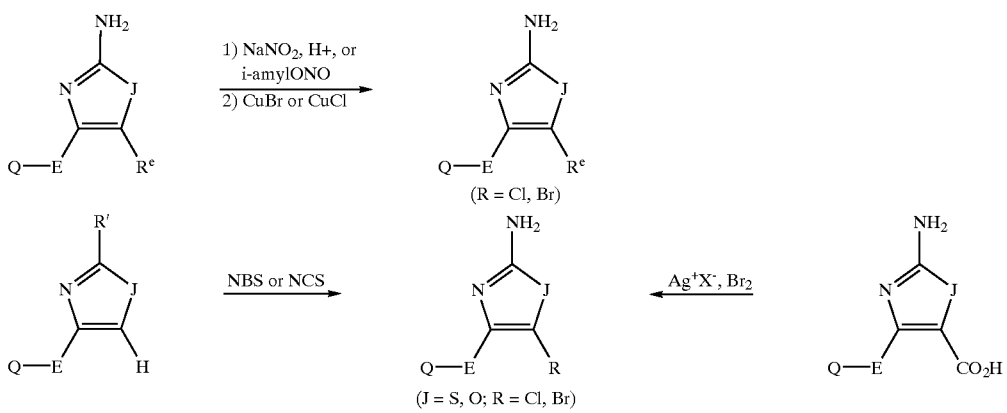

In Scheme 16 is shown how mercapto and sulfonyl derivatives of the thiazoles and oxazoles can be prepared. The 2-mercapto derivatives can be prepared from the corresponding 2-amino heterocycles by diazotization with nitrous acid or isoamyl nitrite followed by reaction with an appropriate thiol. Oxidation of the thiol derivative can afford the sulfonic acid derivatives. The 5-mercapto derivatives can be prepared by thiol displacement of the appropriate 5-bromo derivative. Alternatively, halogen metal exchange of the bromo derivative with n-BuLi followed by quenching with sulfur can afford the required 5-mercapto derivatives. The sulfonyl derivatives are available by oxidation of the mercapto derivatives. In some cases direct sulfonation of the thiazole or oxazole ring can be possible. When R' is an activating group such as amino or alkoxy, treatment with chlorosulfonic acid should give the sulfonyl derivative (Mann et. al. J. Prakt. Chem. 1978, 320, 715). The 4-mercapto and sulfonyl derivatives can be prepared in the same manner as shown for the 5-derivatives from the regioisomers in which the group Q—E occupies position 5 on the ring.

Scheme 16

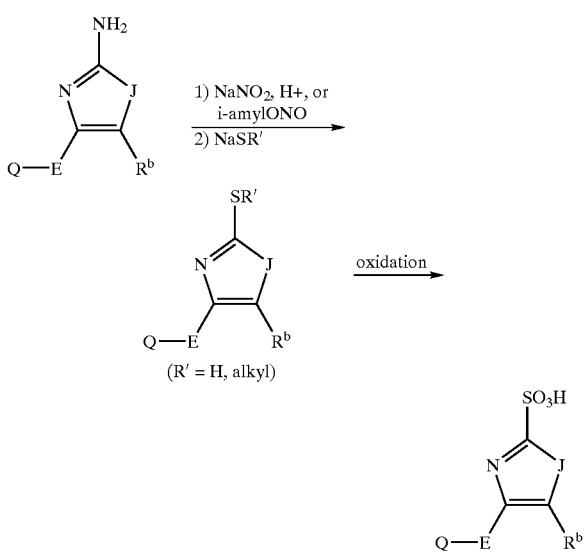

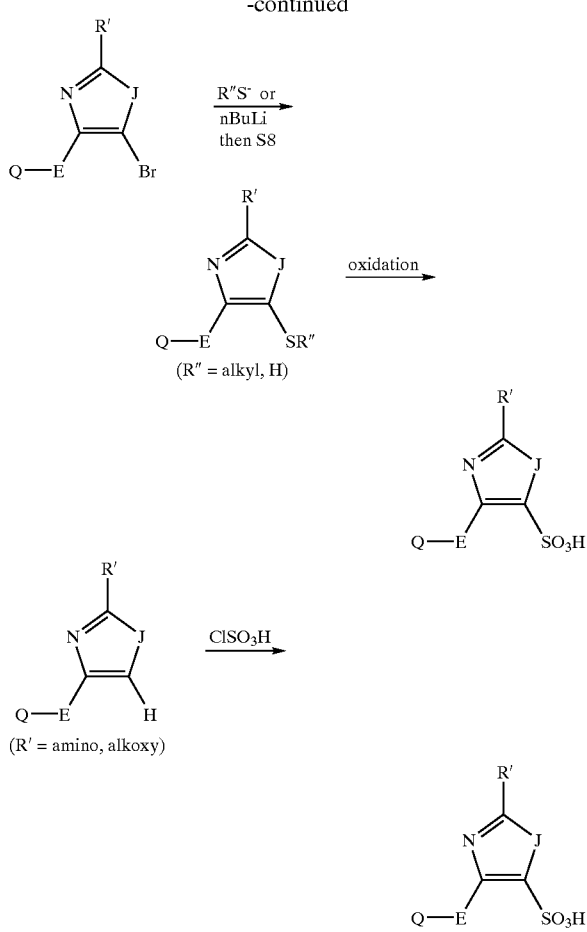

By the cyclization strategies described in Schemes 10–16, and by other strategies not described but familiar to those skilled in the art of organic synthesis, a wide variety of highly substituted thiazoles and oxazoles can be prepared. Proper manipulation of the starting materials for these cyclizations by procedures known to those skilled in the art also allows for the synthesis of oxazoles (Scheme 17, J=O) and thiazoles (Scheme 17, J=S), which are regioisomers of the thiazoles and oxazoles of Scheme 10, containing a wide variety of substituents $R^e$ and $R^f$ which by proper manipulation described in preceeding and following schemes can be converted into $R^{1a}$ and Z—A—B of compounds of Formula I.

Scheme 17

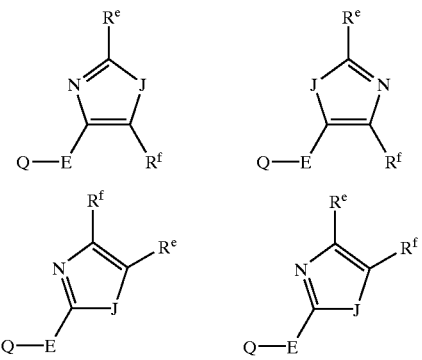

The present invention also describes compounds of Formula I in which ring M is 1,2,3- and 1,2,5-thiadiazole and 1,2,5-oxadiazole. The following schemes provide methods for synthesizing these heterocycles. In Scheme 18 is shown how 1,2,3-thiadiazoles can be prepared. The ketones from Scheme 10 can be converted by standard procedures into semicarbazones ($R^f$=NH$_2$) or acylhydrazones ($R^f$=alkyl, alkoxy) which can then be treated with thionyl chloride to prepare the 1,2,3-thiadiazoles (J. Med. Chem. 1985, 28, 442). Alternatively, diazo ketones can be prepared by treatment with base and a suitable diazo transfer reagent such as tosyl azide. Treatment of these diazo intermediates with hydrogen sulfide or Lawesson's reagent can afford the 1,2,3-thiadiazoles.

Scheme 18

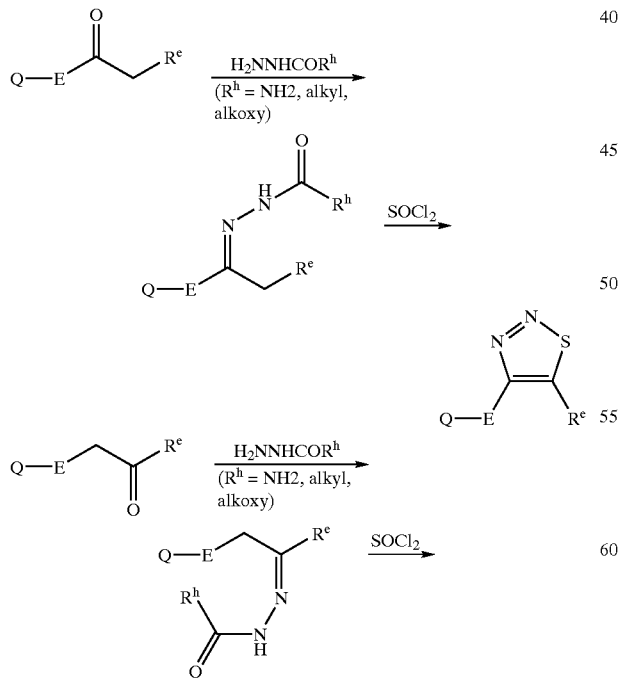

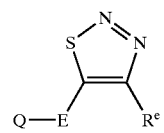

In Scheme 19 is shown how to prepare the 1,2,5-thiadiazoles contained in compounds of Formula I. The disubstituted alkynes, which are readily available by standard alkyne coupling procedures known to those skilled in the art of organic synthesis, can be treated with sulfur nitride in refluxing toluene to afford the 1,2,5-thiadiazoles (J. Het. Chem. 1979, 16, 1009).

Scheme 19

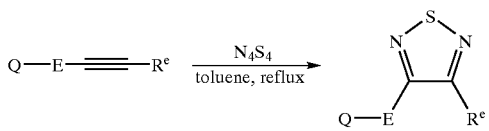

In Scheme 20 is shown how 1,2,5-oxadiazole heterocycles can be prepared. Diazotization of ketones followed by treatment with hydroxylamine can afford the bisoximes. Alternatively, diketones can be treated with hydroxylamine to afford the bisoximes. Dehydration of these readily prepared intermediates with acetic acid or thionyl chloride can then afford the 1,2,5-oxadiazoles.

Scheme 20

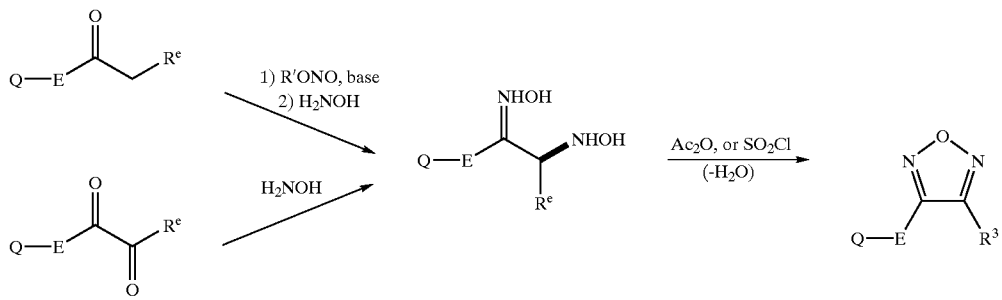

In the cyclization sequences and strategies described above, in general the substituents Q—E and $R^e$ and $R^f$ can be varied widely. In some cases $R^e$ can be chosen so that it corresponds to Z—A—B in Formula I. In other cases $R^b$ can be chosen so that it is hydrogen, carboxylic ester, amino, alkyl, cyano, alkoxy, hydroxy, thioalkoxy, sulfonyl, etc. which can subsequently be converted into the group Z—A—B of Formula I.

In the following schemes are described some methods by which the various groups Z of Formula I can be prepared from various groups Re. In these schemes the heterocycle is denoted as ring M and it is understood that the reactions described will generally be applicable to all of the different heterocycles previously described. It is also understood that the reactions described may require some modification of the reaction conditions, change in the reaction order or suitable protecting groups, depending upon the functionality contained in the compound of interest. One skilled in the art of organic synthesis will understand this and be able to modify the reaction sequence to obtain the desired products.

In Scheme 21 is shown how the heterocyclic compounds from above where $R^e$ is a carboxylic ester group can be converted into compounds containing the Z—A—B residue. For the amide linker (Formula I, Z=—CONH—)ring M where $R^e$=carboalkoxy can be hydrolyzed to the acid. Formation of the acid chloride with thionyl chloride followed by the addition of an appropriate amine $H_2N$—A—B can afford the amide-linked compounds. Alternatively, the acid can be combined with the amine $H_2N$—A—B in the presence of a suitable peptide coupling agent, such as BOP-Cl, HBTU or DCC to afford the corresponding amides. In another method the ester can be directly coupled with an aluminum reagent, prepared by the addition of trimethylaluminum to the amine $H_2N$—A—B, to afford the amide. To form ether- and thioether-linked compounds of Formula I (Z=—$CH_2O$—, —$CH_2S$—) the acid can be reduced to the alcohol. Preferred procedures for this transformation are reduction with borane THF complex, or a procedure involving the reduction of the mixed anhydride of the acid with sodium borohydride. Completion of the ether and thioether linked compounds of Formula I can be readily accomplished by the Mitsonobu protocol with an appropriate phenol, thiophenol or hydroxy- or mercaptoheterocycle HZ—A—B (Formula I, A=aryl or heteroaryl). Other ethers or thioethers can be prepared following initial conversion of the alcohol to a suitable leaving group, such as tosylate. Where J=S, thioethers can be further oxidized to prepare the sulfones (Formula I, Z=—$CH_2SO_2$—). To prepare the amine-linked compounds of Formula I (Z=—$CH_2NH$—) the alcohol can be oxidized to the aldehyde by a number of procedures, two preferred methods of which are the Swern oxidation and oxidation with pyridinium chlorochromate (PCC). Reductive amination of aldehyde with an appropriate amine $H_2N$—A—B and sodium cyanoborohydride can then afford the amine linked compounds. The aldehyde also can be used to prepare the ketone-linked compounds of Formula I (Z=—$COCH_2$—). Treatment of the aldehyde with an organometallic species can afford the alcohol. The organo metallic species (where M=magnesium or zinc) can be best prepared from the corresponding halide by treatment with metallic magnesium or zinc. These reagents readily react with aldehydes to afford alcohols. Oxidation of the resulting alcohol by any of a number of procedures, such as the Swern oxidation or PCC oxidation, can afford the ketone.

Scheme 21

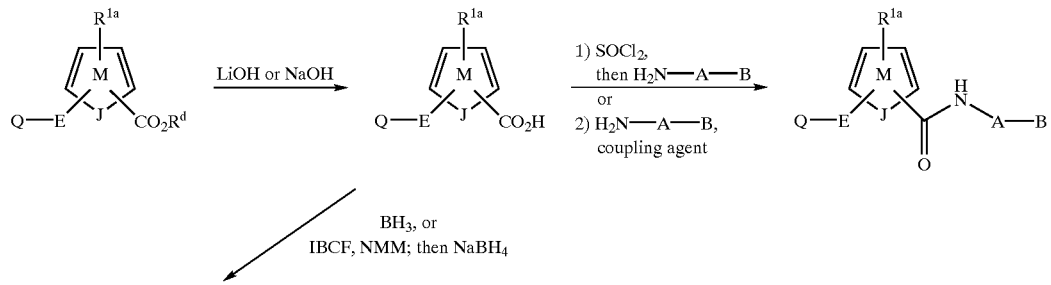

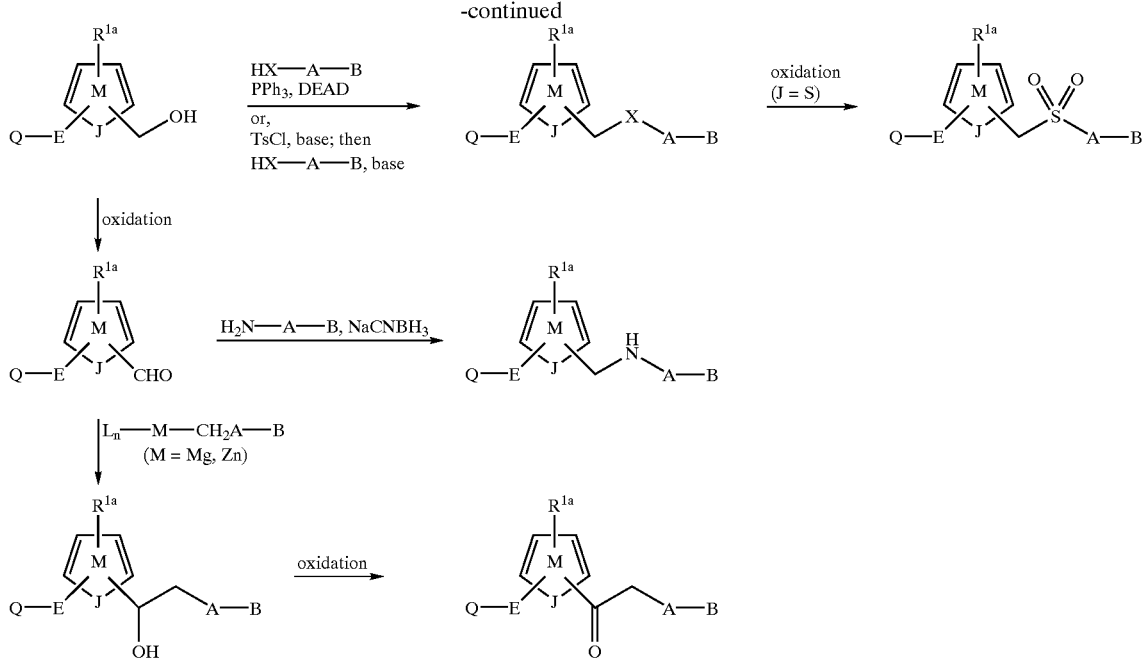

Additional compounds of Formula I in which the linking group Z contains a nitrogen atom attached to ring M can be prepared by the procedures described in Scheme 22. The amines can be converted to the sulfonamides (Formula I, Z=—NHSO$_2$—) by treatment with an appropriate sulfonyl chloride B—A—SO$_2$Cl in the presence of a base such as triethylamine. The amines can be converted into the amides (Formula I, Z=—NHCO—) by treatment with an appropriate acid chloride Cl—CO—A—B in the presence of a base or by treatment with an appropriate carboxylic acid HO—CO—A—B in the presence of a suitable peptide coupling agent, such as DCC, HBTU or BOP-Cl. The amine can be converted into amines of Formula I (Z=—NHCH$_2$—) by reductive amination with an appropriate aldehyde OHC—A—B.

Scheme 22

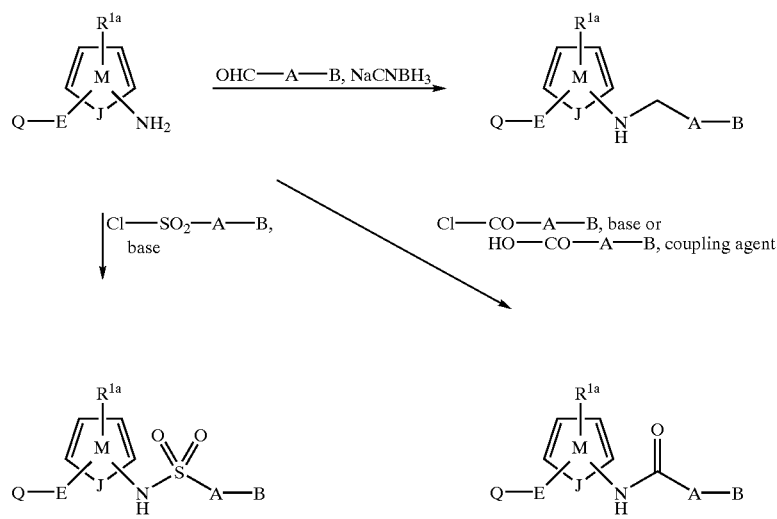

Additional compounds of Formula I in which the linking group Z contains a sulfur atom attached to ring M can be prepared by the procedures described in Scheme 23. Treatment of sulfonyls with phosphorous pentachloride followed by treatment with an appropriate amine H$_2$N—A—B can afford the sulfonamide-linked compounds (Formula I, Z=—SO$_2$NH—). The thiols can be alkylated with a suitable alkylating reagent in the presence of a base to afford thioethers (Formula I, Z=—SCH$_2$—). These compounds can be further oxidized by a variety of reagents to afford the sulfone-linked compounds (Formula I, Z=—SO$_2$CH$_2$—).

Scheme 23

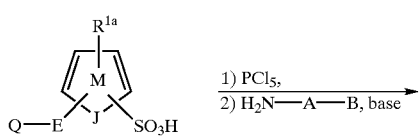

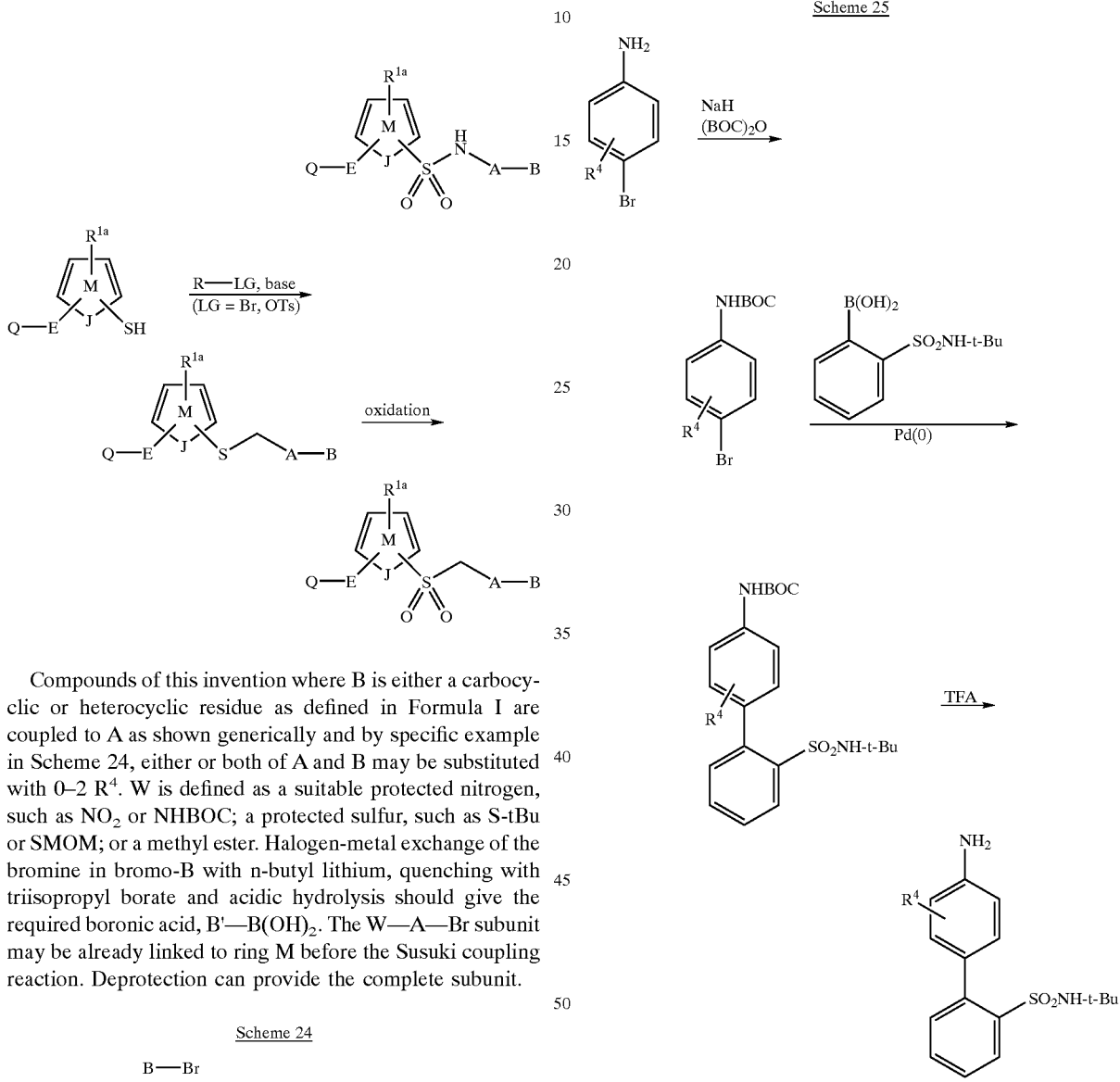

Compounds of this invention where B is either a carbocyclic or heterocyclic residue as defined in Formula I are coupled to A as shown generically and by specific example in Scheme 24, either or both of A and B may be substituted with 0–2 $R^4$. W is defined as a suitable protected nitrogen, such as $NO_2$ or NHBOC; a protected sulfur, such as S-tBu or SMOM; or a methyl ester. Halogen-metal exchange of the bromine in bromo-B with n-butyl lithium, quenching with triisopropyl borate and acidic hydrolysis should give the required boronic acid, B'—$B(OH)_2$. The W—A—Br subunit may be already linked to ring M before the Susuki coupling reaction. Deprotection can provide the complete subunit.

Scheme 24

Scheme 25 describes a typical example of how the A—B subunit can be prepared for attachment to ring M. 4-Bromoaniline can be protected as Boc-derivative and the coupled to 2-(t-butylamino)sulfonylphenylboronic acid under Suzuki conditions. 2-(t-Butylamino) sulfonylphenylboronic acid can be prepared by the method described by Rivero (Bioorg. Med. Chem. Lett. 1994, 189). Deprotection with TFA can provide the aminobiphenyl compound. The aminobiphenyl can then be coupled to the core ring structures as described below.

Scheme 25

When B is defined as X–Y, the following description applies. Groups A and B are available either through commercial sources, known in the literature or readily synthesized by the adaptation of standard procedures known to practioners skilled in the art of organic synthesis. The required reactive functional groups appended to analogs of A and B are also available either through commercial sources, known in the literature or readily synthesized by the adaptation of standard procedures known to practioners skilled in the art of organic synthesis. In the tables that follow the chemistry required to effect the coupling of A to B is outlined.

TABLE A

Preparation of Amide, Ester, Urea, Sulfonamide and Sulfamide linkages between A and B.

| Rxn. No. | if A contains: | then the reactive substituent of Y is: | to give the following product A—X—Y: |
|---|---|---|---|
| 1 | A—$NHR^2$ as a substituent | $ClC(O)$—Y | A—$NR^2$—$C(O)$—Y |
| 2 | a secondary NH as part of a ring or chain | $ClC(O)$—Y | A—$C(O)$—Y |
| 3 | A—OH as a substituent | $ClC(O)$—Y | A—O—$C(O)$—Y |
| 4 | A—$NHR^2$ as a substituent | $ClC(O)$—$CR^2R^{2a}$—Y | A—$NR^2$—$C(O)$—$CR^2R^{2a}$—Y |
| 5 | a secondary NH as part of a ring or chain | $ClC(O)$—$CR^2R^{2a}$—Y | A—$C(O)$—$CR^2R^{2a}$—Y |
| 6 | A—OH as a substituent | $ClC(O)$—$CR^2R^{2a}$—Y | A—O—$C(O)$—$CR^2R^{2a}$—Y |
| 7 | A—$NHR^3$ as a substituent | $ClC(O)NR^2$—Y | A—$NR^2$—$C(O)NR^2$—Y |
| 8 | a secondary NH as part of a ring or chain | $ClC(O)NR^2$—Y | A—$C(O)NR^2$—Y |
| 9 | A—OH as a substituent | $ClC(O)NR^2$—Y | A—O—$C(O)NR^2$—Y |
| 10 | A—$NHR^2$ as a substituent | $ClSO_2$—Y | A—$NR^2$—$SO_2$—Y |
| 11 | a secondary NH as part of a ring or chain | $ClSO_2$—Y | A—$SO_2$—Y |
| 12 | A—$NHR^2$ as a substituent | $ClSO_2$—$CR^2R^{2a}$—Y | A—$NR^2$—$SO_2$—$CR^2R^{2a}$—Y |
| 13 | a secondary NH as part of a ring or chain | $ClSO_2$—$CR^2R^{2a}$—Y | A—$SO_2$—$CR^2R^{2a}$—Y |
| 14 | A—$NHR^2$ as a substituent | $ClSO_2$—$NR^2$—Y | A—$NR^2$—$SO_2$—$NR^2$—Y |
| 15 | a secondary NH as part of a ring or chain | $ClSO_2$—$NR^2$—Y | A—$SO_2$—$NR^2$—Y |
| 16 | A—$C(O)Cl$ | HO—Y as a substituent | A—$C(O)$—O—Y |
| 17 | A—$C(O)Cl$ | $NHR^2$—Y as a substituent | A—$C(O)$—$NR^2$—Y |
| 18 | A—$C(O)Cl$ | a secondary NH as part of a ring or chain | A—$C(O)$—Y |
| 19 | A—$CR^2R^{2a}C(O)Cl$ | HO—Y as a substituent | A—$CR^2R^{2a}C(O)$—O—Y |
| 20 | A—$CR^2R^{2a}C(O)Cl$ | $NHR^2$—Y as a substituent | A—$CR^2R^{2a}C(O)$—$NR^2$—Y |
| 21 | A—$CR^2R^{2a}C(O)Cl$ | a secondary NH as part of a ring or chain | A—$CR^2R^{2a}C(O)$—Y |
| 22 | A—$SO_2Cl$ | $NHR^2$—Y as a substituent | A—$SO_2$—$NR^2$—Y |
| 23 | A—$SO_2Cl$ | a secondary NH as part of a ring or chain | A—$SO_2$—Y |
| 24 | A—$CR^2R^{2a}SO_2Cl$ | $NHR^2$—Y as a substituent | A—$CR^2R^{2a}SO_2$—$NR^2$—Y |
| 25 | A—$CR^2R^{2a}SO_2Cl$ | a secondary NH as part of a ring or chain | A—$CR^2R^{2a}SO_2$—Y |

The chemistry of Table A can be carried out in aprotic solvents such as a chlorocarbon, pyridine, benzene or toluene, at temperatures ranging from −20° C. to the reflux point of the solvent and with or without a trialkylamine base.

TABLE B

Preparation of ketone linkages between A and B.

| Rxn. No. | if A contains: | then the reactive substituent of Y is: | to give the following product A—X—Y: |
|---|---|---|---|
| 1 | A—C(O)Cl | BrMg—Y | A—C(O)—Y |
| 2 | A—CR$^2$R$^{2a}$C(O)Cl | BrMg—Y | A—CR$^2$R$^{2a}$2C(O)—Y |
| 3 | A—C(O)Cl | BrMgCR$^2$R$^{2a}$—Y | A—C(O)CR$^2$R$^{2a}$—Y |
| 4 | A—CR$^2$R$^{2a}$C(O)Cl | BrMgCR$^2$R$^{2a}$—Y | A—CR$^2$R$^{2a}$C(O)CR$^2$R$^{2a}$—Y |

The coupling chemistry of Table B can be carried out by a variety of methods. The Grignard reagent required for Y is prepared from a halogen analog of Y in dry ether, dimethoxyethane or tetrahydrofuran at 0° C. to the reflux point of the solvent. This Grignard reagent can be reacted directly under very controlled conditions, that is low temeprature (−20° C. or lower) and with a large excess of acid chloride or with catalytic or stoichiometric copper bromide.dimethyl sulfide complex in dimethyl sulfide as a solvent or with a variant thereof. Other methods available include transforming the Grignard reagent to the cadmium reagent and coupling according to the procedure of Carson and Prout (Org. Syn. Col. Vol. 3 (1955) 601) or a coupling mediated by Fe(acac)$_3$ according to Fiandanese et al (Tetrahedron Lett., (1984) 4805), or a coupling mediated by manganese (II) catalysis (Cahiez and Laboue, Tetrahedron Lett., 33(31), (1992) 4437).

TABLE C

Preparation of ether and thioether linkages between

| Rxn. No. | if A contains: | then the reactive substituent of Y is: | to give the following product A—X—Y: |
|---|---|---|---|
| 1 | A—OH | Br—Y | A—O—Y |
| 2 | A—CR$^2$R$^{2a}$—OH | Br—Y | A—CR$^2$R$^{2a}$O—Y |
| 3 | A—OH | Br—CR$^2$R$^{2a}$—Y | A—OCR$^2$R$^{2a}$—Y |
| 4 | A—SH | Br—Y | A—S—Y |
| 5 | A—CR$^2$R$^{2a}$—SH | Br—Y | A—CR$^2$R$^{2a}$S—Y |
| 6 | A—SH | Br—CR$^2$R$^{2a}$—Y | A—SCR$^2$R$^{2a}$—Y |

The ether and thioether linkages of Table C can be prepared by reacting the two components in a polar aprotic solvent such as acetone, dimethylformamide or dimethylsulfoxide in the presence of a base such as potassium carbonate, sodium hydride or potassium t-butoxide at temperature ranging from ambient temperature to the reflux point of the solvent used.

TABLE D

Preparation of —SO— and —SO2— linkages from thioethers of Table 3.

| Rxn. No. | if the starting material is: | and it is oxidized with Alumina (wet)/Oxone (Greenhalgh, Synlett, (1992) 235) the product is: | and it is oxidized with m-chloroperbenzoic acid (Satoh et al., Chem. Lett. (1992) 381) the product is: |
|---|---|---|---|
| 1 | A—S—Y | A—S(O)—Y | A—SO$_2$—Y |
| 2 | A—CR$^2$R$^{2a}$S—Y | A—CR$^2$R$^{2a}$S(O)—Y | A—CR$^2$R$^{2a}$SO$_2$—Y |
| 3 | A—SCR$^2$R$^{2a}$—Y | A—S(O)CR$^2$R$^{2a}$—Y | A—SO$_2$CR$^2$R$^{2a}$—Y |

The thioethers of Table C serve as a convenient starting material for the preparation of the sulfoxide and sulfone analogs of Table D. A combination of wet alumina and oxone can provide a reliable reagent for the oxidation of the thioether to the sulfoxide while m-chloroperbenzoic acid oxidation will give the sulfone.

Other features of the invention will become apparent in the course of the following descriptions of exemplary embodiments which are given for illustration fo the invention and are not intended to be limiting thereof.

EXAMPLES

Example 1

3-(3-Amidinophenyl)-4-[(2'-aminosulfonyl-[1,1']-biphen-4-yl)aminocarbonyl]-5-(hydroxymethyl) isoxazole, Trifluoroacetic Acid Salt Part A. Preparation of 2-(t-Butylaminosulfonyl) phenylboronic Acid.

To a solution of 206.5 g (0.968 mol) of benzene-(N-t-butyl)sulfonamide in 2500 mL of THF under $N_2$ was added 790 mL (1.98 mol) of 2.5M n-butyllithium in hexane over 35 minutes, keeping the temperature between 0–5° C. The reaction mixture was allowed to warm to 10° C., at which time a thick precipitate formed. Triisopropylborate (305 mL, 1.32 mol) was added keeping the temperature below 35° C. After 1 hour, the reaction mixture was cooled, 1N HCl (1570 mL) was added, and the mixture was stirred overnight. The mixture was extracted with 400 mL of ether three times, and the combined organic extracts were extracted with 500 mL of 1N NaOH three times. The aqueous extracts were acidified to pH 1 with 6N HCl, and then extracted with 500 mL ether three times. The combined ether extracts were dried over $MgSO_4$, and the solvents evaporated in vacuo until the volume was 700 mL. Hexane (150 mL) was added and overnight, a white precipitate formed. The solid was collected and washed with 10% ether/hexane (250 mL), then dried in vacuo to give 216.3 g (87%) of the desired compound as white crystals. m.p. 118–119° C. $^1$H NMR ($CDCl_3$) δ: 8.00 (d, 1H); 7.82 (d, 1H); 7.53 (m, 2H); 6.29 (br s, 2H); 5.13 (s, 1H); 1.18 (s, 9H).

Part B. Preparation of N-(4-Bromophenyl)-4-(tetrahydropyran-2-yloxymethyl)-2-butynamide.

To a solution of 4.98 g (35.5 mmol) of tetrahydro-2-(2-propynyloxy)-2H-pyran in 70 mL of THF under $N_2$ was added 14.2 mL (35.5 mmol) of 2.5 M n-butyllithium in hexane. After 15 minutes, 7.03 g (35.5 mmol) of 4-bromophenylisocyanate was added and then the reaction was allowed to warm to room temperature. Saturated aqueous ammonium chloride (20 mL) was added and the mixture extracted with 30 mL ethyl acetate three times. The combined organic extracts were dried with $MgSO_4$, concentrated to an oil in vacuo and then chromatographed on silica with 20% EtOAc/hexane to give 7.1 g (59%) of the desired alkyne. $^1$H NMR (CDCl$_3$) δ: 7.53 (br s, 1H); 7.43 (d, 2H); 7.42 (d, 2H); 4.80 (m, 1H); 4.43 (d, 1H); 4.40 (d, 1H); 3.83 (m, 1H); 3.59 (m, 1H); 1.7 (m, 6H).

Part C. Preparation of 3-Cyanobenzaldehyde Oxime.

Hydroxylamine hydrochloride (13.5 g, 194 mmol) was added to a solution of 3-cyanobenzaldehyde (25 g, 191 mmol) in 75 mL of pyridine and 75 mL of ethanol under N$_2$. This was allowed to stir at room temperature for 14 hours. Water (50 mL) was added with vigorous stirring and an off-white solid precipitated. The solid was filtered through a glass frit and washed with another 50 mL of water. Evaporation of residual water under high vacuum gave 19.2 g (69%) of title compound. $^1$H NMR (CDCl$_3$) δ: 11.61 (s, 1H); 8.21 (s, 1H); 8.00 (s, 1H); 7.96 (d, 1H); 7.85 (d, 1H); 7.61 (t, 1H).

Part D. Preparation of N-(4-Bromophenyl)-3-(3-cyanophenyl)-5-(tetrahydropyran-2-yloxymethyl)-isoxazo-4-yl-carboxamide and N-(4-Bromophenyl)-3-(3-cyanophenyl)-4-(tetrahydropyran-2-yloxymethyl)-isoxazo-5-yl-carboxamide.

To a solution of 2.54 g (17.2 mmol) of 3-cyanobenzaldehyde oxime and 7.10 g (21.0 mmol) of N-(4-bromophenyl)-4-(tetrahydropyran-2-yloxymethyl)-2-butynamide in 58 mL THF was added 45 mL bleach (0.67M aqueous solution) over a 4-hour period. The solvent was removed in vacuo and the resulting aqueous solution was extracted with 25 mL EtOAc three times. The combined organic extracts were dried with MgSO$_4$ and the solvent removed in vacuo. Chromatography on silica with 20% EtOAc/hexane gave 1.4 g (17%) of N-(4-bromophenyl)-3-(3-cyanophenyl)-5-(tetrahydropyran-2-yloxymethyl) isoxazo-4-yl-carboxamide and 1.67 g (20%) of N-(4-bromophenyl)-3-(3-cyanophenyl)-4-(tetrahydropyran-2-yloxymethyl)-isoxazo-5-yl-carboxamide. $^1$H NMR (CDCl$_3$) δ: 1st isomer: 9.45 (br s, 1H); 8.11 (s, 1H); 8.04 (d, 1H); 7.77 (d, 1H); 7.58 (t, 1H); 7.50 (m, 4H); 4.98 (dd, 2H); 4.88 (m, 1H); 3.72 (m, 1H); 3.58 (m, 1H); 1.7 (m, 6H). 2nd isomer: 8.66 (br s, 1H); 8.31 (m, 1H); 8.14 (d, 1H); 7.95 (d, 1H); 7.75 (t, 1H), 7.57 (m, 4H); 4.94 (dd, 2H); 4.87 (m, 1H); 3.87 (m, 1H); 3.57 (m, 1H); 1.6 (m, 6H).

Part E. Preparation of 4-(N-[2'-t-Butylaminosulfonyl-[1,1']-biphen-4-yl]aminocarbonyl)-3-(3-cyanophenyl)-5-(tetrahydro-pyran-2-yloxymethyl)-isoxazole.

A mixture of 0.31 g (0.60 mmol) of N-(4-bromophenyl)-3-(3-cyanophenyl)-5-(tetrahydropyran-2-yloxymethyl) isoxazo-4-yl-carboxamide, 0.23 g (0.90 mmol) of 2-(t-butylamino-sulfonyl)phenylboronic acid, 0.052 g (0.045 mmol) of tetrakis(triphenylphosphine palladium(0), 0.05 mL of 40% aqueous tetrabutylammonium hydroxide, and 0.9 mL of 2M aqueous sodium carbonate were refluxed with 8 mL of toluene under N$_2$ for 5.5 hours. After cooling, the mixture was separated and the aqueous layer was extracted with 5 mL of ethyl acetate twice. The combined organic extracts were dried with MgSO$_4$ and concentrated. The resulting solid was chromatographed with 50% EtOAc/hexane to give 0.27 g (73%) of the desired product. $^1$H NMR (CDCl$_3$) δ: 9.57 (br s, 1H); 8.15 (m, 2H); 8.07 (d, 1H); 7.77 (d, 1H); 7.71 (d, 2H); 7.60 (t, 1H); 7.52 (m, 3H); 7.31 (m, 2H); 5.02 (dd, 2H); 4.94 (m, 1H); 3.72 (m, 1H); 3.60 (m, 1H); 1.7 (m, 6H); 1.04 (s, 9H).

Part F. Preparation of 4-[2'-Aminosulfonyl-[1,1']-biphen-4-yl]aminocarbonyl-3-(3-cyanophenyl)-5-(hydroxymethyl)-isoxazole.

A solution of 0.27 g (0.56 mmol) of 4-(N-[2'-t-butylaminosulfonyl-[1,1']-biphen-4-yl]aminocarbonyl)-3-(3-cyanophenyl)-5-(tetrahydropyran-2-yloxymethyl) isoxazole in 10 mL of trifluoroacetic acid is allowed to stir under N$_2$ for 16 hours at room temperature. The solvent was removed in vacuo and then chromatographed on silica with 50% EtOAc/hexane to give 0.11 g (51%) of desired product. $^1$H NMR (CDCl$_3$) δ: 9.19 (br s, 1H); 8.12 (d, 1H); 8.05 (m, 1H); 7.99 (d, 1H); 7.81 (d, 1H); 7.64 (t, 1H); 7.58 (m, 3H); 7.50 (m, 1H); 7.42 (d, 2H); 7.31 (d, 1H); 6.77 (m, 1H); 5.03 (d, 2H). HRMS 475.1076 (M+H).

Part G. Preparation of 3-(3-Amidinophenyl)-4-[2'-aminosulfonyl-[1,1']-biphen-4-yl]aminocarbonyl-5-(hydroxy-methyl)-isoxazole, Trifluoroacetic Acid Salt.

4-(N-[2'-aminosulfonyl-[1,1']-biphen-4-yl] aminocarbonyl)-3-(3-cyanophenyl)-5-(hydroxy-methyl) isoxazole (0.11 g, 0.22 mmol) was dissolved in 5 mL of methanol and 10 mL of chloroform. The reaction mixture was cooled in an ice-bath and HCl gas was bubbled-in for 30 minutes to saturate the solution. The mixture was sealed and allowed to stir at room temperature for 14 hours. The solvents were removed in vacuo and the resulting solid was added to 0.5 g (5.2 mmol) of ammonium carbonate and 10 mL of methanol. The mixture was allowed to stir under N$_2$ for 14 hours. The solvent was removed at reduced pressure. The crude benzamidine was purified by HPLC (C18 reversed phase) eluting with 0.5% TFA in H$_2$O/CH$_3$CN to give 0.07 g (53%) of the desired salt. $^1$H NMR (DMSO-d$_6$) δ: 10.60 (s, 1H); 9.43 (br s, 2H); 9.00 (br s, 2H); 8.14 (m, 1H); 7.98 (d, 2H); 7.89 (d, 1H); 7.75 (t, 1H); 7.58 (m, 4H); 7.34 (d, 2H); 7.28 (m, 1H); 4.79 (s, 2H). HRMS 492.1341 (M+H).

Example 2

3-(3-Amidinophenyl)-4-[(2'-aminosulfonyl-[1,1']-biphen-4-yl)aminocarbonyl]isoxazole, Trifluoroacetic Acid Salt Part A. Preparation of 3-Cyanobenzenehydroximinoyl Chloride.

3-Cyanobenzaldehyde oxime (15 g, 103 mmol) was suspended in 90 mL of DMF and then N-chlorosuccinimide (13.7 g, 103 mmol) was added. Approximately 50 mL of gaseous HCl was added via syringe below the liquid surface over a 2 minute period. The reaction was allowed to stir at room temperature for 15 hours and the solution clarified. The solvent was evaporated at 5 torr with a bath temp of 55° C. till viscous and cloudy. Water (100 mL) was added with vigorous stirring. An off-white precipitate formed, was filtered through a glass frit and washed with 50 mL water to give 18.1 g (98%) of the desired product after drying under high vacuum. $^1$H NMR (CDCl$_3$) δ: 8.75 (s, 1H), 8.17 (s, 1H), 8.10 (d, 1H), 7.73 (d, 1H), 7.55 (dd, 1H).

Part B. Preparation of 2'-t-Butylaminosulfonyl-4-amino-[1,1']biphenyl.

A mixture of 3.44 g (20 mmol) of 4-bromoaniline and 5.14 g (20 mmol) of 2-(t-butylaminosulfonyl)phenylboronic acid, 1.16 g of tetrakis(triphenylphosphine) palladium(0) (1 mmol), 0.32 g of tetrabutylammonium bromide (1 mmol) and 20 mL of 2M aqueous sodium carbonate were refluxed with 180 mL of benzene under N$_2$ for 5.5 hours. After cooling, the mixture was diluted with methylene chloride and water. The two phases were separated and the organic phase was washed with water, dried with MgSO$_4$ and concentrated in vacuo. The resulting thick oil was chromatographed on silica with 30% EtOAc/hexane to afford 2.52 g (41%) of the title compound. $^1$H NMR (CDCl$_3$) δ: 8.14 (d, 1H); 7.53 (t, 1H); 7.43 (t, 1H); 7.33 (d, 2H); 7.27 (d, 1H); 6.76 (d, 2H); 3.7 (br s, 1H); 0.99 (s, 9H).

Part C. Preparation of 3-(3-Cyanophenyl)-5-carbomethoxy-isoxazole.

Triethylamine (1.01 g, 10 mmol) is added dropwise over 2 hours to a solution of 0.72 g (4.0 mmol) of 3-cyanobenzene-hydroximinoyl chloride and 0.56 g (4.8 mmol) of methyl methoxyacrylate in 10 mL of $CH_2Cl_2$ under $N_2$. The reaction mixture is diluted with 10 mL of water and the organic layer separated. The aqueous solution is extracted with 10 mL EtOAc twice and the combined organic extracts are dried with $MgSO_4$ and concentrated in vacuo. The resulting thick oil was chromatographed on silica with 30% EtOAc/hexane to give 0.90 g (99%) of the desired product. $^1$H NMR ($CDCl_3$) δ: 9.07 (s, 1H); 8.14 (s, 1H); 8.06 (d, 1H); 7.79 (d, 2H); 7.61 (t, 1H); 3.88 (s, 3H).

Part D. Preparation of 3-(3-Cyanophenyl)-isoxazole-5-carboxylic Acid.

A mixture of 0.90 g (3.9 mmol) of 4-carbomethoxy-3-(3-cyanophenyl)isoxazole, 0.25 g (6.0 mmol) of lithium hydroxide monohydrate in 1 mL water and 2 mL methanol is stirred under $N_2$ for 5 hours. The reaction mixture was acidified to pH 3 with 1N HCl, extracted with 10 mL EtOAc three times, dried with $MgSO_4$ and concentrated in vacuo to give 0.36 g (43%) of the desired acid. $^1$H NMR ($CDCl_3$) δ: 8.94 (s, 1H); 8.01 (s, 1H); 7.94 (d, 1H); 7.60 (d, 2H); 7.43 (t, 1H).

Part E. Preparation of 4-(N-[2'-t-Butylaminosulfonyl-[1,1']-biphen-4-yl]aminocarbonyl)-3-(3-cyanophenyl)-isoxazole.

Thionyl chloride (10 mL) and 3-(3-cyanophenyl) isoxazole-4-carboxylic acid (0.34 g, 1.6 mmol) are stirred at room temperature under $N_2$ for 1 hour. The excess thionyl chloride is removed in vacuo and the resulting solid is resuspended in 10 mL toluene. The toluene is removed in vacuo to remove any residual thionyl chloride. The solid is dissolved in 15 mL $CH_2Cl_2$ and 0.53 g (1.8 mmol) of 2'-t-butylaminosulfonyl-4-amino-[1,1']biphenyl and 0.32 g (3.2 mmol) of triethylamine are added. After 2 hours, the reaction mixture is diluted with 10 mL of water and the organic layer separated. The aqueous solution is extracted with 10 mL EtOAc three times and the combined organic extracts are dried with $MgSO_4$ and concentrated in vacuo. The resulting thick oil was chromatographed on silica with 25% EtOAc/hexane to 0.53 g (66%) of the desired product. $^1$H NMR ($CDCl_3$) δ: 9.07 (s, 1H); 8.14 (m, 1H); 8.06 (m, 1H); 7.81 (d, 1H); 7.55 (m, 9H); 1.03 (s, 9H).

Part F. Preparation of 3-(3-Amidinophenyl)-4-[2'-aminosulfonyl-[1,1']-biphen-4-yl]aminocarbonyl-5-(hydroxy-methyl)-isoxazole, Trifluoroacetic Acid Salt.

4-(N-[2'-aminosulfonyl-[1,1']-biphen-4-yl] aminocarbonyl)-3-(3-cyanophenyl)isoxazole (0.53 g, 1.1 mmol) was dissolved in 10 mL of methanol and 30 mL of chloroform. The reaction mixture was cooled in an ice-bath and HCl gas was bubbled-in for 30 minutes to saturate the solution. The mixture was sealed and allowed to stir at room temperature for 14 hours. The solvents were removed in vacuo and the resulting solid was added to 0.5 g (5.2 mmol) of ammonium carbonate and 20 mL of methanol. The mixture was allowed to stir under $N_2$ for 14 hours. The solvent was removed at reduced pressure. The crude benzamidine was purified by HPLC (C18 reversed phase) eluting with 0.5% TFA in $H_2O/CH_3CN$ to give 0.09 g (15%) of the title salt. $^1$H NMR (DMSO-$d_6$) δ: 10.69 (s, 1H); 9.44 (br s, 2H); 9.06 (br s, 2H); 8.17 (m, 1H); 8.06 (d, 1H); 8.00 (d, 1H); 7.92 (d, 1H); 7.75 (t, 1H); 7.67 (d, 2H); 7.56 (m, 2H); 7.33 (d, 2H); 7.28 (m, 1H). HRMS 462.1252 (M+H).

Example 3

3-(3-Amidinophenyl)-4-[(2'-methylsulfonyl-[1,1']-biphen-4-yl)aminocarbonyl]isoxazole, Trifluoroacetic Acid Salt Part A. Preparation of 2-Methylthiophenylboronic Acid 2-Bromothioanisole (8.56 g, 42 mmol) was dissolved in 90 mL of dry THF and cooled to −78° C. n-Butyllithium (18.6 mL, 2.5M in hexane, 47 mmol) was added dropwise over 20 minutes, and the resulting solution stirred 90 min. Triisopropylborate (13.7 mL, 59 mmol) was added dropwise over 10 minutes, and the resulting solution stirred at −78° C. for 45 minutes before removing the cooling bath. The reaction was stirred overnight at room temperature. HCl (40 mL of a 6M aqueous solution) was added and stirred vigorously 8 h. The reaction was diluted with 100 mL water and extracted three times with $Et_2O$. The organic extracts were combined and extracted twice with 80 mL of 2M NaOH. The basic layers were combined and acidified with 50 mL 6M HCl and 25 ml 2M HCl. The resulting cloudy solution was extracted three times with 50 mL of $Et_2O$, dried over $MgSO_4$, filtered, and evaporated to yield a white solid (5.22 g, 74%). $^1$H NMR ($CDCl_3$) δ: 8.01 (dd, 1H), 7.53 (dd, 1H), 7.43 (td, 1H), 7.34 (td, 1H), 6.22 (s, 2H), 2.50 (s, 3H).

Part B. Preparation of 4-(t-Butoxycarbonyl)amino-2'-methylthio-[1,1']biphenyl

2-Methylthiophenylboronic acid (5.2 g, 31 mmol), N-t-butylcarbonyl-4-bromoaniline (4.0 g, 15 mmol), $Na_2CO_3$ (31 mL, 2M aqueous), tetrabutylammonium bromide (230 mg, 0.7 mmol), and bis(triphenylphosphine)palladium(II) chloride (515 mg, 0.7 mmol) were combined in 300 mL of benzene, placed briefly under vacuum to degas, and heated at reflux under argon overnight. The reaction was cooled to room temperature and diluted with 100 mL water and 100 mL EtOAc. The organic layer was separated, dried over $Na_2SO_4$, filtered through celite, and the solvents evaporated. The crude mixture was chromatographed on silica with 10–30% EtOAc/hexane to yield the desired compound (4.17 g, 90%). $^1$H NMR ($CDCl_3$) δ: 7.42 (d, 2H), 7.35 (d, 2H), 7.28 (m, 2H), 7.19 (m, 2H), 6.53 (bs, 1H), 2.36 (s, 3H), 1.53 (s, 9H).

Part C. Preparation of 4-(t-Butoxycarbonyl)amino-2'-methylsulfonyl-[1,1']biphenyl 4-(t-Butoxycarbonyl)amino-2'-methylthio-[1,1']biphenyl (4.16 g, 13 mmol) was dissolved in 400 mL of $CH_2Cl_2$ and cooled to 0° C. MCPBA (11.2 g 57–86%, 37 mmol min.) was added in 4 portions and stirred 25 minutes before removing the cooling bath. The reaction was stirred at room temp for 3 hours. The reaction mixture was then extracted with 50 mL saturated aqueous $Na_2SO_3$ and then with 50 mL saturated aqueous $NaHCO_3$. The organic layer was removed, dried over $Na_2SO_4$, filtered, and evaporated to yield the desired product (4.80 g). $^1$H NMR ($CDCl_3$) δ: 8.22 (dd, 1H), 7.63 (td, 1H), 7.54 (td, 1H), 7.41 (m, 5H), 6.61 (s, 1H), 2.64 (s, 3H), 1.54 (s, 9H).

Part D. Preparation of 4-Amino-2'-methylsulfonyl-[1,1'] biphenyl 4-(t-butoxycarbonyl)amino-2'-methylsulfonyl-[1,1'] biphenyl (4.6 g, 13 mmol), was suspended in 100 mL of 4M HCl in dioxane and stirred 2.5 days. The resulting mixture was filtered and the cake rinsed with $Et_2O$ to yield a tan solid (3.69 g, 98%). $^1$H NMR (DMSO-$d_6$) δ: 8.04 (d, 1H), 7.71 (t, 1H), 7.61 (t, 1H), 7.31 (m, 3H), 7.06 (m, 2H), 2.79 (s, 3H).

Part E. Preparation of 3-(3-Cyanophenyl)-4-[(2'-methylsulfonyl-[1,1']-biphen-4-yl)aminocarbonyl]isoxazole 4-Amino-2'-methylsulfonyl-[1,1']biphenyl (0.50 g, 2.2 mmol) was suspended in 10 mL of $CH_2Cl_2$ and 4.4 mL of a 2M solution of trimethylaluminum in heptane was added slowly via syringe. The reaction was stirred for 30 minutes at room temperature and then 3-(3-cyanophenyl)-5-carbomethoxy-isoxazole (0.62 g, 2.2 mmol) was added. The reaction mixture was stirred at room temperature for an additional 14 hours. The aluminum reagent was quenched by careful addition of 1N HCl to pH 2, then extracted with 10 mL of $CH_2Cl_2$ three times. The combined organic extracts were washed with water then brine, dried over $MgSO_4$ and the solvent evaporated. The desired product was obtained (0.74 g, 76%) after silica gel chromatography with 30% EtOAc/hexane. $^1H$ NMR ($CDCl_3$) δ: 9.07 (s, 1H); 8.31 (s, 1H); 8.21 (d, 1H); 8.09 (s, 1H); 8.07 (d, 1H); 7.79 (d, 1H); 7.63 (m, 4H); 7.42 (d, 2H); 7.37 (d, 1H); 2.72 (s, 3H).

Part F. Preparation of 3-(3-Amidinophenyl)-4-[(2'-methylsulfonyl-[1,1']-biphen-4-yl)aminocarbonyl] isoxazole, Trifluoroacetic Acid Salt 3-(3-Cyanophenyl)-4-[(2'-methylsulfonyl-[1,1']-biphen-4-yl)aminocarbonyl]isoxazole (0.74 g, 1.7 mmol) was dissolved in 10 mL of methanol and 40 mL of chloroform. The reaction mixture was cooled in an ice-bath and HCl gas was bubbled-in for 1.5 hours to saturate the solution. The mixture was sealed and allowed to stir at room temperature for 14 hours. The solvents were removed in vacuo and the resulting solid was added to 0.66 g (8.5 mmol) of ammonium carbonate and 20 mL of methanol. The mixture was sealed and allowed to stir under Ar for 14 hours. The solvent was removed at reduced pressure. The crude benzamidine was purified by HPLC (C18 reversed phase) eluting with 0.5% TFA in $H_2O/CH_3CN$ to give 0.33 g (43%) of the desired salt. $^1H$ NMR (DMSO-$d_6$) δ: 10.69 (s, 1H); 9.67 (s, 1H); 9.41 (br s, 2H); 9.07 (br s, 2H); 8.18 (t, 1H); 8.06 (dt, 2H); 7.92 (d, 1H); 7.72 (m, 5H); 7.38 (s, 1H); 7.36 (d, 2H); 2.80 (s, 3H). HRMS 461.1284 (M+H).

Example 4

3-(3-Amidinophenyl)-4-[5-(2-aminosulfonyl) phenylpyrid-2-yl)aminocarbonyl]-5-(methoxymethyl)isoxazole, Trifluoroacetic Acid Salt Part A. Preparation of 3-(3-Cyanophenyl)-5-methoxymethyl-4-carbomethoxyisoxazole Methyl 4-methoxyacetoacetate (1.6 mL, 12 mmol) was dissolved in 12 mL of 2M sodium methoxide in methanol. 3-Cyanobenzenehydroximinoyl chloride (2.0 g, 11 mmol) was dissolved in 10 mL methanol and added to the basic solution over a 5-hour period via syringe pump. The reaction was quenched with 20 mL of saturated, aqueous ammonium chloride. The mixture was extracted with 30 mL EtOAc three times and the combined organic extracts washed with 10 mL water three times. The resulting solution was dried with $MgSO_4$, concentrated in vacuo and then chromatographed on silica with 10% $Et_2O$/benzene to 1.14 g (38%) of a white solid. $^1H$ NMR ($CDCl_3$) δ: 7.95 (m, 1H); 7.92 (dd, 1H); 7.98 (dd, 1H); 7.60 (t, 1H); 4.91 (s, 2H); 3.83 (s, 3H); 3.54 (s, 3H).

Part B. Preparation of 2-Amino-5-(2-t-butylaminosulfonyl) phenylpyridine

A mixture of 1.55 g (9.0 mmol) of 2-amino-5-bromopyridine and 2.3 g (9.0 mmol) of 2-(t-butylaminosulfonyl)phenylboronic acid, 0.52 g of tetrakis (triphenylphosphine) palladium(0) (0.45 mmol), 0.15 g of tetrabutylammonium bromide (0.45 mmol) and 9 mL of 2M aqueous sodium carbonate were refluxed with 80 mL of benzene under Ar for 5 hours. After cooling, the mixture was diluted with 25 mL of methylene chloride and 25 mL of water. The two phases were separated and the organic phase was washed with water, dried with $MgSO_4$ and concentrated in vacuo. The resulting thick oil was chromatographed on silica with 50% EtOAc/hexane to afford 1.34 g (49%) of the aniline. $^1H$ NMR ($CDCl_3$) δ: 8.18 (d, 1H); 8.07 (m, 1H); 7.70 (dd, 1H); 7.58 (dt, 1H); 7.48 (dt, 1H); 7.28 (d, 1H); 6.56 (d, 1H); 4.62 (brs, 2H); 3.88 (br s, 1H); 1.06 (s, 9H).

Part C. Preparation of 3-(3-Cyanophenyl)-4-[5-(2-t-butylaminosulfonyl)phenylpyrid-2-yl)aminocarbonyl]-5-(methoxymethyl)isoxazole 3-(3-cyanophenyl)-5-methoxymethyl-4-carbomethoxy-isoxazole (1.12 g, 4.1 mmol) was dissolved in 3 mL of THF and 1 mL water. Lithium hydroxide monohydrate (0.20 g, 4.9 mmol) was added and the reaction stirred at room temperature for 5 hours. The solvent was evaporated in vacuo, 100 mL of water was added and the mixture extracted with 50 mL of EtOAc twice. The combined organic extracts were dried with $MgSO_4$ concentrated in vacuo to give 0.8 g (75%) of a white solid. The crude carboxylic acid (0.4g, 1.6 mmol) was dissolved in 1.2 mL of 2.0M oxalyl chloride in $CH_2Cl_2$ followed by 0.1 mL of DMF. The reaction was allowed to stir at room temperature for 2 hours. The reaction was concentrated under high vacuum for 30 minutes to yield a yellow-orange solid. The crude acid chloride was dissolved in 5 mL $CH_2Cl_2$. 2-Amino-5-(2-t-butylaminosulfonyl)phenylpyridine (0.51 g, 1.86 mmol) followed by triethylamine (0.65 mL, 4.65 mmol) was added to the crude acid chloride solution. The reaction mixture was allowed to stir at room temperature for 14 hours. The solution was diluted with 50 mL $CH_2Cl2$, washed with 25 mL saturated, aqueous $NaHCO_3$, 25 mL 1M HCl then 25 mL brine. The organic layer was dried with $MgSO_4$, concentrated in vacuo, and chromatographed on silica with 20% EtOAc/benzene to give 0.10 g (12%) of the desired product. $^1H$ NMR ($CDCl_3$) δ: 10.07 (br s, 1H); 8.40 (d, 1H); 8.30 (d, 1H); 8.18 (dd, 1H); 8.09 (m, 1H); 8.02 (dt, 1H); 7.84 (dd, 1H); 7.79 (dt, 1H); 7.60 (m, 3H); 7.28 (dd, 1H); 4.89 (s, 2H); 3.71 (s, 3H); 1.07 (s, 9H).

Part D. Preparation of 3-(3-Amidinophenyl)-4-[5-(2-aminosulfonyl)phenylpyrid-2-yl)aminocarbonyl]-5-(methoxymethyl)isoxazole, Trifluoroacetic Acid Salt 3-(3-cyanophenyl)-4-[5-(2-t-butylaminosulfonyl) phenylpyrid-2-yl)aminocarbonyl]-5-(methoxymethyl) isoxazole (0.10 g, 0.18 mmol) was dissolved in 1 mL of methanol and 4 mL of chloroform. The reaction mixture was cooled in an ice-bath and HCl gas was bubbled-in for 2.5 hours to saturate the solution. The mixture was sealed and allowed to stir at room temperature for 14 hours. The solvents were removed in vacuo and the resulting solid was added to 0.07 g (0.90 mmol) of ammonium carbonate and 10 mL of methanol. The mixture was sealed and allowed to stir under Ar for 14 hours. The solvent was removed at reduced pressure. The crude benzamidine was purified by HPLC (C18 reversed phase) eluting with 0.5% TFA in $H_2O$/$CH_3CN$ to give 0.33 g (43%) of the desired salt. $^1H$ NMR (DMSO-$d_6$) δ: 10.69 (s, 1H); 9.67 (s, 1H); 9.41 (br s, 2H); 9.07 (br s, 2H); 8.18 (t, 1H); 8.06 (dt, 2H); 7.92 (d, 1H); 7.72 (m, 5H); 7.38 (s, 1H); 7.36 (d, 2H); 2.80 (s, 3H). HRMS 507.1458 (M+H).

Example 5

3-(3-Amidinophenyl)-4-[(2'-trifluoromethyl-[1,1']-biphen-4-yl)aminocarbonyl]isoxazole, Trifluoroacetic Acid Salt Part A. Preparation of 2-(Trifluoromethyl)phenylboronic Acid To a solution of 58.8 g (0.261 mol) of 1-bromo-2-(trifluoromethyl)benzene in 250 mL of THF under Ar was added 110 mL (0.275 mol) of 2.5M n-butyllithium in hexane over 35 minutes, keeping the temperature between 0–5° C.

The reaction mixture was allowed to warm to 10° C. Triisopropylborate (95 mL, 0.313 mol) was added, keeping the temperature below 35° C. After 1 hour, the reaction mixture was cooled, 1N HCl (425 mL) was added, and the mixture was stirred overnight. The mixture was extracted with 100 mL of ether three times, and the combined organic extracts were extracted with 100 mL of 1N NaOH three times. The aqueous extracts were acidified to pH 1 with 6N HCl, and then extracted with 100 mL ether three times. The combined ether extracts were dried over $MgSO_4$, and the solvents evaporated in vacuo to give 46.1 g (93%) of the desired compound as a light yellow oil. $^1$H NMR ($CDCl_3$) δ: 7.77 (d, 1H); 7.72 (d, 1H); 7.56 (m, 2H); 4.87 (br s, 2H).

Part B. Preparation of 4-Amino-2'-trifluoromethyl-[1,1'] biphenyl

A mixture of 3.44 g (20 mmol) of 4-bromoaniline and 3.80 g (20 mmol) of 2-(trifluoromethyl)phenylboronic acid, 1.16 g of tetrakis(triphenylphosphine) palladium(0) (1 mmol), 0.32 g of tetrabutylammonium bromide (1 mmol) and 20 mL of 2M aqueous sodium carbonate were refluxed with 180 mL of benzene under $N_2$ for 14 hours. After cooling, the mixture was diluted with methylene chloride and water. The two phases were separated and the organic phase was washed with water, dried with $MgSO_4$ and concentrated in vacuo. The resulting thick oil was chromatographed on silica with 10% EtOAc/hexane to afford 2.09 g (44%) of the aniline. $^1$H NMR ($CDCl_3$) δ: 7.72 (d, 1H); 7.53 (t, 1H); 7.41 (t, 1H); 7.32 (d, 1H); 7.13 (d, 2H); 6.73 (d, 2H); 3.74 (br s, 2H).

Part C. Preparation of 3-(3-Cyanophenyl)-4-[(2'-trifluoromethyl-[1,1']-biphen-4-yl)aminocarbonyl]isoxazole 4-Amino-2'-trifluoromethyl-[1,1']biphenyl (0.24 g, 1.0 mmol) was suspended in 5 mL of $CH_2Cl_2$ and 2.5 mL of a 2M solution of trimethylaluminum in heptane was added slowly via syringe. The reaction was stirred for 30 minutes at room temperature and-then 4-carbomethoxy-3-(3-cyanophenyl)isoxazole (0.25 g, 1.0 mmol) was added. The reaction mixture was stirred at room temperature for an additional 14 hours. The aluminum reagent was quenched by careful addition of 1N HCl to pH 2, then extracted with 10 mL of $CH_2Cl_2$ three times. The combined organic extracts were washed with water then brine, dried over $MgSO_4$ and the solvent evaporated. The desired product was obtained (0.35 g, 80%) after silica gel chromatography with 20% EtOAc/hexane. $^1$H NMR ($CDCl_3$) δ: 9.02 (s, 1H); 8.17 (s, 1H); 8.08 (d, 1H); 7.83 (d, 1H); 7.76 (d, 1H); 7.67 (t, 1H); 7.56 (m, 1H); 7.48 (m, 3H); 7.34 (m, 3H).

Part D. Preparation of 3-(3-Amidinophenyl)-4-[(2'-trifluoromethyl-[1,1']-biphen-4-yl)aminocarbonyl] isoxazole, Trifluoroacetic Acid Salt 3-(3-cyanophenyl)-4-[(2'-trifluoromethyl-[1,1']-biphen-4-yl)aminocarbonyl]isoxazole (0.33 g, 0.76 mmol) was dissolved in 1 mL of methanol and 3 mL of chloroform. The reaction mixture was cooled in an ice-bath and HCl gas was bubbled-in for 0.5 hours to saturate the solution. The mixture was sealed and allowed to stir at room temperature for 14 hours. The solvents were removed in vacuo and the resulting solid was added to 0.25 g (2.6 mmol) of ammonium carbonate and 2 mL of methanol. The mixture was sealed and allowed to stir under Ar for 14 hours. The solvent was removed at reduced pressure. The crude benzamidine was purified by HPLC (C18 reversed phase) eluting with 0.5% TFA in $H_2O/CH_3CN$ to give 0.11 g (32%) of the desired salt. $^1$H NMR (DMSO-$d_6$) δ: 10.68 (s, 1H); 9.68 (s, 1H); 9.43 (br s, 2H); 9.06 (br s, 2H); 8.20 (m, 1H); 8.08 (d, 1H); 7.93 (d, 1H); 7.75 (m, 5H); 7.60 (d, 1H); 7.38 (m, 1H); 7.31 (d, 2H). HRMS 451.1399 (M+H).

Example 6

3-(3-Amidinophenyl)-4-[(2'-aminosulfonyl-[1,1']-biphen-4-yl)aminocarbonyl]-5-(trifluoromethyl) isoxazole, Trifluoroacetic Acid Salt Part A. Preparation of Ethyl 3-Methoxy-3-(trifluoromethyl) acylate Diazald® (14.55, 67.9 mmol) was dissolved in 130 mL $Et_2O$ and 30 mL 95% EtOH. Potassium hydroxide (12.37 g, 220 mmol) is dissolved in 23 mL water and added slowly via additional funnel to the ethanol solution which is heated to 65° C. The ether distillate containing diazomethane is condensed into ethyl 4,4,4-trifluoroacetoacetate (10.0 g, 54.3 mmol). The excess diazomethane was decomposed with the addition of 1 drop of acetic acid. The ethereal solution was evaporated at 450 torr for 30 minutes. The crude enol ether (10.7 g, 100%) was used without purification. $^1$H NMR ($CDCl_3$) δ: 5.78 (s, 1H); 4.22 (q, 2H); 4.04 (s, 3H); 1.32 (t, 3H).

Part B. Preparation of 3-(3-Cyanophenyl)-5-(trifluoromethyl-4-carbomethoxyisoxazole Tributylamine (12.6 g, 67.9 mmol) is added dropwise over 2 hours to a solution of 9.81 g (54.3 mmol) of 3-cyanobenzenehydroximinoyl chloride and 10.76 g (54.3 mmol) of ethyl 3-methoxy-3-(trifluoromethyl)acylate in 49 mL of $CH_2Cl_2$ and 1 mL DMSO under $N_2$. The reaction mixture is diluted with 100 mL of water and the organic layer separated. The aqueous solution is extracted with 100 mL EtOAc twice and the combined organic extracts are dried with $MgSO_4$ and concentrated in vacuo. The resulting thick oil was chromatographed on silica with 30% EtOAc/hexane to give 1.60 g (10%) of the desired product. $^1$H NMR ($CDCl_3$) δ: 8.05 (m, 1H); 7.96 (dt, 1H); 7.84 (dt, 1H); 7.63 (t, 1H); 4.37 (q, 2H); 1.33 (t, 3H).

Part C. Preparation of 3-(3-Cyanophenyl)-4-[(2'-t-butylaminosulfonyl-[1,1']-biphen-4-yl)aminocarbonyl]-5-(trifluoromethyl)isoxazole 2'-t-Butylaminosulfonyl-4-amino-[1,1']biphenyl (0.39 g, 1.3 mmol) was suspended in 4 mL of $CH_2Cl_2$ and 1.9 mL of a 2M solution of trimethylaluminum in heptane was added slowly via syringe. The reaction was stirred for 30 minutes at room temperature and then 3-(3-cyanophenyl)-5-(triflouromethyl-4-carbomethoxyisoxazole (0.40 g, 1.3 mmol) was added. The reaction mixture was stirred at room temperature for an additional 14 hours. The aluminum reagent was quenched by careful addition of 1N HCl to pH 2, then extracted with 20 mL of $CH_2Cl_2$ three times. The combined organic extracts were washed with water then brine, dried over $MgSO_4$ and the solvent evaporated. The desired product was obtained (0.31 g, 43%) after silica gel chromatography with 20% EtOAc/hexane. $^1$H NMR ($CDCl_3$) δ: 8.74 (br s, 1H); 8.11 (d, 1H); 8.05 (m, 1H); 8.02 (d, 1H); 7.76 (d, 1H); 7.55 (m, 5H); 7.37 (d, 2H); 7.28 (d, 1H); 1.03 (s, 9H).

Part D. Preparation of 3-(3-Amidinophenyl)-4-[(2'-aminosulfonyl-[1,1']-biphen-4-yl)aminocarbonyl]-5-(trifluoromethyl)isoxazole, Trifluoroacetic Acid Salt 3-(3-cyanophenyl)-4-[(2'-t-butylaminosulfonyl-[1,1']-biphen-4-yl)aminocarbonyl]-5-(trifluoromethyl)isoxazole (0.30 g, 0.53 mmol) was dissolved in 1 mL of methanol and 3 mL of chloroform. The reaction mixture was cooled in an ice-bath and HCl gas was bubbled-in for 0.5 hours to saturate the solution. The mixture was sealed and allowed to stir at room temperature for 14 hours. The solvents were removed in vacuo and the resulting solid was added to 0.25 g (2.6 mmol) of ammonium carbonate and 2 mL of methanol. The mixture was sealed and allowed to stir under Ar for 14 hours. The solvent was removed at reduced pressure. The crude benzamidine was purified by HPLC (C18 reversed phase) eluting with 0.5% TFA in $H_2O/CH_3CN$ to give 0.11 g (36%) of the desired salt. $^1H$ NMR (DMSO-$d_6$) δ: 11.17 (s, 1H); 9.46 (br s, 2H); 9.09 (br s, 2H); 8.19 (m, 1H); 7.98 (m, 3H); 7.84 (t, 1H); 7.56 (m, 2H); 7.55 (d, 2H); 7.37 (d, 2H); 7.26 (m, 1H). HRMS 586.1743 (M+H).

Examples 7 and 8

2-Acetylamino-4-(3-amidinophenyl)-5-[(2'-aminosulfonyl-[1,1']-biphen-4-yl)aminocarbonyl] thiazole, Trifluoroacetic Acid Salt (Example 7) and 2-Amino-4-(3-amidinophenyl)-5-[(2'-aminosulfonyl-[1,1']-biphen-4-yl)aminocarbonyl]thiazole, Trifluoroacetic Acid Salt (Example 8)

Part A. Preparation of Methyl 3-(3-Cyanophenyl)-3-hydroxypropionate.

To a suspension of activated zinc powder (4.3 g, 65.4 mmol) in 100 mL of tetrahydrofuran was added a few drops of dibromoethane. The resulting mixture was heated to 65° C., stirred for 5 min and then was cooled to 25° C. To this solution was added methyl bromoacetate (5.0 g, 32.7 mmol), and 3-cyanobenzaldehyde (4.3 g, 32.7 mmol). The mixture was heated to 65° C. and stirred for 2 h. The reaction was allowed to cool to 25° C. and then was quenched with 10% aq HCl and filtered through celite. The mixture was diluted with ethyl acetate and washed with 10% aq HCl and saturated aq $NaHCO_3$. This wash cycle was repeated until no white precipitate was observed upon addition of saturated aq $NaHCO_3$. The organics were then washed with brine, dried ($MgSO_4$) and concentrated in vacuo. The residue was purified by flash chromatography (elution with 1:1 hexanes/ethyl acetate) to afford 4.5 g (67%) of the title compound as an oil. MS ($NH_3$-DCI) 223.1 (M+H)+.

Part B. Preparation of Methyl 3-(3-Cyanophenyl)-3-oxopropionate.

To a solution of methyl 3-(3-cyanophenyl)-3-hydroxypropionate (2.22 g, 10.8 mmol) in 30 mL of methylene chloride was added activated manganese dioxide (4.7 g, 54.0 mmol). This mixture was allowed to stir at 25° C. for 16 h. The reaction mixture was filtered through a pad of celite and concentrated in vacuo. The residue was purified by flash chromatography (elution with 2:1 hexanes/ethyl acetate) to afford 0.9 g (41%) of the title compound along with 0.8 g (36%) of recovered starting material. MS for title compound ($H_2O$ GC-MS) 204 (M+H)+.

Part C. Preparation of Methyl 2-Bromo-3-(3-cyanophenyl)-3-oxopropionate.

To a solution of methyl 3-(3-cyanophenyl)-3-oxopropionate (0.91 g, 4.48 mmol) in 20 mL of carbon tetrachloride at 0° C. was added N-bromosuccinimide (0.80 g, 4.48 mmol). The resulting solution was allowed warm to 25° C. and was stirred for 2 h. The insoluble succinimide was filtered off and the solution was concentrated in vacuo to afford an oil (1.2 g, 95%) which was sufficiently pure to be used without purification. MS ($H_2O$ GC-MS) 282/284 (M+H)+.

Part D. Preparation of 2-Acetylamino-4-(3-cyanophenyl)-5-carbomethoxythiazole.

To a solution of methyl 2-bromo-3-(3-cyanophenyl)-3-oxopropionate (1.25 g, 4.4 mmol) in 20 mL of tetrahydrofuran was added 1-acetylthiourea (0.52 g, 4.4 mmol). The resulting mixture was stirred at 65° C. for 3 h. The reaction was allowed to cool and the solvent was evaporated in vacuo. The residue was taken up in ethyl acetate, washed with 10% aq HCl, saturated aq $NaHCO_3$ and brine, dried ($MgSO_4$) and concentrated in vacuo to yield a solid. Trituration with hexanes/ethyl acetate left the title compound as a white solid (0.4 g, 30%). MS (ESI) 302.2 (M+H)+.

Part E. Preparation of 2-Acetylamino-4-(3-cyanophenyl)-5-[(2'-tert-butylaminosulfonyl-[1,1']-biphen-4-yl) aminocarbonyl]thiazole.

To a solution of (2'-tert-butylaminosulfonyl-[1,1']-biphen-4-yl)amine (0.27 g, 0.88 mmol) in 5 mL of methylene chloride at 25° C. was added trimethylaluminum (1.76 mL of a 2.0 M solution in toluene, 3.52 mmol) dropwise. The resulting solution was allowed to stir until no more gas evolution was observed (~15 min). To this solution was added 2-acetylamino-4-(3-cyanophenyl)-5-carbomethoxythiazole (0.12 g, 0.40 mmol) as a solution in methylene chloride. The resulting solution was stirred at 40° C. for 2 h and then was cooled to 25° C. and quenched by the addition of saturated aq $NH_4Cl$. After diluting with ethyl acetate, the organic layer was washed with 10% aq HCl, saturated aq $NaHCO_3$ and brine, dried ($MgSO_4$) and concentrated in vacuo. The residue was purified by flash chromatography (elution with 1:1 hexanes/ethyl acetate) to afford 0.15 g (65%) of the title compound as a solid. MS (ESI) 574 (M+H)+.

Part F. Preparation of 2-Acetylamino-4-(3-amidinophenyl)-5-[(2'-aminosulfonyl-[1,1']-biphen-4-yl)aminocarbonyl] thiazole, Trifluoroacetic Acid Salt (Example 7) and 2-Amino-4-(3-amidinophenyl)-5-[(2'-aminosulfonyl-[1,1']-biphen-4-yl)aminocarbonyl]thiazole, Trifluoroacetic Acid Salt (Example 8).

Through a solution of 2-acetylamino-4-(3-cyanophenyl)-5-[(2'-tert-butylaminosulfonyl-[1,1']-biphen-4-yl) aminocarbonyl]thiazole (0.15 g, 0.26 mmol) in 50 mL of absolute methanol at 0° C. was bubbled anhydrous HCl (g) until the solution was saturated. This solution was tightly stoppered and allowed to stand at 0° C. for 16 h. The solution was concentrated in vacuo and then was taken up in 10 mL of absolute methanol and then there was added ammonium carbonate (0.15 g, 1.56 mmol). This mixture was allowed to stir at 25° C. for 16 h. The reaction mixture was then concentrated in vacuo and purified by prep HPLC (C18 reverse phase column, elution with a $H_2O/CH_3CN$ gradient with 0.5% TFA) to afford 2-acetylamino-4-(3-amidinophenyl)-5-[(2'-aminosulfonyl-[1,1']-biphen-4-yl) aminocarbonyl]thiazole, trifluoroacetic acid salt (Example 7) as the major product (0.50 g, 30%). MS (ESI) 535 (M+H)+. There was also isolated 2-amino-4-(3-amidinophenyl)-5-[(2'-aminosulfonyl-[1,1']-biphen-4-yl) aminocarbonyl]thiazole, trifluoroacetic acid salt (Example 8) as a minor product (0.10 g, 6%). MS (ESI) 493 (M+H)+.

Example 9

2-Methyl-4-(3-amidinophenyl)-5-[(2'-aminosulfonyl-[1,1']-biphen-4-yl)aminocarbonyl] thiazole, Trifluoroacetic Acid Salt Part A. Preparation of 2-Methyl-4-(3-cyanophenyl)-5-carbomethoxythiazole.

To a solution of methyl 2-bromo-3-(3-cyanophenyl)-3-oxopropionate from Example 1, Part C (0.50 g, 1.77 mmol) in 10 mL of tetrahydrofuran was added thioacetamide (0.14 g, 1.77 mmol). The resulting solution was stirred at 65° C. for 4h and then was allowed to cool to 25° C. This mixture was diluted with ethyl acetate, washed with 10% aq HCl, saturated aq $NaHCO_3$ and brine, dried ($MgSO_4$) and concentrated in vacuo to a solid. Trituration with ether left 0.14 g (31%) of the title compound as a solid. MS ($NH_3$-CI) 259 (M+H)+.

Part B. Preparation of 2-Methyl-4-(3-cyanophenyl)-5-[(2'-tert-Butylaminosulfonyl-[1,1']-biphen-4-yl)aminocarbonyl] thiazole.

Following the procedure of Example 1, Part E, 2-methyl-4-(3-cyanophenyl)-5-carbomethoxythiazole (0.08 g, 0.31 mmol) was converted into 0.085 g (52%) of the title compound as a solid. MS (ESI) 531.3 (M+H)+.

Part C. Preparation of 2-Methyl-4-(3-amidinophenyl)-5-[(2'-aminosulfonyl-[1,1']-biphen-4-yl)aminocarbonyl]thiazole, Trifluoroacetic Acid Salt.

A solution of 2-methyl-4-(3-cyanophenyl)-5-[(2'-tert-butylaminosulfonyl-[1,1']-biphen-4-yl)aminocarbonyl]thiazole (0.085 g, 0.16 mmol) in 5 mL of trifluoroacetic acid was stirred at 70° C. until gas evolution was no longer observed (~15 min) and then was allowed to cool to room temperature and as concentrated in vacuo. The crude residue was dissolved in 40 mL of absolute methanol and cooled to 0° C. Anhydrous HCl gas was bubbled through the solution until saturated (~30 min). The flask was then sealed and allowed to stand at 0° C. for 16 h. The reaction mixture was concentrated in vacuo, dissolved in 10 mL of absolute methanol and then ammonium carbonate (0.09 g, 0.96 mmol) was added and the mixture was allowed to stir at 25° C. for 24 h. The reaction mixture was concentrated in vacuo and purified by prep HPLC (C18 reverse phase column, elution with a $H_2O/CH_3CN$ gradient with 0.5% TFA) to afford 65 mg (68%) of the title compound as a solid. MS (ESI) 492.3 (N+H)+.

Example 10

5-(3-Amidinophenyl)-4-[(2'-aminosulfonyl-[1,1']-biphen-4-yl)aminocarbonyl]oxazole Part A. Preparation of 5-(3-Cyanophenyl)-4-carboxymethyloxazole.

The title compound was prepared in 50% yield by the condensation of 3-cyanobenzoyl chloride, methylisocyanoacetate and triethylamine in anhydrous THF following the general method of Suzuki et. al. Syn. Comm. 1972, 2, 237. $^1$H NMR (CDCl$_3$) δ: 8.42–8.40 (d, 1H), 7.99 (s, 1H), 9.77–7.75 (d, 1H), 7.63 (t, 1H), 3.99 (s, 3H) ppm; Ammonia mass spectrum analysis m/z (rel intensity) 246 (M+NH$_4^+$, 100), 229(M+H).

Part B. Preparation of 5-(3-Cyanophenyl)-oxazole-4-carboxylic Acid.

Standard LiOH hydrolysis in aqueous THF of the product from part A then provided pure oxazole carboxylic acid in quantitative yield. $^1$H NMR (CDCl$_3$) δ: 8.56–8.34 (d, 1H), 8.51 (s, 1H), 8.03 (s, 1H), 7.77–7.76 (d, 1H), 7.67–7.62 (t, 1H) ppm; Ammonia mass spectrum analysis m/z (rel intensity) 232 (M+NH$_4^+$, 100) ppm.

Part C. Preparation of 5-(3-Cyanophenyl)-4-[(2'-t-butyl-aminosulfonyl-[1,1']-biphen-4-yl)aminocarbonyl]oxazole.

The acid obtained in part B was then coupled (60% yield) to 2'-tert-butylsulfonamide-biphenylaniline acid chloride as described above. $^1$H NMR (CDCl$_3$) δ: 9.24 (s, 1H), 8.71 (s, 1H), 8.67 (s, 1H), 8.19–8.16 (m, 1H), 8.01 (s, 1H), 7.83–7.80 (d, 2H), 7.76 (m, 1H), 7.67 (d, 1H), 7.35–7.32 (m, 1H), 3.62 (s, 1H), 1.03 (s, 9H) ppm; ESI mass spectrum analysis m/z (rel. intensity) 445 (M+H, 100).

Part D. Preparation of 5-(3-Amidinophenyl)-4-[(2'-aminosulfonyl-[1,1']-biphen-4-yl)aminocarbonyl]oxazole.

The compound obtained in part C was subjected to the Pinner-amidine reaction sequence as outlined previously to obtain the title benzamidine compound in 40% yield. Colorless crystals obtained after lyophilization. $^1$H NMR (DMSO d$_6$) δ: 10.49 (s, 1H), 9.45 (bs, 2H), 9.12 (bs, 2H), 8.85 (s, 1H), 8.61 (s, 1H), 8.54–8.51 (d, 1H), 8.05 (d, 1H), 7.91–7.77 (m, 4H), 7.65–7.54 (m, 2H), 7.40–7.37 (d, 2H), 7.35 (d, 1H), 7.27 (s, 2H) ppm; ESI mass spectrum analysis m/z (rel. intensity) 462 (M+H, 100); High resolution mass spectrum analysis calc. for $C_{23}H_{20}N_5SO_4$ 462.123601, found 462.124334.

Example 11

3-(3-Amidinophenyl)-4-[(2'-t-butylaminosulfonyl-[1,1']-biphen-4-yl)aminocarbonyl]isoxazole, Trifluoroacetic Acid Salt 4-(N-[2'-Aminosulfonyl-[1,1']-biphen-4-yl]aminocarbonyl)-3-(3-cyanophenyl)isoxazole (0.53 g, 1.1 mmol) was dissolved in 10 mL of methanol and 30 mL of chloroform. The reaction mixture was cooled in an ice-bath and HCl gas was bubbled for 30 minutes to saturate the solution. The mixture was sealed and allowed to stir at room temperature for 14 hours. The solvents were removed in vacuo and the resulting solid was used in the next step.

The imidate formed above was added with 0.5 g (5.2 mmol) of ammonium carbonate and 20 mL of methanol. The mixture was allowed to stir under $N_2$ for 14 hours. The solvent was removed at reduced pressure. The crude benzamidine was purified by HPLC (C18 reversed phase) eluting with 0.5% TFA in $H_2O/CH_3CN$ to give 0.09 g (16%) of the desired salt. $^1$H NMR (DMSO-d$_6$) δ: 10.69 (s, 1H); 9.70 (s, 1H); 9.43 (br s, 2H); 9.05 (br s, 2H); 8.05 (d, 1H); 8.00 (d, 1H); 7.92 (d, 1H); 7.74 (t, 1H); 7.67 (d, 2H); 7.59 (t, 1H); 7.52 (t, 1H); 7.34 (d, 2H); 7.26 (m, 1H); 0.98 (s, 9H). HRMS 517.1768 (M+H).

Example 12

3-(3-Amidinophenyl)-4-[(2'-aminosulfonyl-[1,1']-biphen-4-yl) aminocarbonyl]-5-(methoxymethyl) isoxazole, Trifluoroacetic Acid Salt Part A. Preparation of Methyl 3-(3-Cyanophenyl)-5-(methoxymethyl)isoxazole-4-carboxylate.

Methyl 4-methoxyacetoacetate (1.6 mL, 12.2 mmol) was added to a solution of 12.2 mL (24.4 mmol) of 0.5 M NaOMe in methanol. A solution of 3-cyanobenzenehydroximinoyl chloride (2.0 g, 11.1 mmol) in 20 mL methanol was added slowly over 12 hours vis a syringe pump. The reaction mixture was diluted with 20 mL of saturated aqueous ammonium chloride and the organic layer separated. The aqueous solution was extracted with 10 mL EtOAc twice. The combined organic extracts were washed with 10 mL water three times then the organic extract was dried with MgSO$_4$ and concentrated in vacuo. The resulting thick oil (3.1 g) was chromatographed on silica with 10% Et$_2$O/benzene to give 1.14 g (38%) of the desired product. $^1$H NMR (CDCl$_3$) δ: 7.98 (m, 1H); 7.91 (dd, J=8.1, 2.9, 1H); 7.79 (dd, J=8.1, 2.9, 1H); 7.59 (t, J=8.1, 1H); 4.91 (s, 2H); 3.83 (s, 3H); 3.53 (s, 3H) MS (NH$_3$-CI) m/z 273.0 (M+H).

Part B. Preparation of 3-(3-Cyanophenyl)-5-(methoxymethyl)-isoxazole-4-carboxylic Acid.

Methyl 3-(3-cyanophenyl)-5-(methoxymethyl)isoxazole-4-carboxylate (1.12 g, 4.1 mmol) was dissolved in 3 mL THF and 1 mL water. Lithium hydroxide monohydrate (0.20 g, 4.9 mmol) was added and the reaction was allowed to stir for 24 hours under $N_2$. The solvent was removed in vacuo and redissolved in 100 mL of water. The resulting solution was extracted with 30 mL EtOAc twice then acidified with 1N HCl to pH 3. The acidic solution was extracted three times with 30 mL of EtOAc. The combined organic were dried with MgSO$_4$ and concentrated in vacuo to give the desired white solid (0.80 g, 75%). $^1$H NMR (CDCl$_3$) δ: 7.98 (m, 1H); 7.91 (dd, J=8.1, 2.9, 1H); 7.79 (dd, J=8.1, 2.9, 1H); 7.59 (t, J=8.1, 1H); 4.89 (s, 2H); 3.53 (s, 3H).

Part C. Preparation of 3-(3-Cyanophenyl)-4-[(2'-t-butylaminosulfonyl-[1,1']-biphen-4-yl)aminocarbonyl]-5-(methoxymethyl)isoxazole.

Oxalyl chloride (1.15 mL of 2.0 M solution in $CH_2Cl_2$, 2.3 mmol) and 3-(3-cyanophenyl)-5-(methoxymethyl)isoxazole-4-carboxylic acid (0.40 g, 1.55 mmol) were stirred at room temperature under $N_2$ for 1 hour. The excess oxalyl chloride was removed in vacuo. The solid was dissolved in 15 mL $CH_2Cl_2$ and 0.58 g (1.9 mmol) of 2'-t-butylaminosulfonyl-4-amino-[1,1']-biphenyl and 0.65 mL (4.7 mmol) of triethylamine were added. After 12 hours, the reaction mixture was diluted with 10 mL of water and the organic layer separated. The aqueous solution was extracted with 10 mL $CH_2Cl_2$ three times and the combined organic extracts were washed with 10 mL of each of the following: saturated aqueous $NaHCO_3$, 1M aqueous HCl and saturate aqueous brine. The organic extract was dried with $MgSO_4$ and concentrated in vacuo to give 0.63 g of an orange-brown solid. The solid was chromatographed on silica with 10% EtOAc/benzene to 0.63 g (74%) of the desired product. $^1H$ NMR ($CDCl_3$) δ: 9.50 (s, 1H); 8.16 (d, J=8.1, 1H); 8.11 (s, 1H); 8.04 (d, J=8.1, 1H); 7.78 (d, J=8.1, 1H); 7.66 (d, j=8.8, 2H); 7.60 (m, 1H); 7.56 (m, 2H); 7.50 (d, J=8.8, 2H); 7.29 (d, J=7.3, 1H); 4.89 (s, 2H); 3.67 (s, 3H); 1.03 (s, 9H).

Part D. Preparation of 3-(3-Amidinophenyl)-4-[(2'-aminosulfonyl-[1,1']-biphen-4-yl)aminocarbonyl]-5-(methoxymethyl)isoxazole, Trifluoroacetic Acid Salt.

3-(3-Cyanophenyl)-4-[(2'-t-butylaminosulfonyl-[1,1']-biphen-4-yl)aminocarbonyl]-5-(methoxymethyl)isoxazole (0.62 g, 1.14 mmol) was dissolved in 7 mL of methanol and 20 mL of chloroform. The reaction mixture was cooled in an ice-bath and HCl gas was bubbled-in for 1.5 hours to saturate the solution. The mixture was sealed and allowed to stir at room temperature for 14 hours. The solvents were removed in vacuo and the resulting solid was used in the next step.

The imidate formed above was added with 0.44 g (5.7 mmol) of ammonium carbonate and 20 mL of methanol. The mixture was allowed to stir under $N_2$ for 14 hours. The solvent was removed at reduced pressure. The crude benzamidine was purified by HPLC (C18 reversed phase) eluting with 0.5% TFA in $H_2O/CH_3CN$ to give 0.37 g (65%) of the desired salt. $^1H$ NMR (DMSO-$d_6$) δ: 10.63 (s, 1H); 9.42 (s, 1H); 9.03 (br s, 2H); 9.05 (br s, 2H); 8.16 (s, 1H); 8.00 (m, 1H); 7.98 (m, 1H); 7.90 (d, J=7.3, 1H); 7.76 (t, J=8.1, 1H); 7.57 (m, 4H); 7.34 (d, J=8.1, 2H); 7.28 (m, 1H); 4.77 (s, 2H); 3.34 (s, 3H). HRMS 506.1487 (M+H).

Example 13

2-Methyl-4-(3-amidinophenyl)-5-[(2'-trifluoromethyl-[1,1']-biphen-4-yl)aminocarbonyl]thiazole, Trifluoroacetic Acid Salt Part A. Preparation of 2-Methyl-4-(3-cyanophenyl)-5-[4-bromophenyl)aminocarbonyl]thiazole.

To a solution of 4-bromoaniline (0.21 g, 1.2 mmol) in 25 mL of methylene chloride at room temperature was added trimethylaluminum (1.02 mL of a 2.0M solution in toluene, 2.04 mmol) dropwise. The reaction was stirred until gas evolution ceased and then 2-methyl-4-(3-cyanophenyl)-5-carbomethoxythiazole from Example 3, Part A (0.26 g, 1.02 mmol) was added in 10 mL of methylene chloride. The resulting solution was stirred at 40° C. for 16 h and then was allowed to cool to 25° C. This mixture was quenched with saturated aq $NH_4Cl$, diluted with ethyl acetate, washed with water and brine, dried ($MgSO_4$) and concentrated in vacuo. The residue was purified by flash chromatography (elution with 4:1 hexanes/ethyl acetate) to afford 0.18 g (44%) of the title compound as a solid. MS (ESI) 398.0/400.0 (M+H)+.

Part B. Preparation of 2-Methyl-4-(3-cyanophenyl)-5-[(2'-trifluoromethyl-[1,1']-biphen-4-yl)aminocarbonyl]thiazole.

To a solution of 2-methyl-4-(3-cyanophenyl)-5-[4-bromophenyl)aminocarbonyl]thiazole (0.175 g, 0.44 mmol) in 25 mL of benzene was added 2-(trifluoromethyl)phenylboronic acid (0.118 g, 0.62 mmol); tetrabutylammonium bromide (0.006 g, 0.02 mmol); sodium carbonate (0.14 g, 1.3 mmol) and 1.2 mL of $H_2O$. This mixture was degassed with a stream of nitrogen and then tetrakis(triphenylphosphine)palladium (0.02 g, 0.02 mmol) was added and the reaction mixture was stirred at 80° C. for 16 h. The mixture was allowed to cool to room temperature and then was diluted with ethyl acetate, washed with $H_2O$ and brine, dried over $MgSO_4$ and was concentrated in vacuo to afford 0.166 g (83%) of the title compound, which was sufficiently pure to be used without purification. MS (ESI) 464.2 (M+H)+.

Part C. Preparation of 2-Methyl-4-(3-amidinophenyl)-5-[(2'-trifluoromethyl-[1,1']-biphen-4-yl)aminocarbonyl]thiazole, Trifluoroacetic Acid Salt.

Following the procedure described in Example 7, Part F, 2-methyl-4-(3-cyanophenyl)-5-[(2'-trifluoromethyl-[1,1']-biphen-4-yl)aminocarbonyl]thiazole (0.166 g, 0.36 mmol) was converted into 45 mg (21%) of the title compound as a white solid following HPLC purification. MS (ESI) 481.3 (M+H)+.

Example 14

2-Phenyl-4-(3-amidinophenyl)-5-[(2'-aminosulfonyl-[1,1']-biphen-4-yl)aminocarbonyl]thiazole, Trifluoroacetic Acid Salt Part A. Preparation of 2-Phenyl-4-(3-cyanophenyl)-5-carbomethoxythiazole.

To a solution of methyl 2-bromo-3-(3-cyanophenyl)-3-oxopropionate from Example 7, Part C (0.51 g, 1.8 mmol) in 20 mL of absolute ethanol was added thiobenzamide (0.25 g, 1.8 mmol). The resulting mixture was stirred at 80° C. for 24 h. The reaction was allowed to cool and then was filtered. The solid was washed with ethanol and dried in vacuo to yield 0.53 g (91%) of the title compound. MS (ESI) 321.1 (M+H)+.

Part B. Preparation of 2-Phenyl-4-(3-cyanophenyl)-5-[(2'-tert-butylaminosulfonyl-[1,1']-biphen-4-yl)aminocarbonyl]thiazole.

Following the procedure of Example 7, Part E, 2-phenyl-4-(3-cyanophenyl)-5-carbomethoxythiazole (0.30 g, 0.94 mmol) was converted into 0.53 g (95%) of the title compound as a solid. MS (ESI) 593.3 (M+H)+.

Part C. Preparation of 2-Phenyl-4-(3-amidinophenyl)-5-[(2'-aminosulfonyl-[1,1']-biphen-4-yl)aminocarbonyl]thiazole, Trifluoroacetic Acid Salt.

Following the procedure of Example 9, Part C, 2-phenyl-4-(3-cyanophenyl)-5-[(2'-tert-butylaminosulfonyl-[1,1']-biphen-4-yl)aminocarbonyl]thiazole (0.53 g, 0.90 mmol) was converted into 61 mg of the title compound (10%) as a white powder following HPLC purification. $^1H$ NMR (DMSO-$d_6$) δ: 10.77 (s, 1H), 9.40 (broad s, 2H), 8.98 (broad s, 2H), 8.28 (broad s, 1H), 8.08 (m, 3H), 7.99 (d, 1H, J=8 Hz), 7.81 (d, 1H, J=8 Hz), 7.71 (t, 1H, J=8 Hz), 7.61–7.52 (m, 7H), 7.38–7.22 (m, 5H). MS (ESI) 554.3 (M+H)+.

Example 15

3-(3-Amidinophenyl)-4-[(3-fluoro-2'-methylsulfonyl-[1,1']-biphen-4-yl)aminocarbonyl]isoxazole, Trifluoroacetic Acid Salt Part A. Preparation of 3-Fluoro-2'-methylthio-[1,1']-biphenylamine.

A benzene solution (100 mL) of 2-methylthiophenylboronic acid (2.07 g, 12.3 mmol);

4-bromo-2-fluoro aniline (1.06 g, 5.6 mmol); aq. Na$_2$CO$_3$ (12.5 mL, 2 M, 25 mmol); and tetra n-butyl ammonium bromide (90 mg, 0.3 mmol) was purged with vacuum and Ar. Bis(triphenylphosphine)palladium (II) chloride (195 mg, 0.3 mmol) was added, and the reaction was refluxed 10 h. After cooling, the reaction was diluted with EtOAc and H$_2$O, the layers were separated, the organic was dried over Na$_2$SO$_4$, filtered, and evaporated. The crude product was chromatographed on silica gel (10% EtOAc/hexanes) to yield the desired product (1.05 g, 81%). $^1$H NMR (CDCl$_3$) δ: 7.29 (m, 2H); 7.18 (m, 2H); 7.09 (dd, 1H, J=11.7, J'=1.8); 7.01 (dd, 1H, J=8.0, J'=1.4); 6.82 (t, 1H, J=9.2); 3.79 (bs, 2H); 2.38 (s, 3H).

Part B. Preparation of 3-(3-Cyanophenyl)-4-[(3-fluoro-21-methylthio-[1,1']-biphen-4-yl)aminocarbonyl]isoxazole.

Trimethyl aluminum (1.3 mL, 2.0 M in heptane, 2.6 mmol) was added to the 4- amino-3-fluoro-2'-methylthio-[1,1']-biphenyl (309 mg, 1.3 mmol) in CH$_2$Cl$_2$ (7 mL) and stirred at room temp 25 min. Then methyl 3-(3-cyanophenyl)isoxazole-4-carboxylate isoxazole (300 mg, 1.3 mmol) was added and stirred 48 h. More trimethyl aluminum (1.3 mL, 2.6 mmol) and CH$_2$Cl$_2$ (5 mL) were added. After an additional 3 days, the reaction was quenched carefully with 1N HCl and extracted into CH$_2$Cl$_2$. The organic layer was further washed with H$_2$O and brine, dried over Na$_2$SO$_4$, filtered, and evaporated. The crude produc was chromatographed on silica gel (20–30% EtOAc/hexanes followed by 2% MeOH/CHCl$_3$) to yield the desired product (0.50 g, 89%). $^1$H NMR (CDCl$_3$, 400 MHz) δ: 9.07 (s, 1H); 8.34 (bt, 1H, J=8.3); 8.13 (t, 1H, J=1.2); 8.04 (dt, 1H, J=7.8, J'=1.2); 7.84 (dt, 1H, J=7.8, J'=1.4); 7.67 (t, 1H, J=8.1); 7.57 (bs, 1H); 7.35 (m, 1H); 7.28 (m, 1H); 7.19 (m, 4H); 2.38 (s, 1H).

Part C. Preparation of 3-(3-Cyanophenyl)-4-[(3-fluoro-2'-methylsulfonyl-[1,1']-biphen-4-yl)aminocarbonyl] isoxazole.

To a chloroform solution (50 mL) of 3-(3-cyanophenyl)-4-[(3-fluoro-2'-methylthio-[1,1']-biphen-4-yl) aminocarbonyl]isoxazole (0.47 g, 1.1 mmol); m-CPBA(351 mg, 57–86%, max 1.7 mmol) was added. The resulting mixture was stirred at room temp under Ar 22 h. Additional m-CPBA (94 mg of 50–60% and 348 mg of 57–86%, max 2.1 mmol) was added and stirred 4 h. The reaction was extracted with sat. aq. Na$_2$SO$_3$ and sat. NaHCO$_3$, dried over Na$_2$SO$_4$, filtered, and evaporated. The crude product was chromatographed on silica gel (30–50% EtOAc/hexanes) to yield the desired sulfone (447 mg, 88%). $^1$H NMR (CDCl$_3$) δ: 9.10 (s, 1H); 8.41 (t, 1H, J=8.4); 8.22 (dd, 1H, J=7.7, J'=1.5); 8.12 (d, 1H, J=1.5); 8.05 (dt, 1H, J=8.1, J'=1.5); 7.86 (dt, 1H, J=7.7, J'=1.5); 7.64 (m, 4H); 7.28 (m, 3H); 2.73 (s, 3H).

Part C. Preparation of 3-(3-Amidinophenyl)-4-[(3-fluoro-2'-methylsulfonyl-[1,1']-biphen-4-yl)aminocarbonyl] isoxazole, Trifluoroacetic Acid Salt.

Solid 3-(3-cyanophenyl)-4-[(3-fluoro-2'-methylsulfonyl-[1,1']-biphen-4-yl)aminocarbonyl]isoxazole (423 mg, 0.92 mmol) was suspended in methanol (15 mL) and cooled to 0° C. HCl (g) was generated by the addtion of conc. H$_2$SO$_4$ (90 mL) into solid NaCl (360 g) over 1 h. The HCl (g) continued bubbling through the reaction an additional 90 min, at which time the generator and ice bath were removed. The reaction stirred under argon 20 h and was evaporated. After a few hours under high vacuum, the reaction was redissolved in methanol (15 mL); and ammonium carbonate (440 mg, 4.6 mmol) was added. The reaction was stirred 22 h and evaporated. The crude product was purified by prep HPLC on a C-18 reverse phase column (20–80% MeCN/H$_2$O/ 0.05% TFA) to yield a white solid (0.14 g, 26%). $^1$H NMR (DMSO-d$_6$) δ: 10.47 (s, 1H); 9.68 (s, 1H); 9.40 (s, 1.5H); 9.01 (s, 1.5 H); 8.16 (s, 1H); 8.06 (m, 2H); 7.91 (d, 1H, J=8.1); 7.72 (m, 4H); 7.37 (m, 2H); 7.21 (d, 1H, J=8.1); 2.90 (s, 3H). HRMS calc. for C$_{24}$H$_{20}$FN$_4$O$_4$S, 479.1189; found, 479.1169.

Example 16

3-(3-Amidinophenyl)-4-[(2'-trifluoromethylthio-[1, 1']-biphen-4-yl)aminocarbonyl]isoxazole, Trifluoroacetic Acid Salt Part A. Preparation of 3-(3-Cyanophenyl)-4-[(2'-trifluoromethylthio-[1,1']-biphen-4-yl)aminocarbonyl]isoxazole.

Trimethyl aluminum (2.6 mL, 2.0 M in heptane, 5.2 mmol) was added to the 4-amino-2'-trifluoromethylthio-[1, 1']-biphenyl (361 mg, 1.3 mmol); in CH$_2$Cl$_2$ (5 mL) and stirred at room temp 8 min. A CH$_2$Cl$_2$ solution (5 mL) of methyl 3-(3-cyanophenyl)isoxazole-4-carboxylate (300 mg, 1.3 mmol) was added and stirred 2 days. No further reaction was observed after adding more trimethyl aluminum (650 mL) and stirring an additional 20 hr. The reaction was quenched cwerefully with 1 M HCl and extracted into CH$_2$Cl$_2$. The organic was extracted again with water and brine, dried over Na$_2$SO$_4$, filtered, and evaporated. The crude mixture was chromatographed on silica gel (30% EtOAc/hexanes) to yield a yellow solid (565 mg, 92%). $^1$H NMR (CDCl$_3$) δ: 9.02 (s, 1H); 8.17 (s, 1H); 8.09 (d, 1H, J=8.1); 7.82 (t, 2H, J=8.1); 7.66 (t, 1H, J=7.7); 7.53 (m, 4H); 7.42 (t, 2H, J=7.7); 7.32 (d, 2H, J=8.4).

Part B. Preparation of 3-(3-Amidinophenyl)-4-[(2'-trifluoromethylthio-[1,1']-biphen-4-yl)aminocarbonyl]isoxazole.

A methanol solution (10 mL) of 3-(3-cyanophenyl)-4-[(2'-trifluoromethylthio-[1,1']-biphen-4-yl)aminocarbonyl] isoxazole (137 mg, 0.29 mmol) was cooled to 0° C. HCl was generated by the slow addition of conc. H$_2$SO$_4$ (60 mL) to solid NaCl (240 g) over 1 h. The HCl thus generated was bubbled into the reaction mixture over 2 h. The generator and ice bath were removed, and the reaction stirred under Ar 16 h. The reaction was evaporated, placed briefly under high vacuum, and redissolved in methanol (10 mL). Ammonium carbonate (138 mg, 1.4 mmol) was added. After stirring 19 h, the reaction was evaporated and purified by prep HPLC on a C-18 reverse phase column (20–80% MeCN/H$_2$O/ 0.05% TFA) to yield a white powder (84 mg, 48%). $^1$H NMR (DMSO-d$_6$) δ: 10.66 (s, 1H); 9.66 (s, 1H); 9.41 (s, 2H); 8.98 (s, 2H); 8.18 (s, 1H); 8.06 (d, 1H, J=7.6); 7.91 (d, 1H, J=8.5); 7.82 (d, 1H, J=6.9); 7.68 (m, 4H); 7.50 (m, 2H); 7.35 (d, 2H, J=8.8). $^{19}$F NMR (DMSO-d$_6$) −42.45, −73.86. HRMS calc. for C$_{24}$H$_{18}$F$_3$N$_4$O$_2$S, 483.1103; found, 483.1101.

Example 17

3-(3-Amidinophenyl)-5-amino-4-[(2'-aminosulfonyl-[1,1']-biphen-4-yl)aminocarbonyl]isoxazole, Trifluoroacetic Acid Salt Part A. Preparation of Methyl N-(2'-t-Butylaminosulfonyl-[1,1']-biphen-4-yl)cyanoacetamide.

Added to the 4-amino-2'-t-butylaminosulfonyl-[1,1']-biphenyl (2.0 g, 6.6 mmol); in CH$_2$Cl$_2$ (10 mL) and stirred at room temp 30 min. A CH$_2$Cl$_2$ solution (5 mL) of methyl cyanoacetate (0.58 mL, 6.6 mmol) was added and stirred 1 day. The reaction was quenched carefully with 1 M HCl and extracted into CH$_2$Cl$_2$. The organic was extracted again with water and brine, dried over MgSO$_4$, filtered, and evaporated. The crude mixture was chromatographed on silica gel (50% EtOAc/hexanes) to yield a yellow solid (0.81 g, 33%). $^1$H NMR (CDCl$_3$) δ: 8.74 (s, 1H); 8.16 (d, J=7.7, 1H); 7.64 (d, J=8.8, 2H); 7.58 (d, J=7.3, 1H); 7.66 (d, J=8.1, 1H); 7.46 (d, J=8.4, 2H); 7.31 (d, J=7.7, 1H); 3.89 (s, 1H); 3.63 (s, 2H); 1.04 (s, 9H). MS (NH$_3$-CI) m/z 389 (M+NH$_3$).

Part B. Preparation of 3-(3-Cyanophenyl)-5-amino-4-[(2'-aminosulfonyl-[1,1']-biphen-4-yl)aminocarbonyl]isoxazole, Trifluoroacetate Salt.

Methyl N-(2'-t-butylaminosulfonyl-[1,1']-biphen-4-yl) cyanoacetamide (0.81 g, 2.18 mmol) was added to a solution of triethylmine (0.33 g, 3.27 mmol) in 25 mL of ethanol and 5 mL of CH$_2$Cl$_2$. A solution of 3-cyanobenzenehydroximinoyl chloride (0.39 g, 2.18 mmol) in 10 mL ethanol was added slowly over 12 hours via a syringe pump. The reaction mixture was diluted with 50 mL of ether and washed three times with 10 mL of water and twice with 10 mL saturated NaHCO$_3$, then dried with MgSO$_4$ and concentrated in vacuo. The resulting off-white solid was purified by prep HPLC on a C-18 reverse phase column (30–100% MeCN/H$_2$O/0.05% TFA) to yield a white powder (0.10 g, 8.3%). $^1$H NMR (CDCl$_3$) δ: 9.09 (s, 1H); 8.03 (s, 1H); 7.99 (d, J=6.2, 1H); 7.92 (t, J=7.7, 2H); 7.72 (br s, 2H); 7.59 (t, J=7.7, 1H); 7.53 (m, 2H); 7.45 (d, J=8.4, 2H); 7.26 (d, J=8.4, 2H); 7.25 (m, 1H); 6.51 (s, 1H), 0.97 (s, 9H). MS (NH$_3$-CI) m/z 273.0 (M+H).

Part C. Preparation of 3-(3-Amidinophenyl)-5-amino-4-[(2'-aminosulfonyl-[1,1']-biphen-4-yl)aminocarbonyl]isoxazole, Trifluoroacetate Salt.

3-(3-cyanophenyl)-5-amino-4-[(2'-aminosulfonyl-[1,1']-biphen-4-yl)aminocarbonyl]isoxazole (0.10 g, 0.19 mmol) was dissolved in 1 mL of methanol and 4 mL of chloroform. The reaction mixture was cooled in an ice-bath and HCl gas was bubbled-in for 10 minutes to saturate the solution. The mixture was sealed and allowed to stir at room temperature for 14 hours. The solvents were removed in vacuo and the resulting solid was used in the next step.

The imidate formed above was added with 0.07 g (0.95 mmol) of ammonium carbonate and 10 mL of methanol. The mixture was allowed to stir under N$_2$ for 14 hours. The solvent was removed at reduced pressure. The crude benzamidine was purified by HPLC (C18 reversed phase) eluting with 0.5% TFA in H$_2$O/CH$_3$CN to give 0.0064 g (7%) of the desired salt. $^1$H NMR (DMSO-d$_6$) δ: 9.39 (br s, 2H); 9.12 (s, 1H); 8.96 (br s, 2H); 8.06 (s, 1H); 7.98 (d, J=7.7, 1H); 7.96 (d, J=7.8, 1H); 7.88 (d, J=7.7, 1H); 7.74 (br s, 2H); 7.70 (t, J=7.8, 1H); 7.54 (m, 3H); 7.42 (d, J=8.8, 2H); 7.26 (d, J=8.8, 2H); 7.25 (m, 1H); 7.21 (br s, 2H); 6.51 (s, 1H). HRMS m/z 477.1338 (M+H).

Example 18

2-(Phenylamino)-4-(3-amidinophenyl)-5-[(2'-aminosulfonyl-[1,1']-biphen-4-yl)aminocarbonyl] thiazole, Trifluoroacetic Acid Salt.

Part A. Preparation of Ethyl 3-(3-Cyanophenyl)-3-oxopropionate.

To a suspension of sodium hydride (1.2 g of 60% suspension in mineral oil, hexane-washed, 30.3 mmol) in 40 mL of tetrahydrofuran was added diethyl carbonate (3.7 mL, 30.3 mmol) and 3-acetyl benzonitrile (2.2 g, 15.2 mmol). The resulting suspension was stirred at 65° C. for 1 h and then was cooled to room temperature. There was added 40 mL of 10% aqueous HCl and the reaction mixture was diluted with ethyl acetate and the layers were separated. The organic layer was washed with brine, dried (MgSO$_4$) and concentrated in vacuo to afford 3.2 g (96%) of the title compound, which was sufficiently pure to be used without purification. MS (NH$_3$-CI) 218.3 (M+H)+.

Part B. Preparation of Ethyl 2-Bromo-3-(3-cyanophenyl)-3-oxopropionate.

According to the procedure of Example 7, Part C, ethyl 3-(3-cyanophenyl)-3-oxopropionate (3.2 g, 14.7 mmol) was converted into the crude bromide, which was purified by flash chromatography (elution with 4:1 hexanes/ethyl acetate) to afford 2.1 g (48%) of the title compound. MS (H$_2$O, GC/MS) 296/298 (M+H)+.

Part C. Preparation of 2-(Phenylamino)-4-(3-cyanophenyl)-5-carboethoxythiazole.

To a solution of ethyl 2-bromo-3-(3-cyanophenyl)-3-oxopropionate (0.60 g, 2.03 mmol) in 20 mL of absolute ethanol was added N-phenylthiourea (0.31 g, 2.03 mmol). The resulting mixture was stirred at 80° C. for 3 h. The reaction was allowed to cool and the solvent was evaporated in vacuo. The residue was taken up in ethyl acetate, washed with saturated aq NaHCO$_3$ and brine, dried (MgSO$_4$) and concentrated in vacuo to yield a solid. Trituration with hexanes/ethyl ether left the title compound as an off-white solid (0.35 g, 49%). MS (NH3-CI) 350 (M+H)+.

Part D. Preparation of 2-(Phenylamino)-4-(3-cyanophenyl)-5-[(2'-tert-butylaminosulfonyl-[1,1']-biphen-4-yl) aminocarbonyl]thiazole.

Following the procedure of Example 7, Part E, 2-(phenylamino)-4-(3-cyanophenyl)-5-carboethoxythiazole (0.29 g, 0.83 mmol) was converted into 0.37 g (74%) of the title compound as a solid. MS (ESI) 608.3 (M+H)+.

Part E. Preparation of 2-(Phenylamino)-4-(3-amidinophenyl)-5-[(2'-aminosulfonyl-[1,1']-biphen-4-yl) aminocarbonyl]thiazole, Trifluoroacetic Acid Salt.

Following the procedure of Example 9, Part C, 2-(phenylamino)-4-(3-cyanophenyl)-5-[(2'-tert-butylaminosulfonyl-[1,1']-biphen-4-yl)aminocarbonyl] thiazole (350 mg, 0.58 mmol) was converted into 50 mg of the title compound (12%) as an off-white powder following HPLC purification. $^1$H NMR (DMSO-d$_6$) δ: 10.70 (s, 1H), 10.25 (s, 1H), 9.41 (broad s, 2H), 9.02 (broad s, 2H), 8.19 (m, 1H), 8.08 (d, 1H, J=7.7 Hz), 8.03 (d, 1H, J=8.0 Hz), 7.73–7.54 (m, 8H), 7.41–7.27 (m, 8H). MS (ESI) 569.0 (M+H)+.

Example 19

2-(Benzylamino)-4-(3-amidinophenyl)-5-[(2'-aminosulfonyl-[1,1']-biphen-4-yl)aminocarbonyl] thiazole, Trifluoroacetic Acid Salt.

Part A. Preparation of 2-(Benzylamino)-4-(3-cyanophenyl)-5-carboethoxythiazole.

To a solution of ethyl 2-bromo-3-(3-cyanophenyl)-3-oxopropionate (0.60 g, 2.03 mmol) in 20 mL of absolute ethanol was added N-benzylthiourea (0.34 g, 2.03 mmol). The resulting mixture was stirred at 80° C. for 3 h. The reaction was allowed to cool and the solvent was evaporated in vacuo. The residue was taken up in ethyl acetate, washed with saturated aq NaHCO$_3$ and brine, dried (MgSO$_4$) and concentrated in vacuo to yield a solid. Trituration with hexanes/ethyl ether left the title compound as an off-white solid (0.36 g, 49%). MS (ESI) 364.1 (M+H)+.

Part B. Preparation of 2-(Benzylamino)-4-(3-cyanophenyl)-5-[(2'-tert-butylaminosulfonyl-[1,1']-biphen-4-yl) aminocarbonyl]thiazole.

Following the procedure of Example 7, Part E, 2-(benzylamino)-4-(3-cyanophenyl)-5-carboethoxythiazole (0.27 g, 0.74 mmol) was converted into 0.30 g (65%) of the title compound as a yellowwash solid. MS (ESI) 622.3 (M+H)+.

Part C. Preparation of 2-(Benzylamino)-4-(3-amidinophenyl)-5-[(2'-aminosulfonyl-[1,1']-biphen-4-yl) aminocarbonyl]thiazole, Trifluoroacetic Acid Salt.

Following the procedure of Example 9, Part C, 2-(benzylamino)-4-(3-cyanophenyl)-5-[(2'-tertbutylaminosulfonyl-[1,1']-biphen-4-yl)aminocarbonyl]thiazole (260 mg, 0.42 mmol) was converted into 95 mg of the title compound (33%) as an off-white powder following HPLC purification. $^1$H NMR (DMSO-$d_6$) δ: 9.97 (s, 1H), 9.36 (broad s, 2H), 8.98 (broad s, 2H), 8.78 (t, 1H, J=5.9 Hz), 8.09 (broad s, 1H), 8.02 (dd, 1H, J=7.8, 1.6 Hz), 7.98 (d, 1H, J=7.8 Hz), 7.76 (d, 1H, J=8.0 Hz), 7.66–7.25 (m, 15H), 4.58 (d, 2H, J=5.9 Hz). MS (ESI) 583.0 (M+H)+.

Examples 20 and 21

2-(Methylamino)-4-(3-amidinophenyl)-5-[(2'-aminosulfonyl-[1,1']-biphen-4-yl)aminocarbonyl]thiazole, Trifluoroacetic Acid Salt (Example 20) and 2-(Methylamino)-4-(3-carboxamidophenyl)-5-[(2'-aminosulfonyl-[1,1']-biphen-4-yl)aminocarbonyl]thiazole (Example 21)

Part A. Preparation of 2-(Methylamino)-4-(3-cyanophenyl)-5-carboethoxythiazole.

To a solution of ethyl 2-bromo-3-(3-cyanophenyl)-3-oxopropionate (0.65 g, 2.2 mmol) in 20 mL of tetrahydrofuran was added N-methylthiourea (0.20 g, 2.2 mmol). The resulting mixture was stirred at 65° C. for 16h. The reaction was allowed to cool and the solvent was evaporated in vacuo. The residue was taken up in ethyl acetate, washed with saturated aq NaHCO$_3$ and brine, dried (MgSO$_4$) and concentrated in vacuo to yield a solid. Trituration with hexanes/ethyl ether left the title compound as an off-white solid (0.46 g, 73%). MS (ESI) 288.3 (M+H)+.

Part B. Preparation of 2-(Methylamino)-4-(3-cyanophenyl)-5-[(2'-tert-butylaminosulfonyl-[1,1']-biphen-4-yl)aminocarbonyl]thiazole.

Following the procedure of Example 7, Part E, 2-(methylamino)-4-(3-cyanophenyl)-5-carboethoxythiazole (0.46 g, 1.6 mmol) was converted into 0.68 g (78%) of the title compound as a yellowish solid. MS (ESI) 546.7 (M+H)+.

Part C. Preparation of 2-(Methylamino)-4-(3-amidinophenyl)-5-[(2'-aminosulfonyl-[1,1']-biphen-4-yl)aminocarbonyl]thiazole, Trifluoroacetic Acid Salt (Example 6) and 2-(Methylamino)-4-(3-carboxamidophenyl)-5-[(2'-aminosulfonyl-[1,1']-biphen-4-yl)aminocarbonyl]thiazole (Example 20).

Following the procedure of Example 9, Part C, 2-(methylamino)-4-(3-cyanophenyl)-5-[(2'-tert-butylaminosulfonyl-[1,1']-biphen-4-yl)aminocarbonyl]thiazole (500 mg, 1.0 mmol) was converted into 85 mg of the title compound (13%), 2-(methylamino)-4-(3-amidinophenyl)-5-[(2'-aminosulfonyl-[1,1']-biphen-4-yl)aminocarbonyl]thiazole, trifluoroacetic acid salt (Example 20) as a white powder following HPLC purification. $^1$H NMR (DMSO-$d_6$) δ: 9.89 (s, 1H), 9.33 (broad s, 2H), 8.96 (broad s, 2H), 8.05 (broad s, 1H), 7.95 (m, 2H), 7.72 (d, 1H, J=8.0 Hz), 7.62–7.44 (m, 6H), 7.29–7.21 (m, 5H), 2.89 (d, 3H). MS (ESI) 507.2 (M+H)+. There was also isolated 50 mg (8%) of 2-(methylamino)-4-(3-carboxamidophenyl)-5-[(2'-aminosulfonyl-[1,1']-biphen-4-yl)aminocarbonyl]thiazole (Example 21). MS (ESI) 508.1 (M+H)+.

Examples 22 and 23

2-Methyl-4-(3-amidinophenyl)-5-[[5-(2'-aminosulfonylphenyl-1-yl)pyridin-2-yl]aminocarbonyl]thiazole, Trifluoroacetic Acid Salt (Example 22) and 2-Methyl-4-(3-carboxamidophenyl)-5-[[5-(2'-aminosulfonylphenyl-1-yl)pyridin-2-yl]aminocarbonyl]thiazole (Example 23)

Part A. Preparation of 2-Methyl-4-(3-cyanophenyl)-5-carboxythiazole.

To a solution of of 2-methyl-4-(3-cyanophenyl)-5-carbomethoxythiazole from Example 9, Part A (0.96 g, 3.7 mmol) in 20 mL of tetrahydrofuran and 10 mL of water was added lithium hydroxide monohydrate (0.31 g, 7.4 mmol). The resulting mixture was stirred at room temperature for 16 h. The mixture was concentrated in vacuo, diluted with H$_2$O and saturated aqueous NaHCO$_3$ and extracted with hexane. The organic layer was discarded and the aqueous layer was acidified and extracted twice with ethyl acetate. The combined ethyl acetate extracts were washed with brine, dried over MgSO$_4$ and concentrated in vacuo to afford 0.90 g (99%) of the title compound, which was sufficiently pure to be used without purification. MS (NH3-CI) 245 (M+H)+.

Part B. Preparation of 2-Methyl-4-(3-cyanophenyl)-5-[[5-(2'-tert-butylaminosulfonylphenyl-1-yl)pyridin-2-yl]aminocarbonyl]thiazole.

To a solution of 2-methyl-4-(3-cyanophenyl)-5-carboxythiazole (0.22 g, 0.89 mmol) in 10 mL of acetonitrile was added thionyl chloride (0.60 g, 5.0 mmol) and 2 drops of dimethylformamide. The resulting solution was allowed to stir at 50° C. for 10 min and then at room temperature for 1 h. The solution was concentrated in vacuo, the residue was dissolved in 20 mL of methylene chloride and then [[5-(2'-tert-butylaminosulfonylphenyl-1-yl)pyridin-2-yl]amine (0.30 g, 0.98 mmol) and triethylamine (1.3 mL, 8.9 mmol) were added. The reaction mixture was allowed to stir at 25° C. for 16 h. The reaction was diluted with ethyl acetate, washed with 10% aq HCl, saturated aq NaHCO$_3$ and brine, dried (MgSO$_4$); filtered through a pad of silica gel and concentrated in vacuo. The residue was purified by flash chromatography (elution with 3:1 hexanes/ethyl acetate) to afford 0.07 g (15%) of the title compound. MS (ESI) 532.2 (M+H)+.

Part C. Preparation of 2-Methyl-4-(3-amidinophenyl)-5-[[5-(2'-aminosulfonylphenyl-1-yl)pyridin-2-yl]aminocarbonyl]thiazole, Trifluoroacetic Acid Salt (Example 22) and 2-Methyl-4-(3-carboxamidophenyl)-5-[[5-(2'-aminosulfonylphenyl-1-yl)pyridin-2-yl]aminocarbonyl]thiazole (Example 23).

Following the procedure described in Example 9, Part C, 2-methyl-4-(3-cyanophenyl)-5-[[5-(2'-tert-butylaminosulfonylphenyl-1-yl)pyridin-2-yl]aminocarbonyl]thiazole (0.07 g, 0.14 mmol) was converted into 10 mg (16%) of 2-methyl-4-(3-amidinophenyl)-5-[[5-(2'-aminosulfonylphenyl-1-yl)pyridin-2-yl]aminocarbonyl]thiazole, trifluoroacetic acid salt (Example 22) following HPLC purification. MS (ESI) 493.1 (M+H)+. There was also isolated 25 mg (29%) of 2-methyl-4-(3-carboxamidophenyl)-5-[[5-(2'-aminosulfonylphenyl-1-yl)pyridin-2-yl]aminocarbonyl]thiazole (Example 23). MS (ESI) 494.1 (M+H)+.

Examples 24 and 25

2-(3-Pyridyl)-4-(3-amidinophenyl)-5-[(2'-aminosulfonyl-[1,1']-biphen-4-yl)aminocarbonyl]thiazole, Trifluoroacetic Acid Salt (Example 24) and 2-(3-Pyridyl)-4-(3-carboxamidophenyl)-5-[(2'-aminosulfonyl-[1,1']-biphen-4-yl)aminocarbonyl]thiazole (Example 25)

Part A. Preparation of 2-(3-Pyridyl)-4-(3-cyanophenyl)-5-carboethoxythiazole.

To a solution of ethyl 2-bromo-3-(3-cyanophenyl)-3-oxopropionate (1.0 g, 3.4 mmol) in 20 mL of tetrahydrofuran was added thionicotinamide (0.46 g, 3.4 mmol). The resulting mixture was stirred at 65° C. for 16 h. The reaction was allowed to cool and the solvent was evaporated in vacuo. The residue was triturated with chloroform, taken up in ethyl acetate, washed with saturated aq $Na_2CO_3$ and brine, dried ($MgSO_4$) and concentrated in vacuo to yield a solid. Trituration with ethyl acetate left the title compound as an off-white solid (0.26 g, 23%). MS (ESI) 336.1 (M+H)+.

Part B. Preparation of 2-(3-Pyridyl)-4-(3-cyanophenyl)-5-[(2'-tert-butylaminosulfonyl-[1,1']-biphen-4-yl)aminocarbonyl]thiazole.

4-(3-cyanophenyl)-5-carboethoxythiazole (0.26 g, 0.77 mmol) was converted into 0.24 g (52%) of the title compound as a yellowish solid. MS (ESI) 594.1 (M+H)+.

Part C. Preparation of 2-(3-Pyridyl)-4-(3-amidinophenyl)-5-[(2'-aminosulfonyl-[1,1']-biphen-4-yl)aminocarbonyl]thiazole, Trifluoroacetic Acid Salt (Example 24) and 2-(3-Pyridyl)-4-(3-carboxamidophenyl)-5-[(2'-aminosulfonyl-[1,1']-biphen-4-yl)aminocarbonyl]thiazole (Example 25).

Following the procedure of Example 9, Part C, 2-(3-pyridyl)-4-(3-cyanophenyl)-5-[(2'-tert-butylaminosulfonyl-[1,1']-biphen-4-yl)aminocarbonyl]thiazole (0.24 g, 0.45 mmol) was converted into 80 mg of the title compound (27%) of 2-(3-pyridyl)-4-(3-amidinophenyl)-5-[(2'-aminosulfonyl-[1,1']-biphen-4-yl)aminocarbonyl]thiazole, trifluoroacetic acid salt (Example 24) as a white powder following HPLC purification. $^1$H NMR (DMSO-$d_6$) δ: 10.82 (s, 1H), 9.41 (broad s, 2H), 9.30 (broad s, 1H), 9.02 (broad s, 2H), 8.75 (d, 1H, J=5.5 Hz), 8.43 (d, 1H, J=8 Hz), 8.30 (broad s, 1H), 8.10 (d, 1H, J=8 Hz), 7.98 (d, 1H, J=8 Hz), 7.82 (d, 1H, J=8 Hz), 7.70 (t, 1H, J=8 Hz), 7.62–7.50 (m, 5H), 7.38–7.22 (m, 5H). MS (ESI) 555.0 (M+H)+. There was also isolated 30 mg (10%) of 2-(3-pyridyl)-4-(3-carboxamidophenyl)-5-[(2'-aminosulfonyl-[1,1']-biphen-4-yl)aminocarbonyl]thiazole (Example 25). $^1$H NMR (DMSO-$d_6$) δ: 10.72 (s, 1H), 9.28 (broad s, 1H), 8.75 (broad s, 1H), 8.42 (m, 2H), 8.09 (broad s, 1H), 7.98 (d, 1H, J=8 Hz), 7.90 (m, 2H), 7.62–7.50 (m, 6H), 7.42 (broad s, 1H), 7.37–7.26 (m, 3H), 7.21 (broad s, 2H). MS (ESI) 578.0 (M+Na)+.

Examples 26 and 27

2-Chloro-4-(3-amidinophenyl)-5-[(2'-aminosulfonyl-[1,1']-biphen-4-yl)aminocarbonyl]thiazole, Trifluoroacetic Acid Salt (Example 26) and 2-Chloro-4-(3-carboxamidophenyl)-5-[(2'-aminosulfonyl-[1,1']-biphen-4-yl)aminocarbonyl] thiazole (Example 27)

Part A. Preparation of 2-Amino-4-(3-cyanophenyl)-5-carboethoxythiazole.

To a solution of ethyl 2-bromo-3-(3-cyanophenyl)-3-oxopropionate (4.0 g, 13.5 mmol) in 100 mL of tetrahydrofuran was added thiourea (1.03 g, 13.5 mmol). The resulting mixture was stirred at 65° C. for 16h. The reaction was allowed to cool and the solvent was evaporated in vacuo. The residue was triturated with ether, taken up in ethyl acetate, washed with saturated aq Na2CO3 and brine, dried ($MgSO_4$) and concentrated in vacuo to yield a solid. Trituration with ethyl ether left the title compound as an off-white solid (3.79 g, 98%).

Part B. Preparation of 2-Chloro-4-(3-cyanophenyl)-5-carboethoxythiazole.

To a suspension of anhydrous copper (II) chloride (1.86 g, 13.9 mmol) in 180 mL of acetonitrile was added tert-butyl nitrite (1.43 g, 1.39 mmol). The solution was warmed to reflux and then 2-amino-4-(3-cyanophenyl)-5-carboethoxythiazole (3.79 g, 13.9 mmol) in 50 mL of acetonitrile was added via addition funnel over 5 min. The mixture was stirred at reflux until gas evoultion ceased (about 30 min). The reaction was cooled to room temperature, poured into 10% aq Hcl and extracted with ether. The ether layer was washed with saturated aq NaHCO3 and brine, dried (MgSO4) and concentrated to afford 3.44 g (82%) of the title compound which was used without purification. MS (NH3-CI) 293.2 (M+H)+.

Part C. Preparation of 2-Chloro-4-(3-cyanophenyl)-5-[(2'-tert-butylaminosulfonyl-[1,1']-biphen-4-yl)aminocarbonyl]thiazole.

Cyanophenyl)-5-carboethoxythiazole (0.084 g, 0.3 mmol) was converted into 0.056 g (34%) of the title compound as a solid. MS (ESI) 551.0 (M+H)+.

Part D. Preparation of 2-Chloro-4-(3-amidinophenyl)-5-[(2'-aminosulfonyl-[1,1']-biphen-4-yl)aminocarbonyl]thiazole, Trifluoroacetic Acid Salt (Example 26) and 2-Chloro-4-(3-carboxamidophenyl)-5-[(2'-aminosulfonyl-[1,1']-biphen-4-yl)aminocarbonyl]thiazole (Example 27).

Following the procedure of Example 9, Part C, 2-chloro-4-(3-cyanophenyl)-5-[(2'-tert-butylaminosulfonyl-[1,1']-biphen-4-yl)aminocarbonyl]thiazole (0.056 g, 0.11 mmol) was converted into 15 mg of the title compound (23%) of 2-chloro-4-(3-amidinophenyl)-5-[(2'-aminosulfonyl-[1,1']-biphen-4-yl)aminocarbonyl]thiazole, trifluoroacetic acid salt (Example 26) as a white powder following HPLC purification. $^1$H NMR (DMSO-$d_6$) δ: 10.77 (s, 1H), 9.40 (broad s, 2H), 8.96 (broad s, 2H), 8.15 (broad s, 1H), 7.98 (m, 2H), 7.80 (d, 1H, J=8 Hz), 7.69 (d, 1H, J=8 Hz), 7.61–7.52 (m, 4H), 7.37–7.23 (m, 5H). MS (ESI) 512.0 (M+H)+. There was also isolated 20 mg (31%) of 2-chloro-4-(3-carboxamidophenyl)-5-[(2'-aminosulfonyl-[1,1']-biphen-4-yl)aminocarbonyl]thiazole (Example 27). $^1$H NMR (DMSO-$d_6$) δ: 10.68 (s, 1H), 8.28 (broad s, 1H), 8.05 (broad s, 1H), 7.98 (d, 1H, J=8 Hz), 7.89 (d, 1H, J=8 Hz), 7.78 (d, 1H, J=8 Hz), 7.61–7.52 (m, 5H), 7.40 (broad s, 1H), 7.37–7.23 (m, 3H), 7.21 (broad s, 2H). MS (ESI) 534.9 (M+Na)+.

Examples 28, 29 and 30

2-Chloro-4-(3-amidinophenyl)-5-[[5-(2'-aminosulfonylphenyl-1-yl)pyridin-2-yl] aminocarbonyl]thiazole, Trifluoroacetic Acid Salt (Example 28), 2-Chloro-4-(3-carboxamidophenyl)-5-[[5-(2'-aminosulfonylphenyl-1-yl)pyridin-2-yl] aminocarbonyl]thiazole (Example 29), and 2-Hydroxy-4-(3-amidinophenyl)-5-[[5-(2'-aminosulfonylphenyl-1-yl)pyridin-2-yl] aminocarbonyl]thiazole, Trifluoroacetic Acid Salt (Example 30)

Part A. Preparation of 2-Chloro-4-(3-cyanophenyl)-5-carboxythiazole.

To a solution of of 2-chloro-4-(3-cyanophenyl)-5-carboethoxythiazole (0.44 g, 1.45 mmol) in 25 mL of methanol and 25 mL of water was added potassium hydroxide (0.09 g, 1.6 mmol). The resulting solution was stirred at reflux for 2 h and then was cooled to room temperature. The methanol was removed in vacuo and the aqueous layer was diluted with water and washed with hexanes. The hexane layer was discarded. The aqueous layer was acidified and extracted with ethyl acetate. The ethyl acetate layer was washed with brine, dried (MgSO4) and concentrated to yield 0.33g (97%) of the title compound which was used without further purification. MS (ESI) –262.9 (M–H)–.

Part B. Preparation of 2-Chloro-4-(3-cyanophenyl)-5-[[5-(2'-tert-butylaminosulfonylphenyl-1-yl)pyridin-2-yl] aminocarbonyl]thiazole.

Following the procedure described in Example 22, Part B, 2-chloro-4-(3-cyanophenyl)-5-carboxythiazole (0.35 g, 1.33 mmol) was converted into 0.20 g (27%) of the title compound. MS (ESI) 552.0 (M+H)+.

Part C. Preparation of 2-Chloro-4-(3-amidinophenyl)-5-[[5-(2'-aminosulfonylphenyl-1-yl)pyridin-2-yl]aminocarbonyl]thiazole, Trifluoroacetic Acid Salt (Example 28) and 2-Chloro-4-(3-carboxamidophenyl)-5-[[5-(2'-aminosulfonylphenyl-1-yl)pyridin-2-yl]aminocarbonyl]thiazole, Trifluoroacetic Acid Salt (Example 29) and 2-Hydroxy-4-(3-amidinophenyl)-5-[[5-(2'-aminosulfonylphenyl-1-yl)pyridin-2-yl]aminocarbonyl]thiazole, Trifluoroacetic Acid Salt (Example 30).

Following the procedure described in Example 3, Part C, 2-chloro-4-(3-cyanophenyl)-5-[[5-(2'-tert-butylaminosulfonylphenyl-1-yl)pyridin-2-yl]aminocarbonyl]thiazole (0.20 g, 0.4 mmol) was converted into 75 mg (32%) of 2-chloro-4-(3-amidinophenyl)-5-[[5-(2'-aminosulfonylphenyl-1-yl)pyridin-2-yl]aminocarbonyl]thiazole, trifluoroacetic acid salt (Example 28) following HPLC purification. $^1$H NMR (DMSO-d$_6$) δ: 9.38 (broad s, 2H), 8.98 (broad s, 2H), 8.28 (d, 1H, J=1.5 Hz), 8.15 (broad s, 1H), 8.03–7.96 (m, 3H), 7.81 (m, 2H), 7.70–7.57 (m, 4H), 7.40 (broad s, 1H), 7.36 (m,2H). MS (ESI) 513.0 (M+H)+. There was also isolated 2-chloro-4-(3-carboxamidophenyl)-5-[[5-(2'-aminosulfonylphenyl-1-yl)pyridin-2-yl]aminocarbonyl]thiazole (Example 29). MS (ESI) 513.9 (M+H)+. There was also isolated 2-hydroxy-4-(3-amidinophenyl)-5-[[5-(2'-aminosulfonylphenyl-1-yl)pyridin-2-yl]aminocarbonyl]thiazole, trifluoroacetic acid salt (Example 30). MS (ESI) 495.0 (M+H)+.

Example 31

2-Chloro-4-(3-aminophenyl)-5-[(2'-aminosulfonyl-[1,1']-biphen-4-yl)aminocarbonyl]thiazole, Trifluoroacetic Acid Salt Part A. Preparation of Ethyl 3-(3-Nitrophenyl)-3-oxopropionate.

To a suspension of anhydrous tin (II) chloride (2.5 g, 13.2 mmol) in 150 mL of methylene chloride was added ethyl diazoacetate (8.3 g, 72.8 mmol). Then 3-nitrobenzaldehyde (10.0 g, 66.2 mmol) was added as a solid in small portions over 30 min. The resulting suspension was stirred at room temperature for 24 h. Additional tin (II) chloride (2.5 g) was added and the reaction was stirred an additional 24 h. The reaction was concentrated in vacuo, diluted with ethyl acetate, washed with water (2 times) and brine, dried (MgSO4) and concentrated. The residue was purified by flash chromatography (elution with 4:1 hexanes/ethyl acetate) to afford 5 g (32%) of the title compound. $^1$H NMR (CDCl$_3$) (approximately 12:1 mixture of enol and keto tautomers, data for enol only) δ: 12.6 (s, 1H); 8.60 (t, 1H, J=1.8 Hz); 8.3 (m, 1H); 8.1 (m, 1H); 7.62 (t, 1H, J=7.9 Hz) 5.77 (s, 1H); 4.30 (q, 2H, J=7.2 Hz); 1.35 (t, 3H, J=7.2 Hz).

Part B. Preparation of 2-Amino-4-(3-nitrophenyl)-5-carboethoxythiazole.

To a solution of ethyl 3-(3-nitrophenyl)-3-oxopropionate (3.45 g, 14.5 mmol) in 100 mL of acetonitrile was added hydroxy(tosyloxy)iodobenzene (6.3 g, 16.0 mmol). The resulting suspension was stirred at 65° C. for 1h at which time the reaction was a homogeneous solution. Thiourea (1.22 g, 16.0 mmol) was added and stirring was continued at 65° C. for 2 h. The mixture was cooled and concentrated, and the residue was taken up in ethyl acetate, washed with saturated aq Na2CO3 and brine, dried (MgSO$_4$) and concentrated. The residue was triturated with ethyl ether to afford 3.0 g (71%) of the title compound as a yellow solid. $^1$H NMR (DMSO-d$_6$) δ: 8.47 (t, 1H, J=1.9 Hz); 8.24 (m, 1H); 8.21 (m, 1H); 7.97 (broad s, 2H); 7.65 (t, 1H, J=8.1 Hz); 4.08 (q, 2H, J=7.1 Hz); 1.11 (t, 3H, J=7.1 Hz).

Part C. Preparation of 2-Amino-4-(3-nitrophenyl)-5-[(2'-tert-butylaminosulfonyl-[1,1']-biphen-4-yl)aminocarbonyl]thiazole.

Following the procedure of Example 7, Part E, 2-amino-4-(3-nitrophenyl)-5-carboethoxythiazole (0.30 g, 1.02 mmol) was converted into 0.22 g (39%) of the title compound as a solid. MS (ESI) 574.0 (M+Na)+.

Part D. Preparation of 2-Chloro-4-(3-nitrophenyl)-5-[(2'-tert-butylaminosulfonyl-[1,1']-biphen-4-yl)aminocarbonyl]thiazole.

Following the procedure described in Example 26, Part B, 2-amino-4-(3-nitrophenyl)-5-[(2'-tert-butylaminosulfonyl-[1,1']-biphen-4-yl)aminocarbonyl]thiazole (155 mg, 0.28 mmol) was converted into 150 mg (94%) of the title compound which was used without purification. MS (NH$_3$-CI) 588 (M+NH4)+.

Part E. Preparation of 2-Chloro-4-(3-aminophenyl)-5-[(2'-aminosulfonyl-[1,1']-biphen-4-yl)aminocarbonyl]thiazole, Trifluoroacetic Acid Salt.

To a solution of 2-chloro-4-(3-nitrophenyl)-5-[(2'-tert-butylaminosulfonyl-[1,1']-biphen-4-yl)aminocarbonyl]thiazole (100 mg, 0.18 mmol) in ethyl acetate was added tin (II) chloride dihydrate (0.32 g, 1.4 mmol). The resulting suspension was stirred at reflux for 2 h and then was cooled and quenched with saturated aq NaHCO$_3$. The reaction was diluted with ethyl acetate, washed with brine, dried (MgSO4) and concentrated to yield 90 mg (93%) of an amine which was used without purification. The residue was taken up in 5 mL of trifluoroacetic acid and stirred at reflux for 15 min. The reaction was concentrated and the residue was purified by prep HPLC to afford 40 mg (37%) of the title compound as a white powder. $^1$H NMR (DMSO-d$_6$) δ: 10.67 (s, 1H), 7.98 (d, 1H, J=8 Hz), 7.60–7.50 (m, 4H), 7.34–7.19 (m, 7H), 7.11 (broad m, 1H), 6.84 (broad m, 1H). MS (ESI) 484.9 (M+H)+.

Example 32

2-Amino-4-[(3-amino-4-chloro)phenyl]-5-[(2'-aminosulfonyl-[1,1']-biphen-4-yl)aminocarbonyl]thiazole, Trifluoroacetic Acid Salt Part A. Preparation of Ethyl 3-[(3-Nitro-4-chloro)phenyl]-3-oxopropionate.

Following the procedure described in Example 31, Part A, 4-chloro-3-nitrobenzaldehyde (10.0 g, 53.9 mmol) was converted into 4.8 g (33%) of the title compound as a yellow solid. $^1$H NMR (CDCl$_3$) (approximately 15:1 mixture of enol and keto tautomers, data for enol only) δ: 12.6 (s, 1H); 8.25 (d, 1H); 7.9 (dd, 1H); 7.6 (d, 1H); 5.7 (s, 1H); 4.27 (q, 2H); 1.35 (t, 3H).

Part B. Preparation of 2-Amino-4-[(3-nitro-4-chloro)phenyl]-5-carboethoxythiazole.

Following the procedure described in Example 31, Part B, ethyl 3-[(3-nitro-4-chloro)phenyl]-3-oxopropionate (1.6 g, 5.9 mmol) was converted into the title compound as a yellow solid. $^1$H NMR (DMSO-d$_6$) δ: 8.32 (d, 1H); 7.98 (s, 2H); 7.95 (d, 1H); 7.75 (d, 1H); 4.08 (q, 2H); 1.13 (t, 3H).

Part C. Preparation of 2-Amino-4-[(3-nitro-4-chloro)phenyl]-5-[(2'-tert-butylaminosulfonyl-[1,1']-biphen-4-yl)aminocarbonyl]thiazole.

Following the procedure of Example 7, Part E, 2-amino-4-[(3-nitro-4-chloro)phenyl]-5-carboethoxythiazole (0.49 g, 1.5 mmol) was converted into 0.79 g (89%) of the title compound as a solid. MS (ESI) 586.0 (M+H)+.

Part D. Preparation of 2-Amino-4-[(3-amino-4-chloro)phenyl]-5-[(2'-aminosulfonyl-[1,1']-biphen-4-yl)aminocarbonyl]thiazole, Trifluoroacetic Acid Salt.

Following the procedure described in Example 31, Part E, 2-amino-4-[(3-nitro-4-chloro)phenyl]-5-[(2'-tert-butylaminosulfonyl-[1,1']-biphen-4-yl)aminocarbonyl]thiazole (100 mg, 0.17 mmol) was converted into 35 mg (41%) of the title compound which was a white powder following HPLC purification. ¹H NMR (DMSO-d₆) δ: 9.68 (s, 1H), 7.98 (d, 1H, J=8 Hz), 7.60–7.43 (m, 5H), 7.30–7.10 (m, 8H), 6.75 (dd, 1H, J=8, 2 Hz). MS (ESI) 499.9 (M+H)+.

Example 33

2-Chloro-4-[(3-amino-4-chloro)phenyl]-5-[(2'-aminosulfonyl-[1,1']-biphen-4-yl)aminocarbonyl]thiazole, Trifluoroacetic Acid Salt Part A. Preparation of 2-Chloro-4-[(3-nitro-4-chloro)phenyl]-5-[(2'-tert-butylaminosulfonyl-[1,1']-biphen-4-yl)aminocarbonyl]thiazole.

Following the procedure described in Example 26, Part B, 2-amino-4-[(3-nitro-4-chloro)phenyl]-5-[(2'-tert-butylaminosulfonyl-[1,1']-biphen-4-yl)aminocarbonyl]thiazole (199 mg, 0.34 mmol) was converted into 150 mg (71%) of the title compound. MS (ESI) 626.9 (M+Na)+.

Part B. Preparation of 2-Chloro-4-[(3-amino-4-chloro)phenyl]-5-[(2'-aminosulfonyl-[1,1']-biphen-4-yl)aminocarbonyl]thiazole, Trifluoroacetic Acid Salt.

Following the procedure described in Example 31, Part E, 2-chloro-4-[(3-nitro-4-chloro)phenyl]-5-[(2'-tert-butylaminosulfonyl-[1,1']-biphen-4-yl)aminocarbonyl]thiazole (107 mg, 0.18 mmol) was converted into 10 mg (11%) of the title compound which was a white powder following HPLC purification. ¹H NMR (DMSO-d₆) δ: 10.66 (s, 1H), 7.99 (d, 1H, J=8.0 Hz), 7.60–7.50 (m, 4H), 7.37–7.20 (m, 7H), 6.81 (dd, 1H, J=8.0, 2 Hz). MS (ESI) 518.9 (M+H)+.

Example 34

2-Amino-4-[(3-aminomethyl)phenyl]-5-[(2'-aminosulfonyl-[1,1']-biphen-4-yl)aminocarbonyl]thiazole, Trifluoroacetic Acid Salt Part A. Preparation of 2-Amino-4-(3-cyanophenyl)-5-carboethoxythiazole.

To a solution of ethyl 2-bromo-3-(3-cyanophenyl)-3-oxopropionate (2.0 g, 6.75 mmol) in 100 mL of absolute ethanol was added thiourea (0.51 g, 6.75 mmol). The resulting mixture was stirred at 80° C. for 3 h. The reaction was allowed to cool and the solvent was evaporated in vacuo. The residue was taken up in ethyl acetate, washed with saturated aq NaHCO₃ and brine, dried (MgSO₄) and concentrated in vacuo to yield a solid. Trituration with hexanes/ethyl ether left the title compound as an off-white solid (1.55 g, 65%). ¹H NMR (DMSO-d₆) δ: 8.03 (s, 1H); 7.93 (s, 2H); 7.91 (d, 1H); 7.82 (d, 1H); 7.58 (t, 1H); 4.05 (q, 2H); 1.10 (t, 3H).

Part B. Preparation of 2-Amino-4-(3-cyanophenyl)-5-[(2'-tert-butylaminosulfonyl-[1,1']-biphen-4-yl)aminocarbonyl]thiazole.

Following the procedure of Example 7, Part E, 2-amino-4-(3-cyanophenyl)-5-carboethoxythiazole (0.49 g, 1.8 mmol) was converted into 0.31 g (32%) of the title compound as a solid. MS (ESI) 532.3 (M+H)+.

Part C. Preparation of 2-Amino-4-[(3-aminomethyl)phenyl]-5-[(2'-aminosulfonyl-[1,1']-biphen-4-yl)aminocarbonyl]thiazole, Trifluoroacetic Acid Salt.

To a solution of lithium aluminum hydride (0.63 mL of a 1.0 M solution in tetrahydrofuran, 0.63 mmol) in 10 mL of tetrahydrofuran at 0° C. was added concentrated H₂SO₄ (0.020 mL, 0.32 mmol). This solution was stirred for 30 min and then 2-amino-4-(3-cyanophenyl)-5-[(2'-tert-butylaminosulfonyl-[1,1']-biphen-4-yl)aminocarbonyl]thiazole (112 mg, 0.21 mmol) was added as a solution in tetrahydrofuran. The resulting mixture was allowed to warm to room temperature and then was stirred for 16 h. The reaction was cooled to 0° C. and quenched by dropwise addition of water. Dilute aqueous NaOH was added and the mixture was extracted with ethyl acetate. The organic layer was washed with brine, dried (MgSO₄) and concentrated. The residue was taken up in 5 mL of trifluoroacetic acid and stirred at reflux for 30 min. This mixture was cooled and concentrated in vacuo. The residue was purified by prep HPLC to afford the title compound as a white powder. ¹H NMR (DMSO-d₆) δ: 9.77 (s, 1H), 8.13 (broad s, 3H), 7.97 (d, 1H, J=8 Hz), 7.71 (s, 1H), 7.60–7.40 (m, 8H), 7.29–7.20 (m, 6H), 3.98 (broad q, 2H). MS (ESI) 480.0 (M+H)+.

TABLE 1

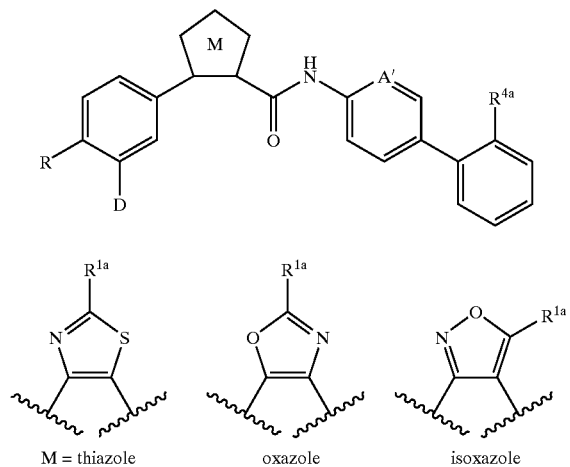

| Ex. | Ring M | D | R | R¹ᵃ | R⁴ᵃ | A' | MS |
|---|---|---|---|---|---|---|---|
| 1 | isoxazole | C(=NH)NH₂ | H | CH₂OH | SO₂NH₂ | CH | 492.1 |
| 2 | isoxazole | C(=NH)NH₂ | H | H | SO₂NH₂ | CH | 462.1 |
| 3 | isoxazole | C(=NH)NH₂ | H | H | SO₂Me | CH | 461.1 |

TABLE 1-continued

[Structure diagram with M ring, showing thiazole, oxazole, and isoxazole variants with R^1a substituents]

M = thiazole    oxazole    isoxazole

| Ex. | Ring M | D | R | R¹ᵃ | R⁴ᵃ | A' | MS |
|---|---|---|---|---|---|---|---|
| 4 | isoxazole | C(=NH)NH₂ | H | CH₂OMe | SO₂NH₂ | N | 506.1 |
| 5 | isoxazole | C(=NH)NH₂ | H | H | CF₃ | CH | 451.1 |
| 6 | isoxazole | C(=NH)NH₂ | H | CF₃ | SO₂NH₂ | CH | 530.1 |
| 7 | thiazole | C(=NH)NH₂ | H | NHAc | SO₂NH₂ | CH | 535.0 |
| 8 | thiazole | C(=NH)NH₂ | H | NH₂ | SO₂NH₂ | CH | 493.0 |
| 9 | thiazole | C(=NH)NH₂ | H | CH₃ | SO₂NH₂ | CH | 492.3 |
| 10 | oxazole | C(=NH)NH₂ | H | H | SO₂NH₂ | CH | 462.1 |
| 11 | isoxazole | C(=NH)NH₂ | H | H | SO₂NHtBu | CH | 518.2 |
| 12 | isoxazole | C(=NH)NH₂ | H | CH₂OMe | SO₂NH₂ | CH | 506.1 |
| 13 | thiazole | C(=NH)NH₂ | H | Me | CF₃ | CH | 481.3 |
| 14 | thiazole | C(=NH)NH₂ | H | Ph | SO₂NH₂ | CH | 554.3 |
| 15 | isoxazole | C(=NH)NH₂ | H | H | SO₂Me | CF | 479.1 |
| 16 | isoxazole | C(=NH)NH₂ | H | H | SCF₃ | CH | 483.1 |
| 17 | isoxazole | C(=NH)NH₂ | H | NH₂ | SO₂NH₂ | CH | 477.1 |
| 18 | thiazole | C(=NH)NH₂ | H | NHPh | SO₂NH₂ | CH | 569.0 |
| 19 | thiazole | C(=NH)NH₂ | H | NHCH₂Ph | SO₂NH₂ | CH | 583.0 |
| 20 | thiazole | C(=NH)NH₂ | H | NHMe | SO₂NH₂ | CH | 507.2 |
| 21 | thiazole | CONH₂ | H | NHMe | SO₂NH₂ | CH | 508.1 |
| 22 | thiazole | C(=NH)NH₂ | H | Me | SO₂NH₂ | N | 493.1 |
| 23 | thiazole | CONH₂ | H | Me | SO₂NH₂ | N | 494.1 |
| 24 | thiazole | C(=NH)NH₂ | H | 3-pyridyl | SO₂NH₂ | CH | 554.3 |
| 25 | thiazole | CONH₂ | H | 3-pyridyl | SO₂NH₂ | CH | 578.0 (M + Na)⁺ |
| 26 | thiazole | C(=NH)NH₂ | H | Cl | SO₂NH₂ | CH | 512.0 |
| 27 | thiazole | CONH₂ | H | Cl | SO₂NH₂ | CH | 534.9 (M + Na)⁺ |
| 28 | thiazole | C(=NH)NH₂ | H | Cl | SO₂NH₂ | N | 513.0 |
| 29 | thiazole | CONH₂ | H | Cl | SO₂NH₂ | N | 513.9 |
| 30 | thiazole | C(=NH)NH₂ | H | OH | SO₂NH₂ | N | 495.0 |
| 31 | thiazole | NH₂ | H | Cl | SO₂NH₂ | CH | 484.9 |
| 32 | thiazole | NH₂ | Cl | NH₂ | SO₂NH₂ | CH | 499.9 |
| 33 | thiazole | NH₂ | Cl | Cl | SO₂NH₂ | CH | 518.9 |
| 34 | thiazole | CH₂NH₂ | H | NH₂ | SO₂NH₂ | CH | 480.0 |

The following tables contain representative examples of the present invention. Each entry in each table is intended to be paired with each formulae at the start of the table. For example, example 1 in Table 2 is intended to be paired with each of formulae A-BB and example 1 in Table 3 is intended to be paired with each of fomulae a-dd.

The following groups are intended for group A in the tables.

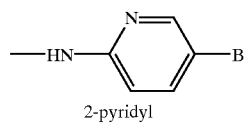

2-pyridyl

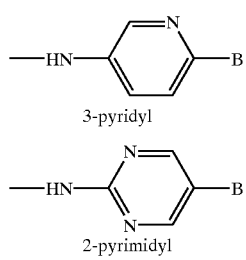

3-pyridyl 2-pyrimidyl

-continued
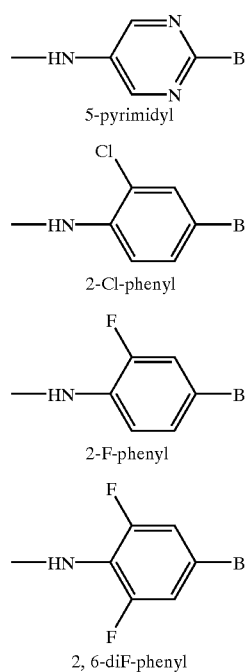
5-pyrimidyl
2-Cl-phenyl
2-F-phenyl
2, 6-diF-phenyl
TABLE 2
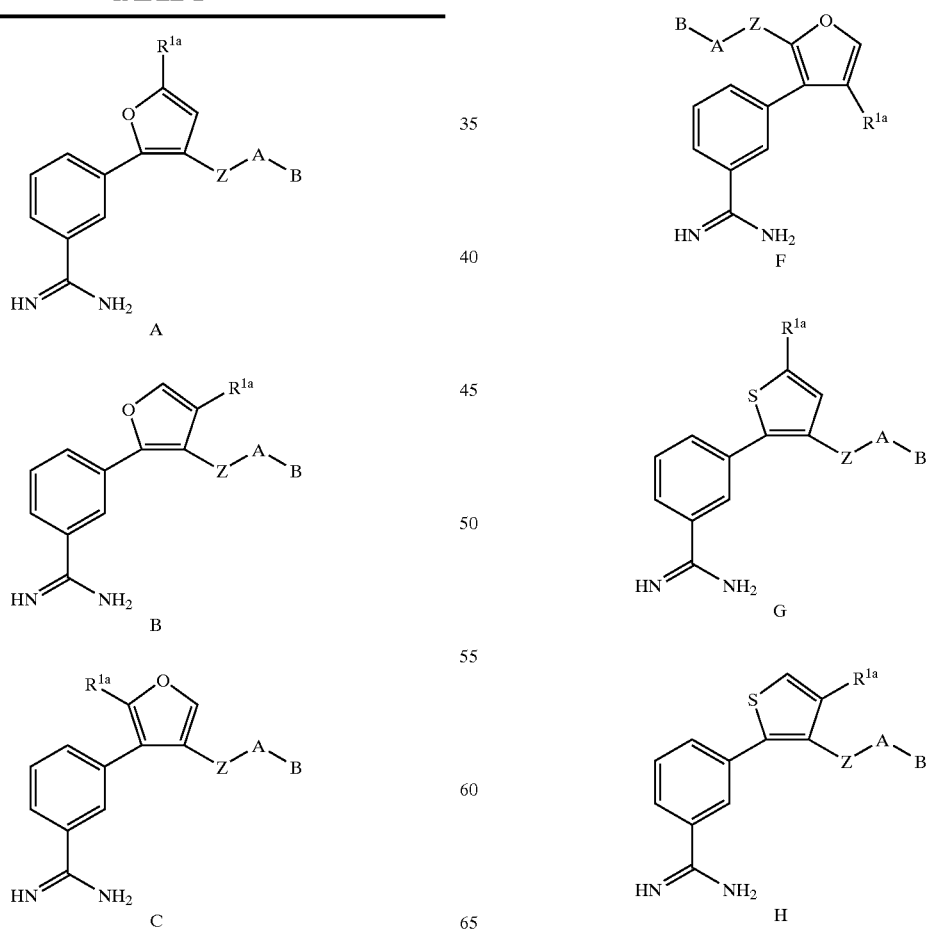
A
B
C
TABLE 2-continued
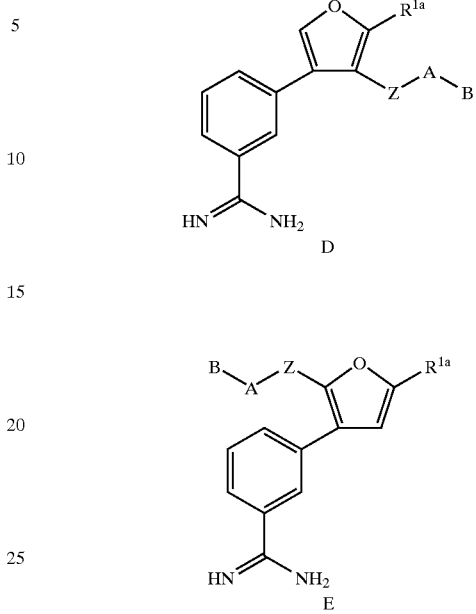
D
E
F
G
H TABLE 2-continued
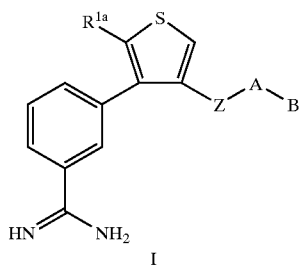
I
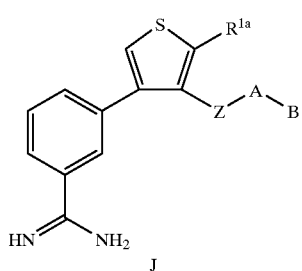
J
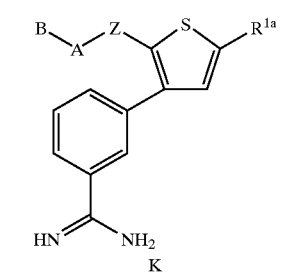
K
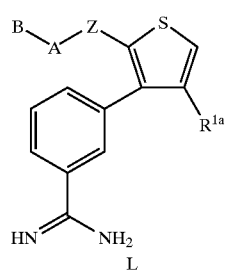
L
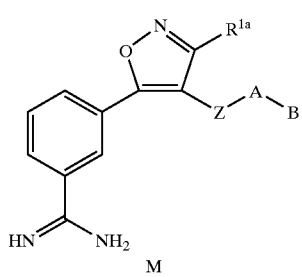
M
TABLE 2-continued
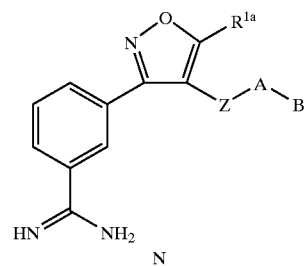
N
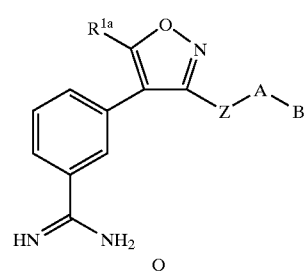
O
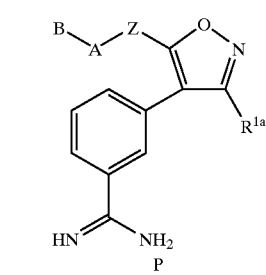
P
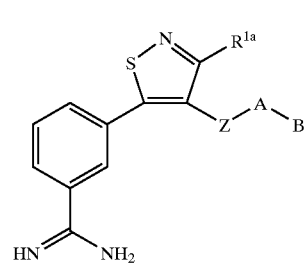
Q
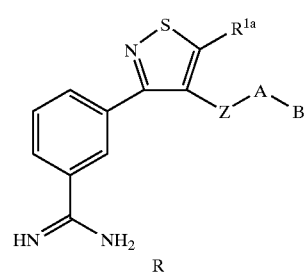
R TABLE 2-continued
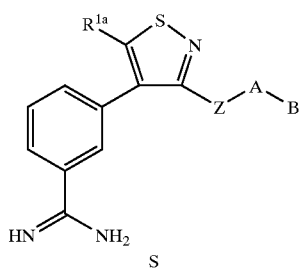
S
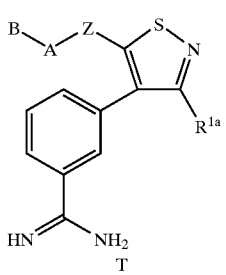
T
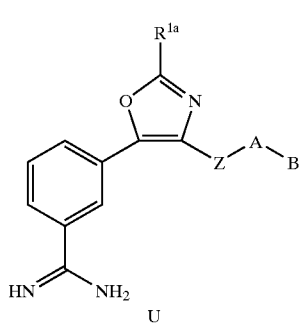
U
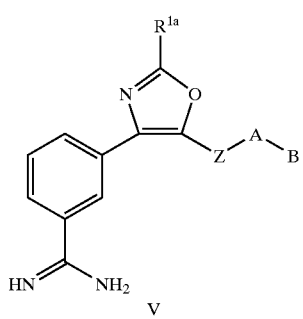
V
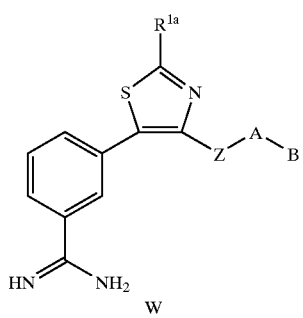
W
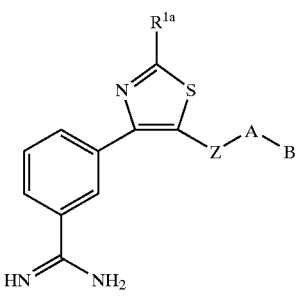
X
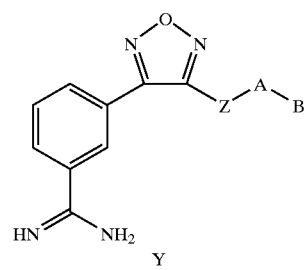
Y
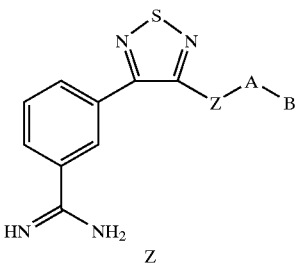
Z
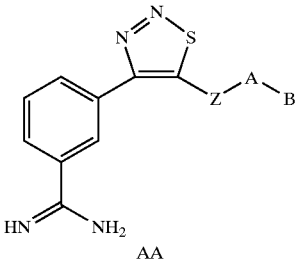
AA
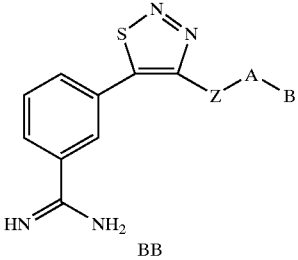
BB
| Ex # | $R^{1a}$ | A | B |
|---|---|---|---|
| 1 | $CH_3$ | phenyl | 2-(aminosulfonyl)phenyl |
| 2 | $CH_3$ | phenyl | 2-(methylaminosulfonyl)phenyl |
| 3 | $CH_3$ | phenyl | 1-pyrrolidinocarbonyl |
| 4 | $CH_3$ | phenyl | 2-(methylsulfonyl)phenyl |
| 5 | $CH_3$ | phenyl | 4-morpholino |
| 6 | $CH_3$ | phenyl | 2-(1'-$CF_3$-tetrazol-2-yl)phenyl |

TABLE 2-continued

| | | | |
|---|---|---|---|
| 7 | $CH_3$ | phenyl | 4-morpholinocarbonyl |
| 8 | $CH_3$ | phenyl | 2-methyl-1-imidazolyl |
| 9 | $CH_3$ | phenyl | 5-methyl-1-imidazolyl |
| 10 | $CH_3$ | phenyl | 2-methylsulfonyl-1-imidazolyl |
| 11 | $CH_3$ | 2-pyridyl | 2-(aminosulfonyl)phenyl |
| 12 | $CH_3$ | 2-pyridyl | 2-(methylaminosulfonyl)phenyl |
| 13 | $CH_3$ | 2-pyridyl | 1-pyrrolidinocarbonyl |
| 14 | $CH_3$ | 2-pyridyl | 2-(methylsulfonyl)phenyl |
| 15 | $CH_3$ | 2-pyridyl | 4-morpholino |
| 16 | $CH_3$ | 2-pyridyl | 2-(1'-$CF_3$-tetrazol-2-yl)phenyl |
| 17 | $CH_3$ | 2-pyridyl | 4-morpholinocarbonyl |
| 18 | $CH_3$ | 2-pyridyl | 2-methyl-1-imidazolyl |
| 19 | $CH_3$ | 2-pyridyl | 5-methyl-1-imidazolyl |
| 20 | $CH_3$ | 2-pyridyl | 2-methylsulfonyl-1-imidazolyl |
| 21 | $CH_3$ | 3-pyridyl | 2-(aminosulfonyl)phenyl |
| 22 | $CH_3$ | 3-pyridyl | 2-(methylaminosulfonyl)phenyl |
| 23 | $CH_3$ | 3-pyridyl | 1-pyrrolidinocarbonyl |
| 24 | $CH_3$ | 3-pyridyl | 2-(methylsulfonyl)phenyl |
| 25 | $CH_3$ | 3-pyridyl | 4-morpholino |
| 26 | $CH_3$ | 3-pyridyl | 2-(1'-$CF_3$-tetrazol-2-yl)phenyl |
| 27 | $CH_3$ | 3-pyridyl | 4-morpholinocarbonyl |
| 28 | $CH_3$ | 3-pyridyl | 2-methyl-1-imidazolyl |
| 29 | $CH_3$ | 3-pyridyl | 5-methyl-1-imidazolyl |
| 30 | $CH_3$ | 3-pyridyl | 2-methylsulfonyl-1-imidazolyl |
| 31 | $CH_3$ | 2-pyrimidyl | 2-(aminosulfonyl)phenyl |
| 32 | $CH_3$ | 2-pyrimidyl | 2-(methylaminosulfonyl)phenyl |
| 33 | $CH_3$ | 2-pyrimidyl | 1-pyrrolidinocarbonyl |
| 34 | $CH_3$ | 2-pyrimidyl | 2-(methylsulfonyl)phenyl |
| 35 | $CH_3$ | 2-pyrimidyl | 4-morpholino |
| 36 | $CH_3$ | 2-pyrimidyl | 2-(1'-$CF_3$-tetrazol-2-yl)phenyl |
| 37 | $CH_3$ | 2-pyrimidyl | 4-morpholinocarbonyl |
| 38 | $CH_3$ | 2-pyrimidyl | 2-methyl-1-imidazolyl |
| 39 | $CH_3$ | 2-pyrimidyl | 5-methyl-1-imidazolyl |
| 40 | $CH_3$ | 2-pyrimidyl | 2-methylsulfonyl-1-imidazolyl |
| 41 | $CH_3$ | 5-pyrimidyl | 2-(aminosulfonyl)phenyl |
| 42 | $CH_3$ | 5-pyrimidyl | 2-(methylaminosulfonyl)phenyl |
| 43 | $CH_3$ | 5-pyrimidyl | 1-pyrrolidinocarbonyl |
| 44 | $CH_3$ | 5-pyrimidyl | 2-(methylsulfonyl)phenyl |
| 45 | $CH_3$ | 5-pyrimidyl | 4-morpholino |
| 46 | $CH_3$ | 5-pyrimidyl | 2-(1'-$CF_3$-tetrazol-2-yl)phenyl |
| 47 | $CH_3$ | 5-pyrimidyl | 4-morpholinocarbonyl |
| 48 | $CH_3$ | 5-pyrimidyl | 2-methyl-1-imidazolyl |
| 49 | $CH_3$ | 5-pyrimidyl | 5-methyl-1-imidazolyl |
| 50 | $CH_3$ | 5-pyrimidyl | 2-methylsulfonyl-1-imidazolyl |
| 51 | $CH_3$ | 2-Cl-phenyl | 2-(aminosulfonyl)phenyl |
| 52 | $CH_3$ | 2-Cl-phenyl | 2-(methylaminosulfonyl)phenyl |
| 53 | $CH_3$ | 2-Cl-phenyl | 1-pyrrolidinocarbonyl |
| 54 | $CH_3$ | 2-Cl-phenyl | 2-(methylsulfonyl)phenyl |
| 55 | $CH_3$ | 2-Cl-phenyl | 4-morpholino |
| 56 | $CH_3$ | 2-Cl-phenyl | 2-(1'-$CF_3$-tetrazol-2-yl)phenyl |
| 57 | $CH_3$ | 2-Cl-phenyl | 4-morpholinocarbonyl |
| 58 | $CH_3$ | 2-Cl-phenyl | 2-methyl-1-imidazolyl |
| 59 | $CH_3$ | 2-Cl-phenyl | 5-methyl-1-imidazolyl |
| 60 | $CH_3$ | 2-Cl-phenyl | 2-methylsulfonyl-1-imidazolyl |
| 61 | $CH_3$ | 2-F-phenyl | 2-(aminosulfonyl)phenyl |
| 62 | $CH_3$ | 2-F-phenyl | 2-(methylaminosulfonyl)phenyl |
| 63 | $CH_3$ | 2-F-phenyl | 1-pyrrolidinocarbonyl |
| 64 | $CH_3$ | 2-F-phenyl | 2-(methylsulfonyl)phenyl |
| 65 | $CH_3$ | 2-F-phenyl | 4-morpholino |
| 66 | $CH_3$ | 2-F-phenyl | 2-(1'-$CF_3$-tetrazol-2-yl)phenyl |
| 67 | $CH_3$ | 2-F-phenyl | 4-morpholinocarbonyl |
| 68 | $CH_3$ | 2-F-phenyl | 2-methyl-1-imidazolyl |
| 69 | $CH_3$ | 2-F-phenyl | 5-methyl-1-imidazolyl |
| 70 | $CH_3$ | 2-F-phenyl | 2-methylsulfonyl-1-imidazolyl |
| 71 | $CH_3$ | 2,6-diF-phenyl | 2-(aminosulfonyl)phenyl |
| 72 | $CH_3$ | 2,6-diF-phenyl | 2-(methylaminosulfonyl)phenyl |
| 73 | $CH_3$ | 2,6-diF-phenyl | 1-pyrrolidinocarbonyl |
| 74 | $CH_3$ | 2,6-diF-phenyl | 2-(methylsulfonyl)phenyl |
| 75 | $CH_3$ | 2,6-diF-phenyl | 4-morpholino |
| 76 | $CH_3$ | 2,6-diF-phenyl | 2-(1'-$CF_3$-tetrazol-2-yl)phenyl |
| 77 | $CH_3$ | 2,6-diF-phenyl | 4-morpholinocarbonyl |
| 78 | $CH_3$ | 2,6-diF-phenyl | 2-methyl-1-imidazolyl |
| 79 | $CH_3$ | 2,6-diF-phenyl | 5-methyl-1-imidazolyl |
| 80 | $CH_3$ | 2,6-diF-phenyl | 2-methylsulfonyl-1-imidazolyl |
| 81 | $CH_2CH_3$ | phenyl | 2-(aminosulfonyl)phenyl |
| 82 | $CH_2CH_3$ | phenyl | 2-(methylaminosulfonyl)phenyl |
| 83 | $CH_2CH_3$ | phenyl | 1-pyrrolidinocarbonyl |
| 84 | $CH_2CH_3$ | phenyl | 2-(methylsulfonyl)phenyl |
| 85 | $CH_2CH_3$ | phenyl | 4-morpholino |
| 86 | $CH_2CH_3$ | phenyl | 2-(1'-$CF_3$-tetrazol-2-yl)phenyl |
| 87 | $CH_2CH_3$ | phenyl | 4-morpholinocarbonyl |
| 88 | $CH_2CH_3$ | phenyl | 2-methyl-1-imidazolyl |
| 89 | $CH_2CH_3$ | phenyl | 5-methyl-1-imidazolyl |
| 90 | $CH_2CH_3$ | phenyl | 2-methylsulfonyl-1-imidazolyl |
| 91 | $CH_2CH_3$ | 2-pyridyl | 2-(aminosulfonyl)phenyl |
| 92 | $CH_2CH_3$ | 2-pyridyl | 2-(methylaminosulfonyl)phenyl |
| 93 | $CH_2CH_3$ | 2-pyridyl | 1-pyrrolidinocarbonyl |
| 94 | $CH_2CH_3$ | 2-pyridyl | 2-(methylsulfonyl)phenyl |
| 95 | $CH_2CH_3$ | 2-pyridyl | 4-morpholino |
| 96 | $CH_2CH_3$ | 2-pyridyl | 2-(1'-$CF_3$-tetrazol-2-yl)phenyl |
| 97 | $CH_2CH_3$ | 2-pyridyl | 4-morpholinocarbonyl |
| 98 | $CH_2CH_3$ | 2-pyridyl | 2-methyl-1-imidazolyl |
| 99 | $CH_2CH_3$ | 2-pyridyl | 5-methyl-1-imidazolyl |
| 100 | $CH_2CH_3$ | 2-pyridyl | 2-methylsulfonyl-1-imidazolyl |
| 101 | $CH_2CH_3$ | 3-pyridyl | 2-(aminosulfonyl)phenyl |
| 102 | $CH_2CH_3$ | 3-pyridyl | 2-(methylaminosulfonyl)phenyl |
| 103 | $CH_2CH_3$ | 3-pyridyl | 1-pyrrolidinocarbonyl |
| 104 | $CH_2CH_3$ | 3-pyridyl | 2-(methylsulfonyl)phenyl |
| 105 | $CH_2CH_3$ | 3-pyridyl | 4-morpholino |
| 106 | $CH_2CH_3$ | 3-pyridyl | 2-(1'-$CF_3$-tetrazol-2-yl)phenyl |
| 107 | $CH_2CH_3$ | 3-pyridyl | 4-morpholinocarbonyl |
| 108 | $CH_2CH_3$ | 3-pyridyl | 2-methyl-1-imidazolyl |
| 109 | $CH_2CH_3$ | 3-pyridyl | 5-methyl-1-imidazolyl |
| 110 | $CH_2CH_3$ | 3-pyridyl | 2-methylsulfonyl-1-imidazolyl |
| 111 | $CH_2CH_3$ | 2-pyrimidyl | 2-(aminosulfonyl)phenyl |
| 112 | $CH_2CH_3$ | 2-pyrimidyl | 2-(methylaminosulfonyl)phenyl |
| 113 | $CH_2CH_3$ | 2-pyrimidyl | 1-pyrrolidinocarbonyl |
| 114 | $CH_2CH_3$ | 2-pyrimidyl | 2-(methylsulfonyl)phenyl |
| 115 | $CH_2CH_3$ | 2-pyrimidyl | 4-morpholino |
| 116 | $CH_2CH_3$ | 2-pyrimidyl | 2-(1'-$CF_3$-tetrazol-2-yl)phenyl |
| 117 | $CH_2CH_3$ | 2-pyrimidyl | 4-morpholinocarbonyl |
| 118 | $CH_2CH_3$ | 2-pyrimidyl | 2-methyl-1-imidazolyl |
| 119 | $CH_2CH_3$ | 2-pyrimidyl | 5-methyl-1-imidazolyl |
| 120 | $CH_2CH_3$ | 2-pyrimidyl | 2-methylsulfonyl-1-imidazolyl |
| 121 | $CH_2CH_3$ | 5-pyrimidyl | 2-(aminosulfonyl)phenyl |
| 122 | $CH_2CH_3$ | 5-pyrimidyl | 2-(methylaminosulfonyl)phenyl |
| 123 | $CH_2CH_3$ | 5-pyrimidyl | 1-pyrrolidinocarbonyl |
| 124 | $CH_2CH_3$ | 5-pyrimidyl | 2-(methylsulfonyl)phenyl |
| 125 | $CH_2CH_3$ | 5-pyrimidyl | 4-morpholino |
| 126 | $CH_2CH_3$ | 5-pyrimidyl | 2-(1'-$CF_3$-tetrazol-2-yl)phenyl |
| 127 | $CH_2CH_3$ | 5-pyrimidyl | 4-morpholinocarbonyl |
| 128 | $CH_2CH_3$ | 5-pyrimidyl | 2-methyl-1-imidazolyl |
| 129 | $CH_2CH_3$ | 5-pyrimidyl | 5-methyl-1-imidazolyl |
| 130 | $CH_2CH_3$ | 5-pyrimidyl | 2-methylsulfonyl-1-imidazolyl |
| 131 | $CH_2CH_3$ | 2-Cl-phenyl | 2-(aminosulfonyl)phenyl |
| 132 | $CH_2CH_3$ | 2-Cl-phenyl | 2-(methylaminosulfonyl)phenyl |
| 133 | $CH_2CH_3$ | 2-Cl-phenyl | 1-pyrrolidinocarbonyl |
| 134 | $CH_2CH_3$ | 2-Cl-phenyl | 2-(methylsulfonyl)phenyl |
| 135 | $CH_2CH_3$ | 2-Cl-phenyl | 4-morpholino |
| 136 | $CH_2CH_3$ | 2-Cl-phenyl | 2-(1'-$CF_3$-tetrazol-2-yl)phenyl |
| 137 | $CH_2CH_3$ | 2-Cl-phenyl | 4-morpholinocarbonyl |
| 138 | $CH_2CH_3$ | 2-Cl-phenyl | 2-methyl-1-imidazolyl |
| 139 | $CH_2CH_3$ | 2-Cl-phenyl | 5-methyl-1-imidazolyl |
| 140 | $CH_2CH_3$ | 2-Cl-phenyl | 2-methylsulfonyl-1-imidazolyl |
| 141 | $CH_2CH_3$ | 2-F-phenyl | 2-(aminosulfonyl)phenyl |
| 142 | $CH_2CH_3$ | 2-F-phenyl | 2-(methylaminosulfonyl)phenyl |
| 143 | $CH_2CH_3$ | 2-F-phenyl | 1-pyrrolidinocarbonyl |
| 144 | $CH_2CH_3$ | 2-F-phenyl | 2-(methylsulfonyl)phenyl |
| 145 | $CH_2CH_3$ | 2-F-phenyl | 4-morpholino |
| 146 | $CH_2CH_3$ | 2-F-phenyl | 2-(1'-$CF_3$-tetrazol-2-yl)phenyl |
| 147 | $CH_2CH_3$ | 2-F-phenyl | 4-morpholinocarbonyl |
| 148 | $CH_2CH_3$ | 2-F-phenyl | 2-methyl-1-imidazolyl |
| 149 | $CH_2CH_3$ | 2-F-phenyl | 5-methyl-1-imidazolyl |
| 150 | $CH_2CH_3$ | 2-F-phenyl | 2-methylsulfonyl-1-imidazolyl |

TABLE 2-continued

| | | | |
|---|---|---|---|
| 151 | CH₂CH₃ | 2,6-diF-phenyl | 2-(aminosulfonyl)phenyl |
| 152 | CH₂CH₃ | 2,6-diF-phenyl | 2-(methylaminosulfonyl)phenyl |
| 153 | CH₂CH₃ | 2,6-diF-phenyl | 1-pyrrolidinocarbonyl |
| 154 | CH₂CH₃ | 2,6-diF-phenyl | 2-(methylsulfonyl)phenyl |
| 155 | CH₂CH₃ | 2,6-diF-phenyl | 4-morpholino |
| 156 | CH₂CH₃ | 2,6-diF-phenyl | 2-(1'-CF₃-tetrazol-2-yl)phenyl |
| 157 | CH₂CH₃ | 2,6-diF-phenyl | 4-morpholinocarbonyl |
| 158 | CH₂CH₃ | 2,6-diF-phenyl | 2-methyl-1-imidazolyl |
| 159 | CH₂CH₃ | 2,6-diF-phenyl | 5-methyl-1-imidazolyl |
| 160 | CH₂CH₃ | 2,6-diF-phenyl | 2-methylsulfonyl-1-imidazolyl |
| 161 | CF₃ | phenyl | 2-(aminosulfonyl)phenyl |
| 162 | CF₃ | phenyl | 2-(methylaminosulfonyl)phenyl |
| 163 | CF₃ | phenyl | 1-pyrrolidinocarbonyl |
| 164 | CF₃ | phenyl | 2-(methylsulfonyl)phenyl |
| 165 | CF₃ | phenyl | 4-morpholino |
| 166 | CF₃ | phenyl | 2-(1'-CF₃-tetrazol-2-yl)phenyl |
| 167 | CF₃ | phenyl | 4-morpholinocarbonyl |
| 168 | CF₃ | phenyl | 2-methyl-1-imidazolyl |
| 169 | CF₃ | phenyl | 5-methyl-1-imidazolyl |
| 170 | CF₃ | phenyl | 2-methylsulfonyl-1-imidazolyl |
| 171 | CF₃ | 2-pyridyl | 2-(aminosulfonyl)phenyl |
| 172 | CF₃ | 2-pyridyl | 2-(methylaminosulfonyl)phenyl |
| 173 | CF₃ | 2-pyridyl | 1-pyrrolidinocarbonyl |
| 174 | CF₃ | 2-pyridyl | 2-(methylsulfonyl)phenyl |
| 175 | CF₃ | 2-pyridyl | 4-morpholino |
| 176 | CF₃ | 2-pyridyl | 2-(1'-CF₃-tetrazol-2-yl)phenyl |
| 177 | CF₃ | 2-pyridyl | 4-morpholinocarbonyl |
| 178 | CF₃ | 2-pyridyl | 2-methyl-1-imidazolyl |
| 179 | CF₃ | 2-pyridyl | 5-methyl-1-imidazolyl |
| 180 | CF₃ | 2-pyridyl | 2-methylsulfonyl-1-imidazolyl |
| 181 | CF₃ | 3-pyridyl | 2-(aminosulfonyl)phenyl |
| 182 | CF₃ | 3-pyridyl | 2-(methylaminosulfonyl)phenyl |
| 183 | CF₃ | 3-pyridyl | 1-pyrrolidinocarbonyl |
| 184 | CF₃ | 3-pyridyl | 2-(methylsulfonyl)phenyl |
| 185 | CF₃ | 3-pyridyl | 4-morpholino |
| 186 | CF₃ | 3-pyridyl | 2-(1'-CF₃-tetrazol-2-yl)phenyl |
| 187 | CF₃ | 3-pyridyl | 4-morpholinocarbonyl |
| 188 | CF₃ | 3-pyridyl | 2-methyl-1-imidazolyl |
| 189 | CF₃ | 3-pyridyl | 5-methyl-1-imidazolyl |
| 190 | CF₃ | 3-pyridyl | 2-methylsulfonyl-1-imidazolyl |
| 191 | CF₃ | 2-pyrimidyl | 2-(aminosulfonyl)phenyl |
| 192 | CF₃ | 2-pyrimidyl | 2-(methylaminosulfonyl)phenyl |
| 193 | CF₃ | 2-pyrimidyl | 1-pyrrolidinocarbonyl |
| 194 | CF₃ | 2-pyrimidyl | 2-(methylsulfonyl)phenyl |
| 195 | CF₃ | 2-pyrimidyl | 4-morpholino |
| 196 | CF₃ | 2-pyrimidyl | 2-(1'-CF₃-tetrazol-2-yl)phenyl |
| 197 | CF₃ | 2-pyrimidyl | 4-morpholinocarbonyl |
| 198 | CF₃ | 2-pyrimidyl | 2-methyl-1-imidazolyl |
| 199 | CF₃ | 2-pyrimidyl | 5-methyl-1-imidazolyl |
| 200 | CF₃ | 2-pyrimidyl | 2-methylsulfonyl-1-imidazolyl |
| 201 | CF₃ | 5-pyrimidyl | 2-(aminosulfonyl)phenyl |
| 202 | CF₃ | 5-pyrimidyl | 2-(methylaminosulfonyl)phenyl |
| 203 | CF₃ | 5-pyrimidyl | 1-pyrrolidinocarbonyl |
| 204 | CF₃ | 5-pyrimidyl | 2-(methylsulfonyl)phenyl |
| 205 | CF₃ | 5-pyrimidyl | 4-morpholino |
| 206 | CF₃ | 5-pyrimidyl | 2-(1'-CF₃-tetrazol-2-yl)phenyl |
| 207 | CF₃ | 5-pyrimidyl | 4-morpholinocarbonyl |
| 208 | CF₃ | 5-pyrimidyl | 2-methyl-1-imidazolyl |
| 209 | CF₃ | 5-pyrimidyl | 5-methyl-1-imidazolyl |
| 210 | CF₃ | 5-pyrimidyl | 2-methylsulfonyl-1-imidazolyl |
| 211 | CF₃ | 2-Cl-phenyl | 2-(aminosulfonyl)phenyl |
| 212 | CF₃ | 2-Cl-phenyl | 2-(methylaminosulfonyl)phenyl |
| 213 | CF₃ | 2-Cl-phenyl | 1-pyrrolidinocarbonyl |
| 214 | CF₃ | 2-Cl-phenyl | 2-(methylsulfonyl)phenyl |
| 215 | CF₃ | 2-Cl-phenyl | 4-morpholino |
| 216 | CF₃ | 2-Cl-phenyl | 2-(1'-CF₃-tetrazol-2-yl)phenyl |
| 217 | CF₃ | 2-Cl-phenyl | 4-morpholinocarbonyl |
| 218 | CF₃ | 2-Cl-phenyl | 2-methyl-1-imidazolyl |
| 219 | CF₃ | 2-Cl-phenyl | 5-methyl-1-imidazolyl |
| 220 | CF₃ | 2-Cl-phenyl | 2-methylsulfonyl-1-imidazolyl |
| 221 | CF₃ | 2-F-phenyl | 2-(aminosulfonyl)phenyl |
| 222 | CF₃ | 2-F-phenyl | 2-(methylaminosulfonyl)phenyl |
| 223 | CF₃ | 2-F-phenyl | 1-pyrrolidinocarbonyl |
| 224 | CF₃ | 2-F-phenyl | 2-(methylsulfonyl)phenyl |
| 225 | CF₃ | 2-F-phenyl | 4-morpholino |
| 226 | CF₃ | 2-F-phenyl | 2-(1'-CF₃-tetrazol-2-yl)phenyl |
| 227 | CF₃ | 2-F-phenyl | 4-morpholinocarbonyl |
| 228 | CF₃ | 2-F-phenyl | 2-methyl-1-imidazolyl |
| 229 | CF₃ | 2-F-phenyl | 5-methyl-1-imidazolyl |
| 230 | CF₃ | 2-F-phenyl | 2-methylsulfonyl-1-imidazolyl |
| 231 | CF₃ | 2,6-diF-phenyl | 2-(aminosulfonyl)phenyl |
| 232 | CF₃ | 2,6-diF-phenyl | 2-(methylaminosulfonyl)phenyl |
| 233 | CF₃ | 2,6-diF-phenyl | 1-pyrrolidinocarbonyl |
| 234 | CF₃ | 2,6-diF-phenyl | 2-(methylsulfonyl)phenyl |
| 235 | CF₃ | 2,6-diF-phenyl | 4-morpholino |
| 236 | CF₃ | 2,6-diF-phenyl | 2-(1'-CF₃-tetrazol-2-yl)phenyl |
| 237 | CF₃ | 2,6-diF-phenyl | 4-morpholinocarbonyl |
| 238 | CF₃ | 2,6-diF-phenyl | 2-methyl-1-imidazolyl |
| 239 | CF₃ | 2,6-diF-phenyl | 5-methyl-1-imidazolyl |
| 240 | CF₃ | 2,6-diF-phenyl | 2-methylsulfonyl-1-imidazolyl |
| 241 | SCH₃ | phenyl | 2-(aminosulfonyl)phenyl |
| 242 | SCH₃ | phenyl | 2-(methylaminosulfonyl)phenyl |
| 243 | SCH₃ | phenyl | 1-pyrrolidinocarbonyl |
| 244 | SCH₃ | phenyl | 2-(methylsulfonyl)phenyl |
| 245 | SCH₃ | phenyl | 4-morpholino |
| 246 | SCH₃ | phenyl | 2-(1'-CF₃-tetrazol-2-yl)phenyl |
| 247 | SCH₃ | phenyl | 4-morpholinocarbonyl |
| 248 | SCH₃ | phenyl | 2-methyl-1-imidazolyl |
| 249 | SCH₃ | phenyl | 5-methyl-1-imidazolyl |
| 250 | SCH₃ | phenyl | 2-methylsulfonyl-1-imidazolyl |
| 251 | SCH₃ | 2-pyridyl | 2-(aminosulfonyl)phenyl |
| 252 | SCH₃ | 2-pyridyl | 2-(methylaminosulfonyl)phenyl |
| 253 | SCH₃ | 2-pyridyl | 1-pyrrolidinocarbonyl |
| 254 | SCH₃ | 2-pyridyl | 2-(methylsulfonyl)phenyl |
| 255 | SCH₃ | 2-pyridyl | 4-morpholino |
| 256 | SCH₃ | 2-pyridyl | 2-(1'-CF₃-tetrazol-2-yl)phenyl |
| 257 | SCH₃ | 2-pyridyl | 4-morpholinocarbonyl |
| 258 | SCH₃ | 2-pyridyl | 2-methyl-1-imidazolyl |
| 259 | SCH₃ | 2-pyridyl | 5-methyl-1-imidazolyl |
| 260 | SCH₃ | 2-pyridyl | 2-methylsulfonyl-1-imidazolyl |
| 261 | SCH₃ | 3-pyridyl | 2-(aminosulfonyl)phenyl |
| 262 | SCH₃ | 3-pyridyl | 2-(methylaminosulfonyl)phenyl |
| 263 | SCH₃ | 3-pyridyl | 1-pyrrolidinocarbonyl |
| 264 | SCH₃ | 3-pyridyl | 2-(methylsulfonyl)phenyl |
| 265 | SCH₃ | 3-pyridyl | 4-morpholino |
| 266 | SCH₃ | 3-pyridyl | 2-(1'-CF₃-tetrazol-2-yl)phenyl |
| 267 | SCH₃ | 3-pyridyl | 4-morpholinocarbonyl |
| 268 | SCH₃ | 3-pyridyl | 2-methyl-1-imidazolyl |
| 269 | SCH₃ | 3-pyridyl | 5-methyl-1-imidazolyl |
| 270 | SCH₃ | 3-pyridyl | 2-methylsulfonyl-1-imidazolyl |
| 271 | SCH₃ | 2-pyrimidyl | 2-(aminosulfonyl)phenyl |
| 272 | SCH₃ | 2-pyrimidyl | 2-(methylaminosulfonyl)phenyl |
| 273 | SCH₃ | 2-pyrimidyl | 1-pyrrolidinocarbonyl |
| 274 | SCH₃ | 2-pyrimidyl | 2-(methylsulfonyl)phenyl |
| 275 | SCH₃ | 2-pyrimidyl | 4-morpholino |
| 276 | SCH₃ | 2-pyrimidyl | 2-(1'-CF₃-tetrazol-2-yl)phenyl |
| 277 | SCH₃ | 2-pyrimidyl | 4-morpholinocarbonyl |
| 278 | SCH₃ | 2-pyrimidyl | 2-methyl-1-imidazolyl |
| 279 | SCH₃ | 2-pyrimidyl | 5-methyl-1-imidazolyl |
| 280 | SCH₃ | 2-pyrimidyl | 2-methylsulfonyl-1-imidazolyl |
| 281 | SCH₃ | 5-pyrimidyl | 2-(aminosulfonyl)phenyl |
| 282 | SCH₃ | 5-pyrimidyl | 2-(methylaminosulfonyl)phenyl |
| 283 | SCH₃ | 5-pyrimidyl | 1-pyrrolidinocarbonyl |
| 284 | SCH₃ | 5-pyrimidyl | 2-(methylsulfonyl)phenyl |
| 285 | SCH₃ | 5-pyrimidyl | 4-morpholino |
| 286 | SCH₃ | 5-pyrimidyl | 2-(1'-CF₃-tetrazol-2-yl)phenyl |
| 287 | SCH₃ | 5-pyrimidyl | 4-morpholinocarbonyl |
| 288 | SCH₃ | 5-pyrimidyl | 2-methyl-1-imidazolyl |
| 289 | SCH₃ | 5-pyrimidyl | 5-methyl-1-imidazolyl |
| 290 | SCH₃ | 5-pyrimidyl | 2-methylsulfonyl-1-imidazolyl |
| 291 | SCH₃ | 2-Cl-phenyl | 2-(aminosulfonyl)phenyl |
| 292 | SCH₃ | 2-Cl-phenyl | 2-(methylaminosulfonyl)phenyl |
| 293 | SCH₃ | 2-Cl-phenyl | 1-pyrrolidinocarbonyl |
| 294 | SCH₃ | 2-Cl-phenyl | 2-(methylsulfonyl)phenyl |

TABLE 2-continued

| | | | |
|---|---|---|---|
| 295 | SCH$_3$ | 2-Cl-phenyl | 4-morpholino |
| 296 | SCH$_3$ | 2-Cl-phenyl | 2-(1'-CF$_3$-tetrazol-2-yl)phenyl |
| 297 | SCH$_3$ | 2-Cl-phenyl | 4-morpholinocarbonyl |
| 298 | SCH$_3$ | 2-Cl-phenyl | 2-methyl-1-imidazolyl |
| 299 | SCH$_3$ | 2-Cl-phenyl | 5-methyl-1-imidazolyl |
| 300 | SCH$_3$ | 2-Cl-phenyl | 2-methylsulfonyl-1-imidazolyl |
| 301 | SCH$_3$ | 2-F-phenyl | 2-(aminosulfonyl)phenyl |
| 302 | SCH$_3$ | 2-F-phenyl | 2-(methylaminosulfonyl)phenyl |
| 303 | SCH$_3$ | 2-F-phenyl | 1-pyrrolidinocarbonyl |
| 304 | SCH$_3$ | 2-F-phenyl | 2-(methylsulfonyl)phenyl |
| 305 | SCH$_3$ | 2-F-phenyl | 4-morpholino |
| 306 | SCH$_3$ | 2-F-phenyl | 2-(1'-CF$_3$-tetrazol-2-yl)phenyl |
| 307 | SCH$_3$ | 2-F-phenyl | 4-morpholinocarbonyl |
| 308 | SCH$_3$ | 2-F-phenyl | 2-methyl-1-imidazolyl |
| 309 | SCH$_3$ | 2-F-phenyl | 5-methyl-1-imidazolyl |
| 310 | SCH$_3$ | 2-F-phenyl | 2-methylsulfonyl-1-imidazolyl |
| 311 | SCH$_3$ | 2,6-diF-phenyl | 2-(aminosulfonyl)phenyl |
| 312 | SCH$_3$ | 2,6-diF-phenyl | 2-(methylaminosulfonyl)phenyl |
| 313 | SCH$_3$ | 2,6-diF-phenyl | 1-pyrrolidinocarbonyl |
| 314 | SCH$_3$ | 2,6-diF-phenyl | 2-(methylsulfonyl)phenyl |
| 315 | SCH$_3$ | 2,6-diF-phenyl | 4-morpholino |
| 316 | SCH$_3$ | 2,6-diF-phenyl | 2-(1'-CF$_3$-tetrazol-2-yl)phenyl |
| 317 | SCH$_3$ | 2,6-diF-phenyl | 4-morpholinocarbonyl |
| 318 | SCH$_3$ | 2,6-diF-phenyl | 2-methyl-1-imidazolyl |
| 319 | SCH$_3$ | 2,6-diF-phenyl | 5-methyl-1-imidazolyl |
| 320 | SCH$_3$ | 2,6-diF-phenyl | 2-methylsulfonyl-1-imidazolyl |
| 321 | SOCH$_3$ | phenyl | 2-(aminosulfonyl)phenyl |
| 322 | SOCH$_3$ | phenyl | 2-(methylaminosulfonyl)phenyl |
| 323 | SOCH$_3$ | phenyl | 1-pyrrolidinocarbonyl |
| 324 | SOCH$_3$ | phenyl | 2-(methylsulfonyl)phenyl |
| 325 | SOCH$_3$ | phenyl | 4-morpholino |
| 326 | SOCH$_3$ | phenyl | 2-(1'-CF$_3$-tetrazol-2-yl)phenyl |
| 327 | SOCH$_3$ | phenyl | 4-morpholinocarbonyl |
| 328 | SOCH$_3$ | phenyl | 2-methyl-1-imidazolyl |
| 329 | SOCH$_3$ | phenyl | 5-methyl-1-imidazolyl |
| 330 | SOCH$_3$ | phenyl | 2-methylsulfonyl-1-imidazolyl |
| 331 | SOCH$_3$ | 2-pyridyl | 2-(aminosulfonyl)phenyl |
| 332 | SOCH$_3$ | 2-pyridyl | 2-(methylaminosulfonyl)phenyl |
| 333 | SOCH$_3$ | 2-pyridyl | 1-pyrrolidinocarbonyl |
| 334 | SOCH$_3$ | 2-pyridyl | 2-(methylsulfonyl)phenyl |
| 335 | SOCH$_3$ | 2-pyridyl | 4-morpholino |
| 336 | SOCH$_3$ | 2-pyridyl | 2-(1'-CF$_3$-tetrazol-2-yl)phenyl |
| 337 | SOCH$_3$ | 2-pyridyl | 4-morpholinocarbonyl |
| 338 | SOCH$_3$ | 2-pyridyl | 2-methyl-1-imidazolyl |
| 339 | SOCH$_3$ | 2-pyridyl | 5-methyl-1-imidazolyl |
| 340 | SOCH$_3$ | 2-pyridyl | 2-methylsulfonyl-1-imidazolyl |
| 341 | SOCH$_3$ | 3-pyridyl | 2-(aminosulfonyl)phenyl |
| 342 | SOCH$_3$ | 3-pyridyl | 2-(methylaminosulfonyl)phenyl |
| 343 | SOCH$_3$ | 3-pyridyl | 1-pyrrolidinocarbonyl |
| 344 | SOCH$_3$ | 3-pyridyl | 2-(methylsulfonyl)phenyl |
| 345 | SOCH$_3$ | 3-pyridyl | 4-morpholino |
| 346 | SOCH$_3$ | 3-pyridyl | 2-(1'-CF$_3$-tetrazol-2-yl)phenyl |
| 347 | SOCH$_3$ | 3-pyridyl | 4-morpholinocarbonyl |
| 348 | SOCH$_3$ | 3-pyridyl | 2-methyl-1-imidazolyl |
| 349 | SOCH$_3$ | 3-pyridyl | 5-methyl-1-imidazolyl |
| 350 | SOCH$_3$ | 3-pyridyl | 2-methylsulfonyl-1-imidazolyl |
| 351 | SOCH$_3$ | 2-pyrimidyl | 2-(aminosulfonyl)phenyl |
| 352 | SOCH$_3$ | 2-pyrimidyl | 2-(methylaminosulfonyl)phenyl |
| 353 | SOCH$_3$ | 2-pyrimidyl | 1-pyrrolidinocarbonyl |
| 354 | SOCH$_3$ | 2-pyrimidyl | 2-(methylsulfonyl)phenyl |
| 355 | SOCH$_3$ | 2-pyrimidyl | 4-morpholino |
| 356 | SOCH$_3$ | 2-pyrimidyl | 2-(1'-CF$_3$-tetrazol-2-yl)phenyl |
| 357 | SOCH$_3$ | 2-pyrimidyl | 4-morpholinocarbonyl |
| 358 | SOCH$_3$ | 2-pyrimidyl | 2-methyl-1-imidazolyl |
| 359 | SOCH$_3$ | 2-pyrimidyl | 5-methyl-1-imidazolyl |
| 360 | SOCH$_3$ | 2-pyrimidyl | 2-methylsulfonyl-1-imidazolyl |
| 361 | SOCH$_3$ | 5-pyrimidyl | 2-(aminosulfonyl)phenyl |
| 362 | SOCH$_3$ | 5-pyrimidyl | 2-(methylaminosulfonyl)phenyl |
| 363 | SOCH$_3$ | 5-pyrimidyl | 1-pyrrolidinocarbonyl |
| 364 | SOCH$_3$ | 5-pyrimidyl | 2-(methylsulfonyl)phenyl |
| 365 | SOCH$_3$ | 5-pyrimidyl | 4-morpholino |
| 366 | SOCH$_3$ | 5-pyrimidyl | 2-(1'-CF$_3$-tetrazol-2-yl)phenyl |
| 367 | SOCH$_3$ | 5-pyrimidyl | 4-morpholinocarbonyl |
| 368 | SOCH$_3$ | 5-pyrimidyl | 2-methyl-1-imidazolyl |
| 369 | SOCH$_3$ | 5-pyrimidyl | 5-methyl-1-imidazolyl |
| 370 | SOCH$_3$ | 5-pyrimidyl | 2-methylsulfonyl-1-imidazolyl |
| 371 | SOCH$_3$ | 2-Cl-phenyl | 2-(aminosulfonyl)phenyl |
| 372 | SOCH$_3$ | 2-Cl-phenyl | 2-(methylaminosulfonyl)phenyl |
| 373 | SOCH$_3$ | 2-Cl-phenyl | 1-pyrrolidinocarbonyl |
| 374 | SOCH$_3$ | 2-Cl-phenyl | 2-(methylsulfonyl)phenyl |
| 375 | SOCH$_3$ | 2-Cl-phenyl | 4-morpholino |
| 376 | SOCH$_3$ | 2-Cl-phenyl | 2-(1'-CF$_3$-tetrazol-2-yl)phenyl |
| 377 | SOCH$_3$ | 2-Cl-phenyl | 4-morpholinocarbonyl |
| 378 | SOCH$_3$ | 2-Cl-phenyl | 2-methyl-1-imidazolyl |
| 379 | SOCH$_3$ | 2-Cl-phenyl | 5-methyl-1-imidazolyl |
| 380 | SOCH$_3$ | 2-Cl-phenyl | 2-methylsulfonyl-1-imidazolyl |
| 381 | SOCH$_3$ | 2-F-phenyl | 2-(aminosulfonyl)phenyl |
| 382 | SOCH$_3$ | 2-F-phenyl | 2-(methylaminosulfonyl)phenyl |
| 383 | SOCH$_3$ | 2-F-phenyl | 1-pyrrolidinocarbonyl |
| 384 | SOCH$_3$ | 2-F-phenyl | 2-(methylsulfonyl)phenyl |
| 385 | SOCH$_3$ | 2-F-phenyl | 4-morpholino |
| 386 | SOCH$_3$ | 2-F-phenyl | 2-(1'-CF$_3$-tetrazol-2-yl)phenyl |
| 387 | SOCH$_3$ | 2-F-phenyl | 4-morpholinocarbonyl |
| 388 | SOCH$_3$ | 2-F-phenyl | 2-methyl-1-imidazolyl |
| 389 | SOCH$_3$ | 2-F-phenyl | 5-methyl-1-imidazolyl |
| 390 | SOCH$_3$ | 2-F-phenyl | 2-methylsulfonyl-1-imidazolyl |
| 391 | SOCH$_3$ | 2,6-diF-phenyl | 2-(aminosulfonyl)phenyl |
| 392 | SOCH$_3$ | 2,6-diF-phenyl | 2-(methylaminosulfonyl)phenyl |
| 393 | SOCH$_3$ | 2,6-diF-phenyl | 1-pyrrolidinocarbonyl |
| 394 | SOCH$_3$ | 2,6-diF-phenyl | 2-(methylsulfonyl)phenyl |
| 395 | SOCH$_3$ | 2,6-diF-phenyl | 4-morpholino |
| 396 | SOCH$_3$ | 2,6-diF-phenyl | 2-(1'-CF$_3$-tetrazol-2-yl)phenyl |
| 397 | SOCH$_3$ | 2,6-diF-phenyl | 4-morpholinocarbonyl |
| 398 | SOCH$_3$ | 2,6-diF-phenyl | 2-methyl-1-imidazolyl |
| 399 | SOCH$_3$ | 2,6-diF-phenyl | 5-methyl-1-imidazolyl |
| 400 | SOCH$_3$ | 2,6-diF-phenyl | 2-methylsulfonyl-1-imidazolyl |
| 401 | SO$_2$CH$_3$ | phenyl | 2-(aminosulfonyl)phenyl |
| 402 | SO$_2$CH$_3$ | phenyl | 2-(methylaminosulfonyl)phenyl |
| 403 | SO$_2$CH$_3$ | phenyl | 1-pyrrolidinocarbonyl |
| 404 | SO$_2$CH$_3$ | phenyl | 2-(methylsulfonyl)phenyl |
| 405 | SO$_2$CH$_3$ | phenyl | 4-morpholino |
| 406 | SO$_2$CH$_3$ | phenyl | 2-(1'-CF$_3$-tetrazol-2-yl)phenyl |
| 407 | SO$_2$CH$_3$ | phenyl | 4-morpholinocarbonyl |
| 408 | SO$_2$CH$_3$ | phenyl | 2-methyl-1-imidazolyl |
| 409 | SO$_2$CH$_3$ | phenyl | 5-methyl-1-imidazolyl |
| 410 | SO$_2$CH$_3$ | phenyl | 2-methylsulfonyl-1-imidazolyl |
| 411 | SO$_2$CH$_3$ | 2-pyridyl | 2-(aminosulfonyl)phenyl |
| 412 | SO$_2$CH$_3$ | 2-pyridyl | 2-(methylaminosulfonyl)phenyl |
| 413 | SO$_2$CH$_3$ | 2-pyridyl | 1-pyrrolidinocarbonyl |
| 414 | SO$_2$CH$_3$ | 2-pyridyl | 2-(methylsulfonyl)phenyl |
| 415 | SO$_2$CH$_3$ | 2-pyridyl | 4-morpholino |
| 416 | SO$_2$CH$_3$ | 2-pyridyl | 2-(1'-CF$_3$-tetrazol-2-yl)phenyl |
| 417 | SO$_2$CH$_3$ | 2-pyridyl | 4-morpholinocarbonyl |
| 418 | SO$_2$CH$_3$ | 2-pyridyl | 2-methyl-1-imidazolyl |
| 419 | SO$_2$CH$_3$ | 2-pyridyl | 5-methyl-1-imidazolyl |
| 420 | SO$_2$CH$_3$ | 2-pyridyl | 2-methylsulfonyl-1-imidazolyl |
| 421 | SO$_2$CH$_3$ | 3-pyridyl | 2-(aminosulfonyl)phenyl |
| 422 | SO$_2$CH$_3$ | 3-pyridyl | 2-(methylaminosulfonyl)phenyl |
| 423 | SO$_2$CH$_3$ | 3-pyridyl | 1-pyrrolidinocarbonyl |
| 424 | SO$_2$CH$_3$ | 3-pyridyl | 2-(methylsulfonyl)phenyl |
| 425 | SO$_2$CH$_3$ | 3-pyridyl | 4-morpholino |
| 426 | SO$_2$CH$_3$ | 3-pyridyl | 2-(1'-CF$_3$-tetrazol-2-yl)phenyl |
| 427 | SO$_2$CH$_3$ | 3-pyridyl | 4-morpholinocarbonyl |
| 428 | SO$_2$CH$_3$ | 3-pyridyl | 2-methyl-1-imidazolyl |
| 429 | SO$_2$CH$_3$ | 3-pyridyl | 5-methyl-1-imidazolyl |
| 430 | SO$_2$CH$_3$ | 3-pyridyl | 2-methylsulfonyl-1-imidazolyl |
| 431 | SO$_2$CH$_3$ | 2-pyrimidyl | 2-(aminosulfonyl)phenyl |
| 432 | SO$_2$CH$_3$ | 2-pyrimidyl | 2-(methylaminosulfonyl)phenyl |
| 433 | SO$_2$CH$_3$ | 2-pyrimidyl | 1-pyrrolidinocarbonyl |
| 434 | SO$_2$CH$_3$ | 2-pyrimidyl | 2-(methylsulfonyl)phenyl |
| 435 | SO$_2$CH$_3$ | 2-pyrimidyl | 4-morpholino |
| 436 | SO$_2$CH$_3$ | 2-pyrimidyl | 2-(1'-CF$_3$-tetrazol-2-yl)phenyl |
| 437 | SO$_2$CH$_3$ | 2-pyrimidyl | 4-morpholinocarbonyl |

TABLE 2-continued

| | | | |
|---|---|---|---|
| 438 | SO$_2$CH$_3$ | 2-pyrimidyl | 2-methyl-1-imidazolyl |
| 439 | SO$_2$CH$_3$ | 2-pyrimidyl | 5-methyl-1-imidazolyl |
| 440 | SO$_2$CH$_3$ | 2-pyrimidyl | 2-methylsulfonyl-1-imidazolyl |
| 441 | SO$_2$CH$_3$ | 5-pyrimidyl | 2-(aminosulfonyl)phenyl |
| 442 | SO$_2$CH$_3$ | 5-pyrimidyl | 2-(methylaminosulfonyl)phenyl |
| 443 | SO$_2$CH$_3$ | 5-pyrimidyl | 1-pyrrolidinocarbonyl |
| 444 | SO$_2$CH$_3$ | 5-pyrimidyl | 2-(methylsulfonyl)phenyl |
| 445 | SO$_2$CH$_3$ | 5-pyrimidyl | 4-morpholino |
| 446 | SO$_2$CH$_3$ | 5-pyrimidyl | 2-(1'-CF$_3$-tetrazol-2-yl)phenyl |
| 447 | SO$_2$CH$_3$ | 5-pyrimidyl | 4-morpholinocarbonyl |
| 448 | SO$_2$CH$_3$ | 5-pyrimidyl | 2-methyl-1-imidazolyl |
| 449 | SO$_2$CH$_3$ | 5-pyrimidyl | 5-methyl-1-imidazolyl |
| 450 | SO$_2$CH$_3$ | 5-pyrimidyl | 2-methylsulfonyl-1-imidazolyl |
| 451 | SO$_2$CH$_3$ | 2-Cl-phenyl | 2-(aminosulfonyl)phenyl |
| 452 | SO$_2$CH$_3$ | 2-Cl-phenyl | 2-(methylaminosulfonyl)phenyl |
| 453 | SO$_2$CH$_3$ | 2-Cl-phenyl | 1-pyrrolidinocarbonyl |
| 454 | SO$_2$CH$_3$ | 2-Cl-phenyl | 2-(methylsulfonyl)phenyl |
| 455 | SO$_2$CH$_3$ | 2-Cl-phenyl | 4-morpholino |
| 456 | SO$_2$CH$_3$ | 2-Cl-phenyl | 2-(1'-CF$_3$-tetrazol-2-yl)phenyl |
| 457 | SO$_2$CH$_3$ | 2-Cl-phenyl | 4-morpholinocarbonyl |
| 458 | SO$_2$CH$_3$ | 2-Cl-phenyl | 2-methyl-1-imidazolyl |
| 459 | SO$_2$CH$_3$ | 2-Cl-phenyl | 5-methyl-1-imidazolyl |
| 460 | SO$_2$CH$_3$ | 2-Cl-phenyl | 2-methylsulfonyl-1-imidazolyl |
| 461 | SO$_2$CH$_3$ | 2-F-phenyl | 2-(aminosulfonyl)phenyl |
| 462 | SO$_2$CH$_3$ | 2-F-phenyl | 2-(methylaminosulfonyl)phenyl |
| 463 | SO$_2$CH$_3$ | 2-F-phenyl | 1-pyrrolidinocarbonyl |
| 464 | SO$_2$CH$_3$ | 2-F-phenyl | 2-(methylsulfonyl)phenyl |
| 465 | SO$_2$CH$_3$ | 2-F-phenyl | 4-morpholino |
| 466 | SO$_2$CH$_3$ | 2-F-phenyl | 2-(1'-CF$_3$-tetrazol-2-yl)phenyl |
| 467 | SO$_2$CH$_3$ | 2-F-phenyl | 4-morpholinocarbonyl |
| 468 | SO$_2$CH$_3$ | 2-F-phenyl | 2-methyl-1-imidazolyl |
| 469 | SO$_2$CH$_3$ | 2-F-phenyl | 5-methyl-1-imidazolyl |
| 470 | SO$_2$CH$_3$ | 2-F-phenyl | 2-methylsulfonyl-1-imidazolyl |
| 471 | SO$_2$CH$_3$ | 2,6-diF-phenyl | 2-(aminosulfonyl)phenyl |
| 472 | SO$_2$CH$_3$ | 2,6-diF-phenyl | 2-(methylaminosulfonyl)phenyl |
| 473 | SO$_2$CH$_3$ | 2,6-diF-phenyl | 1-pyrrolidinocarbonyl |
| 474 | SO$_2$CH$_3$ | 2,6-diF-phenyl | 2-(methylsulfonyl)phenyl |
| 475 | SO$_2$CH$_3$ | 2,6-diF-phenyl | 4-morpholino |
| 476 | SO$_2$CH$_3$ | 2,6-diF-phenyl | 2-(1'-CF$_3$-tetrazol-2-yl)phenyl |
| 477 | SO$_2$CH$_3$ | 2,6-diF-phenyl | 4-morpholinocarbonyl |
| 478 | SO$_2$CH$_3$ | 2,6-diF-phenyl | 2-methyl-1-imidazolyl |
| 479 | SO$_2$CH$_3$ | 2,6-diF-phenyl | 5-methyl-1-imidazolyl |
| 480 | SO$_2$CH$_3$ | 2,6-diF-phenyl | 2-methylsulfonyl-1-imidazolyl |
| 481 | CH$_2$NH—SO$_2$CH$_3$ | phenyl | 2-(aminosulfonyl)phenyl |
| 482 | CH$_2$NH—SO$_2$CH$_3$ | phenyl | 2-(methylaminosulfonyl)phenyl |
| 483 | CH$_2$NH—SO$_2$CH$_3$ | phenyl | 1-pyrrolidinocarbonyl |
| 484 | CH$_2$NH—SO$_2$CH$_3$ | phenyl | 2-(methylsulfonyl)phenyl |
| 485 | CH$_2$NH—SO$_2$CH$_3$ | phenyl | 4-morpholino |
| 486 | CH$_2$NH—SO$_2$CH$_3$ | phenyl | 2-(1'-CF$_3$-tetrazol-2-yl)phenyl |
| 487 | CH$_2$NH—SO$_2$CH$_3$ | phenyl | 4-morpholinocarbonyl |
| 488 | CH$_2$NH—SO$_2$CH$_3$ | phenyl | 2-methyl-1-imidazolyl |
| 489 | CH$_2$NH—SO$_2$CH$_3$ | phenyl | 5-methyl-1-imidazolyl |
| 490 | CH$_2$NH—SO$_2$CH$_3$ | phenyl | 2-methylsulfonyl-1-imidazolyl |
| 491 | CH$_2$NH—SO$_2$CH$_3$ | 2-pyridyl | 2-(aminosulfonyl)phenyl |
| 492 | CH$_2$NH—SO$_2$CH$_3$ | 2-pyridyl | 2-(methylaminosulfonyl)phenyl |
| 493 | CH$_2$NH—SO$_2$CH$_3$ | 2-pyridyl | 1-pyrrolidinocarbonyl |
| 494 | CH$_2$NH—SO$_2$CH$_3$ | 2-pyridyl | 2-(methylsulfonyl)phenyl |
| 495 | CH$_2$NH—SO$_2$CH$_3$ | 2-pyridyl | 4-morpholino |
| 496 | CH$_2$NH—SO$_2$CH$_3$ | 2-pyridyl | 2-(1'-CF$_3$-tetrazol-2-yl)phenyl |
| 497 | CH$_2$NH—SO$_2$CH$_3$ | 2-pyridyl | 4-morpholinocarbonyl |
| 498 | CH$_2$NH—SO$_2$CH$_3$ | 2-pyridyl | 2-methyl-1-imidazolyl |
| 499 | CH$_2$NH—SO$_2$CH$_3$ | 2-pyridyl | 5-methyl-1-imidazolyl |
| 500 | CH$_2$NH—SO$_2$CH$_3$ | 2-pyridyl | 2-methylsulfonyl-1-imidazolyl |
| 501 | CH$_2$NH—SO$_2$CH$_3$ | 3-pyridyl | 2-(aminosulfonyl)phenyl |
| 502 | CH$_2$NH—SO$_2$CH$_3$ | 3-pyridyl | 2-(methylaminosulfonyl)phenyl |
| 503 | CH$_2$NH—SO$_2$CH$_3$ | 3-pyridyl | 1-pyrrolidinocarbonyl |
| 504 | CH$_2$NH—SO$_2$CH$_3$ | 3-pyridyl | 2-(methylsulfonyl)phenyl |
| 505 | CH$_2$NH—SO$_2$CH$_3$ | 3-pyridyl | 4-morpholino |
| 506 | CH$_2$NH—SO$_2$CH$_3$ | 3-pyridyl | 2-(1'-CF$_3$-tetrazol-2-yl)phenyl |
| 507 | CH$_2$NH—SO$_2$CH$_3$ | 3-pyridyl | 4-morpholinocarbonyl |
| 508 | CH$_2$NH—SO$_2$CH$_3$ | 3-pyridyl | 2-methyl-1-imidazolyl |
| 509 | CH$_2$NH—SO$_2$CH$_3$ | 3-pyridyl | 5-methyl-1-imidazolyl |
| 510 | CH$_2$NH—SO$_2$CH$_3$ | 3-pyridyl | 2-methylsulfonyl-1-imidazolyl |
| 511 | CH$_2$NH—SO$_2$CH$_3$ | 2-pyrimidyl | 2-(aminosulfonyl)phenyl |
| 512 | CH$_2$NH—SO$_2$CH$_3$ | 2-pyrimidyl | 2-(methylaminosulfonyl)phenyl |
| 513 | CH$_2$NH—SO$_2$CH$_3$ | 2-pyrimidyl | 1-pyrrolidinocarbonyl |
| 514 | CH$_2$NH—SO$_2$CH$_3$ | 2-pyrimidyl | 2-(methylsulfonyl)phenyl |
| 515 | CH$_2$NH—SO$_2$CH$_3$ | 2-pyrimidyl | 4-morpholino |
| 516 | CH$_2$NH—SO$_2$CH$_3$ | 2-pyrimidyl | 2-(1'-CF$_3$-tetrazol-2-yl)phenyl |
| 517 | CH$_2$NH—SO$_2$CH$_3$ | 2-pyrimidyl | 4-morpholinocarbonyl |
| 518 | CH$_2$NH—SO$_2$CH$_3$ | 2-pyrimidyl | 2-methyl-1-imidazolyl |
| 519 | CH$_2$NH—SO$_2$CH$_3$ | 2-pyrimidyl | 5-methyl-1-imidazolyl |
| 520 | CH$_2$NH—SO$_2$CH$_3$ | 2-pyrimidyl | 2-methylsulfonyl-1-imidazolyl |
| 521 | CH$_2$NH—SO$_2$CH$_3$ | 5-pyrimidyl | 2-(aminosulfonyl)phenyl |
| 522 | CH$_2$NH—SO$_2$CH$_3$ | 5-pyrimidyl | 2-(methylaminosulfonyl)phenyl |
| 523 | CH$_2$NH—SO$_2$CH$_3$ | 5-pyrimidyl | 1-pyrrolidinocarbonyl |
| 524 | CH$_2$NH—SO$_2$CH$_3$ | 5-pyrimidyl | 2-(methylsulfonyl)phenyl |
| 525 | CH$_2$NH—SO$_2$CH$_3$ | 5-pyrimidyl | 4-morpholino |
| 526 | CH$_2$NH—SO$_2$CH$_3$ | 5-pyrimidyl | 2-(1'-CF$_3$-tetrazol-2-yl)phenyl |
| 527 | CH$_2$NH—SO$_2$CH$_3$ | 5-pyrimidyl | 4-morpholinocarbonyl |
| 528 | CH$_2$NH—SO$_2$CH$_3$ | 5-pyrimidyl | 2-methyl-1-imidazolyl |
| 529 | CH$_2$NH—SO$_2$CH$_3$ | 5-pyrimidyl | 5-methyl-1-imidazolyl |
| 530 | CH$_2$NH—SO$_2$CH$_3$ | 5-pyrimidyl | 2-methylsulfonyl-1-imidazolyl |
| 531 | CH$_2$NH—SO$_2$CH$_3$ | 2-Cl-phenyl | 2-(aminosulfonyl)phenyl |
| 532 | CH$_2$NH—SO$_2$CH$_3$ | 2-Cl-phenyl | 2-(methylaminosulfonyl)phenyl |
| 533 | CH$_2$NH—SO$_2$CH$_3$ | 2-Cl-phenyl | 1-pyrrolidinocarbonyl |
| 534 | CH$_2$NH—SO$_2$CH$_3$ | 2-Cl-phenyl | 2-(methylsulfonyl)phenyl |
| 535 | CH$_2$NH—SO$_2$CH$_3$ | 2-Cl-phenyl | 4-morpholino |

TABLE 2-continued

| | | | |
|---|---|---|---|
| 536 | CH₂NH—SO₂CH₃ | 2-Cl-phenyl | 2-(1'-CF₃-tetrazol-2-yl)phenyl |
| 537 | CH₂NH—SO₂CH₃ | 2-Cl-phenyl | 4-morpholinocarbonyl |
| 538 | CH₂NH—SO₂CH₃ | 2-Cl-phenyl | 2-methyl-1-imidazolyl |
| 539 | CH₂NH—SO₂CH₃ | 2-Cl-phenyl | 5-methyl-1-imidazolyl |
| 540 | CH₂NH—SO₂CH₃ | 2-Cl-phenyl | 2-methylsulfonyl-1-imidazolyl |
| 541 | CH₂NH—SO₂CH₃ | 2-F-phenyl | 2-(aminosulfonyl)phenyl |
| 542 | CH₂NH—SO₂CH₃ | 2-F-phenyl | 2-(methylaminosulfonyl)phenyl |
| 543 | CH₂NH—SO₂CH₃ | 2-F-phenyl | 1-pyrrolidinocarbonyl |
| 544 | CH₂NH—SO₂CH₃ | 2-F-phenyl | 2-(methylsulfonyl)phenyl |
| 545 | CH₂NH—SO₂CH₃ | 2-F-phenyl | 4-morpholino |
| 546 | CH₂NH—SO₂CH₃ | 2-F-phenyl | 2-(1'-CF₃-tetrazol-2-yl)phenyl |
| 547 | CH₂NH—SO₂CH₃ | 2-F-phenyl | 4-morpholinocarbonyl |
| 548 | CH₂NH—SO₂CH₃ | 2-F-phenyl | 2-methyl-1-imidazolyl |
| 549 | CH₂NH—SO₂CH₃ | 2-F-phenyl | 5-methyl-1-imidazolyl |
| 550 | CH₂NH—SO₂CH₃ | 2-F-phenyl | 2-methylsulfonyl-1-imidazolyl |
| 551 | CH₂NH—SO₂CH₃ | 2,6-diF-phenyl | 2-(aminosulfonyl)phenyl |
| 552 | CH₂NH—SO₂CH₃ | 2,6-diF-phenyl | 2-(methylaminosulfonyl)phenyl |
| 553 | CH₂NH—SO₂CH₃ | 2,6-diF-phenyl | 1-pyrrolidinocarbonyl |
| 554 | CH₂NH—SO₂CH₃ | 2,6-diF-phenyl | 2-(methylsulfonyl)phenyl |
| 555 | CH₂NH—SO₂CH₃ | 2,6-diF-phenyl | 4-morpholino |
| 556 | CH₂NH—SO₂CH₃ | 2,6-diF-phenyl | 2-(1'-CF₃-tetrazol-2-yl)phenyl |
| 557 | CH₂NH—SO₂CH₃ | 2,6-diF-phenyl | 4-morpholinocarbonyl |
| 558 | CH₂NH—SO₂CH₃ | 2,6-diF-phenyl | 2-methyl-1-imidazolyl |
| 559 | CH₂NH—SO₂CH₃ | 2,6-diF-phenyl | 5-methyl-1-imidazolyl |
| 560 | CH₂NH—SO₂CH₃ | 2,6-diF-phenyl | 2-methylsulfonyl-1-imidazolyl |
| 561 | Cl | phenyl | 2-(aminosulfonyl)phenyl |
| 562 | Cl | phenyl | 2-(methylaminosulfonyl)phenyl |
| 563 | Cl | phenyl | 1-pyrrolidinocarbonyl |
| 564 | Cl | phenyl | 2-(methylsulfonyl)phenyl |
| 565 | Cl | phenyl | 4-morpholino |
| 566 | Cl | phenyl | 2-(1'-CF₃-tetrazol-2-yl)phenyl |
| 567 | Cl | phenyl | 4-morpholinocarbonyl |
| 568 | Cl | phenyl | 2-methyl-1-imidazolyl |
| 569 | Cl | phenyl | 5-methyl-1-imidazolyl |
| 570 | Cl | phenyl | 2-methylsulfonyl-1-imidazolyl |
| 571 | Cl | 2-pyridyl | 2-(aminosulfonyl)phenyl |
| 572 | Cl | 2-pyridyl | 2-(methylaminosulfonyl)phenyl |
| 573 | Cl | 2-pyridyl | 1-pyrrolidinocarbonyl |
| 574 | Cl | 2-pyridyl | 2-(methylsulfonyl)phenyl |
| 575 | Cl | 2-pyridyl | 4-morpholino |
| 576 | Cl | 2-pyridyl | 2-(1'-CF₃-tetrazol-2-yl)phenyl |
| 577 | Cl | 2-pyridyl | 4-morpholinocarbonyl |
| 578 | Cl | 2-pyridyl | 2-methyl-1-imidazolyl |
| 579 | Cl | 2-pyridyl | 5-methyl-1-imidazolyl |
| 580 | Cl | 2-pyridyl | 2-methylsulfonyl-1-imidazolyl |
| 581 | Cl | 3-pyridyl | 2-(aminosulfonyl)phenyl |
| 582 | Cl | 3-pyridyl | 2-(methylaminosulfonyl)phenyl |
| 583 | Cl | 3-pyridyl | 1-pyrrolidinocarbonyl |
| 584 | Cl | 3-pyridyl | 2-(methylsulfonyl)phenyl |
| 585 | Cl | 3-pyridyl | 4-morpholino |
| 586 | Cl | 3-pyridyl | 2-(1'-CF₃-tetrazol-2-yl)phenyl |
| 587 | Cl | 3-pyridyl | 4-morpholinocarbonyl |
| 588 | Cl | 3-pyridyl | 2-methyl-1-imidazolyl |
| 589 | Cl | 3-pyridyl | 5-methyl-1-imidazolyl |
| 590 | Cl | 3-pyridyl | 2-methylsulfonyl-1-imidazolyl |
| 591 | Cl | 2-pyrimidyl | 2-(aminosulfonyl)phenyl |
| 592 | Cl | 2-pyrimidyl | 2-(methylaminosulfonyl)phenyl |
| 593 | Cl | 2-pyrimidyl | 1-pyrrolidinocarbonyl |
| 594 | Cl | 2-pyrimidyl | 2-(methylsulfonyl)phenyl |
| 595 | Cl | 2-pyrimidyl | 4-morpholino |
| 596 | Cl | 2-pyrimidyl | 2-(1'-CF₃-tetrazol-2-yl)phenyl |
| 597 | Cl | 2-pyrimidyl | 4-morpholinocarbonyl |
| 598 | Cl | 2-pyrimidyl | 2-methyl-1-imidazolyl |
| 599 | Cl | 2-pyrimidyl | 5-methyl-1-imidazolyl |
| 600 | Cl | 2-pyrimidyl | 2-methylsulfonyl-1-imidazolyl |
| 601 | Cl | 5-pyrimidyl | 2-(aminosulfonyl)phenyl |
| 602 | Cl | 5-pyrimidyl | 2-(methylaminosulfonyl)phenyl |
| 603 | Cl | 5-pyrimidyl | 1-pyrrolidinocarbonyl |
| 604 | Cl | 5-pyrimidyl | 2-(methylsulfonyl)phenyl |
| 605 | Cl | 5-pyrimidyl | 4-morpholino |
| 606 | Cl | 5-pyrimidyl | 2-(1'-CF₃-tetrazol-2-yl)phenyl |
| 607 | Cl | 5-pyrimidyl | 4-morpholinocarbonyl |
| 608 | Cl | 5-pyrimidyl | 2-methyl-1-imidazolyl |
| 609 | Cl | 5-pyrimidyl | 5-methyl-1-imidazolyl |
| 610 | Cl | 5-pyrimidyl | 2-methylsulfonyl-1-imidazolyl |
| 611 | Cl | 2-Cl-phenyl | 2-(aminosulfonyl)phenyl |
| 612 | Cl | 2-Cl-phenyl | 2-(methylaminosulfonyl)phenyl |
| 613 | Cl | 2-Cl-phenyl | 1-pyrrolidinocarbonyl |
| 614 | Cl | 2-Cl-phenyl | 2-(methylsulfonyl)phenyl |
| 615 | Cl | 2-Cl-phenyl | 4-morpholino |
| 616 | Cl | 2-Cl-phenyl | 2-(1'-CF₃-tetrazol-2-yl)phenyl |
| 617 | Cl | 2-Cl-phenyl | 4-morpholinocarbonyl |
| 618 | Cl | 2-Cl-phenyl | 2-methyl-1-imidazolyl |
| 619 | Cl | 2-Cl-phenyl | 5-methyl-1-imidazolyl |
| 620 | Cl | 2-Cl-phenyl | 2-methylsulfonyl-1-imidazolyl |
| 621 | Cl | 2-F-phenyl | 2-(aminosulfonyl)phenyl |
| 622 | Cl | 2-F-phenyl | 2-(methylaminosulfonyl)phenyl |
| 623 | Cl | 2-F-phenyl | 1-pyrrolidinocarbonyl |
| 624 | Cl | 2-F-phenyl | 2-(methylsulfonyl)phenyl |
| 625 | Cl | 2-F-phenyl | 4-morpholino |
| 626 | Cl | 2-F-phenyl | 2-(1'-CF₃-tetrazol-2-yl)phenyl |
| 627 | Cl | 2-F-phenyl | 4-morpholinocarbonyl |
| 628 | Cl | 2-F-phenyl | 2-methyl-1-imidazolyl |
| 629 | Cl | 2-F-phenyl | 5-methyl-1-imidazolyl |
| 630 | Cl | 2-F-phenyl | 2-methylsulfonyl-1-imidazolyl |
| 631 | Cl | 2,6-diF-phenyl | 2-(aminosulfonyl)phenyl |
| 632 | Cl | 2,6-diF-phenyl | 2-(methylaminosulfonyl)phenyl |
| 633 | Cl | 2,6-diF-phenyl | 1-pyrrolidinocarbonyl |
| 634 | Cl | 2,6-diF-phenyl | 2-(methylsulfonyl)phenyl |
| 635 | Cl | 2,6-diF-phenyl | 4-morpholino |
| 636 | Cl | 2,6-diF-phenyl | 2-(1'-CF₃-tetrazol-2-yl)phenyl |
| 637 | Cl | 2,6-diF-phenyl | 4-morpholinocarbonyl |
| 638 | Cl | 2,6-diF-phenyl | 2-methyl-1-imidazolyl |
| 639 | Cl | 2,6-diF-phenyl | 5-methyl-1-imidazolyl |
| 640 | Cl | 2,6-diF-phenyl | 2-methylsulfonyl-1-imidazolyl |
| 641 | F | phenyl | 2-(aminosulfonyl)phenyl |
| 642 | F | phenyl | 2-(methylaminosulfonyl)phenyl |
| 643 | F | phenyl | 1-pyrrolidinocarbonyl |
| 644 | F | phenyl | 2-(methylsulfonyl)phenyl |
| 645 | F | phenyl | 4-morpholino |
| 646 | F | phenyl | 2-(1'-CF₃-tetrazol-2-yl)phenyl |
| 647 | F | phenyl | 4-morpholinocarbonyl |
| 648 | F | phenyl | 2-methyl-1-imidazolyl |
| 649 | F | phenyl | 5-methyl-1-imidazolyl |
| 650 | F | phenyl | 2-methylsulfonyl-1-imidazolyl |
| 651 | F | 2-pyridyl | 2-(aminosulfonyl)phenyl |
| 652 | F | 2-pyridyl | 2-(methylaminosulfonyl)phenyl |
| 653 | F | 2-pyridyl | 1-pyrrolidinocarbonyl |
| 654 | F | 2-pyridyl | 2-(methylsulfonyl)phenyl |
| 655 | F | 2-pyridyl | 4-morpholino |
| 656 | F | 2-pyridyl | 2-(1'-CF₃-tetrazol-2-yl)phenyl |
| 657 | F | 2-pyridyl | 4-morpholinocarbonyl |
| 658 | F | 2-pyridyl | 2-methyl-1-imidazolyl |

TABLE 2-continued

| | | | |
|---|---|---|---|
| 659 | F | 2-pyridyl | 5-methyl-1-imidazolyl |
| 660 | F | 2-pyridyl | 2-methylsulfonyl-1-imidazolyl |
| 661 | F | 3-pyridyl | 2-(aminosulfonyl)phenyl |
| 662 | F | 3-pyridyl | 2-(methylaminosulfonyl)phenyl |
| 663 | F | 3-pyridyl | 1-pyrrolidinocarbonyl |
| 664 | F | 3-pyridyl | 2-(methylsulfonyl)phenyl |
| 665 | F | 3-pyridyl | 4-morpholino |
| 666 | F | 3-pyridyl | 2-(1'-CF$_3$-tetrazol-2-yl)phenyl |
| 667 | F | 3-pyridyl | 4-morpholinocarbonyl |
| 668 | F | 3-pyridyl | 2-methyl-1-imidazolyl |
| 669 | F | 3-pyridyl | 5-methyl-1-imidazolyl |
| 670 | F | 3-pyridyl | 2-methylsulfonyl-1-imidazolyl |
| 671 | F | 2-pyrimidyl | 2-(aminosulfonyl)phenyl |
| 672 | F | 2-pyrimidyl | 2-(methylaminosulfonyl)phenyl |
| 673 | F | 2-pyrimidyl | 1-pyrrolidinocarbonyl |
| 674 | F | 2-pyrimidyl | 2-(methylsulfonyl)phenyl |
| 675 | F | 2-pyrimidyl | 4-morpholino |
| 676 | F | 2-pyrimidyl | 2-(1'-CF$_3$-tetrazol-2-yl)phenyl |
| 677 | F | 2-pyrimidyl | 4-morpholinocarbonyl |
| 678 | F | 2-pyrimidyl | 2-methyl-1-imidazolyl |
| 679 | F | 2-pyrimidyl | 5-methyl-1-imidazolyl |
| 680 | F | 2-pyrimidyl | 2-methylsulfonyl-1-imidazolyl |
| 681 | F | 5-pyrimidyl | 2-(aminosulfonyl)phenyl |
| 682 | F | 5-pyrimidyl | 2-(methylaminosulfonyl)phenyl |
| 683 | F | 5-pyrimidyl | 1-pyrrolidinocarbonyl |
| 684 | F | 5-pyrimidyl | 2-(methylsulfonyl)phenyl |
| 685 | F | 5-pyrimidyl | 4-morpholino |
| 686 | F | 5-pyrimidyl | 2-(1'-CF$_3$-tetrazol-2-yl)phenyl |
| 687 | F | 5-pyrimidyl | 4-morpholinocarbonyl |
| 688 | F | 5-pyrimidyl | 2-methyl-1-imidazolyl |
| 689 | F | 5-pyrimidyl | 5-methyl-1-imidazolyl |
| 690 | F | 5-pyrimidyl | 2-methylsulfonyl-1-imidazolyl |
| 691 | F | 2-Cl-phenyl | 2-(aminosulfonyl)phenyl |
| 692 | F | 2-Cl-phenyl | 2-(methylaminosulfonyl)phenyl |
| 693 | F | 2-Cl-phenyl | 1-pyrrolidinocarbonyl |
| 694 | F | 2-Cl-phenyl | 2-(methylsulfonyl)phenyl |
| 695 | F | 2-Cl-phenyl | 4-morpholino |
| 696 | F | 2-Cl-phenyl | 2-(1'-CF$_3$-tetrazol-2-yl)phenyl |
| 697 | F | 2-Cl-phenyl | 4-morpholinocarbonyl |
| 698 | F | 2-Cl-phenyl | 2-methyl-1-imidazolyl |
| 699 | F | 2-Cl-phenyl | 5-methyl-1-imidazolyl |
| 700 | F | 2-Cl-phenyl | 2-methylsulfonyl-1-imidazolyl |
| 701 | F | 2-F-phenyl | 2-(aminosulfonyl)phenyl |
| 702 | F | 2-F-phenyl | 2-(methylaminosulfonyl)phenyl |
| 703 | F | 2-F-phenyl | 1-pyrrolidinocarbonyl |
| 704 | F | 2-F-phenyl | 2-(methylsulfonyl)phenyl |
| 705 | F | 2-F-phenyl | 4-morpholino |
| 706 | F | 2-F-phenyl | 2-(1'-CF$_3$-tetrazol-2-yl)phenyl |
| 707 | F | 2-F-phenyl | 4-morpholinocarbonyl |
| 708 | F | 2-F-phenyl | 2-methyl-1-imidazolyl |
| 709 | F | 2-F-phenyl | 5-methyl-1-imidazolyl |
| 710 | F | 2-F-phenyl | 2-methylsulfonyl-1-imidazolyl |
| 711 | F | 2,6-diF-phenyl | 2-(aminosulfonyl)phenyl |
| 712 | F | 2,6-diF-phenyl | 2-(methylaminosulfonyl)phenyl |
| 713 | F | 2,6-diF-phenyl | 1-pyrrolidinocarbonyl |
| 714 | F | 2,6-diF-phenyl | 2-(methylsulfonyl)phenyl |
| 715 | F | 2,6-diF-phenyl | 4-morpholino |
| 716 | F | 2,6-diF-phenyl | 2-(1'-CF$_3$-tetrazol-2-yl)phenyl |
| 717 | F | 2,6-diF-phenyl | 4-morpholinocarbonyl |
| 718 | F | 2,6-diF-phenyl | 2-methyl-1-imidazolyl |
| 719 | F | 2,6-diF-phenyl | 5-methyl-1-imidazolyl |
| 720 | F | 2,6-diF-phenyl | 2-methylsulfonyl-1-imidazolyl |
| 721 | CO$_2$CH$_3$ | phenyl | 2-(aminosulfonyl)phenyl |
| 722 | CO$_2$CH$_3$ | phenyl | 2-(methylaminosulfonyl)phenyl |
| 723 | CO$_2$CH$_3$ | phenyl | 1-pyrrolidinocarbonyl |
| 724 | CO$_2$CH$_3$ | phenyl | 2-(methylsulfonyl)phenyl |
| 725 | CO$_2$CH$_3$ | phenyl | 4-morpholino |
| 726 | CO$_2$CH$_3$ | phenyl | 2-(1'-CF$_3$-tetrazol-2-yl)phenyl |
| 727 | CO$_2$CH$_3$ | phenyl | 4-morpholinocarbonyl |
| 728 | CO$_2$CH$_3$ | phenyl | 2-methyl-1-imidazolyl |
| 729 | CO$_2$CH$_3$ | phenyl | 5-methyl-1-imidazolyl |
| 730 | CO$_2$CH$_3$ | phenyl | 2-methylsulfonyl-1-imidazolyl |
| 731 | CO$_2$CH$_3$ | 2-pyridyl | 2-(aminosulfonyl)phenyl |
| 732 | CO$_2$CH$_3$ | 2-pyridyl | 2-(methylaminosulfonyl)phenyl |
| 733 | CO$_2$CH$_3$ | 2-pyridyl | 1-pyrrolidinocarbonyl |
| 734 | CO$_2$CH$_3$ | 2-pyridyl | 2-(methylsulfonyl)phenyl |
| 735 | CO$_2$CH$_3$ | 2-pyridyl | 4-morpholino |
| 736 | CO$_2$CH$_3$ | 2-pyridyl | 2-(1'-CF$_3$-tetrazol-2-yl)phenyl |
| 737 | CO$_2$CH$_3$ | 2-pyridyl | 4-morpholinocarbonyl |
| 738 | CO$_2$CH$_3$ | 2-pyridyl | 2-methyl-1-imidazolyl |
| 739 | CO$_2$CH$_3$ | 2-pyridyl | 5-methyl-1-imidazolyl |
| 740 | CO$_2$CH$_3$ | 2-pyridyl | 2-methylsulfonyl-1-imidazolyl |
| 741 | CO$_2$CH$_3$ | 3-pyridyl | 2-(aminosulfonyl)phenyl |
| 742 | CO$_2$CH$_3$ | 3-pyridyl | 2-(methylaminosulfonyl)phenyl |
| 743 | CO$_2$CH$_3$ | 3-pyridyl | 1-pyrrolidinocarbonyl |
| 744 | CO$_2$CH$_3$ | 3-pyridyl | 2-(methylsulfonyl)phenyl |
| 745 | CO$_2$CH$_3$ | 3-pyridyl | 4-morpholino |
| 746 | CO$_2$CH$_3$ | 3-pyridyl | 2-(1'-CF$_3$-tetrazol-2-yl)phenyl |
| 747 | CO$_2$CH$_3$ | 3-pyridyl | 4-morpholinocarbonyl |
| 748 | CO$_2$CH$_3$ | 3-pyridyl | 2-methyl-1-imidazolyl |
| 749 | CO$_2$CH$_3$ | 3-pyridyl | 5-methyl-1-imidazolyl |
| 750 | CO$_2$CH$_3$ | 3-pyridyl | 2-methylsulfonyl-1-imidazolyl |
| 751 | CO$_2$CH$_3$ | 2-pyrimidyl | 2-(aminosulfonyl)phenyl |
| 752 | CO$_2$CH$_3$ | 2-pyrimidyl | 2-(methylaminosulfonyl)phenyl |
| 753 | CO$_2$CH$_3$ | 2-pyrimidyl | 1-pyrrolidinocarbonyl |
| 754 | CO$_2$CH$_3$ | 2-pyrimidyl | 2-(methylsulfonyl)phenyl |
| 755 | CO$_2$CH$_3$ | 2-pyrimidyl | 4-morpholino |
| 756 | CO$_2$CH$_3$ | 2-pyrimidyl | 2-(1'-CF$_3$-tetrazol-2-yl)phenyl |
| 757 | CO$_2$CH$_3$ | 2-pyrimidyl | 4-morpholinocarbonyl |
| 758 | CO$_2$CH$_3$ | 2-pyrimidyl | 2-methyl-1-imidazolyl |
| 759 | CO$_2$CH$_3$ | 2-pyrimidyl | 5-methyl-1-imidazolyl |
| 760 | CO$_2$CH$_3$ | 2-pyrimidyl | 2-methylsulfonyl-1-imidazolyl |
| 761 | CO$_2$CH$_3$ | 5-pyrimidyl | 2-(aminosulfonyl)phenyl |
| 762 | CO$_2$CH$_3$ | 5-pyrimidyl | 2-(methylaminosulfonyl)phenyl |
| 763 | CO$_2$CH$_3$ | 5-pyrimidyl | 1-pyrrolidinocarbonyl |
| 764 | CO$_2$CH$_3$ | 5-pyrimidyl | 2-(methylsulfonyl)phenyl |
| 765 | CO$_2$CH$_3$ | 5-pyrimidyl | 4-morpholino |
| 766 | CO$_2$CH$_3$ | 5-pyrimidyl | 2-(1'-CF$_3$-tetrazol-2-yl)phenyl |
| 767 | CO$_2$CH$_3$ | 5-pyrimidyl | 4-morpholinocarbonyl |
| 768 | CO$_2$CH$_3$ | 5-pyrimidyl | 2-methyl-1-imidazolyl |
| 769 | CO$_2$CH$_3$ | 5-pyrimidyl | 5-methyl-1-imidazolyl |
| 770 | CO$_2$CH$_3$ | 5-pyrimidyl | 2-methylsulfonyl-1-imidazolyl |
| 771 | CO$_2$CH$_3$ | 2-Cl-phenyl | 2-(aminosulfonyl)phenyl |
| 772 | CO$_2$CH$_3$ | 2-Cl-phenyl | 2-(methylaminosulfonyl)phenyl |
| 773 | CO$_2$CH$_3$ | 2-Cl-phenyl | 1-pyrrolidinocarbonyl |
| 774 | CO$_2$CH$_3$ | 2-Cl-phenyl | 2-(methylsulfonyl)phenyl |
| 775 | CO$_2$CH$_3$ | 2-Cl-phenyl | 4-morpholino |
| 776 | CO$_2$CH$_3$ | 2-Cl-phenyl | 2-(1'-CF$_3$-tetrazol-2-yl)phenyl |
| 777 | CO$_2$CH$_3$ | 2-Cl-phenyl | 4-morpholinocarbonyl |
| 778 | CO$_2$CH$_3$ | 2-Cl-phenyl | 2-methyl-1-imidazolyl |
| 779 | CO$_2$CH$_3$ | 2-Cl-phenyl | 5-methyl-1-imidazolyl |
| 780 | CO$_2$CH$_3$ | 2-Cl-phenyl | 2-methylsulfonyl-1-imidazolyl |
| 781 | CO$_2$CH$_3$ | 2-F-phenyl | 2-(aminosulfonyl)phenyl |
| 782 | CO$_2$CH$_3$ | 2-F-phenyl | 2-(methylaminosulfonyl)phenyl |
| 783 | CO$_2$CH$_3$ | 2-F-phenyl | 1-pyrrolidinocarbonyl |
| 784 | CO$_2$CH$_3$ | 2-F-phenyl | 2-(methylsulfonyl)phenyl |
| 785 | CO$_2$CH$_3$ | 2-F-phenyl | 4-morpholino |
| 786 | CO$_2$CH$_3$ | 2-F-phenyl | 2-(1'-CF$_3$-tetrazol-2-yl)phenyl |
| 787 | CO$_2$CH$_3$ | 2-F-phenyl | 4-morpholinocarbonyl |
| 788 | CO$_2$CH$_3$ | 2-F-phenyl | 2-methyl-1-imidazolyl |
| 789 | CO$_2$CH$_3$ | 2-F-phenyl | 5-methyl-1-imidazolyl |
| 790 | CO$_2$CH$_3$ | 2-F-phenyl | 2-methylsulfonyl-1-imidazolyl |
| 791 | CO$_2$CH$_3$ | 2,6-diF-phenyl | 2-(aminosulfonyl)phenyl |
| 792 | CO$_2$CH$_3$ | 2,6-diF-phenyl | 2-(methylaminosulfonyl)phenyl |
| 793 | CO$_2$CH$_3$ | 2,6-diF-phenyl | 1-pyrrolidinocarbonyl |
| 794 | CO$_2$CH$_3$ | 2,6-diF-phenyl | 2-(methylsulfonyl)phenyl |
| 795 | CO$_2$CH$_3$ | 2,6-diF-phenyl | 4-morpholino |
| 796 | CO$_2$CH$_3$ | 2,6-diF-phenyl | 2-(1'-CF$_3$-tetrazol-2-yl)phenyl |
| 797 | CO$_2$CH$_3$ | 2,6-diF-phenyl | 4-morpholinocarbonyl |
| 798 | CO$_2$CH$_3$ | 2,6-diF-phenyl | 2-methyl-1-imidazolyl |
| 799 | CO$_2$CH$_3$ | 2,6-diF-phenyl | 5-methyl-1-imidazolyl |
| 800 | CO$_2$CH$_3$ | 2,6-diF-phenyl | 2-methylsulfonyl-1-imidazolyl |
| 801 | CH$_2$OCH$_3$ | phenyl | 2-(aminosulfonyl)phenyl |
| 802 | CH$_2$OCH$_3$ | phenyl | 2-(methylaminosulfonyl)phenyl |

TABLE 2-continued

| | | | |
|---|---|---|---|
| 803 | $CH_2OCH_3$ | phenyl | 1-pyrrolidinocarbonyl |
| 804 | $CH_2OCH_3$ | phenyl | 2-(methylsulfonyl)phenyl |
| 805 | $CH_2OCH_3$ | phenyl | 4-morpholino |
| 806 | $CH_2OCH_3$ | phenyl | 2-(1'-$CF_3$-tetrazol-2-yl)phenyl |
| 807 | $CH_2OCH_3$ | phenyl | 4-morpholinocarbonyl |
| 808 | $CH_2OCH_3$ | phenyl | 2-methyl-1-imidazolyl |
| 809 | $CH_2OCH_3$ | phenyl | 5-methyl-1-imidazolyl |
| 810 | $CH_2OCH_3$ | phenyl | 2-methylsulfonyl-1-imidazolyl |
| 811 | $CH_2OCH_3$ | 2-pyridyl | 2-(aminosulfonyl)phenyl |
| 812 | $CH_2OCH_3$ | 2-pyridyl | 2-(methylaminosulfonyl)phenyl |
| 813 | $CH_2OCH_3$ | 2-pyridyl | 1-pyrrolidinocarbonyl |
| 814 | $CH_2OCH_3$ | 2-pyridyl | 2-(methylsulfonyl)phenyl |
| 815 | $CH_2OCH_3$ | 2-pyridyl | 4-morpholino |
| 816 | $CH_2OCH_3$ | 2-pyridyl | 2-(1'-$CF_3$-tetrazol-2-yl)phenyl |
| 817 | $CH_2OCH_3$ | 2-pyridyl | 4-morpholinocarbonyl |
| 818 | $CH_2OCH_3$ | 2-pyridyl | 2-methyl-1-imidazolyl |
| 819 | $CH_2OCH_3$ | 2-pyridyl | 5-methyl-1-imidazolyl |
| 820 | $CH_2OCH_3$ | 2-pyridyl | 2-methylsulfonyl-1-imidazolyl |
| 821 | $CH_2OCH_3$ | 3-pyridyl | 2-(aminosulfonyl)phenyl |
| 822 | $CH_2OCH_3$ | 3-pyridyl | 2-(methylaminosulfonyl)phenyl |
| 823 | $CH_2OCH_3$ | 3-pyridyl | 1-pyrrolidinocarbonyl |
| 824 | $CH_2OCH_3$ | 3-pyridyl | 2-(methylsulfonyl)phenyl |
| 825 | $CH_2OCH_3$ | 3-pyridyl | 4-morpholino |
| 826 | $CH_2OCH_3$ | 3-pyridyl | 2-(1'-$CF_3$-tetrazol-2-yl)phenyl |
| 827 | $CH_2OCH_3$ | 3-pyridyl | 4-morpholinocarbonyl |
| 828 | $CH_2OCH_3$ | 3-pyridyl | 2-methyl-1-imidazolyl |
| 829 | $CH_2OCH_3$ | 3-pyridyl | 5-methyl-1-imidazolyl |
| 830 | $CH_2OCH_3$ | 3-pyridyl | 2-methylsulfonyl-1-imidazolyl |
| 831 | $CH_2OCH_3$ | 2-pyrimidyl | 2-(aminosulfonyl)phenyl |
| 832 | $CH_2OCH_3$ | 2-pyrimidyl | 2-(methylaminosulfonyl)phenyl |
| 833 | $CH_2OCH_3$ | 2-pyrimidyl | 1-pyrrolidinocarbonyl |
| 834 | $CH_2OCH_3$ | 2-pyrimidyl | 2-(methylsulfonyl)phenyl |
| 835 | $CH_2OCH_3$ | 2-pyrimidyl | 4-morpholino |
| 836 | $CH_2OCH_3$ | 2-pyrimidyl | 2-(1'-$CF_3$-tetrazol-2-yl)phenyl |
| 837 | $CH_2OCH_3$ | 2-pyrimidyl | 4-morpholinocarbonyl |
| 838 | $CH_2OCH_3$ | 2-pyrimidyl | 2-methyl-1-imidazolyl |
| 839 | $CH_2OCH_3$ | 2-pyrimidyl | 5-methyl-1-imidazolyl |
| 840 | $CH_2OCH_3$ | 2-pyrimidyl | 2-methylsulfonyl-1-imidazolyl |
| 841 | $CH_2OCH_3$ | 5-pyrimidyl | 2-(aminosulfonyl)phenyl |
| 842 | $CH_2OCH_3$ | 5-pyrimidyl | 2-(methylaminosulfonyl)phenyl |
| 843 | $CH_2OCH_3$ | 5-pyrimidyl | 1-pyrrolidinocarbonyl |
| 844 | $CH_2OCH_3$ | 5-pyrimidyl | 2-(methylsulfonyl)phenyl |
| 845 | $CH_2OCH_3$ | 5-pyrimidyl | 4-morpholino |
| 846 | $CH_2OCH_3$ | 5-pyrimidyl | 2-(1'-$CF_3$-tetrazol-2-yl)phenyl |
| 847 | $CH_2OCH_3$ | 5-pyrimidyl | 4-morpholinocarbonyl |
| 848 | $CH_2OCH_3$ | 5-pyrimidyl | 2-methyl-1-imidazolyl |
| 849 | $CH_2OCH_3$ | 5-pyrimidyl | 5-methyl-1-imidazolyl |
| 850 | $CH_2OCH_3$ | 5-pyrimidyl | 2-methylsulfonyl-1-imidazolyl |
| 851 | $CH_2OCH_3$ | 2-Cl-phenyl | 2-(aminosulfonyl)phenyl |
| 852 | $CH_2OCH_3$ | 2-Cl-phenyl | 2-(methylaminosulfonyl)phenyl |
| 853 | $CH_2OCH_3$ | 2-Cl-phenyl | 1-pyrrolidinocarbonyl |
| 854 | $CH_2OCH_3$ | 2-Cl-phenyl | 2-(methylsulfonyl)phenyl |
| 855 | $CH_2OCH_3$ | 2-Cl-phenyl | 4-morpholino |
| 856 | $CH_2OCH_3$ | 2-Cl-phenyl | 2-(1'-$CF_3$-tetrazol-2-yl)phenyl |
| 857 | $CH_2OCH_3$ | 2-Cl-phenyl | 4-morpholinocarbonyl |
| 858 | $CH_2OCH_3$ | 2-Cl-phenyl | 2-methyl-1-imidazolyl |
| 859 | $CH_2OCH_3$ | 2-Cl-phenyl | 5-methyl-1-imidazolyl |
| 860 | $CH_2OCH_3$ | 2-Cl-phenyl | 2-methylsulfonyl-1-imidazolyl |
| 861 | $CH_2OCH_3$ | 2-F-phenyl | 2-(aminosulfonyl)phenyl |
| 862 | $CH_2OCH_3$ | 2-F-phenyl | 2-(methylaminosulfonyl)phenyl |
| 863 | $CH_2OCH_3$ | 2-F-phenyl | 1-pyrrolidinocarbonyl |
| 864 | $CH_2OCH_3$ | 2-F-phenyl | 2-(methylsulfonyl)phenyl |
| 865 | $CH_2OCH_3$ | 2-F-phenyl | 4-morpholino |
| 866 | $CH_2OCH_3$ | 2-F-phenyl | 2-(1'-$CF_3$-tetrazol-2-yl)phenyl |
| 867 | $CH_2OCH_3$ | 2-F-phenyl | 4-morpholinocarbonyl |
| 868 | $CH_2OCH_3$ | 2-F-phenyl | 2-methyl-1-imidazolyl |
| 869 | $CH_2OCH_3$ | 2-F-phenyl | 5-methyl-1-imidazolyl |
| 870 | $CH_2OCH_3$ | 2-F-phenyl | 2-methylsulfonyl-1-imidazolyl |
| 871 | $CH_2OCH_3$ | 2,6-diF-phenyl | 2-(aminosulfonyl)phenyl |
| 872 | $CH_2OCH_3$ | 2,6-diF-phenyl | 2-(methylaminosulfonyl)phenyl |
| 873 | $CH_2OCH_3$ | 2,6-diF-phenyl | 1-pyrrolidinocarbonyl |
| 874 | $CH_2OCH_3$ | 2,6-diF-phenyl | 2-(methylsulfonyl)phenyl |
| 875 | $CH_2OCH_3$ | 2,6-diF-phenyl | 4-morpholino |
| 876 | $CH_2OCH_3$ | 2,6-diF-phenyl | 2-(1'-$CF_3$-tetrazol-2-yl)phenyl |
| 877 | $CH_2OCH_3$ | 2,6-diF-phenyl | 4-morpholinocarbonyl |
| 878 | $CH_2OCH_3$ | 2,6-diF-phenyl | 2-methyl-1-imidazolyl |
| 879 | $CH_2OCH_3$ | 2,6-diF-phenyl | 5-methyl-1-imidazolyl |
| 880 | $CH_2OCH_3$ | 2,6-diF-phenyl | 2-methylsulfonyl-1-imidazolyl |
| 881 | $CONH_2$ | phenyl | 2-(aminosulfonyl)phenyl |
| 882 | $CONH_2$ | phenyl | 2-(methylaminosulfonyl)phenyl |
| 883 | $CONH_2$ | phenyl | 1-pyrrolidinocarbonyl |
| 884 | $CONH_2$ | phenyl | 2-(methylsulfonyl)phenyl |
| 885 | $CONH_2$ | phenyl | 4-morpholino |
| 886 | $CONH_2$ | phenyl | 2-(1'-$CF_3$-tetrazol-2-yl)phenyl |
| 887 | $CONH_2$ | phenyl | 4-morpholinocarbonyl |
| 888 | $CONH_2$ | phenyl | 2-methyl-1-imidazolyl |
| 889 | $CONH_2$ | phenyl | 5-methyl-1-imidazolyl |
| 890 | $CONH_2$ | phenyl | 2-methylsulfonyl-1-imidazolyl |
| 891 | $CONH_2$ | 2-pyridyl | 2-(aminosulfonyl)phenyl |
| 892 | $CONH_2$ | 2-pyridyl | 2-(methylaminosulfonyl)phenyl |
| 893 | $CONH_2$ | 2-pyridyl | 1-pyrrolidinocarbonyl |
| 894 | $CONH_2$ | 2-pyridyl | 2-(methylsulfonyl)phenyl |
| 895 | $CONH_2$ | 2-pyridyl | 4-morpholino |
| 896 | $CONH_2$ | 2-pyridyl | 2-(1'-$CF_3$-tetrazol-2-yl)phenyl |
| 897 | $CONH_2$ | 2-pyridyl | 4-morpholinocarbonyl |
| 898 | $CONH_2$ | 2-pyridyl | 2-methyl-1-imidazolyl |
| 899 | $CONH_2$ | 2-pyridyl | 5-methyl-1-imidazolyl |
| 900 | $CONH_2$ | 2-pyridyl | 2-methylsulfonyl-1-imidazolyl |
| 901 | $CONH_2$ | 3-pyridyl | 2-(aminosulfonyl)phenyl |
| 902 | $CONH_2$ | 3-pyridyl | 2-(methylaminosulfonyl)phenyl |
| 903 | $CONH_2$ | 3-pyridyl | 1-pyrrolidinocarbonyl |
| 904 | $CONH_2$ | 3-pyridyl | 2-(methylsulfonyl)phenyl |
| 905 | $CONH_2$ | 3-pyridyl | 4-morpholino |
| 906 | $CONH_2$ | 3-pyridyl | 2-(1'-$CF_3$-tetrazol-2-yl)phenyl |
| 907 | $CONH_2$ | 3-pyridyl | 4-morpholinocarbonyl |
| 908 | $CONH_2$ | 3-pyridyl | 2-methyl-1-imidazolyl |
| 909 | $CONH_2$ | 3-pyridyl | 5-methyl-1-imidazolyl |
| 910 | $CONH_2$ | 3-pyridyl | 2-methylsulfonyl-1-imidazolyl |
| 911 | $CONH_2$ | 2-pyrimidyl | 2-(aminosulfonyl)phenyl |
| 912 | $CONH_2$ | 2-pyrimidyl | 2-(methylaminosulfonyl)phenyl |
| 913 | $CONH_2$ | 2-pyrimidyl | 1-pyrrolidinocarbonyl |
| 914 | $CONH_2$ | 2-pyrimidyl | 2-(methylsulfonyl)phenyl |
| 915 | $CONH_2$ | 2-pyrimidyl | 4-morpholino |
| 916 | $CONH_2$ | 2-pyrimidyl | 2-(1'-$CF_3$-tetrazol-2-yl)phenyl |
| 917 | $CONH_2$ | 2-pyrimidyl | 4-morpholinocarbonyl |
| 918 | $CONH_2$ | 2-pyrimidyl | 2-methyl-1-imidazolyl |
| 919 | $CONH_2$ | 2-pyrimidyl | 5-methyl-1-imidazolyl |
| 920 | $CONH_2$ | 2-pyrimidyl | 2-methylsulfonyl-1-imidazolyl |
| 921 | $CONH_2$ | 5-pyrimidyl | 2-(aminosulfonyl)phenyl |
| 922 | $CONH_2$ | 5-pyrimidyl | 2-(methylaminosulfonyl)phenyl |
| 923 | $CONH_2$ | 5-pyrimidyl | 1-pyrrolidinocarbonyl |
| 924 | $CONH_2$ | 5-pyrimidyl | 2-(methylsulfonyl)phenyl |
| 925 | $CONH_2$ | 5-pyrimidyl | 4-morpholino |
| 926 | $CONH_2$ | 5-pyrimidyl | 2-(1'-$CF_3$-tetrazol-2-yl)phenyl |
| 927 | $CONH_2$ | 5-pyrimidyl | 4-morpholinocarbonyl |
| 928 | $CONH_2$ | 5-pyrimidyl | 2-methyl-1-imidazolyl |
| 929 | $CONH_2$ | 5-pyrimidyl | 5-methyl-1-imidazolyl |
| 930 | $CONH_2$ | 5-pyrimidyl | 2-methylsulfonyl-1-imidazolyl |
| 931 | $CONH_2$ | 2-Cl-phenyl | 2-(aminosulfonyl)phenyl |
| 932 | $CONH_2$ | 2-Cl-phenyl | 2-(methylaminosulfonyl)phenyl |
| 933 | $CONH_2$ | 2-Cl-phenyl | 1-pyrrolidinocarbonyl |
| 934 | $CONH_2$ | 2-Cl-phenyl | 2-(methylsulfonyl)phenyl |
| 935 | $CONH_2$ | 2-Cl-phenyl | 4-morpholino |
| 936 | $CONH_2$ | 2-Cl-phenyl | 2-(1'-$CF_3$-tetrazol-2-yl)phenyl |
| 937 | $CONH_2$ | 2-Cl-phenyl | 4-morpholinocarbonyl |
| 938 | $CONH_2$ | 2-Cl-phenyl | 2-methyl-1-imidazolyl |
| 939 | $CONH_2$ | 2-Cl-phenyl | 5-methyl-1-imidazolyl |
| 940 | $CONH_2$ | 2-Cl-phenyl | 2-methylsulfonyl-1-imidazolyl |
| 941 | $CONH_2$ | 2-F-phenyl | 2-(aminosulfonyl)phenyl |
| 942 | $CONH_2$ | 2-F-phenyl | 2-(methylaminosulfonyl)phenyl |
| 943 | $CONH_2$ | 2-F-phenyl | 1-pyrrolidinocarbonyl |
| 944 | $CONH_2$ | 2-F-phenyl | 2-(methylsulfonyl)phenyl |
| 945 | $CONH_2$ | 2-F-phenyl | 4-morpholino |
| 946 | $CONH_2$ | 2-F-phenyl | 2-(1'-$CF_3$-tetrazol-2- |

TABLE 2-continued

| | | | |
|---|---|---|---|
| | | | yl)phenyl |
| 947 | CONH₂ | 2-F-phenyl | 4-morpholinocarbonyl |
| 948 | CONH₂ | 2-F-phenyl | 2-methyl-1-imidazolyl |
| 949 | CONH₂ | 2-F-phenyl | 5-methyl-1-imidazolyl |
| 950 | CONH₂ | 2-F-phenyl | 2-methylsulfonyl-1-imidazolyl |
| 951 | CONH₂ | 2,6-diF-phenyl | 2-(aminosulfonyl)phenyl |
| 952 | CONH₂ | 2,6-diF-phenyl | 2-(methylaminosulfonyl)phenyl |
| 953 | CONH₂ | 2,6-diF-phenyl | 1-pyrrolidinocarbonyl |
| 954 | CONH₂ | 2,6-diF-phenyl | 2-(methylsulfonyl)phenyl |
| 955 | CONH₂ | 2,6-diF-phenyl | 4-morpholino |
| 956 | CONH₂ | 2,6-diF-phenyl | 2-(1'-CF₃-tetrazol-2-yl)phenyl |
| 957 | CONH₂ | 2,6-diF-phenyl | 4-morpholinocarbonyl |
| 958 | CONH₂ | 2,6-diF-phenyl | 2-methyl-1-imidazolyl |
| 959 | CONH₂ | 2,6-diF-phenyl | 5-methyl-1-imidazolyl |
| 960 | CONH₂ | 2,6-diF-phenyl | 2-methylsulfonyl-1-imidazolyl |

TABLE 3

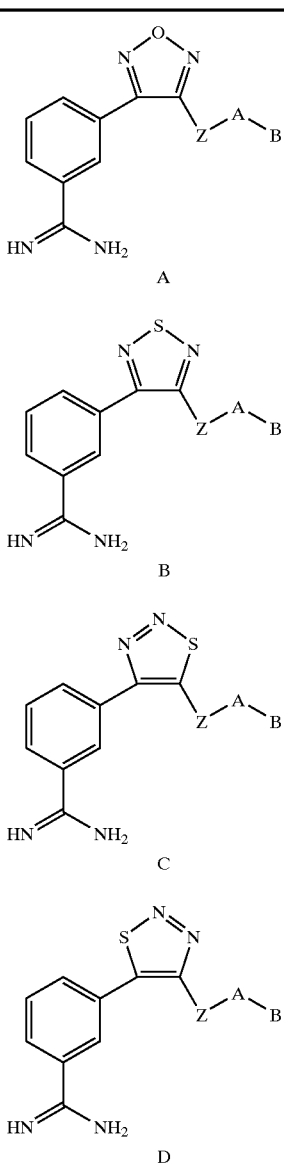

Ex #    A    B

TABLE 3-continued

| Ex # | A | B |
|---|---|---|
| 1 | phenyl | 2-(aminosulfonyl)phenyl |
| 2 | phenyl | 2-(methylaminosulfonyl)phenyl |
| 3 | phenyl | 1-pyrrolidinocarbonyl |
| 4 | phenyl | 2-(methylsulfonyl)phenyl |
| 5 | phenyl | 4-morpholino |
| 6 | phenyl | 2-(1'-CF₃-tetrazol-2-yl)phenyl |
| 7 | phenyl | 4-morpholinocarbonyl |
| 8 | phenyl | 2-methyl-1-imidazolyl |
| 9 | phenyl | 5-methyl-1-imidazolyl |
| 10 | phenyl | 2-methylsulfonyl-1-imidazolyl |
| 11 | 2-pyridyl | 2-(aminosulfonyl)phenyl |
| 12 | 2-pyridyl | 2-(methylaminosulfonyl)phenyl |
| 13 | 2-pyridyl | 1-pyrrolidinocarbonyl |
| 14 | 2-pyridyl | 2-(methylsulfonyl)phenyl |
| 15 | 2-pyridyl | 4-morpholino |
| 16 | 2-pyridyl | 2-(1'-CF₃-tetrazol-2-yl)phenyl |
| 17 | 2-pyridyl | 4-morpholinocarbonyl |
| 18 | 2-pyridyl | 2-methyl-1-imidazolyl |
| 19 | 2-pyridyl | 5-methyl-1-imidazolyl |
| 20 | 2-pyridyl | 2-methylsulfonyl-1-imidazolyl |
| 21 | 3-pyridyl | 2-(aminosulfonyl)phenyl |
| 22 | 3-pyridyl | 2-(methylaminosulfonyl)phenyl |
| 23 | 3-pyridyl | 1-pyrrolidinocarbonyl |
| 24 | 3-pyridyl | 2-(methylsulfonyl)phenyl |
| 25 | 3-pyridyl | 4-morpholino |
| 26 | 3-pyridyl | 2-(1'-CF₃-tetrazol-2-yl)phenyl |
| 27 | 3-pyridyl | 4-morpholinocarbonyl |
| 28 | 3-pyridyl | 2-methyl-1-imidazolyl |
| 29 | 3-pyridyl | 5-methyl-1-imidazolyl |
| 30 | 3-pyridyl | 2-methylsulfonyl-1-imidazolyl |
| 31 | 2-pyrimidyl | 2-(aminosulfonyl)phenyl |
| 32 | 2-pyrimidyl | 2-(methylaminosulfonyl)phenyl |
| 33 | 2-pyrimidyl | 1-pyrrolidinocarbonyl |
| 34 | 2-pyrimidyl | 2-(methylsulfonyl)phenyl |
| 35 | 2-pyrimidyl | 4-morpholino |
| 36 | 2-pyrimidyl | 2-(1'-CF₃-tetrazol-2-yl)phenyl |
| 37 | 2-pyrimidyl | 4-morpholinocarbonyl |
| 38 | 2-pyrimidyl | 2-methyl-1-imidazolyl |
| 39 | 2-pyrimidyl | 5-methyl-1-imidazolyl |
| 40 | 2-pyrimidyl | 2-methylsulfonyl-1-imidazolyl |
| 41 | 5-pyrimidyl | 2-(aminosulfonyl)phenyl |
| 42 | 5-pyrimidyl | 2-(methylaminosulfonyl)phenyl |
| 43 | 5-pyrimidyl | 1-pyrrolidinocarbonyl |
| 44 | 5-pyrimidyl | 2-(methylsulfonyl)phenyl |
| 45 | 5-pyrimidyl | 4-morpholino |
| 46 | 5-pyrimidyl | 2-(1'-CF₃-tetrazol-2-yl)phenyl |
| 47 | 5-pyrimidyl | 4-morpholinocarbonyl |
| 48 | 5-pyrimidyl | 2-methyl-1-imidazolyl |
| 49 | 5-pyrimidyl | 5-methyl-1-imidazolyl |
| 50 | 5-pyrimidyl | 2-methylsulfonyl-1-imidazolyl |
| 51 | 2-Cl-phenyl | 2-(aminosulfonyl)phenyl |
| 52 | 2-Cl-phenyl | 2-(methylaminosulfonyl)phenyl |
| 53 | 2-Cl-phenyl | 1-pyrrolidinocarbonyl |
| 54 | 2-Cl-phenyl | 2-(methylsulfonyl)phenyl |
| 55 | 2-Cl-phenyl | 4-morpholino |
| 56 | 2-Cl-phenyl | 2-(1'-CF₃-tetrazol-2-yl)phenyl |
| 57 | 2-Cl-phenyl | 4-morpholinocarbonyl |
| 58 | 2-Cl-phenyl | 2-methyl-1-imidazolyl |
| 59 | 2-Cl-phenyl | 5-methyl-1-imidazolyl |
| 60 | 2-Cl-phenyl | 2-methylsulfonyl-1-imidazolyl |
| 61 | 2-F-phenyl | 2-(aminosulfonyl)phenyl |
| 62 | 2-F-phenyl | 2-(methylaminosulfonyl)phenyl |
| 63 | 2-F-phenyl | 1-pyrrolidinocarbonyl |
| 64 | 2-F-phenyl | 2-(methylsulfonyl)phenyl |
| 65 | 2-F-phenyl | 4-morpholino |
| 66 | 2-F-phenyl | 2-(1'-CF₃-tetrazol-2-yl)phenyl |
| 67 | 2-F-phenyl | 4-morpholinocarbonyl |
| 68 | 2-F-phenyl | 2-methyl-1-imidazolyl |
| 69 | 2-F-phenyl | 5-methyl-1-imidazolyl |
| 70 | 2-F-phenyl | 2-methylsulfonyl-1-imidazolyl |
| 71 | 2,6-diF-phenyl | 2-(aminosulfonyl)phenyl |
| 72 | 2,6-diF-phenyl | 2-(methylaminosulfonyl)phenyl |

TABLE 3-continued
| | | |
|---|---|---|
| 73 | 2,6-diF-phenyl | 1-pyrrolidinocarbonyl |
| 74 | 2,6-diF-phenyl | 2-(methylsulfonyl)phenyl |
| 75 | 2,6-diF-phenyl | 4-morpholino |
| 76 | 2,6-diF-phenyl | 2-(1'-CF$_3$-tetrazol-2-yl)phenyl |
| 77 | 2,6-diF-phenyl | 4-morpholinocarbonyl |
| 78 | 2,6-diF-phenyl | 2-methyl-1-imidazolyl |
| 79 | 2,6-diF-phenyl | 5-methyl-1-imidazolyl |
| 80 | 2,6-diF-phenyl | 2-methylsulfonyl-1-imidazolyl |
TABLE 4
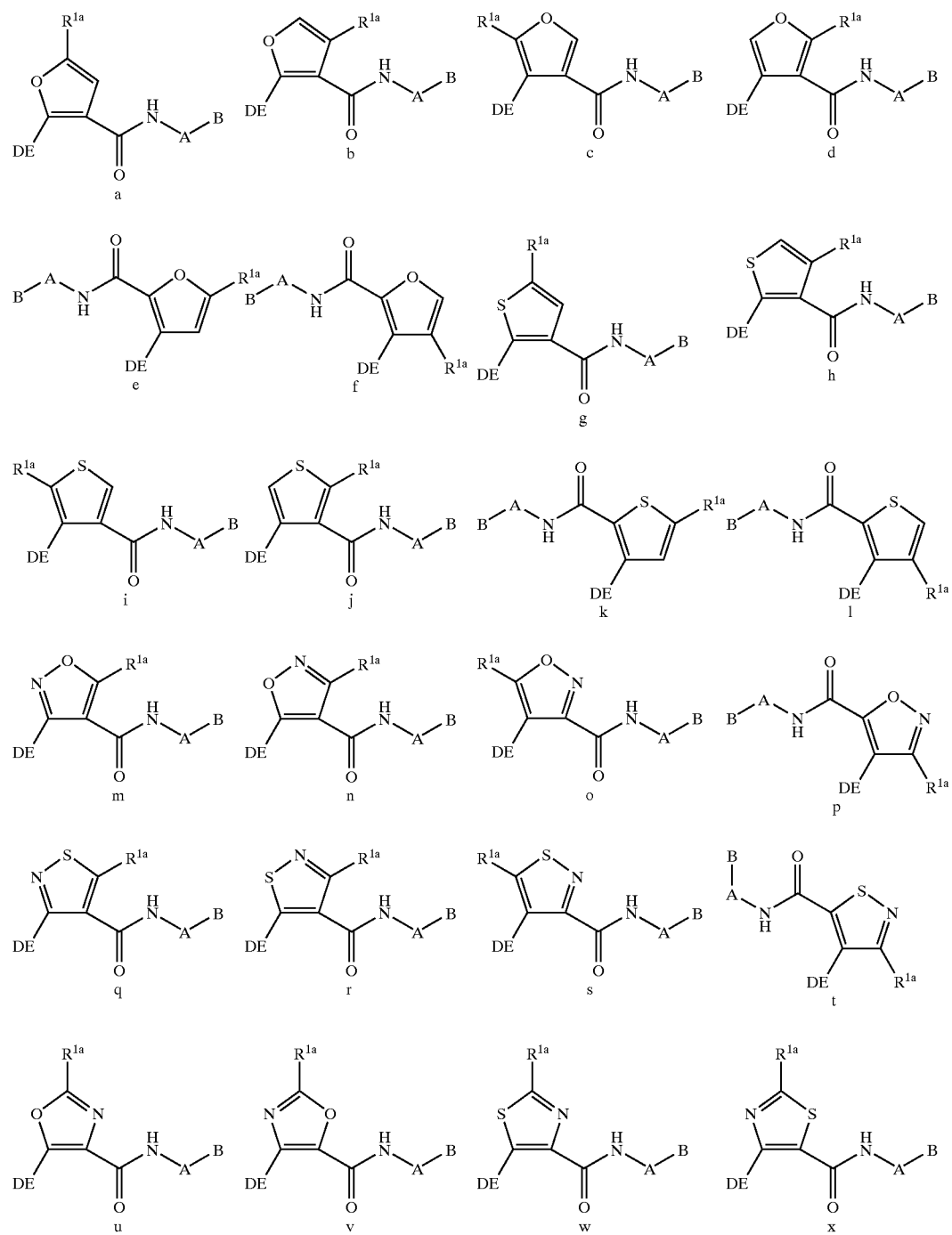

TABLE 4-continued

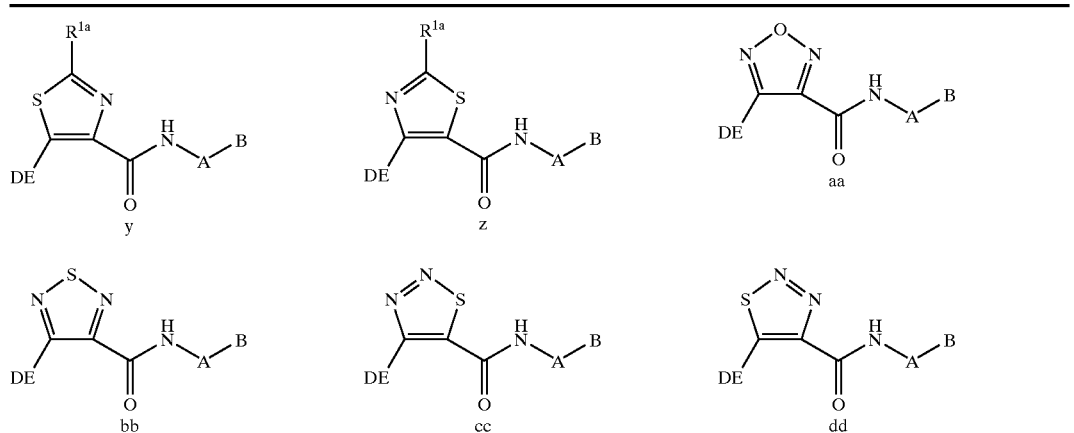

For each example, DE is:
(A) pyridin-4-yl-CH$_2$,
(B) 2-amino-pyrimidin-4-yl,
(C) 6-amino-pyridin-2-yl,
(D) 3-amidino-4-F-phenyl, or
(E) N-amidino-3-piperidinyl.

| Ex # | R$^{1a}$ | A | B |
|---|---|---|---|
| 1 | CH$_3$ | phenyl | 2-(aminosulfonyl)phenyl |
| 2 | CH$_3$ | phenyl | 2-(methylaminosulfonyl)phenyl |
| 3 | CH$_3$ | phenyl | 1-pyrrolidinocarbonyl |
| 4 | CH$_3$ | phenyl | 2-(methylsulfonyl)phenyl |
| 5 | CH$_3$ | phenyl | 4-morpholino |
| 6 | CH$_3$ | phenyl | 2-(1'-CF$_3$-tetrazol-2-yl)phenyl |
| 7 | CH$_3$ | phenyl | 4-morpholinocarbonyl |
| 8 | CH$_3$ | phenyl | 2-methyl-1-imidazolyl |
| 9 | CH$_3$ | phenyl | 5-methyl-1-imidazolyl |
| 10 | CH$_3$ | phenyl | 2-methylsulfonyl-1-imidazolyl |
| 11 | CH$_3$ | 2-pyridyl | 2-(aminosulfonyl)phenyl |
| 12 | CH$_3$ | 2-pyridyl | 2-(methylaminosulfonyl)phenyl |
| 13 | CH$_3$ | 2-pyridyl | 1-pyrrolidinocarbonyl |
| 14 | CH$_3$ | 2-pyridyl | 2-(methylsulfonyl)phenyl |
| 15 | CH$_3$ | 2-pyridyl | 4-morpholino |
| 16 | CH$_3$ | 2-pyridyl | 2-(1'-CF$_3$-tetrazol-2-yl)phenyl |
| 17 | CH$_3$ | 2-pyridyl | 4-morpholinocarbonyl |
| 18 | CH$_3$ | 2-pyridyl | 2-methyl-1-imidazolyl |
| 19 | CH$_3$ | 2-pyridyl | 5-methyl-1-imidazolyl |
| 20 | CH$_3$ | 2-pyridyl | 2-methylsulfonyl-1-imidazolyl |
| 21 | CH$_3$ | 3-pyridyl | 2-(aminosulfonyl)phenyl |
| 22 | CH$_3$ | 3-pyridyl | 2-(methylaminosulfonyl)phenyl |
| 23 | CH$_3$ | 3-pyridyl | 1-pyrrolidinocarbonyl |
| 24 | CH$_3$ | 3-pyridyl | 2-(methylsulfonyl)phenyl |
| 25 | CH$_3$ | 3-pyridyl | 4-morpholino |
| 26 | CH$_3$ | 3-pyridyl | 2-(1'-CF$_3$-tetrazol-2-yl)phenyl |
| 27 | CH$_3$ | 3-pyridyl | 4-morpholinocarbonyl |
| 28 | CH$_3$ | 3-pyridyl | 2-methyl-1-imidazolyl |
| 29 | CH$_3$ | 3-pyridyl | 5-methyl-1-imidazolyl |
| 30 | CH$_3$ | 3-pyridyl | 2-methylsulfonyl-1-imidazolyl |
| 31 | CH$_3$ | 2-pyrimidyl | 2-(aminosulfonyl)phenyl |
| 32 | CH$_3$ | 2-pyrimidyl | 2-(methylaminosulfonyl)phenyl |
| 33 | CH$_3$ | 2-pyrimidyl | 1-pyrrolidinocarbonyl |
| 34 | CH$_3$ | 2-pyrimidyl | 2-(methylsulfonyl)phenyl |
| 35 | CH$_3$ | 2-pyrimidyl | 4-morpholino |
| 36 | CH$_3$ | 2-pyrimidyl | 2-(1'-CF$_3$-tetrazol-2-yl)phenyl |
| 37 | CH$_3$ | 2-pyrimidyl | 4-morpholinocarbonyl |
| 38 | CH$_3$ | 2-pyrimidyl | 2-methyl-1-imidazolyl |
| 39 | CH$_3$ | 2-pyrimidyl | 5-methyl-1-imidazolyl |
| 40 | CH$_3$ | 2-pyrimidyl | 2-methylsulfonyl-1-imidazolyl |
| 41 | CH$_3$ | 5-pyrimidyl | 2-(aminosulfonyl)phenyl |
| 42 | CH$_3$ | 5-pyrimidyl | 2-(methylaminosulfonyl)phenyl |
| 43 | CH$_3$ | 5-pyrimidyl | 1-pyrrolidinocarbonyl |
| 44 | CH$_3$ | 5-pyrimidyl | 2-(methylsulfonyl)phenyl |
| 45 | CH$_3$ | 5-pyrimidyl | 4-morpholino |
| 46 | CH$_3$ | 5-pyrimidyl | 2-(1'-CF$_3$-tetrazol-2-yl)phenyl |
| 47 | CH$_3$ | 5-pyrimidyl | 4-morpholinocarbonyl |
| 48 | CH$_3$ | 5-pyrimidyl | 2-methyl-1-imidazolyl |
| 49 | CH$_3$ | 5-pyrimidyl | 5-methyl-1-imidazolyl |
| 50 | CH$_3$ | 5-pyrimidyl | 2-methylsulfonyl-1-imidazolyl |

TABLE 4-continued

| | | | |
|---|---|---|---|
| 51 | CH$_3$ | 2-Cl-phenyl | 2-(aminosulfonyl)phenyl |
| 52 | CH$_3$ | 2-Cl-phenyl | 2-(methylaminosulfonyl)phenyl |
| 53 | CH$_3$ | 2-Cl-phenyl | 1-pyrrolidinocarbonyl |
| 54 | CH$_3$ | 2-Cl-phenyl | 2-(methylsulfonyl)phenyl |
| 55 | CH$_3$ | 2-Cl-phenyl | 4-morpholino |
| 56 | CH$_3$ | 2-Cl-phenyl | 2-(1'-CF$_3$-tetrazol-2-yl)phenyl |
| 57 | CH$_3$ | 2-Cl-phenyl | 4-morpholinocarbonyl |
| 58 | CH$_3$ | 2-Cl-phenyl | 2-methyl-1-imidazolyl |
| 59 | CH$_3$ | 2-Cl-phenyl | 5-methyl-1-imidazolyl |
| 60 | CH$_3$ | 2-Cl-phenyl | 2-methylsulfonyl-1-imidazolyl |
| 61 | CH$_3$ | 2-F-phenyl | 2-(aminosulfonyl)phenyl |
| 62 | CH$_3$ | 2-F-phenyl | 2-(methylaminosulfonyl)phenyl |
| 63 | CH$_3$ | 2-F-phenyl | 1-pyrrolidinocarbonyl |
| 64 | CH$_3$ | 2-F-phenyl | 2-(methylsulfonyl)phenyl |
| 65 | CH$_3$ | 2-F-phenyl | 4-morpholino |
| 66 | CH$_3$ | 2-F-phenyl | 2-(1'-CF$_3$-tetrazol-2-yl)phenyl |
| 67 | CH$_3$ | 2-F-phenyl | 4-morpholinocarbonyl |
| 68 | CH$_3$ | 2-F-phenyl | 2-methyl-1-imidazolyl |
| 69 | CH$_3$ | 2-F-phenyl | 5-methyl-1-imidazolyl |
| 70 | CH$_3$ | 2-F-phenyl | 2-methylsulfonyl-1-imidazolyl |
| 71 | CH$_3$ | 2,6-diF-phenyl | 2-(aminosulfonyl)phenyl |
| 72 | CH$_3$ | 2,6-diF-phenyl | 2-(methylaminosulfonyl)phenyl |
| 73 | CH$_3$ | 2,6-diF-phenyl | 1-pyrrolidinocarbonyl |
| 74 | CH$_3$ | 2,6-diF-phenyl | 2-(methylsulfonyl)phenyl |
| 75 | CH$_3$ | 2,6-diF-phenyl | 4-morpholino |
| 76 | CH$_3$ | 2,6-diF-phenyl | 2-(1'-CF$_3$-tetrazol-2-yl)phenyl |
| 77 | CH$_3$ | 2,6-diF-phenyl | 4-morpholinocarbonyl |
| 78 | CH$_3$ | 2,6-diF-phenyl | 2-methyl-1-imidazolyl |
| 79 | CH$_3$ | 2,6-diF-phenyl | 5-methyl-1-imidazolyl |
| 80 | CH$_3$ | 2,6-diF-phenyl | 2-methylsulfonyl-1-imidazolyl |
| 81 | CH$_2$CH$_3$ | phenyl | 2-(aminosulfonyl)phenyl |
| 82 | CH$_2$CH$_3$ | phenyl | 2-(methylaminosulfonyl)phenyl |
| 83 | CH$_2$CH$_3$ | phenyl | 1-pyrrolidinocarbonyl |
| 84 | CH$_2$CH$_3$ | phenyl | 2-(methylsulfonyl)phenyl |
| 85 | CH$_2$CH$_3$ | phenyl | 4-morpholino |
| 86 | CH$_2$CH$_3$ | phenyl | 2-(1'-CF$_3$-tetrazol-2-yl)phenyl |
| 87 | CH$_2$CH$_3$ | phenyl | 4-morpholinocarbonyl |
| 88 | CH$_2$CH$_3$ | phenyl | 2-methyl-1-imidazolyl |
| 89 | CH$_2$CH$_3$ | phenyl | 5-methyl-1-imidazolyl |
| 90 | CH$_2$CH$_3$ | phenyl | 2-methylsulfonyl-1-imidazolyl |
| 91 | CH$_2$CH$_3$ | 2-pyridyl | 2-(aminosulfonyl)phenyl |
| 92 | CH$_2$CH$_3$ | 2-pyridyl | 2-(methylaminosulfonyl)phenyl |
| 93 | CH$_2$CH$_3$ | 2-pyridyl | 1-pyrrolidinocarbonyl |
| 94 | CH$_2$CH$_3$ | 2-pyridyl | 2-(methylsulfonyl)phenyl |
| 95 | CH$_2$CH$_3$ | 2-pyridyl | 4-morpholino |
| 96 | CH$_2$CH$_3$ | 2-pyridyl | 2-(1'-CF$_3$-tetrazol-2-yl)phenyl |
| 97 | CH$_2$CH$_3$ | 2-pyridyl | 4-morpholinocarbonyl |
| 98 | CH$_2$CH$_3$ | 2-pyridyl | 2-methyl-1-imidazolyl |
| 99 | CH$_2$CH$_3$ | 2-pyridyl | 5-methyl-1-imidazolyl |
| 100 | CH$_2$CH$_3$ | 2-pyridyl | 2-methylsulfonyl-1-imidazolyl |
| 101 | CH$_2$CH$_3$ | 3-pyridyl | 2-(aminosulfonyl)phenyl |
| 102 | CH$_2$CH$_3$ | 3-pyridyl | 2-(methylaminosulfonyl)phenyl |
| 103 | CH$_2$CH$_3$ | 3-pyridyl | 1-pyrrolidinocarbonyl |
| 104 | CH$_2$CH$_3$ | 3-pyridyl | 2-(methylsulfonyl)phenyl |
| 105 | CH$_2$CH$_3$ | 3-pyridyl | 4-morpholino |
| 106 | CH$_2$CH$_3$ | 3-pyridyl | 2-(1'-CF$_3$-tetrazol-2-yl)phenyl |
| 107 | CH$_2$CH$_3$ | 3-pyridyl | 4-morpholinocarbonyl |
| 108 | CH$_2$CH$_3$ | 3-pyridyl | 2-methyl-1-imidazolyl |
| 109 | CH$_2$CH$_3$ | 3-pyridyl | 5-methyl-1-imidazolyl |
| 110 | CH$_2$CH$_3$ | 3-pyridyl | 2-methylsulfonyl-1-imidazolyl |
| 111 | CH$_2$CH$_3$ | 2-pyrimidyl | 2-(aminosulfonyl)phenyl |
| 112 | CH$_2$CH$_3$ | 2-pyrimidyl | 2-(methylaminosulfonyl)phenyl |
| 113 | CH$_2$CH$_3$ | 2-pyrimidyl | 1-pyrrolidinocarbonyl |
| 114 | CH$_2$CH$_3$ | 2-pyrimidyl | 2-(methylsulfonyl)phenyl |
| 115 | CH$_2$CH$_3$ | 2-pyrimidyl | 4-morpholino |
| 116 | CH$_2$CH$_3$ | 2-pyrimidyl | 2-(1'-CF$_3$-tetrazol-2-yl)phenyl |
| 117 | CH$_2$CH$_3$ | 2-pyrimidyl | 4-morpholinocarbonyl |
| 118 | CH$_2$CH$_3$ | 2-pyrimidyl | 2-methyl-1-imidazolyl |
| 119 | CH$_2$CH$_3$ | 2-pyrimidyl | 5-methyl-1-imidazolyl |
| 120 | CH$_2$CH$_3$ | 2-pyrimidyl | 2-methylsulfonyl-1-imidazolyl |
| 121 | CH$_2$CH$_3$ | 5-pyrimidyl | 2-(aminosulfonyl)phenyl |
| 122 | CH$_2$CH$_3$ | 5-pyrimidyl | 2-(methylaminosulfonyl)phenyl |
| 123 | CH$_2$CH$_3$ | 5-pyrimidyl | 1-pyrrolidinocarbonyl |
| 124 | CH$_2$CH$_3$ | 5-pyrimidyl | 2-(methylsulfonyl)phenyl |
| 125 | CH$_2$CH$_3$ | 5-pyrimidyl | 4-morpholino |
| 126 | CH$_2$CH$_3$ | 5-pyrimidyl | 2-(1'-CF$_3$-tetrazol-2-yl)phenyl |
| 127 | CH$_2$CH$_3$ | 5-pyrimidyl | 4-morpholinocarbonyl |
| 128 | CH$_2$CH$_3$ | 5-pyrimidyl | 2-methyl-1-imidazolyl |
| 129 | CH$_2$CH$_3$ | 5-pyrimidyl | 5-methyl-1-imidazolyl |

TABLE 4-continued

| | | | |
|---|---|---|---|
| 130 | $CH_2CH_3$ | 5-pyrimidyl | 2-methylsulfonyl-1-imidazolyl |
| 131 | $CH_2CH_3$ | 2-Cl-phenyl | 2-(aminosulfonyl)phenyl |
| 132 | $CH_2CH_3$ | 2-Cl-phenyl | 2-(methylaminosulfonyl)phenyl |
| 133 | $CH_2CH_3$ | 2-Cl-phenyl | 1-pyrrolidinocarbonyl |
| 134 | $CH_2CH_3$ | 2-Cl-phenyl | 2-(methylsulfonyl)phenyl |
| 135 | $CH_2CH_3$ | 2-Cl-phenyl | 4-morpholino |
| 136 | $CH_2CH_3$ | 2-Cl-phenyl | 2-(1'-$CF_3$-tetrazol-2-yl)phenyl |
| 137 | $CH_2CH_3$ | 2-Cl-phenyl | 4-morpholinocarbonyl |
| 138 | $CH_2CH_3$ | 2-Cl-phenyl | 2-methyl-1-imidazolyl |
| 139 | $CH_2CH_3$ | 2-Cl-phenyl | 5-methyl-1-imidazolyl |
| 140 | $CH_2CH_3$ | 2-Cl-phenyl | 2-methylsulfonyl-1-imidazolyl |
| 141 | $CH_2CH_3$ | 2-F-phenyl | 2-(aminosulfonyl)phenyl |
| 142 | $CH_2CH_3$ | 2-F-phenyl | 2-(methylaminosulfonyl)phenyl |
| 143 | $CH_2CH_3$ | 2-F-phenyl | 1-pyrrolidinocarbonyl |
| 144 | $CH_2CH_3$ | 2-F-phenyl | 2-(methylsulfonyl)phenyl |
| 145 | $CH_2CH_3$ | 2-F-phenyl | 4-morpholino |
| 146 | $CH_2CH_3$ | 2-F-phenyl | 2-(1'-$CF_3$-tetrazol-2-yl)phenyl |
| 147 | $CH_2CH_3$ | 2-F-phenyl | 4-morpholinocarbonyl |
| 148 | $CH_2CH_3$ | 2-F-phenyl | 2-methyl-1-imidazolyl |
| 149 | $CH_2CH_3$ | 2-F-phenyl | 5-methyl-1-imidazolyl |
| 150 | $CH_2CH_3$ | 2-F-phenyl | 2-methylsulfonyl-1-imidazolyl |
| 151 | $CH_2CH_3$ | 2,6-diF-phenyl | 2-(aminosulfonyl)phenyl |
| 152 | $CH_2CH_3$ | 2,6-diF-phenyl | 2-(methylaminosulfonyl)phenyl |
| 153 | $CH_2CH_3$ | 2,6-diF-phenyl | 1-pyrrolidinocarbonyl |
| 154 | $CH_2CH_3$ | 2,6-diF-phenyl | 2-(methylsulfonyl)phenyl |
| 155 | $CH_2CH_3$ | 2,6-diF-phenyl | 4-morpholino |
| 156 | $CH_2CH_3$ | 2,6-diF-phenyl | 2-(1'-$CF_3$-tetrazol-2-yl)phenyl |
| 157 | $CH_2CH_3$ | 2,6-diF-phenyl | 4-morpholinocarbonyl |
| 158 | $CH_2CH_3$ | 2,6-diF-phenyl | 2-methyl-1-imidazolyl |
| 159 | $CH_2CH_3$ | 2,6-diF-phenyl | 5-methyl-1-imidazolyl |
| 160 | $CH_2CH_3$ | 2,6-diF-phenyl | 2-methylsulfonyl-1-imidazolyl |
| 161 | $CF_3$ | phenyl | 2-(aminosulfonyl)phenyl |
| 162 | $CF_3$ | phenyl | 2-(methylaminosulfonyl)phenyl |
| 163 | $CF_3$ | phenyl | 1-pyrrolidinocarbonyl |
| 164 | $CF_3$ | phenyl | 2-(methylsulfonyl)phenyl |
| 165 | $CF_3$ | phenyl | 4-morpholino |
| 166 | $CF_3$ | phenyl | 2-(1'-$CF_3$-tetrazol-2-yl)phenyl |
| 167 | $CF_3$ | phenyl | 4-morpholinocarbonyl |
| 168 | $CF_3$ | phenyl | 2-methyl-1-imidazolyl |
| 169 | $CF_3$ | phenyl | 5-methyl-1-imidazolyl |
| 170 | $CF_3$ | phenyl | 2-methylsulfonyl-1-imidazolyl |
| 171 | $CF_3$ | 2-pyridyl | 2-(aminosulfonyl)phenyl |
| 172 | $CF_3$ | 2-pyridyl | 2-(methylaminosulfonyl)phenyl |
| 173 | $CF_3$ | 2-pyridyl | 1-pyrrolidinocarbonyl |
| 174 | $CF_3$ | 2-pyridyl | 2-(methylsulfonyl)phenyl |
| 175 | $CF_3$ | 2-pyridyl | 4-morpholino |
| 176 | $CF_3$ | 2-pyridyl | 2-(1'-$CF_3$-tetrazol-2-yl)phenyl |
| 177 | $CF_3$ | 2-pyridyl | 4-morpholinocarbonyl |
| 178 | $CF_3$ | 2-pyridyl | 2-methyl-1-imidazolyl |
| 179 | $CF_3$ | 2-pyridyl | 5-methyl-1-imidazolyl |
| 180 | $CF_3$ | 2-pyridyl | 2-methylsulfonyl-1-imidazolyl |
| 181 | $CF_3$ | 3-pyridyl | 2-(aminosulfonyl)phenyl |
| 182 | $CF_3$ | 3-pyridyl | 2-(methylaminosulfonyl)phenyl |
| 183 | $CF_3$ | 3-pyridyl | 1-pyrrolidinocarbonyl |
| 184 | $CF_3$ | 3-pyridyl | 2-(methylsulfonyl)phenyl |
| 185 | $CF_3$ | 3-pyridyl | 4-morpholino |
| 186 | $CF_3$ | 3-pyridyl | 2-(1'-$CF_3$-tetrazol-2-yl)phenyl |
| 187 | $CF_3$ | 3-pyridyl | 4-morpholinocarbonyl |
| 188 | $CF_3$ | 3-pyridyl | 2-methyl-1-imidazolyl |
| 189 | $CF_3$ | 3-pyridyl | 5-methyl-1-imidazolyl |
| 190 | $CF_3$ | 3-pyridyl | 2-methylsulfonyl-1-imidazolyl |
| 191 | $CF_3$ | 2-pyrimidyl | 2-(aminosulfonyl)phenyl |
| 192 | $CF_3$ | 2-pyrimidyl | 2-(methylaminosulfonyl)phenyl |
| 193 | $CF_3$ | 2-pyrimidyl | 1-pyrrolidinocarbonyl |
| 194 | $CF_3$ | 2-pyrimidyl | 2-(methylsulfonyl)phenyl |
| 195 | $CF_3$ | 2-pyrimidyl | 4-morpholino |
| 196 | $CF_3$ | 2-pyrimidyl | 2-(1'-$CF_3$-tetrazol-2-yl)phenyl |
| 197 | $CF_3$ | 2-pyrimidyl | 4-morpholinocarbonyl |
| 198 | $CF_3$ | 2-pyrimidyl | 2-methyl-1-imidazolyl |
| 199 | $CF_3$ | 2-pyrimidyl | 5-methyl-1-imidazolyl |
| 200 | $CF_3$ | 2-pyrimidyl | 2-methylsulfonyl-1-imidazolyl |
| 201 | $CF_3$ | 5-pyrimidyl | 2-(aminosulfonyl)phenyl |
| 202 | $CF_3$ | 5-pyrimidyl | 2-(methylaminosulfonyl)phenyl |
| 203 | $CF_3$ | 5-pyrimidyl | 1-pyrrolidinocarbonyl |
| 204 | $CF_3$ | 5-pyrimidyl | 2-(methylsulfonyl)phenyl |
| 205 | $CF_3$ | 5-pyrimidyl | 4-morpholino |
| 206 | $CF_3$ | 5-pyrimidyl | 2-(1'-$CF_3$-tetrazol-2-yl)phenyl |
| 207 | $CF_3$ | 5-pyrimidyl | 4-morpholinocarbonyl |
| 208 | $CF_3$ | 5-pyrimidyl | 2-methyl-1-imidazolyl |

TABLE 4-continued

| | | | |
|---|---|---|---|
| 209 | CF$_3$ | 5-pyrimidyl | 5-methyl-1-imidazolyl |
| 210 | CF$_3$ | 5-pyrimidyl | 2-methylsulfonyl-1-imidazolyl |
| 211 | CF$_3$ | 2-Cl-phenyl | 2-(aminosulfonyl)phenyl |
| 212 | CF$_3$ | 2-Cl-phenyl | 2-(methylaminosulfonyl)phenyl |
| 213 | CF$_3$ | 2-Cl-phenyl | 1-pyrrolidinocarbonyl |
| 214 | CF$_3$ | 2-Cl-phenyl | 2-(methylsulfonyl)phenyl |
| 215 | CF$_3$ | 2-Cl-phenyl | 4-morpholino |
| 216 | CF$_3$ | 2-Cl-phenyl | 2-(1'-CF$_3$-tetrazol-2-yl)phenyl |
| 217 | CF$_3$ | 2-Cl-phenyl | 4-morpholinocarbonyl |
| 218 | CF$_3$ | 2-Cl-phenyl | 2-methyl-1-imidazolyl |
| 219 | CF$_3$ | 2-Cl-phenyl | 5-methyl-1-imidazolyl |
| 220 | CF$_3$ | 2-Cl-phenyl | 2-methylsulfonyl-1-imidazolyl |
| 221 | CF$_3$ | 2-F-phenyl | 2-(aminosulfonyl)phenyl |
| 222 | CF$_3$ | 2-F-phenyl | 2-(methylaminosulfonyl)phenyl |
| 223 | CF$_3$ | 2-F-phenyl | 1-pyrrolidinocarbonyl |
| 224 | CF$_3$ | 2-F-phenyl | 2-(methylsulfonyl)phenyl |
| 225 | CF$_3$ | 2-F-phenyl | 4-morpholino |
| 226 | CF$_3$ | 2-F-phenyl | 2-(1'-CF$_3$-tetrazol-2-yl)phenyl |
| 227 | CF$_3$ | 2-F-phenyl | 4-morpholinocarbonyl |
| 228 | CF$_3$ | 2-F-phenyl | 2-methyl-1-imidazolyl |
| 229 | CF$_3$ | 2-F-phenyl | 5-methyl-1-imidazolyl |
| 230 | CF$_3$ | 2-F-phenyl | 2-methylsulfonyl-1-imidazolyl |
| 231 | CF$_3$ | 2,6-diF-phenyl | 2-(aminosulfonyl)phenyl |
| 232 | CF$_3$ | 2,6-diF-phenyl | 2-(methylaminosulfonyl)phenyl |
| 233 | CF$_3$ | 2,6-diF-phenyl | 1-pyrrolidinocarbonyl |
| 234 | CF$_3$ | 2,6-diF-phenyl | 2-(methylsulfonyl)phenyl |
| 235 | CF$_3$ | 2,6-diF-phenyl | 4-morpholino |
| 236 | CF$_3$ | 2,6-diF-phenyl | 2-(1'-CF$_3$-tetrazol-2-yl)phenyl |
| 237 | CF$_3$ | 2,6-diF-phenyl | 4-morpholinocarbonyl |
| 238 | CF$_3$ | 2,6-diF-phenyl | 2-methyl-1-imidazolyl |
| 239 | CF$_3$ | 2,6-diF-phenyl | 5-methyl-1-imidazolyl |
| 240 | CF$_3$ | 2,6-diF-phenyl | 2-methylsulfonyl-1-imidazolyl |
| 241 | SCH$_3$ | phenyl | 2-(aminosulfonyl)phenyl |
| 242 | SCH$_3$ | phenyl | 2-(methylaminosulfonyl)phenyl |
| 243 | SCH$_3$ | phenyl | 1-pyrrolidinocarbonyl |
| 244 | SCH$_3$ | phenyl | 2-(methylsulfonyl)phenyl |
| 245 | SCH$_3$ | phenyl | 4-morpholino |
| 246 | SCH$_3$ | phenyl | 2-(1'-CF$_3$-tetrazol-2-yl)phenyl |
| 247 | SCH$_3$ | phenyl | 4-morpholinocarbonyl |
| 248 | SCH$_3$ | phenyl | 2-methyl-1-imidazolyl |
| 249 | SCH$_3$ | phenyl | 5-methyl-1-imidazolyl |
| 250 | SCH$_3$ | phenyl | 2-methylsulfonyl-1-imidazolyl |
| 251 | SCH$_3$ | 2-pyridyl | 2-(aminosulfonyl)phenyl |
| 252 | SCH$_3$ | 2-pyridyl | 2-(methylaminosulfonyl)phenyl |
| 253 | SCH$_3$ | 2-pyridyl | 1-pyrrolidinocarbonyl |
| 254 | SCH$_3$ | 2-pyridyl | 2-(methylsulfonyl)phenyl |
| 255 | SCH$_3$ | 2-pyridyl | 4-morpholino |
| 256 | SCH$_3$ | 2-pyridyl | 2-(1'-CF$_3$-tetrazol-2-yl)phenyl |
| 257 | SCH$_3$ | 2-pyridyl | 4-morpholinocarbonyl |
| 258 | SCH$_3$ | 2-pyridyl | 2-methyl-1-imidazolyl |
| 259 | SCH$_3$ | 2-pyridyl | 5-methyl-1-imidazolyl |
| 260 | SCH$_3$ | 2-pyridyl | 2-methylsulfonyl-1-imidazolyl |
| 261 | SCH$_3$ | 3-pyridyl | 2-(aminosulfonyl)phenyl |
| 262 | SCH$_3$ | 3-pyridyl | 2-(methylaminosulfonyl)phenyl |
| 263 | SCH$_3$ | 3-pyridyl | 1-pyrrolidinocarbonyl |
| 264 | SCH$_3$ | 3-pyridyl | 2-(methylsulfonyl)phenyl |
| 265 | SCH$_3$ | 3-pyridyl | 4-morpholino |
| 266 | SCH$_3$ | 3-pyridyl | 2-(1'-CF$_3$-tetrazol-2-yl)phenyl |
| 267 | SCH$_3$ | 3-pyridyl | 4-morpholinocarbonyl |
| 268 | SCH$_3$ | 3-pyridyl | 2-methyl-1-imidazolyl |
| 269 | SCH$_3$ | 3-pyridyl | 5-methyl-1-imidazolyl |
| 270 | SCH$_3$ | 3-pyridyl | 2-methylsulfonyl-1-imidazolyl |
| 271 | SCH$_3$ | 2-pyrimidyl | 2-(aminosulfonyl)phenyl |
| 272 | SCH$_3$ | 2-pyrimidyl | 2-(methylaminosulfonyl)phenyl |
| 273 | SCH$_3$ | 2-pyrimidyl | 1-pyrrolidinocarbonyl |
| 274 | SCH$_3$ | 2-pyrimidyl | 2-(methylsulfonyl)phenyl |
| 275 | SCH$_3$ | 2-pyrimidyl | 4-morpholino |
| 276 | SCH$_3$ | 2-pyrimidyl | 2-(1'-CF$_3$-tetrazol-2-yl)phenyl |
| 277 | SCH$_3$ | 2-pyrimidyl | 4-morpholinocarbonyl |
| 278 | SCH$_3$ | 2-pyrimidyl | 2-methyl-1-imidazolyl |
| 279 | SCH$_3$ | 2-pyrimidyl | 5-methyl-1-imidazolyl |
| 280 | SCH$_3$ | 2-pyrimidyl | 2-methylsulfonyl-1-imidazolyl |
| 281 | SCH$_3$ | 5-pyrimidyl | 2-(aminosulfonyl)phenyl |
| 282 | SCH$_3$ | 5-pyrimidyl | 2-(methylaminosulfonyl)phenyl |
| 283 | SCH$_3$ | 5-pyrimidyl | 1-pyrrolidinocarbonyl |
| 284 | SCH$_3$ | 5-pyrimidyl | 2-(methylsulfonyl)phenyl |
| 285 | SCH$_3$ | 5-pyrimidyl | 4-morpholino |
| 286 | SCH$_3$ | 5-pyrimidyl | 2-(1'-CF$_3$-tetrazol-2-yl)phenyl |
| 287 | SCH$_3$ | 5-pyrimidyl | 4-morpholinocarbonyl |

TABLE 4-continued

| | | | |
|---|---|---|---|
| 288 | SCH$_3$ | 5-pyrimidyl | 2-methyl-1-imidazolyl |
| 289 | SCH$_3$ | 5-pyrimidyl | 5-methyl-1-imidazolyl |
| 290 | SCH$_3$ | 5-pyrimidyl | 2-methylsulfonyl-1-imidazolyl |
| 291 | SCH$_3$ | 2-Cl-phenyl | 2-(aminosulfonyl)phenyl |
| 292 | SCH$_3$ | 2-Cl-phenyl | 2-(methylaminosulfonyl)phenyl |
| 293 | SCH$_3$ | 2-Cl-phenyl | 1-pyrrolidinocarbonyl |
| 294 | SCH$_3$ | 2-Cl-phenyl | 2-(methylsulfonyl)phenyl |
| 295 | SCH$_3$ | 2-Cl-phenyl | 4-morpholino |
| 296 | SCH$_3$ | 2-Cl-phenyl | 2-(1'-CF$_3$-tetrazol-2-yl)phenyl |
| 297 | SCH$_3$ | 2-Cl-phenyl | 4-morpholinocarbonyl |
| 298 | SCH$_3$ | 2-Cl-phenyl | 2-methyl-1-imidazolyl |
| 299 | SCH$_3$ | 2-Cl-phenyl | 5-methyl-1-imidazolyl |
| 300 | SCH$_3$ | 2-Cl-phenyl | 2-methylsulfonyl-1-imidazolyl |
| 301 | SCH$_3$ | 2-F-phenyl | 2-(aminosulfonyl)phenyl |
| 302 | SCH$_3$ | 2-F-phenyl | 2-(methylaminosulfonyl)phenyl |
| 303 | SCH$_3$ | 2-F-phenyl | 1-pyrrolidinocarbonyl |
| 304 | SCH$_3$ | 2-F-phenyl | 2-(methylsulfonyl)phenyl |
| 305 | SCH$_3$ | 2-F-phenyl | 4-morpholino |
| 306 | SCH$_3$ | 2-F-phenyl | 2-(1'-CF$_3$-tetrazol-2-yl)phenyl |
| 307 | SCH$_3$ | 2-F-phenyl | 4-morpholinocarbonyl |
| 308 | SCH$_3$ | 2-F-phenyl | 2-methyl-1-imidazolyl |
| 309 | SCH$_3$ | 2-F-phenyl | 5-methyl-1-imidazolyl |
| 310 | SCH$_3$ | 2-F-phenyl | 2-methylsulfonyl-1-imidazolyl |
| 311 | SCH$_3$ | 2,6-diF-phenyl | 2-(aminosulfonyl)phenyl |
| 312 | SCH$_3$ | 2,6-diF-phenyl | 2-(methylaminosulfonyl)phenyl |
| 313 | SCH$_3$ | 2,6-diF-phenyl | 1-pyrrolidinocarbonyl |
| 314 | SCH$_3$ | 2,6-diF-phenyl | 2-(methylsulfonyl)phenyl |
| 315 | SCH$_3$ | 2,6-diF-phenyl | 4-morpholino |
| 316 | SCH$_3$ | 2,6-diF-phenyl | 2-(1'-CF$_3$-tetrazol-2-yl)phenyl |
| 317 | SCH$_3$ | 2,6-diF-phenyl | 4-morpholinocarbonyl |
| 318 | SCH$_3$ | 2,6-diF-phenyl | 2-methyl-1-imidazolyl |
| 319 | SCH$_3$ | 2,6-diF-phenyl | 5-methyl-1-imidazolyl |
| 320 | SCH$_3$ | 2,6-diF-phenyl | 2-methylsulfonyl-1-imidazolyl |
| 321 | SOCH$_3$ | phenyl | 2-(aminosulfonyl)phenyl |
| 322 | SOCH$_3$ | phenyl | 2-(methylaminosulfonyl)phenyl |
| 323 | SOCH$_3$ | phenyl | 1-pyrrolidinocarbonyl |
| 324 | SOCH$_3$ | phenyl | 2-(methylsulfonyl)phenyl |
| 325 | SOCH$_3$ | phenyl | 4-morpholino |
| 326 | SOCH$_3$ | phenyl | 2-(1'-CF$_3$-tetrazol-2-yl)phenyl |
| 327 | SOCH$_3$ | phenyl | 4-morpholinocarbonyl |
| 328 | SOCH$_3$ | phenyl | 2-methyl-1-imidazolyl |
| 329 | SOCH$_3$ | phenyl | 5-methyl-1-imidazolyl |
| 330 | SOCH$_3$ | phenyl | 2-methylsulfonyl-1-imidazolyl |
| 331 | SOCH$_3$ | 2-pyridyl | 2-(aminosulfonyl)phenyl |
| 332 | SOCH$_3$ | 2-pyridyl | 2-(methylaminosulfonyl)phenyl |
| 333 | SOCH$_3$ | 2-pyridyl | 1-pyrrolidinocarbonyl |
| 334 | SOCH$_3$ | 2-pyridyl | 2-(methylsulfonyl)phenyl |
| 335 | SOCH$_3$ | 2-pyridyl | 4-morpholino |
| 336 | SOCH$_3$ | 2-pyridyl | 2-(1'-CF$_3$-tetrazol-2-yl)phenyl |
| 337 | SOCH$_3$ | 2-pyridyl | 4-morpholinocarbonyl |
| 338 | SOCH$_3$ | 2-pyridyl | 2-methyl-1-imidazolyl |
| 339 | SOCH$_3$ | 2-pyridyl | 5-methyl-1-imidazolyl |
| 340 | SOCH$_3$ | 2-pyridyl | 2-methylsulfonyl-1-imidazolyl |
| 341 | SOCH$_3$ | 3-pyridyl | 2-(aminosulfonyl)phenyl |
| 342 | SOCH$_3$ | 3-pyridyl | 2-(methylaminosulfonyl)phenyl |
| 343 | SOCH$_3$ | 3-pyridyl | 1-pyrrolidinocarbonyl |
| 344 | SOCH$_3$ | 3-pyridyl | 2-(methylsulfonyl)phenyl |
| 345 | SOCH$_3$ | 3-pyridyl | 4-morpholino |
| 346 | SOCH$_3$ | 3-pyridyl | 2-(1'-CF$_3$-tetrazol-2-yl)phenyl |
| 347 | SOCH$_3$ | 3-pyridyl | 4-morpholinocarbonyl |
| 348 | SOCH$_3$ | 3-pyridyl | 2-methyl-1-imidazolyl |
| 349 | SOCH$_3$ | 3-pyridyl | 5-methyl-1-imidazolyl |
| 350 | SOCH$_3$ | 3-pyridyl | 2-methylsulfonyl-1-imidazolyl |
| 351 | SOCH$_3$ | 2-pyrimidyl | 2-(aminosulfonyl)phenyl |
| 352 | SOCH$_3$ | 2-pyrimidyl | 2-(methylaminosulfonyl)phenyl |
| 353 | SOCH$_3$ | 2-pyrimidyl | 1-pyrrolidinocarbonyl |
| 354 | SOCH$_3$ | 2-pyrimidyl | 2-(methylsulfonyl)phenyl |
| 355 | SOCH$_3$ | 2-pyrimidyl | 4-morpholino |
| 356 | SOCH$_3$ | 2-pyrimidyl | 2-(1'-CF$_3$-tetrazol-2-yl)phenyl |
| 357 | SOCH$_3$ | 2-pyrimidyl | 4-morpholinocarbonyl |
| 358 | SOCH$_3$ | 2-pyrimidyl | 2-methyl-1-imidazolyl |
| 359 | SOCH$_3$ | 2-pyrimidyl | 5-methyl-1-imidazolyl |
| 360 | SOCH$_3$ | 2-pyrimidyl | 2-methylsulfonyl-1-imidazolyl |
| 361 | SOCH$_3$ | 5-pyrimidyl | 2-(aminosulfonyl)phenyl |
| 362 | SOCH$_3$ | 5-pyrimidyl | 2-(methylaminosulfonyl)phenyl |
| 363 | SOCH$_3$ | 5-pyrimidyl | 1-pyrrolidinocarbonyl |
| 364 | SOCH$_3$ | 5-pyrimidyl | 2-(methylsulfonyl)phenyl |
| 365 | SOCH$_3$ | 5-pyrimidyl | 4-morpholino |
| 366 | SOCH$_3$ | 5-pyrimidyl | 2-(1'-CF$_3$-tetrazol-2-yl)phenyl |

TABLE 4-continued

| | | | |
|---|---|---|---|
| 367 | SOCH$_3$ | 5-pyrimidyl | 4-morpholinocarbonyl |
| 368 | SOCH$_3$ | 5-pyrimidyl | 2-methyl-1-imidazolyl |
| 369 | SOCH$_3$ | 5-pyrimidyl | 5-methyl-1-imidazolyl |
| 370 | SOCH$_3$ | 5-pyrimidyl | 2-methylsulfonyl-1-imidazolyl |
| 371 | SOCH$_3$ | 2-Cl-phenyl | 2-(aminosulfonyl)phenyl |
| 372 | SOCH$_3$ | 2-Cl-phenyl | 2-(methylaminosulfonyl)phenyl |
| 373 | SOCH$_3$ | 2-Cl-phenyl | 1-pyrrolidinocarbonyl |
| 374 | SOCH$_3$ | 2-Cl-phenyl | 2-(methylsulfonyl)phenyl |
| 375 | SOCH$_3$ | 2-Cl-phenyl | 4-morpholino |
| 376 | SOCH$_3$ | 2-Cl-phenyl | 2-(1'-CF$_3$-tetrazol-2-yl)phenyl |
| 377 | SOCH$_3$ | 2-Cl-phenyl | 4-morpholinocarbonyl |
| 378 | SOCH$_3$ | 2-Cl-phenyl | 2-methyl-1-imidazolyl |
| 379 | SOCH$_3$ | 2-Cl-phenyl | 5-methyl-1-imidazolyl |
| 380 | SOCH$_3$ | 2-Cl-phenyl | 2-methylsulfonyl-1-imidazolyl |
| 381 | SOCH$_3$ | 2-F-phenyl | 2-(aminosulfonyl)phenyl |
| 382 | SOCH$_3$ | 2-F-phenyl | 2-(methylaminosulfonyl)phenyl |
| 383 | SOCH$_3$ | 2-F-phenyl | 1-pyrrolidinocarbonyl |
| 384 | SOCH$_3$ | 2-F-phenyl | 2-(methylsulfonyl)phenyl |
| 385 | SOCH$_3$ | 2-F-phenyl | 4-morpholino |
| 386 | SOCH$_3$ | 2-F-phenyl | 2-(1'-CF$_3$-tetrazol-2-yl)phenyl |
| 387 | SOCH$_3$ | 2-F-phenyl | 4-morpholinocarbonyl |
| 388 | SOCH$_3$ | 2-F-phenyl | 2-methyl-1-imidazolyl |
| 389 | SOCH$_3$ | 2-F-phenyl | 5-methyl-1-imidazolyl |
| 390 | SOCH$_3$ | 2-F-phenyl | 2-methylsulfonyl-1-imidazolyl |
| 391 | SOCH$_3$ | 2,6-diF-phenyl | 2-(aminosulfonyl)phenyl |
| 392 | SOCH$_3$ | 2,6-diF-phenyl | 2-(methylaminosulfonyl)phenyl |
| 393 | SOCH$_3$ | 2,6-diF-phenyl | 1-pyrrolidinocarbonyl |
| 394 | SOCH$_3$ | 2,6-diF-phenyl | 2-(methylsulfonyl)phenyl |
| 395 | SOCH$_3$ | 2,6-diF-phenyl | 4-morpholino |
| 396 | SOCH$_3$ | 2,6-diF-phenyl | 2-(1'-CF$_3$-tetrazol-2-yl)phenyl |
| 397 | SOCH$_3$ | 2,6-diF-phenyl | 4-morpholinocarbonyl |
| 398 | SOCH$_3$ | 2,6-diF-phenyl | 2-methyl-1-imidazolyl |
| 399 | SOCH$_3$ | 2,6-diF-phenyl | 5-methyl-1-imidazolyl |
| 400 | SOCH$_3$ | 2,6-diF-phenyl | 2-methylsulfonyl-1-imidazolyl |
| 401 | SO$_2$CH$_3$ | phenyl | 2-(aminosulfonyl)phenyl |
| 402 | SO$_2$CH$_3$ | phenyl | 2-(methylaminosulfonyl)phenyl |
| 403 | SO$_2$CH$_3$ | phenyl | 1-pyrrolidinocarbonyl |
| 404 | SO$_2$CH$_3$ | phenyl | 2-(methylsulfonyl)phenyl |
| 405 | SO$_2$CH$_3$ | phenyl | 4-morpholino |
| 406 | SO$_2$CH$_3$ | phenyl | 2-(1'-CF$_3$-tetrazol-2-yl)phenyl |
| 407 | SO$_2$CH$_3$ | phenyl | 4-morpholinocarbonyl |
| 408 | SO$_2$CH$_3$ | phenyl | 2-methyl-1-imidazolyl |
| 409 | SO$_2$CH$_3$ | phenyl | 5-methyl-1-imidazolyl |
| 410 | SO$_2$CH$_3$ | phenyl | 2-methylsulfonyl-1-imidazolyl |
| 411 | SO$_2$CH$_3$ | 2-pyridyl | 2-(aminosulfonyl)phenyl |
| 412 | SO$_2$CH$_3$ | 2-pyridyl | 2-(methylaminosulfonyl)phenyl |
| 413 | SO$_2$CH$_3$ | 2-pyridyl | 1-pyrrolidinocarbonyl |
| 414 | SO$_2$CH$_3$ | 2-pyridyl | 2-(methylsulfonyl)phenyl |
| 415 | SO$_2$CH$_3$ | 2-pyridyl | 4-morpholino |
| 416 | SO$_2$CH$_3$ | 2-pyridyl | 2-(1'-CF$_3$-tetrazol-2-yl)phenyl |
| 417 | SO$_2$CH$_3$ | 2-pyridyl | 4-morpholinocarbonyl |
| 418 | SO$_2$CH$_3$ | 2-pyridyl | 2-methyl-1-imidazolyl |
| 419 | SO$_2$CH$_3$ | 2-pyridyl | 5-methyl-1-imidazolyl |
| 420 | SO$_2$CH$_3$ | 2-pyridyl | 2-methylsulfonyl-1-imidazolyl |
| 421 | SO$_2$CH$_3$ | 3-pyridyl | 2-(aminosulfonyl)phenyl |
| 422 | SO$_2$CH$_3$ | 3-pyridyl | 2-(methylaminosulfonyl)phenyl |
| 423 | SO$_2$CH$_3$ | 3-pyridyl | 1-pyrrolidinocarbonyl |
| 424 | SO$_2$CH$_3$ | 3-pyridyl | 2-(methylsulfonyl)phenyl |
| 425 | SO$_2$CH$_3$ | 3-pyridyl | 4-morpholino |
| 426 | SO$_2$CH$_3$ | 3-pyridyl | 2-(1'-CF$_3$-tetrazol-2-yl)phenyl |
| 427 | SO$_2$CH$_3$ | 3-pyridyl | 4-morpholinocarbonyl |
| 428 | SO$_2$CH$_3$ | 3-pyridyl | 2-methyl-1-imidazolyl |
| 429 | SO$_2$CH$_3$ | 3-pyridyl | 5-methyl-1-imidazolyl |
| 430 | SO$_2$CH$_3$ | 3-pyridyl | 2-methylsulfonyl-1-imidazolyl |
| 431 | SO$_2$CH$_3$ | 2-pyrimidyl | 2-(aminosulfonyl)phenyl |
| 432 | SO$_2$CH$_3$ | 2-pyrimidyl | 2-(methylaminosulfonyl)phenyl |
| 433 | SO$_2$CH$_3$ | 2-pyrimidyl | 1-pyrrolidinocarbonyl |
| 434 | SO$_2$CH$_3$ | 2-pyrimidyl | 2-(methylsulfonyl)phenyl |
| 435 | SO$_2$CH$_3$ | 2-pyrimidyl | 4-morpholino |
| 436 | SO$_2$CH$_3$ | 2-pyrimidyl | 2-(1'-CF$_3$-tetrazol-2-yl)phenyl |
| 437 | SO$_2$CH$_3$ | 2-pyrimidyl | 4-morpholinocarbonyl |
| 438 | SO$_2$CH$_3$ | 2-pyrimidyl | 2-methyl-1-imidazolyl |
| 439 | SO$_2$CH$_3$ | 2-pyrimidyl | 5-methyl-1-imidazolyl |
| 440 | SO$_2$CH$_3$ | 2-pyrimidyl | 2-methylsulfonyl-1-imidazolyl |
| 441 | SO$_2$CH$_3$ | 5-pyrimidyl | 2-(aminosulfonyl)phenyl |
| 442 | SO$_2$CH$_3$ | 5-pyrimidyl | 2-(methylaminosulfonyl)phenyl |
| 443 | SO$_2$CH$_3$ | 5-pyrimidyl | 1-pyrrolidinocarbonyl |
| 444 | SO$_2$CH$_3$ | 5-pyrimidyl | 2-(methylsulfonyl)phenyl |
| 445 | SO$_2$CH$_3$ | 5-pyrimidyl | 4-morpholino |

TABLE 4-continued

| | | | |
|---|---|---|---|
| 446 | $SO_2CH_3$ | 5-pyrimidyl | 2-(1'-$CF_3$-tetrazol-2-yl)phenyl |
| 447 | $SO_2CH_3$ | 5-pyrimidyl | 4-morpholinocarbonyl |
| 448 | $SO_2CH_3$ | 5-pyrimidyl | 2-methyl-1-imidazolyl |
| 449 | $SO_2CH_3$ | 5-pyrimidyl | 5-methyl-1-imidazolyl |
| 450 | $SO_2CH_3$ | 5-pyrimidyl | 2-methylsulfonyl-1-imidazolyl |
| 451 | $SO_2CH_3$ | 2-Cl-phenyl | 2-(aminosulfonyl)phenyl |
| 452 | $SO_2CH_3$ | 2-Cl-phenyl | 2-(methylaminosulfonyl)phenyl |
| 453 | $SO_2CH_3$ | 2-Cl-phenyl | 1-pyrrolidinocarbonyl |
| 454 | $SO_2CH_3$ | 2-Cl-phenyl | 2-(methylsulfonyl)phenyl |
| 455 | $SO_2CH_3$ | 2-Cl-phenyl | 4-morpholino |
| 456 | $SO_2CH_3$ | 2-Cl-phenyl | 2-(1'-$CF_3$-tetrazol-2-yl)phenyl |
| 457 | $SO_2CH_3$ | 2-Cl-phenyl | 4-morpholinocarbonyl |
| 458 | $SO_2CH_3$ | 2-Cl-phenyl | 2-methyl-1-imidazolyl |
| 459 | $SO_2CH_3$ | 2-Cl-phenyl | 5-methyl-1-imidazolyl |
| 460 | $SO_2CH_3$ | 2-Cl-phenyl | 2-methylsulfonyl-1-imidazolyl |
| 461 | $SO_2CH_3$ | 2-F-phenyl | 2-(aminosulfonyl)phenyl |
| 462 | $SO_2CH_3$ | 2-F-phenyl | 2-(methylaminosulfonyl)phenyl |
| 463 | $SO_2CH_3$ | 2-F-phenyl | 1-pyrrolidinocarbonyl |
| 464 | $SO_2CH_3$ | 2-F-phenyl | 2-(methylsulfonyl)phenyl |
| 465 | $SO_2CH_3$ | 2-F-phenyl | 4-morpholino |
| 466 | $SO_2CH_3$ | 2-F-phenyl | 2-(1'-$CF_3$-tetrazol-2-yl)phenyl |
| 467 | $SO_2CH_3$ | 2-F-phenyl | 4-morpholinocarbonyl |
| 468 | $SO_2CH_3$ | 2-F-phenyl | 2-methyl-1-imidazolyl |
| 469 | $SO_2CH_3$ | 2-F-phenyl | 5-methyl-1-imidazolyl |
| 470 | $SO_2CH_3$ | 2-F-phenyl | 2-methylsulfonyl-1-imidazolyl |
| 471 | $SO_2CH_3$ | 2,6-diF-phenyl | 2-(aminosulfonyl)phenyl |
| 472 | $SO_2CH_3$ | 2,6-diF-phenyl | 2-(methylaminosulfonyl)phenyl |
| 473 | $SO_2CH_3$ | 2,6-diF-phenyl | 1-pyrrolidinocarbonyl |
| 474 | $SO_2CH_3$ | 2,6-diF-phenyl | 2-(methylsulfonyl)phenyl |
| 475 | $SO_2CH_3$ | 2,6-diF-phenyl | 4-morpholino |
| 476 | $SO_2CH_3$ | 2,6-diF-phenyl | 2-(1'-$CF_3$-tetrazol-2-yl)phenyl |
| 477 | $SO_2CH_3$ | 2,6-diF-phenyl | 4-morpholinocarbonyl |
| 478 | $SO_2CH_3$ | 2,6-diF-phenyl | 2-methyl-1-imidazolyl |
| 479 | $SO_2CH_3$ | 2,6-diF-phenyl | 5-methyl-1-imidazolyl |
| 480 | $SO_2CH_3$ | 2,6-diF-phenyl | 2-methylsulfonyl-1-imidazolyl |
| 481 | $CH_2NHSO_2CH_3$ | phenyl | 2-(aminosulfonyl)phenyl |
| 482 | $CH_2NHSO_2CH_3$ | phenyl | 2-(methylaminosulfonyl)phenyl |
| 483 | $CH_2NHSO_2CH_3$ | phenyl | 1-pyrrolidinocarbonyl |
| 484 | $CH_2NHSO_2CH_3$ | phenyl | 2-(methylsulfonyl)phenyl |
| 485 | $CH_2NHSO_2CH_3$ | phenyl | 4-morpholino |
| 486 | $CH_2NHSO_2CH_3$ | phenyl | 2-(1'-$CF_3$-tetrazol-2-yl)phenyl |
| 487 | $CH_2NHSO_2CH_3$ | phenyl | 4-morpholinocarbonyl |
| 488 | $CH_2NHSO_2CH_3$ | phenyl | 2-methyl-1-imidazolyl |
| 489 | $CH_2NHSO_2CH_3$ | phenyl | 5-methyl-1-imidazolyl |
| 490 | $CH_2NHSO_2CH_3$ | phenyl | 2-methylsulfonyl-1-imidazolyl |
| 491 | $CH_2NHSO_2CH_3$ | 2-pyridyl | 2-(aminosulfonyl)phenyl |
| 492 | $CH_2NHSO_2CH_3$ | 2-pyridyl | 2-(methylaminosulfonyl)phenyl |
| 493 | $CH_2NHSO_2CH_3$ | 2-pyridyl | 1-pyrrolidinocarbonyl |
| 494 | $CH_2NHSO_2CH_3$ | 2-pyridyl | 2-(methylsulfonyl)phenyl |
| 495 | $CH_2NHSO_2CH_3$ | 2-pyridyl | 4-morpholino |
| 496 | $CH_2NHSO_2CH_3$ | 2-pyridyl | 2-(1'-$CF_3$-tetrazol-2-yl)phenyl |
| 497 | $CH_2NHSO_2CH_3$ | 2-pyridyl | 4-morpholinocarbonyl |
| 498 | $CH_2NHSO_2CH_3$ | 2-pyridyl | 2-methyl-1-imidazolyl |
| 499 | $CH_2NHSO_2CH_3$ | 2-pyridyl | 5-methyl-1-imidazolyl |
| 500 | $CH_2NHSO_2CH_3$ | 2-pyridyl | 2-methylsulfonyl-1-imidazolyl |
| 501 | $CH_2NHSO_2CH_3$ | 3-pyridyl | 2-(aminosulfonyl)phenyl |
| 502 | $CH_2NHSO_2CH_3$ | 3-pyridyl | 2-(methylaminosulfonyl)phenyl |
| 503 | $CH_2NHSO_2CH_3$ | 3-pyridyl | 1-pyrrolidinocarbonyl |
| 504 | $CH_2NHSO_2CH_3$ | 3-pyridyl | 2-(methylsulfonyl)phenyl |
| 505 | $CH_2NHSO_2CH_3$ | 3-pyridyl | 4-morpholino |
| 506 | $CH_2NHSO_2CH_3$ | 3-pyridyl | 2-(1'-$CF_3$-tetrazol-2-yl)phenyl |
| 507 | $CH_2NHSO_2CH_3$ | 3-pyridyl | 4-morpholinocarbonyl |
| 508 | $CH_2NHSO_2CH_3$ | 3-pyridyl | 2-methyl-1-imidazolyl |
| 509 | $CH_2NHSO_2CH_3$ | 3-pyridyl | 5-methyl-1-imidazolyl |
| 510 | $CH_2NHSO_2CH_3$ | 3-pyridyl | 2-methylsulfonyl-1-imidazolyl |
| 511 | $CH_2NHSO_2CH_3$ | 2-pyrimidyl | 2-(aminosulfonyl)phenyl |
| 512 | $CH_2NHSO_2CH_3$ | 2-pyrimidyl | 2-(methylaminosulfonyl)phenyl |
| 513 | $CH_2NHSO_2CH_3$ | 2-pyrimidyl | 1-pyrrolidinocarbonyl |
| 514 | $CH_2NHSO_2CH_3$ | 2-pyrimidyl | 2-(methylsulfonyl)phenyl |
| 515 | $CH_2NHSO_2CH_3$ | 2-pyrimidyl | 4-morpholino |
| 516 | $CH_2NHSO_2CH_3$ | 2-pyrimidyl | 2-(1'-$CF_3$-tetrazol-2-yl)phenyl |
| 517 | $CH_2NHSO_2CH_3$ | 2-pyrimidyl | 4-morpholinocarbonyl |
| 518 | $CH_2NHSO_2CH_3$ | 2-pyrimidyl | 2-methyl-1-imidazolyl |
| 519 | $CH_2NHSO_2CH_3$ | 2-pyrimidyl | 5-methyl-1-imidazolyl |
| 520 | $CH_2NHSO_2CH_3$ | 2-pyrimidyl | 2-methylsulfonyl-1-imidazolyl |
| 521 | $CH_2NHSO_2CH_3$ | 5-pyrimidyl | 2-(aminosulfonyl)phenyl |
| 522 | $CH_2NHSO_2CH_3$ | 5-pyrimidyl | 2-(methylaminosulfonyl)phenyl |
| 523 | $CH_2NHSO_2CH_3$ | 5-pyrimidyl | 1-pyrrolidinocarbonyl |
| 524 | $CH_2NHSO_2CH_3$ | 5-pyrimidyl | 2-(methylsulfonyl)phenyl |

TABLE 4-continued

| | | | |
|---|---|---|---|
| 525 | $CH_2NHSO_2CH_3$ | 5-pyrimidyl | 4-morpholino |
| 526 | $CH_2NHSO_2CH_3$ | 5-pyrimidyl | 2-(1'-$CF_3$-tetrazol-2-yl)phenyl |
| 527 | $CH_2NHSO_2CH_3$ | 5-pyrimidyl | 4-morpholinocarbonyl |
| 528 | $CH_2NHSO_2CH_3$ | 5-pyrimidyl | 2-methyl-1-imidazolyl |
| 529 | $CH_2NHSO_2CH_3$ | 5-pyrimidyl | 5-methyl-1-imidazolyl |
| 530 | $CH_2NHSO_2CH_3$ | 5-pyrimidyl | 2-methylsulfonyl-1-imidazolyl |
| 531 | $CH_2NHSO_2CH_3$ | 2-Cl-phenyl | 2-(aminosulfonyl)phenyl |
| 532 | $CH_2NHSO_2CH_3$ | 2-Cl-phenyl | 2-(methylaminosulfonyl)phenyl |
| 533 | $CH_2NHSO_2CH_3$ | 2-Cl-phenyl | 1-pyrrolidinocarbonyl |
| 534 | $CH_2NHSO_2CH_3$ | 2-Cl-phenyl | 2-(methylsulfonyl)phenyl |
| 535 | $CH_2NHSO_2CH_3$ | 2-Cl-phenyl | 4-morpholino |
| 536 | $CH_2NHSO_2CH_3$ | 2-Cl-phenyl | 2-(1'-$CF_3$-tetrazol-2-yl)phenyl |
| 537 | $CH_2NHSO_2CH_3$ | 2-Cl-phenyl | 4-morpholinocarbonyl |
| 538 | $CH_2NHSO_2CH_3$ | 2-Cl-phenyl | 2-methyl-1-imidazolyl |
| 539 | $CH_2NHSO_2CH_3$ | 2-Cl-phenyl | 5-methyl-1-imidazolyl |
| 540 | $CH_2NHSO_2CH_3$ | 2-Cl-phenyl | 2-methylsulfonyl-1-imidazolyl |
| 541 | $CH_2NHSO_2CH_3$ | 2-F-phenyl | 2-(aminosulfonyl)phenyl |
| 542 | $CH_2NHSO_2CH_3$ | 2-F-phenyl | 2-(methylaminosulfonyl)phenyl |
| 543 | $CH_2NHSO_2CH_3$ | 2-F-phenyl | 1-pyrrolidinocarbonyl |
| 544 | $CH_2NHSO_2CH_3$ | 2-F-phenyl | 2-(methylsulfonyl)phenyl |
| 545 | $CH_2NHSO_2CH_3$ | 2-F-phenyl | 4-morpholino |
| 546 | $CH_2NHSO_2CH_3$ | 2-F-phenyl | 2-(1'-$CF_3$-tetrazol-2-yl)phenyl |
| 547 | $CH_2NHSO_2CH_3$ | 2-F-phenyl | 4-morpholinocarbonyl |
| 548 | $CH_2NHSO_2CH_3$ | 2-F-phenyl | 2-methyl-1-imidazolyl |
| 549 | $CH_2NHSO_2CH_3$ | 2-F-phenyl | 5-methyl-1-imidazolyl |
| 550 | $CH_2NHSO_2CH_3$ | 2-F-phenyl | 2-methylsulfonyl-1-imidazolyl |
| 551 | $CH_2NHSO_2CH_3$ | 2,6-diF-phenyl | 2-(aminosulfonyl)phenyl |
| 552 | $CH_2NHSO_2CH_3$ | 2,6-diF-phenyl | 2-(methylaminosulfonyl)phenyl |
| 553 | $CH_2NHSO_2CH_3$ | 2,6-diF-phenyl | 1-pyrrolidinocarbonyl |
| 554 | $CH_2NHSO_2CH_3$ | 2,6-diF-phenyl | 2-(methylsulfonyl)phenyl |
| 555 | $CH_2NHSO_2CH_3$ | 2,6-diF-phenyl | 4-morpholino |
| 556 | $CH_2NHSO_2CH_3$ | 2,6-diF-phenyl | 2-(1'-$CF_3$-tetrazol-2-yl)phenyl |
| 557 | $CH_2NHSO_2CH_3$ | 2,6-diF-phenyl | 4-morpholinocarbonyl |
| 558 | $CH_2NHSO_2CH_3$ | 2,6-diF-phenyl | 2-methyl-1-imidazolyl |
| 559 | $CH_2NHSO_2CH_3$ | 2,6-diF-phenyl | 5-methyl-1-imidazolyl |
| 560 | $CH_2NHSO_2CH_3$ | 2,6-diF-phenyl | 2-methylsulfonyl-1-imidazolyl |
| 561 | Cl | phenyl | 2-(aminosulfonyl)phenyl |
| 562 | Cl | phenyl | 2-(methylaminosulfonyl)phenyl |
| 563 | Cl | phenyl | 1-pyrrolidinocarbonyl |
| 564 | Cl | phenyl | 2-(methylsulfonyl)phenyl |
| 565 | Cl | phenyl | 4-morpholino |
| 566 | Cl | phenyl | 2-(1'-$CF_3$-tetrazol-2-yl)phenyl |
| 567 | Cl | phenyl | 4-morpholinocarbonyl |
| 568 | Cl | phenyl | 2-methyl-1-imidazolyl |
| 569 | Cl | phenyl | 5-methyl-1-imidazolyl |
| 570 | Cl | phenyl | 2-methylsulfonyl-1-imidazolyl |
| 571 | Cl | 2-pyridyl | 2-(aminosulfonyl)phenyl |
| 572 | Cl | 2-pyridyl | 2-(methylaminosulfonyl)phenyl |
| 573 | Cl | 2-pyridyl | 1-pyrrolidinocarbonyl |
| 574 | Cl | 2-pyridyl | 2-(methylsulfonyl)phenyl |
| 575 | Cl | 2-pyridyl | 4-morpholino |
| 576 | Cl | 2-pyridyl | 2-(1'-$CF_3$-tetrazol-2-yl)phenyl |
| 577 | Cl | 2-pyridyl | 4-morpholinocarbonyl |
| 578 | Cl | 2-pyridyl | 2-methyl-1-imidazolyl |
| 579 | Cl | 2-pyridyl | 5-methyl-1-imidazolyl |
| 580 | Cl | 2-pyridyl | 2-methylsulfonyl-1-imidazolyl |
| 581 | Cl | 3-pyridyl | 2-(aminosulfonyl)phenyl |
| 582 | Cl | 3-pyridyl | 2-(methylaminosulfonyl)phenyl |
| 583 | Cl | 3-pyridyl | 1-pyrrolidinocarbonyl |
| 584 | Cl | 3-pyridyl | 2-(methylsulfonyl)phenyl |
| 585 | Cl | 3-pyridyl | 4-morpholino |
| 586 | Cl | 3-pyridyl | 2-(1'-$CF_3$-tetrazol-2-yl)phenyl |
| 587 | Cl | 3-pyridyl | 4-morpholinocarbonyl |
| 588 | Cl | 3-pyridyl | 2-methyl-1-imidazolyl |
| 589 | Cl | 3-pyridyl | 5-methyl-1-imidazolyl |
| 590 | Cl | 3-pyridyl | 2-methylsulfonyl-1-imidazolyl |
| 591 | Cl | 2-pyrimidyl | 2-(aminosulfonyl)phenyl |
| 592 | Cl | 2-pyrimidyl | 2-(methylaminosulfonyl)phenyl |
| 593 | Cl | 2-pyrimidyl | 1-pyrrolidinocarbonyl |
| 594 | Cl | 2-pyrimidyl | 2-(methylsulfonyl)phenyl |
| 595 | Cl | 2-pyrimidyl | 4-morpholino |
| 596 | Cl | 2-pyrimidyl | 2-(1'-$CF_3$-tetrazol-2-yl)phenyl |
| 597 | Cl | 2-pyrimidyl | 4-morpholinocarbonyl |
| 598 | Cl | 2-pyrimidyl | 2-methyl-1-imidazolyl |
| 599 | Cl | 2-pyrimidyl | 5-methyl-1-imidazolyl |
| 600 | Cl | 2-pyrimidyl | 2-methylsulfonyl-1-imidazolyl |
| 601 | Cl | 5-pyrimidyl | 2-(aminosulfonyl)phenyl |
| 602 | Cl | 5-pyrimidyl | 2-(methylaminosulfonyl)phenyl |
| 603 | Cl | 5-pyrimidyl | 1-pyrrolidinocarbonyl |

TABLE 4-continued

| | | | |
|---|---|---|---|
| 604 | Cl | 5-pyrimidyl | 2-(methylsulfonyl)phenyl |
| 605 | Cl | 5-pyrimidyl | 4-morpholino |
| 606 | Cl | 5-pyrimidyl | 2-(1'-CF$_3$-tetrazol-2-yl)phenyl |
| 607 | Cl | 5-pyrimidyl | 4-morpholinocarbonyl |
| 608 | Cl | 5-pyrimidyl | 2-methyl-1-imidazolyl |
| 609 | Cl | 5-pyrimidyl | 5-methyl-1-imidazolyl |
| 610 | Cl | 5-pyrimidyl | 2-methylsulfonyl-1-imidazolyl |
| 611 | Cl | 2-Cl-phenyl | 2-(aminosulfonyl)phenyl |
| 612 | Cl | 2-Cl-phenyl | 2-(methylaminosulfonyl)phenyl |
| 613 | Cl | 2-Cl-phenyl | 1-pyrrolidinocarbonyl |
| 614 | Cl | 2-Cl-phenyl | 2-(methylsulfonyl)phenyl |
| 615 | Cl | 2-Cl-phenyl | 4-morpholino |
| 616 | Cl | 2-Cl-phenyl | 2-(1'-CF$_3$-tetrazol-2-yl)phenyl |
| 617 | Cl | 2-Cl-phenyl | 4-morpholinocarbonyl |
| 618 | Cl | 2-Cl-phenyl | 2-methyl-1-imidazolyl |
| 619 | Cl | 2-Cl-phenyl | 5-methyl-1-imidazolyl |
| 620 | Cl | 2-Cl-phenyl | 2-methylsulfonyl-1-imidazolyl |
| 621 | Cl | 2-F-phenyl | 2-(aminosulfonyl)phenyl |
| 622 | Cl | 2-F-phenyl | 2-(methylaminosulfonyl)phenyl |
| 623 | Cl | 2-F-phenyl | 1-pyrrolidinocarbonyl |
| 624 | Cl | 2-F-phenyl | 2-(methylsulfonyl)phenyl |
| 625 | Cl | 2-F-phenyl | 4-morpholino |
| 626 | Cl | 2-F-phenyl | 2-(1'-CF$_3$-tetrazol-2-yl)phenyl |
| 627 | Cl | 2-F-phenyl | 4-morpholinocarbonyl |
| 628 | Cl | 2-F-phenyl | 2-methyl-1-imidazolyl |
| 629 | Cl | 2-F-phenyl | 5-methyl-1-imidazolyl |
| 630 | Cl | 2-F-phenyl | 2-methylsulfonyl-1-imidazolyl |
| 631 | Cl | 2,6-diF-phenyl | 2-(aminosulfonyl)phenyl |
| 632 | Cl | 2,6-diF-phenyl | 2-(methylaminosulfonyl)phenyl |
| 633 | Cl | 2,6-diF-phenyl | 1-pyrrolidinocarbonyl |
| 634 | Cl | 2,6-diF-phenyl | 2-(methylsulfonyl)phenyl |
| 635 | Cl | 2,6-diF-phenyl | 4-morpholino |
| 636 | Cl | 2,6-diF-phenyl | 2-(1'-CF$_3$-tetrazol-2-yl)phenyl |
| 637 | Cl | 2,6-diF-phenyl | 4-morpholinocarbonyl |
| 638 | Cl | 2,6-diF-phenyl | 2-methyl-1-imidazolyl |
| 639 | Cl | 2,6-diF-phenyl | 5-methyl-1-imidazolyl |
| 640 | Cl | 2,6-diF-phenyl | 2-methylsulfonyl-1-imidazolyl |
| 641 | F | phenyl | 2-(aminosulfonyl)phenyl |
| 642 | F | phenyl | 2-(methylaminosulfonyl)phenyl |
| 643 | F | phenyl | 1-pyrrolidinocarbonyl |
| 644 | F | phenyl | 2-(methylsulfonyl)phenyl |
| 645 | F | phenyl | 4-morpholino |
| 646 | F | phenyl | 2-(1'-CF$_3$-tetrazol-2-yl)phenyl |
| 647 | F | phenyl | 4-morpholinocarbonyl |
| 648 | F | phenyl | 2-methyl-1-imidazolyl |
| 649 | F | phenyl | 5-methyl-1-imidazolyl |
| 650 | F | phenyl | 2-methylsulfonyl-1-imidazolyl |
| 651 | F | 2-pyridyl | 2-(aminosulfonyl)phenyl |
| 652 | F | 2-pyridyl | 2-(methylaminosulfonyl)phenyl |
| 653 | F | 2-pyridyl | 1-pyrrolidinocarbonyl |
| 654 | F | 2-pyridyl | 2-(methylsulfonyl)phenyl |
| 655 | F | 2-pyridyl | 4-morpholino |
| 656 | F | 2-pyridyl | 2-(1'-CF$_3$-tetrazol-2-yl)phenyl |
| 657 | F | 2-pyridyl | 4-morpholinocarbonyl |
| 658 | F | 2-pyridyl | 2-methyl-1-imidazolyl |
| 659 | F | 2-pyridyl | 5-methyl-1-imidazolyl |
| 660 | F | 2-pyridyl | 2-methylsulfonyl-1-imidazolyl |
| 661 | F | 3-pyridyl | 2-(aminosulfonyl)phenyl |
| 662 | F | 3-pyridyl | 2-(methylaminosulfonyl)phenyl |
| 663 | F | 3-pyridyl | 1-pyrrolidinocarbonyl |
| 664 | F | 3-pyridyl | 2-(methylsulfonyl)phenyl |
| 665 | F | 3-pyridyl | 4-morpholino |
| 666 | F | 3-pyridyl | 2-(1'-CF$_3$-tetrazol-2-yl)phenyl |
| 667 | F | 3-pyridyl | 4-morpholinocarbonyl |
| 668 | F | 3-pyridyl | 2-methyl-1-imidazolyl |
| 669 | F | 3-pyridyl | 5-methyl-1-imidazolyl |
| 670 | F | 3-pyridyl | 2-methylsulfonyl-1-imidazolyl |
| 671 | F | 2-pyrimidyl | 2-(aminosulfonyl)phenyl |
| 672 | F | 2-pyrimidyl | 2-(methylaminosulfonyl)phenyl |
| 673 | F | 2-pyrimidyl | 1-pyrrolidinocarbonyl |
| 674 | F | 2-pyrimidyl | 2-(methylsulfonyl)phenyl |
| 675 | F | 2-pyrimidyl | 4-morpholino |
| 676 | F | 2-pyrimidyl | 2-(1'-CF$_3$-tetrazol-2-yl)phenyl |
| 677 | F | 2-pyrimidyl | 4-morpholinocarbonyl |
| 678 | F | 2-pyrimidyl | 2-methyl-1-imidazolyl |
| 679 | F | 2-pyrimidyl | 5-methyl-1-imidazolyl |
| 680 | F | 2-pyrimidyl | 2-methylsulfonyl-1-imidazolyl |
| 681 | F | 5-pyrimidyl | 2-(aminosulfonyl)phenyl |
| 682 | F | 5-pyrimidyl | 2-(methylaminosulfonyl)phenyl |

TABLE 4-continued

| | | | |
|---|---|---|---|
| 683 | F | 5-pyrimidyl | 1-pyrrolidinocarbonyl |
| 684 | F | 5-pyrimidyl | 2-(methylsulfonyl)phenyl |
| 685 | F | 5-pyrimidyl | 4-morpholino |
| 686 | F | 5-pyrimidyl | 2-(1'-$CF_3$-tetrazol-2-yl)phenyl |
| 687 | F | 5-pyrimidyl | 4-morpholinocarbonyl |
| 688 | F | 5-pyrimidyl | 2-methyl-1-imidazolyl |
| 689 | F | 5-pyrimidyl | 5-methyl-1-imidazolyl |
| 690 | F | 5-pyrimidyl | 2-methylsulfonyl-1-imidazolyl |
| 691 | F | 2-Cl-phenyl | 2-(aminosulfonyl)phenyl |
| 692 | F | 2-Cl-phenyl | 2-(methylaminosulfonyl)phenyl |
| 693 | F | 2-Cl-phenyl | 1-pyrrolidinocarbonyl |
| 694 | F | 2-Cl-phenyl | 2-(methylsulfonyl)phenyl |
| 695 | F | 2-Cl-phenyl | 4-morpholino |
| 696 | F | 2-Cl-phenyl | 2-(1'-$CF_3$-tetrazol-2-yl)phenyl |
| 697 | F | 2-Cl-phenyl | 4-morpholinocarbonyl |
| 698 | F | 2-Cl-phenyl | 2-methyl-1-imidazolyl |
| 699 | F | 2-Cl-phenyl | 5-methyl-1-imidazolyl |
| 700 | F | 2-Cl-phenyl | 2-methylsulfonyl-1-imidazolyl |
| 701 | F | 2-F-phenyl | 2-(aminosulfonyl)phenyl |
| 702 | F | 2-F-phenyl | 2-(methylaminosulfonyl)phenyl |
| 703 | F | 2-F-phenyl | 1-pyrrolidinocarbonyl |
| 704 | F | 2-F-phenyl | 2-(methylsulfonyl)phenyl |
| 705 | F | 2-F-phenyl | 4-morpholino |
| 706 | F | 2-F-phenyl | 2-(1'-$CF_3$-tetrazol-2-yl)phenyl |
| 707 | F | 2-F-phenyl | 4-morpholinocarbonyl |
| 708 | F | 2-F-phenyl | 2-methyl-1-imidazolyl |
| 709 | F | 2-F-phenyl | 5-methyl-1-imidazolyl |
| 710 | F | 2-F-phenyl | 2-methylsulfonyl-1-imidazolyl |
| 711 | F | 2,6-diF-phenyl | 2-(aminosulfonyl)phenyl |
| 712 | F | 2,6-diF-phenyl | 2-(methylaminosulfonyl)phenyl |
| 713 | F | 2,6-diF-phenyl | 1-pyrrolidinocarbonyl |
| 714 | F | 2,6-diF-phenyl | 2-(methylsulfonyl)phenyl |
| 715 | F | 2,6-diF-phenyl | 4-morpholino |
| 716 | F | 2,6-diF-phenyl | 2-(1'-$CF_3$-tetrazol-2-yl)phenyl |
| 717 | F | 2,6-diF-phenyl | 4-morpholinocarbonyl |
| 718 | F | 2,6-diF-phenyl | 2-methyl-1-imidazolyl |
| 719 | F | 2,6-diF-phenyl | 5-methyl-1-imidazolyl |
| 720 | F | 2,6-diF-phenyl | 2-methylsulfonyl-1-imidazolyl |
| 721 | $CO_2CH_3$ | phenyl | 2-(aminosulfonyl)phenyl |
| 722 | $CO_2CH_3$ | phenyl | 2-(methylsulfonyl)phenyl |
| 723 | $CO_2CH_3$ | phenyl | 1-pyrrolidinocarbonyl |
| 724 | $CO_2CH_3$ | phenyl | 2-(methylsulfonyl)phenyl |
| 725 | $CO_2CH_3$ | phenyl | 4-morpholino |
| 726 | $CO_2CH_3$ | phenyl | 2-(1'-$CF_3$-tetrazol-2-yl)phenyl |
| 727 | $CO_2CH_3$ | phenyl | 4-morpholinocarbonyl |
| 728 | $CO_2CH_3$ | phenyl | 2-methyl-1-imidazolyl |
| 729 | $CO_2CH_3$ | phenyl | 5-methyl-1-imidazolyl |
| 730 | $CO_2CH_3$ | phenyl | 2-methylsulfonyl-1-imidazolyl |
| 731 | $CO_2CH_3$ | 2-pyridyl | 2-(aminosulfonyl)phenyl |
| 732 | $CO_2CH_3$ | 2-pyridyl | 2-(methylaminosulfonyl)phenyl |
| 733 | $CO_2CH_3$ | 2-pyridyl | 1-pyrrolidinocarbonyl |
| 734 | $CO_2CH_3$ | 2-pyridyl | 2-(methylsulfonyl)phenyl |
| 735 | $CO_2CH_3$ | 2-pyridyl | 4-morpholino |
| 736 | $CO_2CH_3$ | 2-pyridyl | 2-(1'-$CF_3$-tetrazol-2-yl)phenyl |
| 737 | $CO_2CH_3$ | 2-pyridyl | 4-morpholinocarbonyl |
| 738 | $CO_2CH_3$ | 2-pyridyl | 2-methyl-1-imidazolyl |
| 739 | $CO_2CH_3$ | 2-pyridyl | 5-methyl-1-imidazolyl |
| 740 | $CO_2CH_3$ | 2-pyridyl | 2-methylsulfonyl-1-imidazolyl |
| 741 | $CO_2CH_3$ | 3-pyridyl | 2-(aminosulfonyl)phenyl |
| 742 | $CO_2CH_3$ | 3-pyridyl | 2-(methylaminosulfonyl)phenyl |
| 743 | $CO_2CH_3$ | 3-pyridyl | 1-pyrrolidinocarbonyl |
| 744 | $CO_2CH_3$ | 3-pyridyl | 2-(methylsulfonyl)phenyl |
| 745 | $CO_2CH_3$ | 3-pyridyl | 4-morpholino |
| 746 | $CO_2CH_3$ | 3-pyridyl | 2-(1'-$CF_3$-tetrazol-2-yl)phenyl |
| 747 | $CO_2CH_3$ | 3-pyridyl | 4-morpholinocarbonyl |
| 748 | $CO_2CH_3$ | 3-pyridyl | 2-methyl-1-imidazolyl |
| 749 | $CO_2CH_3$ | 3-pyridyl | 5-methyl-1-imidazolyl |
| 750 | $CO_2CH_3$ | 3-pyridyl | 2-methylsulfonyl-1-imidazolyl |
| 751 | $CO_2CH_3$ | 2-pyrimidyl | 2-(aminosulfonyl)phenyl |
| 752 | $CO_2CH_3$ | 2-pyrimidyl | 2-(methylaminosulfonyl)phenyl |
| 753 | $CO_2CH_3$ | 2-pyrimidyl | 1-pyrrolidinocarbonyl |
| 754 | $CO_2CH_3$ | 2-pyrimidyl | 2-(methylsulfonyl)phenyl |
| 755 | $CO_2CH_3$ | 2-pyrimidyl | 4-morpholino |
| 756 | $CO_2CH_3$ | 2-pyrimidyl | 2-(1'-$CF_3$-tetrazol-2-yl)phenyl |
| 757 | $CO_2CH_3$ | 2-pyrimidyl | 4-morpholinocarbonyl |
| 758 | $CO_2CH_3$ | 2-pyrimidyl | 2-methyl-1-imidazolyl |
| 759 | $CO_2CH_3$ | 2-pyrimidyl | 5-methyl-1-imidazolyl |
| 760 | $CO_2CH_3$ | 2-pyrimidyl | 2-methylsulfonyl-1-imidazolyl |
| 761 | $CO_2CH_3$ | 5-pyrimidyl | 2-(aminosulfonyl)phenyl |

TABLE 4-continued

| | | | |
|---|---|---|---|
| 762 | $CO_2CH_3$ | 5-pyrimidyl | 2-(methylaminosulfonyl)phenyl |
| 763 | $CO_2CH_3$ | 5-pyrimidyl | 1-pyrrolidinocarbonyl |
| 764 | $CO_2CH_3$ | 5-pyrimidyl | 2-(methylsulfonyl)phenyl |
| 765 | $CO_2CH_3$ | 5-pyrimidyl | 4-morpholino |
| 766 | $CO_2CH_3$ | 5-pyrimidyl | 2-(1'-$CF_3$-tetrazol-2-yl)phenyl |
| 767 | $CO_2CH_3$ | 5-pyrimidyl | 4-morpholinocarbonyl |
| 768 | $CO_2CH_3$ | 5-pyrimidyl | 2-methyl-1-imidazolyl |
| 769 | $CO_2CH_3$ | 5-pyrimidyl | 5-methyl-1-imidazolyl |
| 770 | $CO_2CH_3$ | 5-pyrimidyl | 2-methylsulfonyl-1-imidazolyl |
| 771 | $CO_2CH_3$ | 2-Cl-phenyl | 2-(aminosulfonyl)phenyl |
| 772 | $CO_2CH_3$ | 2-Cl-phenyl | 2-(methylaminosulfonyl)phenyl |
| 773 | $CO_2CH_3$ | 2-Cl-phenyl | 1-pyrrolidinocarbonyl |
| 774 | $CO_2CH_3$ | 2-Cl-phenyl | 2-(methylsulfonyl)phenyl |
| 775 | $CO_2CH_3$ | 2-Cl-phenyl | 4-morpholino |
| 776 | $CO_2CH_3$ | 2-Cl-phenyl | 2-(1'-$CF_3$-tetrazol-2-yl)phenyl |
| 777 | $CO_2CH_3$ | 2-Cl-phenyl | 4-morpholinocarbonyl |
| 778 | $CO_2CH_3$ | 2-Cl-phenyl | 2-methyl-1-imidazolyl |
| 779 | $CO_2CH_3$ | 2-Cl-phenyl | 5-methyl-1-imidazolyl |
| 780 | $CO_2CH_3$ | 2-Cl-phenyl | 2-methylsulfonyl-1-imidazolyl |
| 781 | $CO_2CH_3$ | 2-F-phenyl | 2-(aminosulfonyl)phenyl |
| 782 | $CO_2CH_3$ | 2-F-phenyl | 2-(methylaminosulfonyl)phenyl |
| 783 | $CO_2CH_3$ | 2-F-phenyl | 1-pyrrolidinocarbonyl |
| 784 | $CO_2CH_3$ | 2-F-phenyl | 2-(methylsulfonyl)phenyl |
| 785 | $CO_2CH_3$ | 2-F-phenyl | 4-morpholino |
| 786 | $CO_2CH_3$ | 2-F-phenyl | 2-(1'-$CF_3$-tetrazol-2-yl)phenyl |
| 787 | $CO_2CH_3$ | 2-F-phenyl | 4-morpholinocarbonyl |
| 788 | $CO_2CH_3$ | 2-F-phenyl | 2-methyl-1-imidazolyl |
| 789 | $CO_2CH_3$ | 2-F-phenyl | 5-methyl-1-imidazolyl |
| 790 | $CO_2CH_3$ | 2-F-phenyl | 2-methylsulfonyl-1-imidazolyl |
| 791 | $CO_2CH_3$ | 2,6-diF-phenyl | 2-(aminosulfonyl)phenyl |
| 792 | $CO_2CH_3$ | 2,6-diF-phenyl | 2-(methylaminosulfonyl)phenyl |
| 793 | $CO_2CH_3$ | 2,6-diF-phenyl | 1-pyrrolidinocarbonyl |
| 794 | $CO_2CH_3$ | 2,6-diF-phenyl | 2-(methylsulfonyl)phenyl |
| 795 | $CO_2CH_3$ | 2,6-diF-phenyl | 4-morpholino |
| 796 | $CO_2CH_3$ | 2,6-diF-phenyl | 2-(1'-$CF_3$-tetrazol-2-yl)phenyl |
| 797 | $CO_2CH_3$ | 2,6-diF-phenyl | 4-morpholinocarbonyl |
| 798 | $CO_2CH_3$ | 2,6-diF-phenyl | 2-methyl-1-imidazolyl |
| 799 | $CO_2CH_3$ | 2,6-diF-phenyl | 5-methyl-1-imidazolyl |
| 800 | $CO_2CH_3$ | 2,6-diF-phenyl | 2-methylsulfonyl-1-imidazolyl |
| 801 | $CH_2OCH_3$ | phenyl | 2-(aminosulfonyl)phenyl |
| 802 | $CH_2OCH_3$ | phenyl | 2-(methylaminosulfonyl)phenyl |
| 803 | $CH_2OCH_3$ | phenyl | 1-pyrrolidinocarbonyl |
| 804 | $CH_2OCH_3$ | phenyl | 2-(methylsulfonyl)phenyl |
| 805 | $CH_2OCH_3$ | phenyl | 4-morpholino |
| 806 | $CH_2OCH_3$ | phenyl | 2-(1'-$CF_3$-tetrazol-2-yl)phenyl |
| 807 | $CH_2OCH_3$ | phenyl | 4-morpholinocarbonyl |
| 808 | $CH_2OCH_3$ | phenyl | 2-methyl-1-imidazolyl |
| 809 | $CH_2OCH_3$ | phenyl | 5-methyl-1-imidazolyl |
| 810 | $CH_2OCH_3$ | phenyl | 2-methylsulfonyl-1-imidazolyl |
| 811 | $CH_2OCH_3$ | 2-pyridyl | 2-(aminosulfonyl)phenyl |
| 812 | $CH_2OCH_3$ | 2-pyridyl | 2-(methylaminosulfonyl)phenyl |
| 813 | $CH_2OCH_3$ | 2-pyridyl | 1-pyrrolidinocarbonyl |
| 814 | $CH_2OCH_3$ | 2-pyridyl | 2-(methylsulfonyl)phenyl |
| 815 | $CH_2OCH_3$ | 2-pyridyl | 4-morpholino |
| 816 | $CH_2OCH_3$ | 2-pyridyl | 2-(1'-$CF_3$-tetrazol-2-yl)phenyl |
| 817 | $CH_2OCH_3$ | 2-pyridyl | 4-morpholinocarbonyl |
| 818 | $CH_2OCH_3$ | 2-pyridyl | 2-methyl-1-imidazolyl |
| 819 | $CH_2OCH_3$ | 2-pyridyl | 5-methyl-1-imidazolyl |
| 820 | $CH_2OCH_3$ | 2-pyridyl | 2-methylsulfonyl-1-imidazolyl |
| 821 | $CH_2OCH_3$ | 3-pyridyl | 2-(aminosulfonyl)phenyl |
| 822 | $CH_2OCH_3$ | 3-pyridyl | 2-(methylaminosulfonyl)phenyl |
| 823 | $CH_2OCH_3$ | 3-pyridyl | 1-pyrrolidinocarbonyl |
| 824 | $CH_2OCH_3$ | 3-pyridyl | 2-(methylsulfonyl)phenyl |
| 825 | $CH_2OCH_3$ | 3-pyridyl | 4-morpholino |
| 826 | $CH_2OCH_3$ | 3-pyridyl | 2-(1'-$CF_3$-tetrazol-2-yl)phenyl |
| 827 | $CH_2OCH_3$ | 3-pyridyl | 4-morpholinocarbonyl |
| 828 | $CH_2OCH_3$ | 3-pyridyl | 2-methyl-1-imidazolyl |
| 829 | $CH_2OCH_3$ | 3-pyridyl | 5-methyl-1-imidazolyl |
| 830 | $CH_2OCH_3$ | 3-pyridyl | 2-methylsulfonyl-1-imidazolyl |
| 831 | $CH_2OCH_3$ | 2-pyrimidyl | 2-(aminosulfonyl)phenyl |
| 832 | $CH_2OCH_3$ | 2-pyrimidyl | 2-(methylaminosulfonyl)phenyl |
| 833 | $CH_2OCH_3$ | 2-pyrimidyl | 1-pyrrolidinocarbonyl |
| 834 | $CH_2OCH_3$ | 2-pyrimidyl | 2-(methylsulfonyl)phenyl |
| 835 | $CH_2OCH_3$ | 2-pyrimidyl | 4-morpholino |
| 836 | $CH_2OCH_3$ | 2-pyrimidyl | 2-(1'-$CF_3$-tetrazol-2-yl)phenyl |
| 837 | $CH_2OCH_3$ | 2-pyrimidyl | 4-morpholinocarbonyl |
| 838 | $CH_2OCH_3$ | 2-pyrimidyl | 2-methyl-1-imidazolyl |
| 839 | $CH_2OCH_3$ | 2-pyrimidyl | 5-methyl-1-imidazolyl |
| 840 | $CH_2OCH_3$ | 2-pyrimidyl | 2-methylsulfonyl-1-imidazolyl |

TABLE 4-continued

| | | | |
|---|---|---|---|
| 841 | CH$_2$OCH$_3$ | 5-pyrimidyl | 2-(aminosulfonyl)phenyl |
| 842 | CH$_2$OCH$_3$ | 5-pyrimidyl | 2-(methylaminosulfonyl)phenyl |
| 843 | CH$_2$OCH$_3$ | 5-pyrimidyl | 1-pyrrolidinocarbonyl |
| 844 | CH$_2$OCH$_3$ | 5-pyrimidyl | 2-(methylsulfonyl)phenyl |
| 845 | CH$_2$OCH$_3$ | 5-pyrimidyl | 4-morpholino |
| 846 | CH$_2$OCH$_3$ | 5-pyrimidyl | 2-(1'-CF$_3$-tetrazol-2-yl)phenyl |
| 847 | CH$_2$OCH$_3$ | 5-pyrimidyl | 4-morpholinocarbonyl |
| 848 | CH$_2$OCH$_3$ | 5-pyrimidyl | 2-methyl-1-imidazolyl |
| 849 | CH$_2$OCH$_3$ | 5-pyrimidyl | 5-methyl-1-imidazolyl |
| 850 | CH$_2$OCH$_3$ | 5-pyrimidyl | 2-methylsulfonyl-1-imidazolyl |
| 851 | CH$_2$OCH$_3$ | 2-Cl-phenyl | 2-(aminosulfonyl)phenyl |
| 852 | CH$_2$OCH$_3$ | 2-Cl-phenyl | 2-(methylaminosulfonyl)phenyl |
| 853 | CH$_2$OCH$_3$ | 2-Cl-phenyl | 1-pyrrolidinocarbonyl |
| 854 | CH$_2$OCH$_3$ | 2-Cl-phenyl | 2-(methylsulfonyl)phenyl |
| 855 | CH$_2$OCH$_3$ | 2-Cl-phenyl | 4-morpholino |
| 856 | CH$_2$OCH$_3$ | 2-Cl-phenyl | 2-(1'-CF$_3$-tetrazol-2-yl)phenyl |
| 857 | CH$_2$OCH$_3$ | 2-Cl-phenyl | 4-morpholinocarbonyl |
| 858 | CH$_2$OCH$_3$ | 2-Cl-phenyl | 2-methyl-1-imidazolyl |
| 859 | CH$_2$OCH$_3$ | 2-Cl-phenyl | 5-methyl-1-imidazolyl |
| 860 | CH$_2$OCH$_3$ | 2-Cl-phenyl | 2-methylsulfonyl-1-imidazolyl |
| 861 | CH$_2$OCH$_3$ | 2-F-phenyl | 2-(aminosulfonyl)phenyl |
| 862 | CH$_2$OCH$_3$ | 2-F-phenyl | 2-(methylaminosulfonyl)phenyl |
| 863 | CH$_2$OCH$_3$ | 2-F-phenyl | 1-pyrrolidinocarbonyl |
| 864 | CH$_2$OCH$_3$ | 2-F-phenyl | 2-(methylsulfonyl)phenyl |
| 865 | CH$_2$OCH$_3$ | 2-F-phenyl | 4-morpholino |
| 866 | CH$_2$OCH$_3$ | 2-F-phenyl | 2-(1'-CF$_3$-tetrazol-2-yl)phenyl |
| 867 | CH$_2$OCH$_3$ | 2-F-phenyl | 4-morpholinocarbonyl |
| 868 | CH$_2$OCH$_3$ | 2-F-phenyl | 2-methyl-1-imidazolyl |
| 869 | CH$_2$OCH$_3$ | 2-F-phenyl | 5-methyl-1-imidazolyl |
| 870 | CH$_2$OCH$_3$ | 2-F-phenyl | 2-methylsulfonyl-1-imidazolyl |
| 871 | CH$_2$OCH$_3$ | 2,6-diF-phenyl | 2-(aminosulfonyl)phenyl |
| 872 | CH$_2$OCH$_3$ | 2,6-diF-phenyl | 2-(methylaminosulfonyl)phenyl |
| 873 | CH$_2$OCH$_3$ | 2,6-diF-phenyl | 1-pyrrolidinocarbonyl |
| 874 | CH$_2$OCH$_3$ | 2,6-diF-phenyl | 2-(methylsulfonyl)phenyl |
| 875 | CH$_2$OCH$_3$ | 2,6-diF-phenyl | 4-morpholino |
| 876 | CH$_2$OCH$_3$ | 2,6-diF-phenyl | 2-(1'-CF$_3$-tetrazol-2-yl)phenyl |
| 877 | CH$_2$OCH$_3$ | 2,6-diF-phenyl | 4-morpholinocarbonyl |
| 878 | CH$_2$OCH$_3$ | 2,6-diF-phenyl | 2-methyl-1-imidazolyl |
| 879 | CH$_2$OCH$_3$ | 2,6-diF-phenyl | 5-methyl-1-imidazolyl |
| 880 | CH$_2$OCH$_3$ | 2,6-diF-phenyl | 2-methylsulfonyl-1-imidazolyl |
| 881 | CONH$_2$ | phenyl | 2-(aminosulfonyl)phenyl |
| 882 | CONH$_2$ | phenyl | 2-(methylaminosulfonyl)phenyl |
| 883 | CONH$_2$ | phenyl | 1-pyrrolidinocarbonyl |
| 884 | CONH$_2$ | phenyl | 2-(methylsulfonyl)phenyl |
| 885 | CONH$_2$ | phenyl | 4-morpholino |
| 886 | CONH$_2$ | phenyl | 2-(1'-CF$_3$-tetrazol-2-yl)phenyl |
| 887 | CONH$_2$ | phenyl | 4-morpholinocarbonyl |
| 888 | CONH$_2$ | phenyl | 2-methyl-1-imidazolyl |
| 889 | CONH$_2$ | phenyl | 5-methyl-1-imidazolyl |
| 890 | CONH$_2$ | phenyl | 2-methylsulfonyl-1-imidazolyl |
| 891 | CONH$_2$ | 2-pyridyl | 2-(aminosulfonyl)phenyl |
| 892 | CONH$_2$ | 2-pyridyl | 2-(methylaminosulfonyl)phenyl |
| 893 | CONH$_2$ | 2-pyridyl | 1-pyrrolidinocarbonyl |
| 894 | CONH$_2$ | 2-pyridyl | 2-(methylsulfonyl)phenyl |
| 895 | CONH$_2$ | 2-pyridyl | 4-morpholino |
| 896 | CONH$_2$ | 2-pyridyl | 2-(1'-CF$_3$-tetrazol-2-yl)phenyl |
| 897 | CONH$_2$ | 2-pyridyl | 4-morpholinocarbonyl |
| 898 | CONH$_2$ | 2-pyridyl | 2-methyl-1-imidazolyl |
| 899 | CONH$_2$ | 2-pyridyl | 5-methyl-1-imidazolyl |
| 900 | CONH$_2$ | 2-pyridyl | 2-methylsulfonyl-1-imidazolyl |
| 901 | CONH$_2$ | 3-pyridyl | 2-(aminosulfonyl)phenyl |
| 902 | CONH$_2$ | 3-pyridyl | 2-(methylaminosulfonyl)phenyl |
| 903 | CONH$_2$ | 3-pyridyl | 1-pyrrolidinocarbonyl |
| 904 | CONH$_2$ | 3-pyridyl | 2-(methylsulfonyl)phenyl |
| 905 | CONH$_2$ | 3-pyridyl | 4-morpholino |
| 906 | CONH$_2$ | 3-pyridyl | 2-(1'-CF$_3$-tetrazol-2-yl)phenyl |
| 907 | CONH$_2$ | 3-pyridyl | 4-morpholinocarbonyl |
| 908 | CONH$_2$ | 3-pyridyl | 2-methyl-1-imidazolyl |
| 909 | CONH$_2$ | 3-pyridyl | 5-methyl-1-imidazolyl |
| 910 | CONH$_2$ | 3-pyridyl | 2-methylsulfonyl-1-imidazolyl |
| 911 | CONH$_2$ | 2-pyrimidyl | 2-(aminosulfonyl)phenyl |
| 912 | CONH$_2$ | 2-pyrimidyl | 2-(methylaminosulfonyl)phenyl |
| 913 | CONH$_2$ | 2-pyrimidyl | 1-pyrrolidinocarbonyl |
| 914 | CONH$_2$ | 2-pyrimidyl | 2-(methylsulfonyl)phenyl |
| 915 | CONH$_2$ | 2-pyrimidyl | 4-morpholino |
| 916 | CONH$_2$ | 2-pyrimidyl | 2-(1'-CF$_3$-tetrazol-2-yl)phenyl |
| 917 | CONH$_2$ | 2-pyrimidyl | 4-morpholinocarbonyl |
| 918 | CONH$_2$ | 2-pyrimidyl | 2-methyl-1-imidazolyl |
| 919 | CONH$_2$ | 2-pyrimidyl | 5-methyl-1-imidazolyl |

TABLE 4-continued

| | | | |
|---|---|---|---|
| 920 | CONH$_2$ | 2-pyrimidyl | 2-methylsulfonyl-1-imidazolyl |
| 921 | CONH$_2$ | 5-pyrimidyl | 2-(aminosulfonyl)phenyl |
| 922 | CONH$_2$ | 5-pyrimidyl | 2-(methylaminosulfonyl)phenyl |
| 923 | CONH$_2$ | 5-pyrimidyl | 1-pyrrolidinocarbonyl |
| 924 | CONH$_2$ | 5-pyrimidyl | 2-(methylsulfonyl)phenyl |
| 925 | CONH$_2$ | 5-pyrimidyl | 4-morpholino |
| 926 | CONH$_2$ | 5-pyrimidyl | 2-(1'-CF$_3$-tetrazol-2-yl)phenyl |
| 927 | CONH$_2$ | 5-pyrimidyl | 4-morpholinocarbonyl |
| 928 | CONH$_2$ | 5-pyrimidyl | 2-methyl-1-imidazolyl |
| 929 | CONH$_2$ | 5-pyrimidyl | 5-methyl-1-imidazolyl |
| 930 | CONH$_2$ | 5-pyrimidyl | 2-methylsulfonyl-1-imidazolyl |
| 931 | CONH$_2$ | 2-Cl-phenyl | 2-(aminosulfonyl)phenyl |
| 932 | CONH$_2$ | 2-Cl-phenyl | 2-(methylaminosulfonyl)phenyl |
| 933 | CONH$_2$ | 2-Cl-phenyl | 1-pyrrolidinocarbonyl |
| 934 | CONH$_2$ | 2-Cl-phenyl | 2-(methylsulfonyl)phenyl |
| 935 | CONH$_2$ | 2-Cl-phenyl | 4-morpholino |
| 936 | CONH$_2$ | 2-Cl-phenyl | 2-(1'-CF$_3$-tetrazol-2-yl)phenyl |
| 937 | CONH$_2$ | 2-Cl-phenyl | 4-morpholinocarbonyl |
| 938 | CONH$_2$ | 2-Cl-phenyl | 2-methyl-1-imidazolyl |
| 939 | CONH$_2$ | 2-Cl-phenyl | 5-methyl-1-imidazolyl |
| 940 | CONH$_2$ | 2-Cl-phenyl | 2-methylsulfonyl-1-imidazolyl |
| 941 | CONH$_2$ | 2-F-phenyl | 2-(aminosulfonyl)phenyl |
| 942 | CONH$_2$ | 2-F-phenyl | 2-(methylaminosulfonyl)phenyl |
| 943 | CONH$_2$ | 2-F-phenyl | 1-pyrrolidinocarbonyl |
| 944 | CONH$_2$ | 2-F-phenyl | 2-(methylsulfonyl)phenyl |
| 945 | CONH$_2$ | 2-F-phenyl | 4-morpholino |
| 946 | CONH$_2$ | 2-F-phenyl | 2-(1'-CF$_3$-tetrazol-2-yl)phenyl |
| 947 | CONH$_2$ | 2-F-phenyl | 4-morpholinocarbonyl |
| 948 | CONH$_2$ | 2-F-phenyl | 2-methyl-1-imidazolyl |
| 949 | CONH$_2$ | 2-F-phenyl | 5-methyl-1-imidazolyl |
| 950 | CONH$_2$ | 2-F-phenyl | 2-methylsulfonyl-1-imidazolyl |
| 951 | CONH$_2$ | 2,6-diF-phenyl | 2-(aminosulfonyl)phenyl |
| 952 | CONH$_2$ | 2,6-diF-phenyl | 2-(methylaminosulfonyl)phenyl |
| 953 | CONH$_2$ | 2,6-diF-phenyl | 1-pyrrolidinocarbonyl |
| 954 | CONH$_2$ | 2,6-diF-phenyl | 2-(methylsulfonyl)phenyl |
| 955 | CONH$_2$ | 2,6-diF-phenyl | 4-morpholino |
| 956 | CONH$_2$ | 2,6-diF-phenyl | 2-(1'-CF$_3$-tetrazol-2-yl)phenyl |
| 957 | CONH$_2$ | 2,6-diF-phenyl | 4-morpholinocarbonyl |
| 958 | CONH$_2$ | 2,6-diF-phenyl | 2-methyl-1-imidazolyl |
| 959 | CONH$_2$ | 2,6-diF-phenyl | 5-methyl-1-imidazolyl |
| 960 | CONH$_2$ | 2,6-diF-phenyl | 2-methylsulfonyl-1-imidazolyl |

TABLE 5

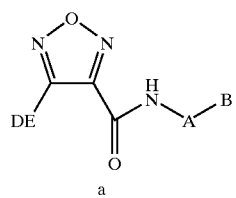

a

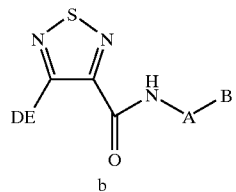

b

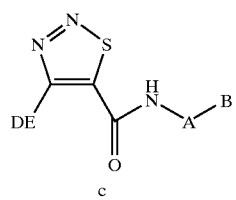

c

TABLE 5-continued

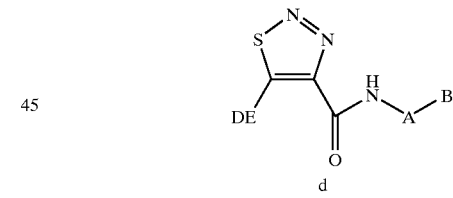

d

| Ex # | A | B |
|---|---|---|
| 1 | phenyl | 2-(aminosulfonyl)phenyl |
| 2 | phenyl | 2-(methylaminosulfonyl)phenyl |
| 3 | phenyl | 1-pyrrolidinocarbonyl |
| 4 | phenyl | 2-(methylsulfonyl)phenyl |
| 5 | phenyl | 4-morpholino |
| 6 | phenyl | 2-(1'-CF$_3$-tetrazol-2-yl)phenyl |
| 7 | phenyl | 4-morpholinocarbonyl |
| 8 | phenyl | 2-methyl-1-imidazolyl |
| 9 | phenyl | 5-methyl-1-imidazolyl |
| 10 | phenyl | 2-methylsulfonyl-1-imidazolyl |
| 11 | 2-pyridyl | 2-(aminosulfonyl)phenyl |
| 12 | 2-pyridyl | 2-(methylaminosulfonyl)phenyl |
| 13 | 2-pyridyl | 1-pyrrolidinocarbonyl |
| 14 | 2-pyridyl | 2-(methylsulfonyl)phenyl |
| 15 | 2-pyridyl | 4-morpholino |
| 16 | 2-pyridyl | 2-(1'-CF$_3$-tetrazol-2-yl)phenyl |
| 17 | 2-pyridyl | 4-morpholinocarbonyl |

TABLE 5-continued

| | | |
|---|---|---|
| 18 | 2-pyridyl | 2-methyl-1-imidazolyl |
| 19 | 2-pyridyl | 5-methyl-1-imidazolyl |
| 20 | 2-pyridyl | 2-methylsulfonyl-1-imidazolyl |
| 21 | 3-pyridyl | 2-(aminosulfonyl)phenyl |
| 22 | 3-pyridyl | 2-(methylaminosulfonyl)phenyl |
| 23 | 3-pyridyl | 1-pyrrolidinocarbonyl |
| 24 | 3-pyridyl | 2-(methylsulfonyl)phenyl |
| 25 | 3-pyridyl | 4-morpholino |
| 26 | 3-pyridyl | 2-(1'-CF$_3$-tetrazol-2-yl)phenyl |
| 27 | 3-pyridyl | 4-morpholinocarbonyl |
| 28 | 3-pyridyl | 2-methyl-1-imidazolyl |
| 29 | 3-pyridyl | 5-methyl-1-imidazolyl |
| 30 | 3-pyridyl | 2-methylsulfonyl-1-imidazolyl |
| 31 | 2-pyrimidyl | 2-(aminosulfonyl)phenyl |
| 32 | 2-pyrimidyl | 2-(methylaminosulfonyl)phenyl |
| 33 | 2-pyrimidyl | 1-pyrrolidinocarbonyl |
| 34 | 2-pyrimidyl | 2-(methylsulfonyl)phenyl |
| 35 | 2-pyrimidyl | 4-morpholino |
| 36 | 2-pyrimidyl | 2-(1'-CF$_3$-tetrazol-2-yl)phenyl |
| 37 | 2-pyrimidyl | 4-morpholinocarbonyl |
| 38 | 2-pyrimidyl | 2-methyl-1-imidazolyl |
| 39 | 2-pyrimidyl | 5-methyl-1-imidazolyl |
| 40 | 2-pyrimidyl | 2-methylsulfonyl-1-imidazolyl |
| 41 | 5-pyrimidyl | 2-(aminosulfonyl)phenyl |
| 42 | 5-pyrimidyl | 2-(methylaminosulfonyl)phenyl |
| 43 | 5-pyrimidyl | 1-pyrrolidinocarbonyl |
| 44 | 5-pyrimidyl | 2-(methylsulfonyl)phenyl |
| 45 | 5-pyrimidyl | 4-morpholino |
| 46 | 5-pyrimidyl | 2-(1'-CF$_3$-tetrazol-2-yl)phenyl |
| 47 | 5-pyrimidyl | 4-morpholinocarbonyl |
| 48 | 5-pyrimidyl | 2-methyl-1-imidazolyl |
| 49 | 5-pyrimidyl | 5-methyl-1-imidazolyl |
| 50 | 5-pyrimidyl | 2-methylsulfonyl-1-imidazolyl |
| 51 | 2-Cl-phenyl | 2-(aminosulfonyl)phenyl |
| 52 | 2-Cl-phenyl | 2-(methylaminosulfonyl)phenyl |
| 53 | 2-Cl-phenyl | 1-pyrrolidinocarbonyl |
| 54 | 2-Cl-phenyl | 2-(methylsulfonyl)phenyl |
| 55 | 2-Cl-phenyl | 4-morpholino |
| 56 | 2-Cl-phenyl | 2-(1'-CF$_3$-tetrazol-2-yl)phenyl |
| 57 | 2-Cl-phenyl | 4-morpholinocarbonyl |
| 58 | 2-Cl-phenyl | 2-methyl-1-imidazolyl |
| 59 | 2-Cl-phenyl | 5-methyl-1-imidazolyl |
| 60 | 2-Cl-phenyl | 2-methylsulfonyl-1-imidazolyl |
| 61 | 2-F-phenyl | 2-(aminosulfonyl)phenyl |
| 62 | 2-F-phenyl | 2-(methylaminosulfonyl)phenyl |
| 63 | 2-F-phenyl | 1-pyrrolidinocarbonyl |
| 64 | 2-F-phenyl | 2-(methylsulfonyl)phenyl |
| 65 | 2-F-phenyl | 4-morpholino |
| 66 | 2-F-phenyl | 2-(1'-CF$_3$-tetrazol-2-yl)phenyl |
| 67 | 2-F-phenyl | 4-morpholinocarbonyl |
| 68 | 2-F-phenyl | 2-methyl-1-imidazolyl |
| 69 | 2-F-phenyl | 5-methyl-1-imidazolyl |
| 70 | 2-F-phenyl | 2-methylsulfonyl-1-imidazolyl |
| 71 | 2,6-diF-phenyl | 2-(aminosulfonyl)phenyl |
| 72 | 2,6-diF-phenyl | 2-(methylaminosulfonyl)phenyl |
| 73 | 2,6-diF-phenyl | 1-pyrrolidinocarbonyl |
| 74 | 2,6-diF-phenyl | 2-(methylsulfonyl)phenyl |
| 75 | 2,6-diF-phenyl | 4-morpholino |
| 76 | 2,6-diF-phenyl | 2-(1'-CF$_3$-tetrazol-2-yl)phenyl |
| 77 | 2,6-diF-phenyl | 4-morpholinocarbonyl |
| 78 | 2,6-diF-phenyl | 2-methyl-1-imidazolyl |
| 79 | 2,6-diF-phenyl | 5-methyl-1-imidazolyl |
| 80 | 2,6-diF-phenyl | 2-methylsulfonyl-1-imidazolyl |

For each example, DE is:
(A) pyridin-4-yl-CH$_2$,
(B) 2-amino-pyrimidin-4-yl,
(C) 6-amino-pyridin-2-yl,
(D) 3-amidino-4-F-phenyl, or
(E) N-amidino-3-piperidinyl.

TABLE 6

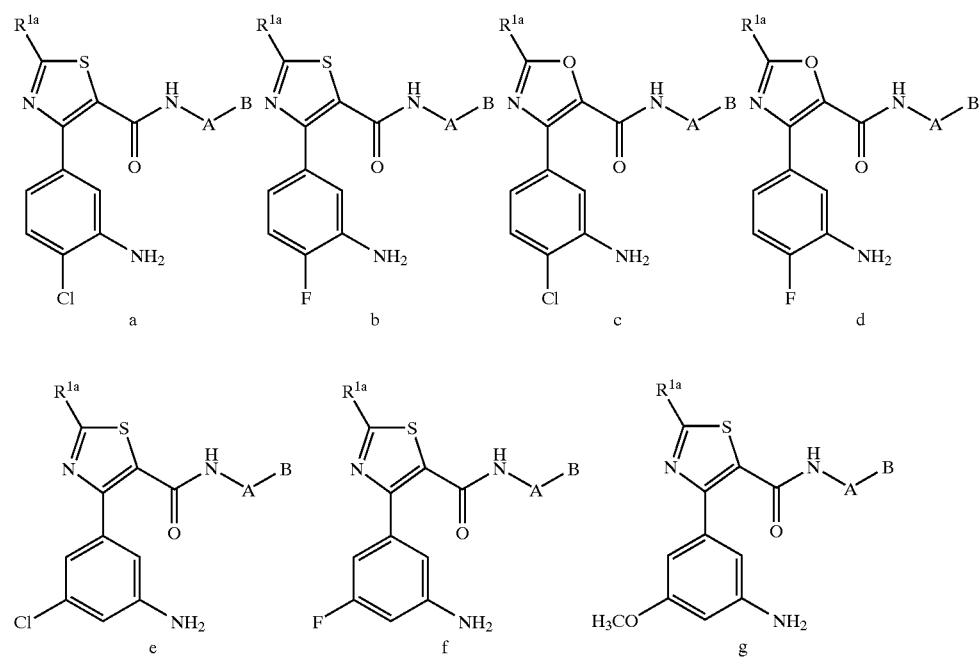

TABLE 6-continued
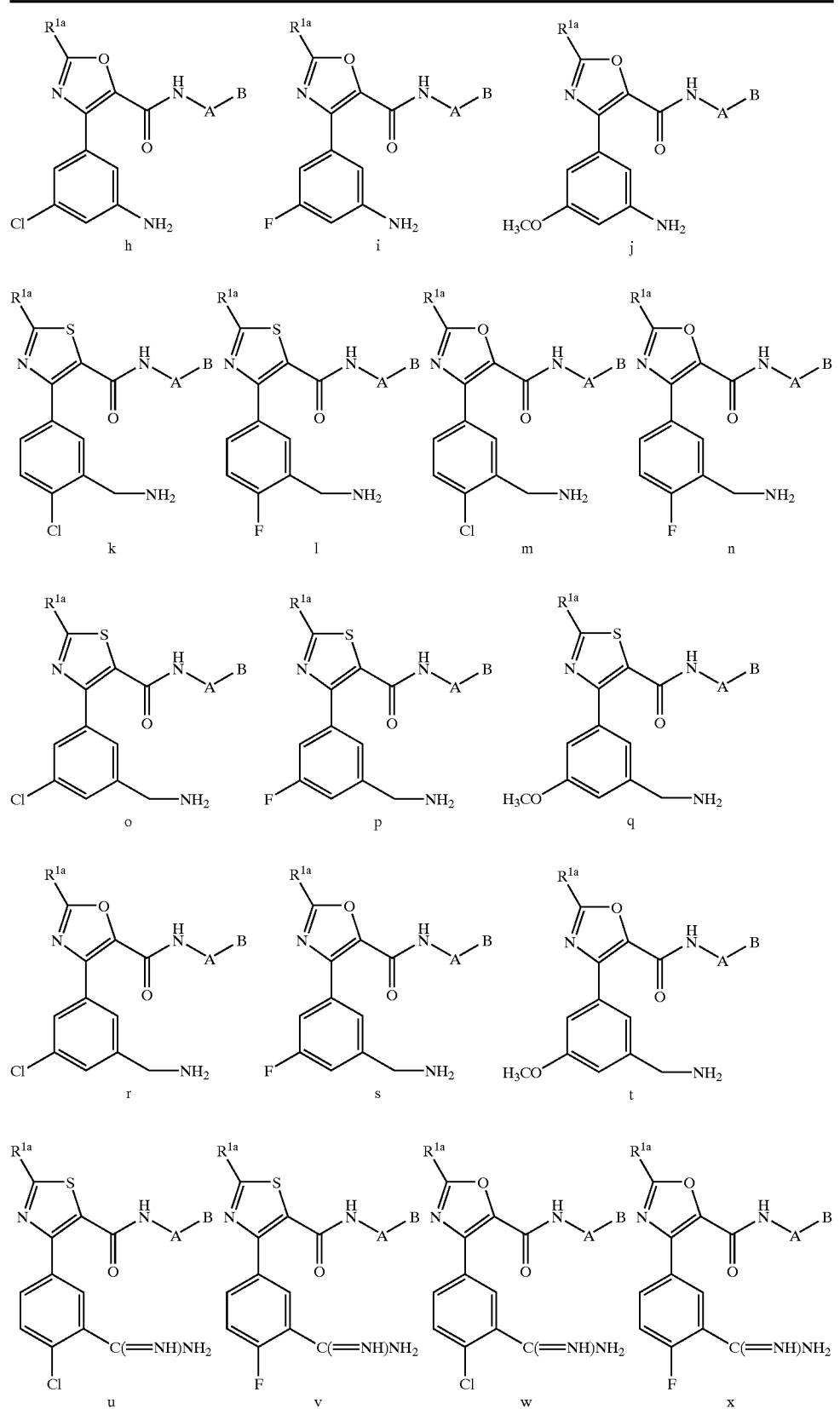

TABLE 6-continued
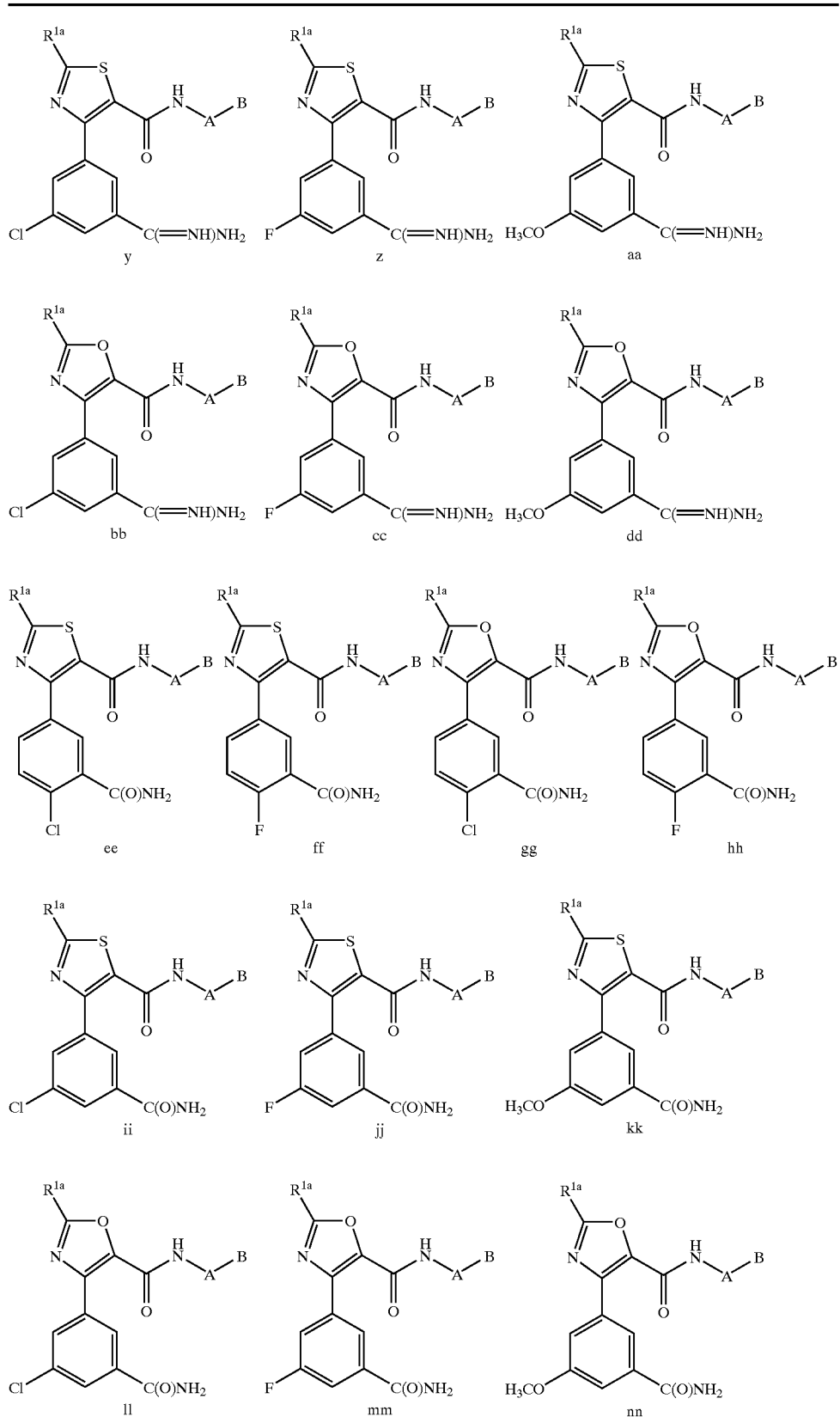

TABLE 6-continued

| Ex # | R¹ᵃ | A | B |
| --- | --- | --- | --- |
| 1 | CH₃ | phenyl | 2-(aminosulfonyl)phenyl |
| 2 | CH₃ | phenyl | 2-(methylaminosulfonyl)phenyl |
| 3 | CH₃ | phenyl | 1-pyrrolidinocarbonyl |
| 4 | CH₃ | phenyl | 2-(methylsulfonyl)phenyl |
| 5 | CH₃ | phenyl | 4-morpholino |
| 6 | CH₃ | phenyl | 2-(1'-CF₃-tetrazol-2-yl)phenyl |
| 7 | CH₃ | phenyl | 4-morpholinocarbonyl |
| 8 | CH₃ | phenyl | 2-methyl-1-imidazolyl |
| 9 | CH₃ | phenyl | 5-methyl-1-imidazolyl |
| 10 | CH₃ | phenyl | 2-methylsulfonyl-1-imidazolyl |
| 11 | CH₃ | 2-pyridyl | 2-(aminosulfonyl)phenyl |
| 12 | CH₃ | 2-pyridyl | 2-(methylaminosulfonyl)phenyl |
| 13 | CH₃ | 2-pyridyl | 1-pyrrolidinocarbonyl |
| 14 | CH₃ | 2-pyridyl | 2-(methylsulfonyl)phenyl |
| 15 | CH₃ | 2-pyridyl | 4-morpholino |
| 16 | CH₃ | 2-pyridyl | 2-(1'-CF₃-tetrazol-2-yl)phenyl |
| 17 | CH₃ | 2-pyridyl | 4-morpholinocarbonyl |
| 18 | CH₃ | 2-pyridyl | 2-methyl-1-imidazolyl |
| 19 | CH₃ | 2-pyridyl | 5-methyl-1-imidazolyl |
| 20 | CH₃ | 2-pyridyl | 2-methylsulfonyl-1-imidazolyl |
| 21 | CH₃ | 3-pyridyl | 2-(aminosulfonyl)phenyl |
| 22 | CH₃ | 3-pyridyl | 2-(methylaminosulfonyl)phenyl |
| 23 | CH₃ | 3-pyridyl | 1-pyrrolidinocarbonyl |
| 24 | CH₃ | 3-pyridyl | 2-(methylsulfonyl)phenyl |
| 25 | CH₃ | 3-pyridyl | 4-morpholino |
| 26 | CH₃ | 3-pyridyl | 2-(1'-CF₃-tetrazol-2-yl)phenyl |
| 27 | CH₃ | 3-pyridyl | 4-morpholinocarbonyl |
| 28 | CH₃ | 3-pyridyl | 2-methyl-1-imidazolyl |
| 29 | CH₃ | 3-pyridyl | 5-methyl-1-imidazolyl |
| 30 | CH₃ | 3-pyridyl | 2-methylsulfonyl-1-imidazolyl |
| 31 | CH₃ | 2-pyrimidyl | 2-(aminosulfonyl)phenyl |
| 32 | CH₃ | 2-pyrimidyl | 2-(methylaminosulfonyl)phenyl |
| 33 | CH₃ | 2-pyrimidyl | 1-pyrrolidinocarbonyl |
| 34 | CH₃ | 2-pyrimidyl | 2-(methylsulfonyl)phenyl |
| 35 | CH₃ | 2-pyrimidyl | 4-morpholino |
| 36 | CH₃ | 2-pyrimidyl | 2-(1'-CF₃-tetrazol-2-yl)phenyl |
| 37 | CH₃ | 2-pyrimidyl | 4-morpholinocarbonyl |
| 38 | CH₃ | 2-pyrimidyl | 2-methyl-1-imidazolyl |
| 39 | CH₃ | 2-pyrimidyl | 5-methyl-1-imidazolyl |
| 40 | CH₃ | 2-pyrimidyl | 2-methylsulfonyl-1-imidazolyl |
| 41 | CH₃ | 5-pyrimidyl | 2-(aminosulfonyl)phenyl |
| 42 | CH₃ | 5-pyrimidyl | 2-(methylaminosulfonyl)phenyl |
| 43 | CH₃ | 5-pyrimidyl | 1-pyrrolidinocarbonyl |
| 44 | CH₃ | 5-pyrimidyl | 2-(methylsulfonyl)phenyl |
| 45 | CH₃ | 5-pyrimidyl | 4-morpholino |
| 46 | CH₃ | 5-pyrimidyl | 2-(1'-CF₃-tetrazol-2-yl)phenyl |
| 47 | CH₃ | 5-pyrimidyl | 4-morpholinocarbonyl |

TABLE 6-continued

| | | | |
|---|---|---|---|
| 48 | CH$_3$ | 5-pyrimidyl | 2-methyl-1-imidazolyl |
| 49 | CH$_3$ | 5-pyrimidyl | 5-methyl-1-imidazolyl |
| 50 | CH$_3$ | 5-pyrimidyl | 2-methylsulfonyl-1-imidazolyl |
| 51 | CH$_3$ | 2-Cl-phenyl | 2-(aminosulfonyl)phenyl |
| 52 | CH$_3$ | 2-Cl-phenyl | 2-(methylaminosulfonyl)phenyl |
| 53 | CH$_3$ | 2-Cl-phenyl | 1-pyrrolidinocarbonyl |
| 54 | CH$_3$ | 2-Cl-phenyl | 2-(methylsulfonyl)phenyl |
| 55 | CH$_3$ | 2-Cl-phenyl | 4-morpholino |
| 56 | CH$_3$ | 2-Cl-phenyl | 2-(1'-CF$_3$-tetrazol-2-yl)phenyl |
| 57 | CH$_3$ | 2-Cl-phenyl | 4-morpholinocarbonyl |
| 58 | CH$_3$ | 2-Cl-phenyl | 2-methyl-1-imidazolyl |
| 59 | CH$_3$ | 2-Cl-phenyl | 5-methyl-1-imidazolyl |
| 60 | CH$_3$ | 2-Cl-phenyl | 2-methylsulfonyl-1-imidazolyl |
| 61 | CH$_3$ | 2-F-phenyl | 2-(aminosulfonyl)phenyl |
| 62 | CH$_3$ | 2-F-phenyl | 2-(methylaminosulfonyl)phenyl |
| 63 | CH$_3$ | 2-F-phenyl | 1-pyrrolidinocarbonyl |
| 64 | CH$_3$ | 2-F-phenyl | 2-(methylsulfonyl)phenyl |
| 65 | CH$_3$ | 2-F-phenyl | 4-morpholino |
| 66 | CH$_3$ | 2-F-phenyl | 2-(1'-CF$_3$-tetrazol-2-yl)phenyl |
| 67 | CH$_3$ | 2-F-phenyl | 4-morpholinocarbonyl |
| 68 | CH$_3$ | 2-F-phenyl | 2-methyl-1-imidazolyl |
| 69 | CH$_3$ | 2-F-phenyl | 5-methyl-1-imidazolyl |
| 70 | CH$_3$ | 2-F-phenyl | 2-methylsulfonyl-1-imidazolyl |
| 71 | CH$_3$ | 2,6-diF-phenyl | 2-(aminosulfonyl)phenyl |
| 72 | CH$_3$ | 2,6-diF-phenyl | 2-(methylaminosulfonyl)phenyl |
| 73 | CH$_3$ | 2,6-diF-phenyl | 1-pyrrolidinocarbonyl |
| 74 | CH$_3$ | 2,6-diF-phenyl | 2-(methylsulfonyl)phenyl |
| 75 | CH$_3$ | 2,6-diF-phenyl | 4-morpholino |
| 76 | CH$_3$ | 2,6-diF-phenyl | 2-(1'-CF$_3$-tetrazol-2-yl)phenyl |
| 77 | CH$_3$ | 2,6-diF-phenyl | 4-morpholinocarbonyl |
| 78 | CH$_3$ | 2,6-diF-phenyl | 2-methyl-1-imidazolyl |
| 79 | CH$_3$ | 2,6-diF-phenyl | 5-methyl-1-imidazolyl |
| 80 | CH$_3$ | 2,6-diF-phenyl | 2-methylsulfonyl-1-imidazolyl |
| 81 | CH$_2$CH$_3$ | phenyl | 2-(aminosulfonyl)phenyl |
| 82 | CH$_2$CH$_3$ | phenyl | 2-(methylaminosulfonyl)phenyl |
| 83 | CH$_2$CH$_3$ | phenyl | 1-pyrrolidinocarbonyl |
| 84 | CH$_2$CH$_3$ | phenyl | 2-(methylsulfonyl)phenyl |
| 85 | CH$_2$CH$_3$ | phenyl | 4-morpholino |
| 86 | CH$_2$CH$_3$ | phenyl | 2-(1'-CF$_3$-tetrazol-2-yl)phenyl |
| 87 | CH$_2$CH$_3$ | phenyl | 4-morpholinocarbonyl |
| 88 | CH$_2$CH$_3$ | phenyl | 2-methyl-1-imidazolyl |
| 89 | CH$_2$CH$_3$ | phenyl | 5-methyl-1-imidazolyl |
| 90 | CH$_2$CH$_3$ | phenyl | 2-methylsulfonyl-1-imidazolyl |
| 91 | CH$_2$CH$_3$ | 2-pyridyl | 2-(aminosulfonyl)phenyl |
| 92 | CH$_2$CH$_3$ | 2-pyridyl | 2-(methylaminosulfonyl)phenyl |
| 93 | CH$_2$CH$_3$ | 2-pyridyl | 1-pyrrolidinocarbonyl |
| 94 | CH$_2$CH$_3$ | 2-pyridyl | 2-(methylsulfonyl)phenyl |
| 95 | CH$_2$CH$_3$ | 2-pyridyl | 4-morpholino |
| 96 | CH$_2$CH$_3$ | 2-pyridyl | 2-(1'-CF$_3$-tetrazol-2-yl)phenyl |
| 97 | CH$_2$CH$_3$ | 2-pyridyl | 4-morpholinocarbonyl |
| 98 | CH$_2$CH$_3$ | 2-pyridyl | 2-methyl-1-imidazolyl |
| 99 | CH$_2$CH$_3$ | 2-pyridyl | 5-methyl-1-imidazolyl |
| 100 | CH$_2$CH$_3$ | 2-pyridyl | 2-methylsulfonyl-1-imidazolyl |
| 101 | CH$_2$CH$_3$ | 3-pyridyl | 2-(aminosulfonyl)phenyl |
| 102 | CH$_2$CH$_3$ | 3-pyridyl | 2-(methylaminosulfonyl)phenyl |
| 103 | CH$_2$CH$_3$ | 3-pyridyl | 1-pyrrolidinocarbonyl |
| 104 | CH$_2$CH$_3$ | 3-pyridyl | 2-(methylsulfonyl)phenyl |
| 105 | CH$_2$CH$_3$ | 3-pyridyl | 4-morpholino |
| 106 | CH$_2$CH$_3$ | 3-pyridyl | 2-(1'-CF$_3$-tetrazol-2-yl)phenyl |
| 107 | CH$_2$CH$_3$ | 3-pyridyl | 4-morpholinocarbonyl |
| 108 | CH$_2$CH$_3$ | 3-pyridyl | 2-methyl-1-imidazolyl |
| 109 | CH$_2$CH$_3$ | 3-pyridyl | 5-methyl-1-imidazolyl |
| 110 | CH$_2$CH$_3$ | 3-pyridyl | 2-methylsulfonyl-1-imidazolyl |
| 111 | CH$_2$CH$_3$ | 2-pyrimidyl | 2-(aminosulfonyl)phenyl |
| 112 | CH$_2$CH$_3$ | 2-pyrimidyl | 2-(methylaminosulfonyl)phenyl |
| 113 | CH$_2$CH$_3$ | 2-pyrimidyl | 1-pyrrolidinocarbonyl |
| 114 | CH$_2$CH$_3$ | 2-pyrimidyl | 2-(methylsulfonyl)phenyl |
| 115 | CH$_2$CH$_3$ | 2-pyrimidyl | 4-morpholino |
| 116 | CH$_2$CH$_3$ | 2-pyrimidyl | 2-(1'-CF$_3$-tetrazol-2-yl)phenyl |
| 117 | CH$_2$CH$_3$ | 2-pyrimidyl | 4-morpholinocarbonyl |
| 118 | CH$_2$CH$_3$ | 2-pyrimidyl | 2-methyl-1-imidazolyl |
| 119 | CH$_2$CH$_3$ | 2-pyrimidyl | 5-methyl-1-imidazolyl |
| 120 | CH$_2$CH$_3$ | 2-pyrimidyl | 2-methylsulfonyl-1-imidazolyl |
| 121 | CH$_2$CH$_3$ | 5-pyrimidyl | 2-(aminosulfonyl)phenyl |
| 122 | CH$_2$CH$_3$ | 5-pyrimidyl | 2-(methylaminosulfonyl)phenyl |
| 123 | CH$_2$CH$_3$ | 5-pyrimidyl | 1-pyrrolidinocarbonyl |
| 124 | CH$_2$CH$_3$ | 5-pyrimidyl | 2-(methylsulfonyl)phenyl |
| 125 | CH$_2$CH$_3$ | 5-pyrimidyl | 4-morpholino |
| 126 | CH$_2$CH$_3$ | 5-pyrimidyl | 2-(1'-CF$_3$-tetrazol-2-yl)phenyl |

TABLE 6-continued

| | | | |
|---|---|---|---|
| 127 | $CH_2CH_3$ | 5-pyrimidyl | 4-morpholinocarbonyl |
| 128 | $CH_2CH_3$ | 5-pyrimidyl | 2-methyl-1-imidazolyl |
| 129 | $CH_2CH_3$ | 5-pyrimidyl | 5-methyl-1-imidazolyl |
| 130 | $CH_2CH_3$ | 5-pyrimidyl | 2-methylsulfonyl-1-imidazolyl |
| 131 | $CH_2CH_3$ | 2-Cl-phenyl | 2-(aminosulfonyl)phenyl |
| 132 | $CH_2CH_3$ | 2-Cl-phenyl | 2-(methylaminosulfonyl)phenyl |
| 133 | $CH_2CH_3$ | 2-Cl-phenyl | 1-pyrrolidinocarbonyl |
| 134 | $CH_2CH_3$ | 2-Cl-phenyl | 2-(methylsulfonyl)phenyl |
| 135 | $CH_2CH_3$ | 2-Cl-phenyl | 4-morpholino |
| 136 | $CH_2CH_3$ | 2-Cl-phenyl | 2-(1'-$CF_3$-tetrazol-2-yl)phenyl |
| 137 | $CH_2CH_3$ | 2-Cl-phenyl | 4-morpholinocarbonyl |
| 138 | $CH_2CH_3$ | 2-Cl-phenyl | 2-methyl-1-imidazolyl |
| 139 | $CH_2CH_3$ | 2-Cl-phenyl | 5-methyl-1-imidazolyl |
| 140 | $CH_2CH_3$ | 2-Cl-phenyl | 2-methylsulfonyl-1-imidazolyl |
| 141 | $CH_2CH_3$ | 2-F-phenyl | 2-(aminosulfonyl)phenyl |
| 142 | $CH_2CH_3$ | 2-F-phenyl | 2-(methylaminosulfonyl)phenyl |
| 143 | $CH_2CH_3$ | 2-F-phenyl | 1-pyrrolidinocarbonyl |
| 144 | $CH_2CH_3$ | 2-F-phenyl | 2-(methylsulfonyl)phenyl |
| 145 | $CH_2CH_3$ | 2-F-phenyl | 4-morpholino |
| 146 | $CH_2CH_3$ | 2-F-phenyl | 2-(1'-$CF_3$-tetrazol-2-yl)phenyl |
| 147 | $CH_2CH_3$ | 2-F-phenyl | 4-morpholinocarbonyl |
| 148 | $CH_2CH_3$ | 2-F-phenyl | 2-methyl-1-imidazolyl |
| 149 | $CH_2CH_3$ | 2-F-phenyl | 5-methyl-1-imidazolyl |
| 150 | $CH_2CH_3$ | 2-F-phenyl | 2-methylsulfonyl-1-imidazolyl |
| 151 | $CH_2CH_3$ | 2,6-diF-phenyl | 2-(aminosulfonyl)phenyl |
| 152 | $CH_2CH_3$ | 2,6-diF-phenyl | 2-(methylaminosulfonyl)phenyl |
| 153 | $CH_2CH_3$ | 2,6-diF-phenyl | 1-pyrrolidinocarbonyl |
| 154 | $CH_2CH_3$ | 2,6-diF-phenyl | 2-(methylsulfonyl)phenyl |
| 155 | $CH_2CH_3$ | 2,6-diF-phenyl | 4-morpholino |
| 156 | $CH_2CH_3$ | 2,6-diF-phenyl | 2-(1'-$CF_3$-tetrazol-2-yl)phenyl |
| 157 | $CH_2CH_3$ | 2,6-diF-phenyl | 4-morpholinocarbonyl |
| 158 | $CH_2CH_3$ | 2,6-diF-phenyl | 2-methyl-1-imidazolyl |
| 159 | $CH_2CH_3$ | 2,6-diF-phenyl | 5-methyl-1-imidazolyl |
| 160 | $CH_2CH_3$ | 2,6-diF-phenyl | 2-methylsulfonyl-1-imidazolyl |
| 161 | $CF_3$ | phenyl | 2-(aminosulfonyl)phenyl |
| 162 | $CF_3$ | phenyl | 2-(methylaminosulfonyl)phenyl |
| 163 | $CF_3$ | phenyl | 1-pyrrolidinocarbonyl |
| 164 | $CF_3$ | phenyl | 2-(methylsulfonyl)phenyl |
| 165 | $CF_3$ | phenyl | 4-morpholino |
| 166 | $CF_3$ | phenyl | 2-(1'-$CF_3$-tetrazol-2-yl)phenyl |
| 167 | $CF_3$ | phenyl | 4-morpholinocarbonyl |
| 168 | $CF_3$ | phenyl | 2-methyl-1-imidazolyl |
| 169 | $CF_3$ | phenyl | 5-methyl-1-imidazolyl |
| 170 | $CF_3$ | phenyl | 2-methylsulfonyl-1-imidazolyl |
| 171 | $CF_3$ | 2-pyridyl | 2-(aminosulfonyl)phenyl |
| 172 | $CF_3$ | 2-pyridyl | 2-(methylaminosulfonyl)phenyl |
| 173 | $CF_3$ | 2-pyridyl | 1-pyrrolidinocarbonyl |
| 174 | $CF_3$ | 2-pyridyl | 2-(methylsulfonyl)phenyl |
| 175 | $CF_3$ | 2-pyridyl | 4-morpholino |
| 176 | $CF_3$ | 2-pyridyl | 2-(1'-$CF_3$-tetrazol-2-yl)phenyl |
| 177 | $CF_3$ | 2-pyridyl | 4-morpholinocarbonyl |
| 178 | $CF_3$ | 2-pyridyl | 2-methyl-1-imidazolyl |
| 179 | $CF_3$ | 2-pyridyl | 5-methyl-1-imidazolyl |
| 180 | $CF_3$ | 2-pyridyl | 2-methylsulfonyl-1-imidazolyl |
| 181 | $CF_3$ | 3-pyridyl | 2-(aminosulfonyl)phenyl |
| 182 | $CF_3$ | 3-pyridyl | 2-(methylaminosulfonyl)phenyl |
| 183 | $CF_3$ | 3-pyridyl | 1-pyrrolidinocarbonyl |
| 184 | $CF_3$ | 3-pyridyl | 2-(methylsulfonyl)phenyl |
| 185 | $CF_3$ | 3-pyridyl | 4-morpholino |
| 186 | $CF_3$ | 3-pyridyl | 2-(1'-$CF_3$-tetrazol-2-yl)phenyl |
| 187 | $CF_3$ | 3-pyridyl | 4-morpholinocarbonyl |
| 188 | $CF_3$ | 3-pyridyl | 2-methyl-1-imidazolyl |
| 189 | $CF_3$ | 3-pyridyl | 5-methyl-1-imidazolyl |
| 190 | $CF_3$ | 3-pyridyl | 2-methylsulfonyl-1-imidazolyl |
| 191 | $CF_3$ | 2-pyrimidyl | 2-(aminosulfonyl)phenyl |
| 192 | $CF_3$ | 2-pyrimidyl | 2-(methylaminosulfonyl)phenyl |
| 193 | $CF_3$ | 2-pyrimidyl | 1-pyrrolidinocarbonyl |
| 194 | $CF_3$ | 2-pyrimidyl | 2-(methylsulfonyl)phenyl |
| 195 | $CF_3$ | 2-pyrimidyl | 4-morpholino |
| 196 | $CF_3$ | 2-pyrimidyl | 2-(1'-$CF_3$-tetrazol-2-yl)phenyl |
| 197 | $CF_3$ | 2-pyrimidyl | 4-morpholinocarbonyl |
| 198 | $CF_3$ | 2-pyrimidyl | 2-methyl-1-imidazolyl |
| 199 | $CF_3$ | 2-pyrimidyl | 5-methyl-1-imidazolyl |
| 200 | $CF_3$ | 2-pyrimidyl | 2-methylsulfonyl-1-imidazolyl |
| 201 | $CF_3$ | 5-pyrimidyl | 2-(aminosulfonyl)phenyl |
| 202 | $CF_3$ | 5-pyrimidyl | 2-(methylaminosulfonyl)phenyl |
| 203 | $CF_3$ | 5-pyrimidyl | 1-pyrrolidinocarbonyl |
| 204 | $CF_3$ | 5-pyrimidyl | 2-(methylsulfonyl)phenyl |
| 205 | $CF_3$ | 5-pyrimidyl | 4-morpholino |

TABLE 6-continued

| | | | |
|---|---|---|---|
| 206 | $CF_3$ | 5-pyrimidyl | 2-(1'-$CF_3$-tetrazol-2-yl)phenyl |
| 207 | $CF_3$ | 5-pyrimidyl | 4-morpholinocarbonyl |
| 208 | $CF_3$ | 5-pyrimidyl | 2-methyl-1-imidazolyl |
| 209 | $CF_3$ | 5-pyrimidyl | 5-methyl-1-imidazolyl |
| 210 | $CF_3$ | 5-pyrimidyl | 2-methylsulfonyl-1-imidazolyl |
| 211 | $CF_3$ | 2-Cl-phenyl | 2-(aminosulfonyl)phenyl |
| 212 | $CF_3$ | 2-Cl-phenyl | 2-(methylaminosulfonyl)phenyl |
| 213 | $CF_3$ | 2-Cl-phenyl | 1-pyrrolidinocarbonyl |
| 214 | $CF_3$ | 2-Cl-phenyl | 2-(methylsulfonyl)phenyl |
| 215 | $CF_3$ | 2-Cl-phenyl | 4-morpholino |
| 216 | $CF_3$ | 2-Cl-phenyl | 2-(1'-$CF_3$-tetrazol-2-yl)phenyl |
| 217 | $CF_3$ | 2-Cl-phenyl | 4-morpholinocarbonyl |
| 218 | $CF_3$ | 2-Cl-phenyl | 2-methyl-1-imidazolyl |
| 219 | $CF_3$ | 2-Cl-phenyl | 5-methyl-1-imidazolyl |
| 220 | $CF_3$ | 2-Cl-phenyl | 2-methylsulfonyl-1-imidazolyl |
| 221 | $CF_3$ | 2-F-phenyl | 2-(aminosulfonyl)phenyl |
| 222 | $CF_3$ | 2-F-phenyl | 2-(methylaminosulfonyl)phenyl |
| 223 | $CF_3$ | 2-F-phenyl | 1-pyrrolidinocarbonyl |
| 224 | $CF_3$ | 2-F-phenyl | 2-(methylsulfonyl)phenyl |
| 225 | $CF_3$ | 2-F-phenyl | 4-morpholino |
| 226 | $CF_3$ | 2-F-phenyl | 2-(1'-$CF_3$-tetrazol-2-yl)phenyl |
| 227 | $CF_3$ | 2-F-phenyl | 4-morpholinocarbonyl |
| 228 | $CF_3$ | 2-F-phenyl | 2-methyl-1-imidazolyl |
| 229 | $CF_3$ | 2-F-phenyl | 5-methyl-1-imidazolyl |
| 230 | $CF_3$ | 2-F-phenyl | 2-methylsulfonyl-1-imidazolyl |
| 231 | $CF_3$ | 2,6-diF-phenyl | 2-(aminosulfonyl)phenyl |
| 232 | $CF_3$ | 2,6-diF-phenyl | 2-(methylaminosulfonyl)phenyl |
| 233 | $CF_3$ | 2,6-diF-phenyl | 1-pyrrolidinocarbonyl |
| 234 | $CF_3$ | 2,6-diF-phenyl | 2-(methylsulfonyl)phenyl |
| 235 | $CF_3$ | 2,6-diF-phenyl | 4-morpholino |
| 236 | $CF_3$ | 2,6-diF-phenyl | 2-(1'-$CF_3$-tetrazol-2-yl)phenyl |
| 237 | $CF_3$ | 2,6-diF-phenyl | 4-morpholinocarbonyl |
| 238 | $CF_3$ | 2,6-diF-phenyl | 2-methyl-1-imidazolyl |
| 239 | $CF_3$ | 2,6-diF-phenyl | 5-methyl-1-imidazolyl |
| 240 | $CF_3$ | 2,6-diF-phenyl | 2-methylsulfonyl-1-imidazolyl |
| 241 | $SCH_3$ | phenyl | 2-(aminosulfonyl)phenyl |
| 242 | $SCH_3$ | phenyl | 2-(methylaminosulfonyl)phenyl |
| 243 | $SCH_3$ | phenyl | 1-pyrrolidinocarbonyl |
| 244 | $SCH_3$ | phenyl | 2-(methylsulfonyl)phenyl |
| 245 | $SCH_3$ | phenyl | 4-morpholino |
| 246 | $SCH_3$ | phenyl | 2-(1'-$CF_3$-tetrazol-2-yl)phenyl |
| 247 | $SCH_3$ | phenyl | 4-morpholinocarbonyl |
| 248 | $SCH_3$ | phenyl | 2-methyl-1-imidazolyl |
| 249 | $SCH_3$ | phenyl | 5-methyl-1-imidazolyl |
| 250 | $SCH_3$ | phenyl | 2-methylsulfonyl-1-imidazolyl |
| 251 | $SCH_3$ | 2-pyridyl | 2-(aminosulfonyl)phenyl |
| 252 | $SCH_3$ | 2-pyridyl | 2-(methylaminosulfonyl)phenyl |
| 253 | $SCH_3$ | 2-pyridyl | 1-pyrrolidinocarbonyl |
| 254 | $SCH_3$ | 2-pyridyl | 2-(methylsulfonyl)phenyl |
| 255 | $SCH_3$ | 2-pyridyl | 4-morpholino |
| 256 | $SCH_3$ | 2-pyridyl | 2-(1'-$CF_3$-tetrazol-2-yl)phenyl |
| 257 | $SCH_3$ | 2-pyridyl | 4-morpholinocarbonyl |
| 258 | $SCH_3$ | 2-pyridyl | 2-methyl-1-imidazolyl |
| 259 | $SCH_3$ | 2-pyridyl | 5-methyl-1-imidazolyl |
| 260 | $SCH_3$ | 2-pyridyl | 2-methylsulfonyl-1-imidazolyl |
| 261 | $SCH_3$ | 3-pyridyl | 2-(aminosulfonyl)phenyl |
| 262 | $SCH_3$ | 3-pyridyl | 2-(methylaminosulfonyl)phenyl |
| 263 | $SCH_3$ | 3-pyridyl | 1-pyrrolidinocarbonyl |
| 264 | $SCH_3$ | 3-pyridyl | 2-(methylsulfonyl)phenyl |
| 265 | $SCH_3$ | 3-pyridyl | 4-morpholino |
| 266 | $SCH_3$ | 3-pyridyl | 2-(1'-$CF_3$-tetrazol-2-yl)phenyl |
| 267 | $SCH_3$ | 3-pyridyl | 4-morpholinocarbonyl |
| 268 | $SCH_3$ | 3-pyridyl | 2-methyl-1-imidazolyl |
| 269 | $SCH_3$ | 3-pyridyl | 5-methyl-1-imidazolyl |
| 270 | $SCH_3$ | 3-pyridyl | 2-methylsulfonyl-1-imidazolyl |
| 271 | $SCH_3$ | 2-pyrimidyl | 2-(aminosulfonyl)phenyl |
| 272 | $SCH_3$ | 2-pyrimidyl | 2-(methylaminosulfonyl)phenyl |
| 273 | $SCH_3$ | 2-pyrimidyl | 1-pyrrolidinocarbonyl |
| 274 | $SCH_3$ | 2-pyrimidyl | 2-(methylsulfonyl)phenyl |
| 275 | $SCH_3$ | 2-pyrimidyl | 4-morpholino |
| 276 | $SCH_3$ | 2-pyrimidyl | 2-(1'-$CF_3$-tetrazol-2-yl)phenyl |
| 277 | $SCH_3$ | 2-pyrimidyl | 4-morpholinocarbonyl |
| 278 | $SCH_3$ | 2-pyrimidyl | 2-methyl-1-imidazolyl |
| 279 | $SCH_3$ | 2-pyrimidyl | 5-methyl-1-imidazolyl |
| 280 | $SCH_3$ | 2-pyrimidyl | 2-methylsulfonyl-1-imidazolyl |
| 281 | $SCH_3$ | 5-pyrimidyl | 2-(aminosulfonyl)phenyl |
| 282 | $SCH_3$ | 5-pyrimidyl | 2-(methylaminosulfonyl)phenyl |
| 283 | $SCH_3$ | 5-pyrimidyl | 1-pyrrolidinocarbonyl |
| 284 | $SCH_3$ | 5-pyrimidyl | 2-(methylsulfonyl)phenyl |

TABLE 6-continued

| | | | |
|---|---|---|---|
| 285 | SCH$_3$ | 5-pyrimidyl | 4-morpholino |
| 286 | SCH$_3$ | 5-pyrimidyl | 2-(1'-CF$_3$-tetrazol-2-yl)phenyl |
| 287 | SCH$_3$ | 5-pyrimidyl | 4-morpholinocarbonyl |
| 288 | SCH$_3$ | 5-pyrimidyl | 2-methyl-1-imidazolyl |
| 289 | SCH$_3$ | 5-pyrimidyl | 5-methyl-1-imidazolyl |
| 290 | SCH$_3$ | 5-pyrimidyl | 2-methylsulfonyl-1-imidazolyl |
| 291 | SCH$_3$ | 2-Cl-phenyl | 2-(aminosulfonyl)phenyl |
| 292 | SCH$_3$ | 2-Cl-phenyl | 2-(methylaminosulfonyl)phenyl |
| 293 | SCH$_3$ | 2-Cl-phenyl | 1-pyrrolidinocarbonyl |
| 294 | SCH$_3$ | 2-Cl-phenyl | 2-(methylsulfonyl)phenyl |
| 295 | SCH$_3$ | 2-Cl-phenyl | 4-morpholino |
| 296 | SCH$_3$ | 2-Cl-phenyl | 2-(1'-CF$_3$-tetrazol-2-yl)phenyl |
| 297 | SCH$_3$ | 2-Cl-phenyl | 4-morpholinocarbonyl |
| 298 | SCH$_3$ | 2-Cl-phenyl | 2-methyl-1-imidazolyl |
| 299 | SCH$_3$ | 2-Cl-phenyl | 5-methyl-1-imidazolyl |
| 300 | SCH$_3$ | 2-Cl-phenyl | 2-methylsulfonyl-1-imidazolyl |
| 301 | SCH$_3$ | 2-F-phenyl | 2-(aminosulfonyl)phenyl |
| 302 | SCH$_3$ | 2-F-phenyl | 2-(methylaminosulfonyl)phenyl |
| 303 | SCH$_3$ | 2-F-phenyl | 1-pyrrolidinocarbonyl |
| 304 | SCH$_3$ | 2-F-phenyl | 2-(methylsulfonyl)phenyl |
| 305 | SCH$_3$ | 2-F-phenyl | 4-morpholino |
| 306 | SCH$_3$ | 2-F-phenyl | 2-(1'-CF$_3$-tetrazol-2-yl)phenyl |
| 307 | SCH$_3$ | 2-F-phenyl | 4-morpholinocarbonyl |
| 308 | SCH$_3$ | 2-F-phenyl | 2-methyl-1-imidazolyl |
| 309 | SCH$_3$ | 2-F-phenyl | 5-methyl-1-imidazolyl |
| 310 | SCH$_3$ | 2-F-phenyl | 2-methylsulfonyl-1-imidazolyl |
| 311 | SCH$_3$ | 2,6-diF-phenyl | 2-(aminosulfonyl)phenyl |
| 312 | SCH$_3$ | 2,6-diF-phenyl | 2-(methylaminosulfonyl)phenyl |
| 313 | SCH$_3$ | 2,6-diF-phenyl | 1-pyrrolidinocarbonyl |
| 314 | SCH$_3$ | 2,6-diF-phenyl | 2-(methylsulfonyl)phenyl |
| 315 | SCH$_3$ | 2,6-diF-phenyl | 4-morpholino |
| 316 | SCH$_3$ | 2,6-diF-phenyl | 2-(1'-CF$_3$-tetrazol-2-yl)phenyl |
| 317 | SCH$_3$ | 2,6-diF-phenyl | 4-morpholinocarbonyl |
| 318 | SCH$_3$ | 2,6-diF-phenyl | 2-methyl-1-imidazolyl |
| 319 | SCH$_3$ | 2,6-diF-phenyl | 5-methyl-1-imidazolyl |
| 320 | SCH$_3$ | 2,6-diF-phenyl | 2-methylsulfonyl-1-imidazolyl |
| 321 | SOCH$_3$ | phenyl | 2-(aminosulfonyl)phenyl |
| 322 | SOCH$_3$ | phenyl | 2-(methylaminosulfonyl)phenyl |
| 323 | SOCH$_3$ | phenyl | 1-pyrrolidinocarbonyl |
| 324 | SOCH$_3$ | phenyl | 2-(methylsulfonyl)phenyl |
| 325 | SOCH$_3$ | phenyl | 4-morpholino |
| 326 | SOCH$_3$ | phenyl | 2-(1'-CF$_3$-tetrazol-2-yl)phenyl |
| 327 | SOCH$_3$ | phenyl | 4-morpholinocarbonyl |
| 328 | SOCH$_3$ | phenyl | 2-methyl-1-imidazolyl |
| 329 | SOCH$_3$ | phenyl | 5-methyl-1-imidazolyl |
| 330 | SOCH$_3$ | phenyl | 2-methylsulfonyl-1-imidazolyl |
| 331 | SOCH$_3$ | 2-pyridyl | 2-(aminosulfonyl)phenyl |
| 332 | SOCH$_3$ | 2-pyridyl | 2-(methylaminosulfonyl)phenyl |
| 333 | SOCH$_3$ | 2-pyridyl | 1-pyrrolidinocarbonyl |
| 334 | SOCH$_3$ | 2-pyridyl | 2-(methylsulfonyl)phenyl |
| 335 | SOCH$_3$ | 2-pyridyl | 4-morpholino |
| 336 | SOCH$_3$ | 2-pyridyl | 2-(1'-CF$_3$-tetrazol-2-yl)phenyl |
| 337 | SOCH$_3$ | 2-pyridyl | 4-morpholinocarbonyl |
| 338 | SOCH$_3$ | 2-pyridyl | 2-methyl-1-imidazolyl |
| 339 | SOCH$_3$ | 2-pyridyl | 5-methyl-1-imidazolyl |
| 340 | SOCH$_3$ | 2-pyridyl | 2-methylsulfonyl-1-imidazolyl |
| 341 | SOCH$_3$ | 3-pyridyl | 2-(aminosulfonyl)phenyl |
| 342 | SOCH$_3$ | 3-pyridyl | 2-(methylaminosulfonyl)phenyl |
| 343 | SOCH$_3$ | 3-pyridyl | 1-pyrrolidinocarbonyl |
| 344 | SOCH$_3$ | 3-pyridyl | 2-(methylsulfonyl)phenyl |
| 345 | SOCH$_3$ | 3-pyridyl | 4-morpholino |
| 346 | SOCH$_3$ | 3-pyridyl | 2-(1'-CF$_3$-tetrazol-2-yl)phenyl |
| 347 | SOCH$_3$ | 3-pyridyl | 4-morpholinocarbonyl |
| 348 | SOCH$_3$ | 3-pyridyl | 2-methyl-1-imidazolyl |
| 349 | SOCH$_3$ | 3-pyridyl | 5-methyl-1-imidazolyl |
| 350 | SOCH$_3$ | 3-pyridyl | 2-methylsulfonyl-1-imidazolyl |
| 351 | SOCH$_3$ | 2-pyrimidyl | 2-(aminosulfonyl)phenyl |
| 352 | SOCH$_3$ | 2-pyrimidyl | 2-(methylaminosulfonyl)phenyl |
| 353 | SOCH$_3$ | 2-pyrimidyl | 1-pyrrolidinocarbonyl |
| 354 | SOCH$_3$ | 2-pyrimidyl | 2-(methylsulfonyl)phenyl |
| 355 | SOCH$_3$ | 2-pyrimidyl | 4-morpholino |
| 356 | SOCH$_3$ | 2-pyrimidyl | 2-(1'-CF$_3$-tetrazol-2-yl)phenyl |
| 357 | SOCH$_3$ | 2-pyrimidyl | 4-morpholinocarbonyl |
| 358 | SOCH$_3$ | 2-pyrimidyl | 2-methyl-1-imidazolyl |
| 359 | SOCH$_3$ | 2-pyrimidyl | 5-methyl-1-imidazolyl |
| 360 | SOCH$_3$ | 2-pyrimidyl | 2-methylsulfonyl-1-imidazolyl |
| 361 | SOCH$_3$ | 5-pyrimidyl | 2-(aminosulfonyl)phenyl |
| 362 | SOCH$_3$ | 5-pyrimidyl | 2-(methylaminosulfonyl)phenyl |
| 363 | SOCH$_3$ | 5-pyrimidyl | 1-pyrrolidinocarbonyl |

TABLE 6-continued

| | | | |
|---|---|---|---|
| 364 | SOCH$_3$ | 5-pyrimidyl | 2-(methylsulfonyl)phenyl |
| 365 | SOCH$_3$ | 5-pyrimidyl | 4-morpholino |
| 366 | SOCH$_3$ | 5-pyrimidyl | 2-(1'-CF$_3$-tetrazol-2-yl)phenyl |
| 367 | SOCH$_3$ | 5-pyrimidyl | 4-morpholinocarbonyl |
| 368 | SOCH$_3$ | 5-pyrimidyl | 2-methyl-1-imidazolyl |
| 369 | SOCH$_3$ | 5-pyrimidyl | 5-methyl-1-imidazolyl |
| 370 | SOCH$_3$ | 5-pyrimidyl | 2-methylsulfonyl-1-imidazolyl |
| 371 | SOCH$_3$ | 2-Cl-phenyl | 2-(aminosulfonyl)phenyl |
| 372 | SOCH$_3$ | 2-Cl-phenyl | 2-(methylaminosulfonyl)phenyl |
| 373 | SOCH$_3$ | 2-Cl-phenyl | 1-pyrrolidinocarbonyl |
| 374 | SOCH$_3$ | 2-Cl-phenyl | 2-(methylsulfonyl)phenyl |
| 375 | SOCH$_3$ | 2-Cl-phenyl | 4-morpholino |
| 376 | SOCH$_3$ | 2-Cl-phenyl | 2-(1'-CF$_3$-tetrazol-2-yl)phenyl |
| 377 | SOCH$_3$ | 2-Cl-phenyl | 4-morpholinocarbonyl |
| 378 | SOCH$_3$ | 2-Cl-phenyl | 2-methyl-1-imidazolyl |
| 379 | SOCH$_3$ | 2-Cl-phenyl | 5-methyl-1-imidazolyl |
| 380 | SOCH$_3$ | 2-Cl-phenyl | 2-methylsulfonyl-1-imidazolyl |
| 381 | SOCH$_3$ | 2-F-phenyl | 2-(aminosulfonyl)phenyl |
| 382 | SOCH$_3$ | 2-F-phenyl | 2-(methylaminosulfonyl)phenyl |
| 383 | SOCH$_3$ | 2-F-phenyl | 1-pyrrolidinocarbonyl |
| 384 | SOCH$_3$ | 2-F-phenyl | 2-(methylsulfonyl)phenyl |
| 385 | SOCH$_3$ | 2-F-phenyl | 4-morpholino |
| 386 | SOCH$_3$ | 2-F-phenyl | 2-(1'-CF$_3$-tetrazol-2-yl)phenyl |
| 387 | SOCH$_3$ | 2-F-phenyl | 4-morpholinocarbonyl |
| 388 | SOCH$_3$ | 2-F-phenyl | 2-methyl-1-imidazolyl |
| 389 | SOCH$_3$ | 2-F-phenyl | 5-methyl-1-imidazolyl |
| 390 | SOCH$_3$ | 2-F-phenyl | 2-methylsulfonyl-1-imidazolyl |
| 391 | SOCH$_3$ | 2,6-diF-phenyl | 2-(aminosulfonyl)phenyl |
| 392 | SOCH$_3$ | 2,6-diF-phenyl | 2-(methylaminosulfonyl)phenyl |
| 393 | SOCH$_3$ | 2,6-diF-phenyl | 1-pyrrolidinocarbonyl |
| 394 | SOCH$_3$ | 2,6-diF-phenyl | 2-(methylsulfonyl)phenyl |
| 395 | SOCH$_3$ | 2,6-diF-phenyl | 4-morpholino |
| 396 | SOCH$_3$ | 2,6-diF-phenyl | 2-(1'-CF$_3$-tetrazol-2-yl)phenyl |
| 397 | SOCH$_3$ | 2,6-diF-phenyl | 4-morpholinocarbonyl |
| 398 | SOCH$_3$ | 2,6-diF-phenyl | 2-methyl-1-imidazolyl |
| 399 | SOCH$_3$ | 2,6-diF-phenyl | 5-methyl-1-imidazolyl |
| 400 | SOCH$_3$ | 2,6-diF-phenyl | 2-methylsulfonyl-1-imidazolyl |
| 401 | SO$_2$CH$_3$ | phenyl | 2-(aminosulfonyl)phenyl |
| 402 | SO$_2$CH$_3$ | phenyl | 2-(methylaminosulfonyl)phenyl |
| 403 | SO$_2$CH$_3$ | phenyl | 1-pyrrolidinocarbonyl |
| 404 | SO$_2$CH$_3$ | phenyl | 2-(methylsulfonyl)phenyl |
| 405 | SO$_2$CH$_3$ | phenyl | 4-morpholino |
| 406 | SO$_2$CH$_3$ | phenyl | 2-(1'-CF$_3$-tetrazol-2-yl)phenyl |
| 407 | SO$_2$CH$_3$ | phenyl | 4-morpholinocarbonyl |
| 408 | SO$_2$CH$_3$ | phenyl | 2-methyl-1-imidazolyl |
| 409 | SO$_2$CH$_3$ | phenyl | 5-methyl-1-imidazolyl |
| 410 | SO$_2$CH$_3$ | phenyl | 2-methylsulfonyl-1-imidazolyl |
| 411 | SO$_2$CH$_3$ | 2-pyridyl | 2-(aminosulfonyl)phenyl |
| 412 | SO$_2$CH$_3$ | 2-pyridyl | 2-(methylaminosulfonyl)phenyl |
| 413 | SO$_2$CH$_3$ | 2-pyridyl | 1-pyrrolidinocarbonyl |
| 414 | SO$_2$CH$_3$ | 2-pyridyl | 2-(methylsulfonyl)phenyl |
| 415 | SO$_2$CH$_3$ | 2-pyridyl | 4-morpholino |
| 416 | SO$_2$CH$_3$ | 2-pyridyl | 2-(1'-CF$_3$-tetrazol-2-yl)phenyl |
| 417 | SO$_2$CH$_3$ | 2-pyridyl | 4-morpholinocarbonyl |
| 418 | SO$_2$CH$_3$ | 2-pyridyl | 2-methyl-1-imidazolyl |
| 419 | SO$_2$CH$_3$ | 2-pyridyl | 5-methyl-1-imidazolyl |
| 420 | SO$_2$CH$_3$ | 2-pyridyl | 2-methylsulfonyl-1-imidazolyl |
| 421 | SO$_2$CH$_3$ | 3-pyridyl | 2-(aminosulfonyl)phenyl |
| 422 | SO$_2$CH$_3$ | 3-pyridyl | 2-(methylaminosulfonyl)phenyl |
| 423 | SO$_2$CH$_3$ | 3-pyridyl | 1-pyrrolidinocarbonyl |
| 424 | SO$_2$CH$_3$ | 3-pyridyl | 2-(methylsulfonyl)phenyl |
| 425 | SO$_2$CH$_3$ | 3-pyridyl | 4-morpholino |
| 426 | SO$_2$CH$_3$ | 3-pyridyl | 2-(1'-CF$_3$-tetrazol-2-yl)phenyl |
| 427 | SO$_2$CH$_3$ | 3-pyridyl | 4-morpholinocarbonyl |
| 428 | SO$_2$CH$_3$ | 3-pyridyl | 2-methyl-1-imidazolyl |
| 429 | SO$_2$CH$_3$ | 3-pyridyl | 5-methyl-1-imidazolyl |
| 430 | SO$_2$CH$_3$ | 3-pyridyl | 2-methylsulfonyl-1-imidazolyl |
| 431 | SO$_2$CH$_3$ | 2-pyrimidyl | 2-(aminosulfonyl)phenyl |
| 432 | SO$_2$CH$_3$ | 2-pyrimidyl | 2-(methylaminosulfonyl)phenyl |
| 433 | SO$_2$CH$_3$ | 2-pyrimidyl | 1-pyrrolidinocarbonyl |
| 434 | SO$_2$CH$_3$ | 2-pyrimidyl | 2-(methylsulfonyl)phenyl |
| 435 | SO$_2$CH$_3$ | 2-pyrimidyl | 4-morpholino |
| 436 | SO$_2$CH$_3$ | 2-pyrimidyl | 2-(1'-CF$_3$-tetrazol-2-yl)phenyl |
| 437 | SO$_2$CH$_3$ | 2-pyrimidyl | 4-morpholinocarbonyl |
| 438 | SO$_2$CH$_3$ | 2-pyrimidyl | 2-methyl-1-imidazolyl |
| 439 | SO$_2$CH$_3$ | 2-pyrimidyl | 5-methyl-1-imidazolyl |
| 440 | SO$_2$CH$_3$ | 2-pyrimidyl | 2-methylsulfonyl-1-imidazolyl |
| 441 | SO$_2$CH$_3$ | 5-pyrimidyl | 2-(aminosulfonyl)phenyl |
| 442 | SO$_2$CH$_3$ | 5-pyrimidyl | 2-(methylaminosulfonyl)phenyl |

TABLE 6-continued

| | | | |
|---|---|---|---|
| 443 | $SO_2CH_3$ | 5-pyrimidyl | 1-pyrrolidinocarbonyl |
| 444 | $SO_2CH_3$ | 5-pyrimidyl | 2-(methylsulfonyl)phenyl |
| 445 | $SO_2CH_3$ | 5-pyrimidyl | 4-morpholino |
| 446 | $SO_2CH_3$ | 5-pyrimidyl | 2-(1'-$CF_3$-tetrazol-2-yl)phenyl |
| 447 | $SO_2CH_3$ | 5-pyrimidyl | 4-morpholinocarbonyl |
| 448 | $SO_2CH_3$ | 5-pyrimidyl | 2-methyl-1-imidazolyl |
| 449 | $SO_2CH_3$ | 5-pyrimidyl | 5-methyl-1-imidazolyl |
| 450 | $SO_2CH_3$ | 5-pyrimidyl | 2-methylsulfonyl-1-imidazolyl |
| 451 | $SO_2CH_3$ | 2-Cl-phenyl | 2-(aminosulfonyl)phenyl |
| 452 | $SO_2CH_3$ | 2-Cl-phenyl | 2-(methylaminosulfonyl)phenyl |
| 453 | $SO_2CH_3$ | 2-Cl-phenyl | 1-pyrrolidinocarbonyl |
| 454 | $SO_2CH_3$ | 2-Cl-phenyl | 2-(methylsulfonyl)phenyl |
| 455 | $SO_2CH_3$ | 2-Cl-phenyl | 4-morpholino |
| 456 | $SO_2CH_3$ | 2-Cl-phenyl | 2-(1'-$CF_3$-tetrazol-2-yl)phenyl |
| 457 | $SO_2CH_3$ | 2-Cl-phenyl | 4-morpholinocarbonyl |
| 458 | $SO_2CH_3$ | 2-Cl-phenyl | 2-methyl-1-imidazolyl |
| 459 | $SO_2CH_3$ | 2-Cl-phenyl | 5-methyl-1-imidazolyl |
| 460 | $SO_2CH_3$ | 2-Cl-phenyl | 2-methylsulfonyl-1-imidazolyl |
| 461 | $SO_2CH_3$ | 2-F-phenyl | 2-(aminosulfonyl)phenyl |
| 462 | $SO_2CH_3$ | 2-F-phenyl | 2-(methylaminosulfonyl)phenyl |
| 463 | $SO_2CH_3$ | 2-F-phenyl | 1-pyrrolidinocarbonyl |
| 464 | $SO_2CH_3$ | 2-F-phenyl | 2-(methylsulfonyl)phenyl |
| 465 | $SO_2CH_3$ | 2-F-phenyl | 4-morpholino |
| 466 | $SO_2CH_3$ | 2-F-phenyl | 2-(1'-$CF_3$-tetrazol-2-yl)phenyl |
| 467 | $SO_2CH_3$ | 2-F-phenyl | 4-morpholinocarbonyl |
| 468 | $SO_2CH_3$ | 2-F-phenyl | 2-methyl-1-imidazolyl |
| 469 | $SO_2CH_3$ | 2-F-phenyl | 5-methyl-1-imidazolyl |
| 470 | $SO_2CH_3$ | 2-F-phenyl | 2-methylsulfonyl-1-imidazolyl |
| 471 | $SO_2CH_3$ | 2,6-diF-phenyl | 2-(aminosulfonyl)phenyl |
| 472 | $SO_2CH_3$ | 2,6-diF-phenyl | 2-(methylaminosulfonyl)phenyl |
| 473 | $SO_2CH_3$ | 2,6-diF-phenyl | 1-pyrrolidinocarbonyl |
| 474 | $SO_2CH_3$ | 2,6-diF-phenyl | 2-(methylsulfonyl)phenyl |
| 475 | $SO_2CH_3$ | 2,6-diF-phenyl | 4-morpholino |
| 476 | $SO_2CH_3$ | 2,6-diF-phenyl | 2-(1'-$CF_3$-tetrazol-2-yl)phenyl |
| 477 | $SO_2CH_3$ | 2,6-diF-phenyl | 4-morpholinocarbonyl |
| 478 | $SO_2CH_3$ | 2,6-diF-phenyl | 2-methyl-1-imidazolyl |
| 479 | $SO_2CH_3$ | 2,6-diF-phenyl | 5-methyl-1-imidazolyl |
| 480 | $SO_2CH_3$ | 2,6-diF-phenyl | 2-methylsulfonyl-1-imidazolyl |
| 481 | $CH_2NHSO_2CH_3$ | phenyl | 2-(aminosulfonyl)phenyl |
| 482 | $CH_2NHSO_2CH_3$ | phenyl | 2-(methylaminosulfonyl)phenyl |
| 483 | $CH_2NHSO_2CH_3$ | phenyl | 1-pyrrolidinocarbonyl |
| 484 | $CH_2NHSO_2CH_3$ | phenyl | 2-(methylsulfonyl)phenyl |
| 485 | $CH_2NHSO_2CH_3$ | phenyl | 4-morpholino |
| 486 | $CH_2NHSO_2CH_3$ | phenyl | 2-(1'-$CF_3$-tetrazol-2-yl)phenyl |
| 487 | $CH_2NHSO_2CH_3$ | phenyl | 4-morpholinocarbonyl |
| 488 | $CH_2NHSO_2CH_3$ | phenyl | 2-methyl-1-imidazolyl |
| 489 | $CH_2NHSO_2CH_3$ | phenyl | 5-methyl-1-imidazolyl |
| 490 | $CH_2NHSO_2CH_3$ | phenyl | 2-methylsulfonyl-1-imidazolyl |
| 491 | $CH_2NHSO_2CH_3$ | 2-pyridyl | 2-(aminosulfonyl)phenyl |
| 492 | $CH_2NHSO_2CH_3$ | 2-pyridyl | 2-(methylaminosulfonyl)phenyl |
| 493 | $CH_2NHSO_2CH_3$ | 2-pyridyl | 1-pyrrolidinocarbonyl |
| 494 | $CH_2NHSO_2CH_3$ | 2-pyridyl | 2-(methylsulfonyl)phenyl |
| 495 | $CH_2NHSO_2CH_3$ | 2-pyridyl | 4-morpholino |
| 496 | $CH_2NHSO_2CH_3$ | 2-pyridyl | 2-(1'-$CF_3$-tetrazol-2-yl)phenyl |
| 497 | $CH_2NHSO_2CH_3$ | 2-pyridyl | 4-morpholinocarbonyl |
| 498 | $CH_2NHSO_2CH_3$ | 2-pyridyl | 2-methyl-1-imidazolyl |
| 499 | $CH_2NHSO_2CH_3$ | 2-pyridyl | 5-methyl-1-imidazolyl |
| 500 | $CH_2NHSO_2CH_3$ | 2-pyridyl | 2-methylsulfonyl-1-imidazolyl |
| 501 | $CH_2NHSO_2CH_3$ | 3-pyridyl | 2-(aminosulfonyl)phenyl |
| 502 | $CH_2NHSO_2CH_3$ | 3-pyridyl | 2-(methylaminosulfonyl)phenyl |
| 503 | $CH_2NHSO_2CH_3$ | 3-pyridyl | 1-pyrrolidinocarbonyl |
| 504 | $CH_2NHSO_2CH_3$ | 3-pyridyl | 2-(methylsulfonyl)phenyl |
| 505 | $CH_2NHSO_2CH_3$ | 3-pyridyl | 4-morpholino |
| 506 | $CH_2NHSO_2CH_3$ | 3-pyridyl | 2-(1'-$CF_3$-tetrazol-2-yl)phenyl |
| 507 | $CH_2NHSO_2CH_3$ | 3-pyridyl | 4-morpholinocarbonyl |
| 508 | $CH_2NHSO_2CH_3$ | 3-pyridyl | 2-methyl-1-imidazolyl |
| 509 | $CH_2NHSO_2CH_3$ | 3-pyridyl | 5-methyl-1-imidazolyl |
| 510 | $CH_2NHSO_2CH_3$ | 3-pyridyl | 2-methylsulfonyl-1-imidazolyl |
| 511 | $CH_2NHSO_2CH_3$ | 2-pyrimidyl | 2-(aminosulfonyl)phenyl |
| 512 | $CH_2NHSO_2CH_3$ | 2-pyrimidyl | 2-(methylaminosulfonyl)phenyl |
| 513 | $CH_2NHSO_2CH_3$ | 2-pyrimidyl | 1-pyrrolidinocarbonyl |
| 514 | $CH_2NHSO_2CH_3$ | 2-pyrimidyl | 2-(methylsulfonyl)phenyl |
| 515 | $CH_2NHSO_2CH_3$ | 2-pyrimidyl | 4-morpholino |
| 516 | $CH_2NHSO_2CH_3$ | 2-pyrimidyl | 2-(1'-$CF_3$-tetrazol-2-yl)phenyl |
| 517 | $CH_2NHSO_2CH_3$ | 2-pyrimidyl | 4-morpholinocarbonyl |
| 518 | $CH_2NHSO_2CH_3$ | 2-pyrimidyl | 2-methyl-1-imidazolyl |
| 519 | $CH_2NHSO_2CH_3$ | 2-pyrimidyl | 5-methyl-1-imidazolyl |
| 520 | $CH_2NHSO_2CH_3$ | 2-pyrimidyl | 2-methylsulfonyl-1-imidazolyl |
| 521 | $CH_2NHSO_2CH_3$ | 5-pyrimidyl | 2-(aminosulfonyl)phenyl |

TABLE 6-continued

| | | | |
|---|---|---|---|
| 522 | CH$_2$NHSO$_2$CH$_3$ | 5-pyrimidyl | 2-(methylaminosulfonyl)phenyl |
| 523 | CH$_2$NHSO$_2$CH$_3$ | 5-pyrimidyl | 1-pyrrolidinocarbonyl |
| 524 | CH$_2$NHSO$_2$CH$_3$ | 5-pyrimidyl | 2-(methylsulfonyl)phenyl |
| 525 | CH$_2$NHSO$_2$CH$_3$ | 5-pyrimidyl | 4-morpholino |
| 526 | CH$_2$NHSO$_2$CH$_3$ | 5-pyrimidyl | 2-(1'-CF$_3$-tetrazol-2-yl)phenyl |
| 527 | CH$_2$NHSO$_2$CH$_3$ | 5-pyrimidyl | 4-morpholinocarbonyl |
| 528 | CH$_2$NHSO$_2$CH$_3$ | 5-pyrimidyl | 2-methyl-1-imidazolyl |
| 529 | CH$_2$NHSO$_2$CH$_3$ | 5-pyrimidyl | 5-methyl-1-imidazolyl |
| 530 | CH$_2$NHSO$_2$CH$_3$ | 5-pyrimidyl | 2-methylsulfonyl-1-imidazolyl |
| 531 | CH$_2$NHSO$_2$CH$_3$ | 2-Cl-phenyl | 2-(aminosulfonyl)phenyl |
| 532 | CH$_2$NHSO$_2$CH$_3$ | 2-Cl-phenyl | 2-(methylaminosulfonyl)phenyl |
| 533 | CH$_2$NHSO$_2$CH$_3$ | 2-Cl-phenyl | 1-pyrrolidinocarbonyl |
| 534 | CH$_2$NHSO$_2$CH$_3$ | 2-Cl-phenyl | 2-(methylsulfonyl)phenyl |
| 535 | CH$_2$NHSO$_2$CH$_3$ | 2-Cl-phenyl | 4-morpholino |
| 536 | CH$_2$NHSO$_2$CH$_3$ | 2-Cl-phenyl | 2-(1'-CF$_3$-tetrazol-2-yl)phenyl |
| 537 | CH$_2$NHSO$_2$CH$_3$ | 2-Cl-phenyl | 4-morpholinocarbonyl |
| 538 | CH$_2$NHSO$_2$CH$_3$ | 2-Cl-phenyl | 2-methyl-1-imidazolyl |
| 539 | CH$_2$NHSO$_2$CH$_3$ | 2-Cl-phenyl | 5-methyl-1-imidazolyl |
| 540 | CH$_2$NHSO$_2$CH$_3$ | 2-Cl-phenyl | 2-methylsulfonyl-1-imidazolyl |
| 541 | CH$_2$NHSO$_2$CH$_3$ | 2-F-phenyl | 2-(aminosulfonyl)phenyl |
| 542 | CH$_2$NHSO$_2$CH$_3$ | 2-F-phenyl | 2-(methylaminosulfonyl)phenyl |
| 543 | CH$_2$NHSO$_2$CH$_3$ | 2-F-phenyl | 1-pyrrolidinocarbonyl |
| 544 | CH$_2$NHSO$_2$CH$_3$ | 2-F-phenyl | 2-(methylsulfonyl)phenyl |
| 545 | CH$_2$NHSO$_2$CH$_3$ | 2-F-phenyl | 4-morpholino |
| 546 | CH$_2$NHSO$_2$CH$_3$ | 2-F-phenyl | 2-(1'-CF$_3$-tetrazol-2-yl)phenyl |
| 547 | CH$_2$NHSO$_2$CH$_3$ | 2-F-phenyl | 4-morpholinocarbonyl |
| 548 | CH$_2$NHSO$_2$CH$_3$ | 2-F-phenyl | 2-methyl-1-imidazolyl |
| 549 | CH$_2$NHSO$_2$CH$_3$ | 2-F-phenyl | 5-methyl-1-imidazolyl |
| 550 | CH$_2$NHSO$_2$CH$_3$ | 2-F-phenyl | 2-methylsulfonyl-1-imidazolyl |
| 551 | CH$_2$NHSO$_2$CH$_3$ | 2,6-diF-phenyl | 2-(aminosulfonyl)phenyl |
| 552 | CH$_2$NHSO$_2$CH$_3$ | 2,6-diF-phenyl | 2-(methylaminosulfonyl)phenyl |
| 553 | CH$_2$NHSO$_2$CH$_3$ | 2,6-diF-phenyl | 1-pyrrolidinocarbonyl |
| 554 | CH$_2$NHSO$_2$CH$_3$ | 2,6-diF-phenyl | 2-(methylsulfonyl)phenyl |
| 555 | CH$_2$NHSO$_2$CH$_3$ | 2,6-diF-phenyl | 4-morpholino |
| 556 | CH$_2$NHSO$_2$CH$_3$ | 2,6-diF-phenyl | 2-(1'-CF$_3$-tetrazol-2-yl)phenyl |
| 557 | CH$_2$NHSO$_2$CH$_3$ | 2,6-diF-phenyl | 4-morpholinocarbonyl |
| 558 | CH$_2$NHSO$_2$CH$_3$ | 2,6-diF-phenyl | 2-methyl-1-imidazolyl |
| 559 | CH$_2$NHSO$_2$CH$_3$ | 2,6-diF-phenyl | 5-methyl-1-imidazolyl |
| 560 | CH$_2$NHSO$_2$CH$_3$ | 2,6-diF-phenyl | 2-methylsulfonyl-1-imidazolyl |
| 561 | Cl | phenyl | 2-(aminosulfonyl)phenyl |
| 562 | Cl | phenyl | 2-(methylaminosulfonyl)phenyl |
| 563 | Cl | phenyl | 1-pyrrolidinocarbonyl |
| 564 | Cl | phenyl | 2-(methylsulfonyl)phenyl |
| 565 | Cl | phenyl | 4-morpholino |
| 566 | Cl | phenyl | 2-(1'-CF$_3$-tetrazol-2-yl)phenyl |
| 567 | Cl | phenyl | 4-morpholinocarbonyl |
| 568 | Cl | phenyl | 2-methyl-1-imidazolyl |
| 569 | Cl | phenyl | 5-methyl-1-imidazolyl |
| 570 | Cl | phenyl | 2-methylsulfonyl-1-imidazolyl |
| 571 | Cl | 2-pyridyl | 2-(aminosulfonyl)phenyl |
| 572 | Cl | 2-pyridyl | 2-(methylaminosulfonyl)phenyl |
| 573 | Cl | 2-pyridyl | 1-pyrrolidinocarbonyl |
| 574 | Cl | 2-pyridyl | 2-(methylsulfonyl)phenyl |
| 575 | Cl | 2-pyridyl | 4-morpholino |
| 576 | Cl | 2-pyridyl | 2-(1'-CF$_3$-tetrazol-2-yl)phenyl |
| 577 | Cl | 2-pyridyl | 4-morpholinocarbonyl |
| 578 | Cl | 2-pyridyl | 2-methyl-1-imidazolyl |
| 579 | Cl | 2-pyridyl | 5-methyl-1-imidazolyl |
| 580 | Cl | 2-pyridyl | 2-methylsulfonyl-1-imidazolyl |
| 581 | Cl | 3-pyridyl | 2-(aminosulfonyl)phenyl |
| 582 | Cl | 3-pyridyl | 2-(methylaminosulfonyl)phenyl |
| 583 | Cl | 3-pyridyl | 1-pyrrolidinocarbonyl |
| 584 | Cl | 3-pyridyl | 2-(methylsulfonyl)phenyl |
| 585 | Cl | 3-pyridyl | 4-morpholino |
| 586 | Cl | 3-pyridyl | 2-(1'-CF$_3$-tetrazol-2-yl)phenyl |
| 587 | Cl | 3-pyridyl | 4-morpholinocarbonyl |
| 588 | Cl | 3-pyridyl | 2-methyl-1-imidazolyl |
| 589 | Cl | 3-pyridyl | 5-methyl-1-imidazolyl |
| 590 | Cl | 3-pyridyl | 2-methylsulfonyl-1-imidazolyl |
| 591 | Cl | 2-pyrimidyl | 2-(aminosulfonyl)phenyl |
| 592 | Cl | 2-pyrimidyl | 2-(methylaminosulfonyl)phenyl |
| 593 | Cl | 2-pyrimidyl | 1-pyrrolidinocarbonyl |
| 594 | Cl | 2-pyrimidyl | 2-(methylsulfonyl)phenyl |
| 595 | Cl | 2-pyrimidyl | 4-morpholino |
| 596 | Cl | 2-pyrimidyl | 2-(1'-CF$_3$-tetrazol-2-yl)phenyl |
| 597 | Cl | 2-pyrimidyl | 4-morpholinocarbonyl |
| 598 | Cl | 2-pyrimidyl | 2-methyl-1-imidazolyl |
| 599 | Cl | 2-pyrimidyl | 5-methyl-1-imidazolyl |
| 600 | Cl | 2-pyrimidyl | 2-methylsulfonyl-1-imidazolyl |

TABLE 6-continued

| | | | |
|---|---|---|---|
| 601 | Cl | 5-pyrimidyl | 2-(aminosulfonyl)phenyl |
| 602 | Cl | 5-pyrimidyl | 2-(methylaminosulfonyl)phenyl |
| 603 | Cl | 5-pyrimidyl | 1-pyrrolidinocarbonyl |
| 604 | Cl | 5-pyrimidyl | 2-(methylsulfonyl)phenyl |
| 605 | Cl | 5-pyrimidyl | 4-morpholino |
| 606 | Cl | 5-pyrimidyl | 2-(1'-$CF_3$-tetrazol-2-yl)phenyl |
| 607 | Cl | 5-pyrimidyl | 4-morpholinocarbonyl |
| 608 | Cl | 5-pyrimidyl | 2-methyl-1-imidazolyl |
| 609 | Cl | 5-pyrimidyl | 5-methyl-1-imidazolyl |
| 610 | Cl | 5-pyrimidyl | 2-methylsulfonyl-1-imidazolyl |
| 611 | Cl | 2-Cl-phenyl | 2-(aminosulfonyl)phenyl |
| 612 | Cl | 2-Cl-phenyl | 2-(methylaminosulfonyl)phenyl |
| 613 | Cl | 2-Cl-phenyl | 1-pyrrolidinocarbonyl |
| 614 | Cl | 2-Cl-phenyl | 2-(methylsulfonyl)phenyl |
| 615 | Cl | 2-Cl-phenyl | 4-morpholino |
| 616 | Cl | 2-Cl-phenyl | 2-(1'-$CF_3$-tetrazol-2-yl)phenyl |
| 617 | Cl | 2-Cl-phenyl | 4-morpholinocarbonyl |
| 618 | Cl | 2-Cl-phenyl | 2-methyl-1-imidazolyl |
| 619 | Cl | 2-Cl-phenyl | 5-methyl-1-imidazolyl |
| 620 | Cl | 2-Cl-phenyl | 2-methylsulfonyl-1-imidazolyl |
| 621 | Cl | 2-F-phenyl | 2-(aminosulfonyl)phenyl |
| 622 | Cl | 2-F-phenyl | 2-(methylaminosulfonyl)pheilyl |
| 623 | Cl | 2-F-phenyl | 1-pyrrolidinocarbonyl |
| 624 | Cl | 2-F-phenyl | 2-(methylsulfonyl)phenyl |
| 625 | Cl | 2-F-phenyl | 4-morpholino |
| 626 | Cl | 2-F-phenyl | 2-(1'-$CF_3$-tetrazol-2-yl)phenyl |
| 627 | Cl | 2-F-phenyl | 4-morpholinocarbonyl |
| 628 | Cl | 2-F-phenyl | 2-methyl-1-imidazolyl |
| 629 | Cl | 2-F-phenyl | 5-methyl-1-imidazolyl |
| 630 | Cl | 2-F-phenyl | 2-methylsulfonyl-1-imidazolyl |
| 631 | Cl | 2,6-diF-phenyl | 2-(aminosulfonyl)phenyl |
| 632 | Cl | 2,6-diF-phenyl | 2-(methylaminosulfonyl)phenyl |
| 633 | Cl | 2,6-diF-phenyl | 1-pyrrolidinocarbonyl |
| 634 | Cl | 2,6-diF-phenyl | 2-(methylsulfonyl)phenyl |
| 635 | Cl | 2,6-diF-phenyl | 4-morpholino |
| 636 | Cl | 2,6-diF-phenyl | 2-(1'-$CF_3$-tetrazol-2-yl)phenyl |
| 637 | Cl | 2,6-diF-phenyl | 4-morpholinocarbonyl |
| 638 | Cl | 2,6-diF-phenyl | 2-methyl-1-imidazolyl |
| 639 | Cl | 2,6-diF-phenyl | 5-methyl-1-imidazolyl |
| 640 | Cl | 2,6-diF-phenyl | 2-methylsulfonyl-1-imidazolyl |
| 641 | F | phenyl | 2-(aminosulfonyl)phenyl |
| 642 | F | phenyl | 2-(methylaminosulfonyl)phenyl |
| 643 | F | phenyl | 1-pyrrolidinocarbonyl |
| 644 | F | phenyl | 2-(methylsulfonyl)phenyl |
| 645 | F | phenyl | 4-morpholino |
| 646 | F | phenyl | 2-(1'-$CF_3$-tetrazol-2-yl)phenyl |
| 647 | F | phenyl | 4-morpholinocarbonyl |
| 648 | F | phenyl | 2-methyl-1-imidazolyl |
| 649 | F | phenyl | 5-methyl-1-imidazolyl |
| 650 | F | phenyl | 2-methylsulfonyl-1-imidazolyl |
| 651 | F | 2-pyridyl | 2-(aminosulfonyl)phenyl |
| 652 | F | 2-pyridyl | 2-(methylaminosulfonyl)phenyl |
| 653 | F | 2-pyridyl | 1-pyrrolidinocarbonyl |
| 654 | F | 2-pyridyl | 2-(methylsulfonyl)phenyl |
| 655 | F | 2-pyridyl | 4-morpholino |
| 656 | F | 2-pyridyl | 2-(1'-$CF_3$-tetrazol-2-yl)phenyl |
| 657 | F | 2-pyridyl | 4-morpholinocarbonyl |
| 658 | F | 2-pyridyl | 2-methyl-1-imidazolyl |
| 659 | F | 2-pyridyl | 5-methyl-1-imidazolyl |
| 660 | F | 2-pyridyl | 2-methylsulfonyl-1-imidazolyl |
| 661 | F | 3-pyridyl | 2-(aminosulfonyl)phenyl |
| 662 | F | 3-pyridyl | 2-(methylaminosulfonyl)phenyl |
| 663 | F | 3-pyridyl | 1-pyrrolidinocarbonyl |
| 664 | F | 3-pyridyl | 2-(methylsulfonyl)phenyl |
| 665 | F | 3-pyridyl | 4-morpholino |
| 666 | F | 3-pyridyl | 2-(1'-$CF_3$-tetrazol-2-yl)phenyl |
| 667 | F | 3-pyridyl | 4-morpholinocarbonyl |
| 668 | F | 3-pyridyl | 2-methyl-1-imidazolyl |
| 669 | F | 3-pyridyl | 5-methyl-1-imidazolyl |
| 670 | F | 3-pyridyl | 2-methylsulfonyl-1-imidazolyl |
| 671 | F | 2-pyrimidyl | 2-(aminosulfonyl)phenyl |
| 672 | F | 2-pyrimidyl | 2-(methylaminosulfonyl)phenyl |
| 673 | F | 2-pyrimidyl | 1-pyrrolidinocarbonyl |
| 674 | F | 2-pyrimidyl | 2-(methylsulfonyl)phenyl |
| 675 | F | 2-pyrimidyl | 4-morpholino |
| 676 | F | 2-pyrimidyl | 2-(1'-$CF_3$-tetrazol-2-yl)phenyl |
| 677 | F | 2-pyrimidyl | 4-morpholinocarbonyl |
| 678 | F | 2-pyrimidyl | 2-methyl-1-imidazolyl |
| 679 | F | 2-pyrimidyl | 5-methyl-1-imidazolyl |

TABLE 6-continued

| | | | |
|---|---|---|---|
| 680 | F | 2-pyrimidyl | 2-methylsulfonyl-1-imidazolyl |
| 681 | F | 5-pyrimidyl | 2-(aminosulfonyl)phenyl |
| 682 | F | 5-pyrimidyl | 2-(methylaminosulfonyl)phenyl |
| 683 | F | 5-pyrimidyl | 1-pyrrolidinocarbonyl |
| 684 | F | 5-pyrimidyl | 2-(methylsulfonyl)phenyl |
| 685 | F | 5-pyrimidyl | 4-morpholino |
| 686 | F | 5-pyrimidyl | 2-(1'-$CF_3$-tetrazol-2-yl)phenyl |
| 687 | F | 5-pyrimidyl | 4-morpholinocarbonyl |
| 688 | F | 5-pyrimidyl | 2-methyl-1-imidazolyl |
| 689 | F | 5-pyrimidyl | 5-methyl-1-imidazolyl |
| 690 | F | 5-pyrimidyl | 2-methylsulfonyl-1-imidazolyl |
| 691 | F | 2-Cl-phenyl | 2-(aminosulfonyl)phenyl |
| 692 | F | 2-Cl-phenyl | 2-(methylaminosulfonyl)phenyl |
| 693 | F | 2-Cl-phenyl | 1-pyrrolidinocarbonyl |
| 694 | F | 2-Cl-phenyl | 2-(methylsulfonyl)phenyl |
| 695 | F | 2-Cl-phenyl | 4-morpholino |
| 696 | F | 2-Cl-phenyl | 2-(1'-$CF_3$-tetrazol-2-yl)phenyl |
| 697 | F | 2-Cl-phenyl | 4-morpholinocarbonyl |
| 698 | F | 2-Cl-phenyl | 2-methyl-1-imidazolyl |
| 699 | F | 2-Cl-phenyl | 5-methyl-1-imidazolyl |
| 700 | F | 2-Cl-phenyl | 2-methylsulfonyl-1-imidazolyl |
| 701 | F | 2-F-phenyl | 2-(aminosulfonyl)phenyl |
| 702 | F | 2-F-phenyl | 2-(methylaminosulfonyl)phenyl |
| 703 | F | 2-F-phenyl | 1-pyrrolidinocarbonyl |
| 704 | F | 2-F-phenyl | 2-(methylsulfonyl)phenyl |
| 705 | F | 2-F-phenyl | 4-morpholino |
| 706 | F | 2-F-phenyl | 2-(1'-$CF_3$-tetrazol-2-yl)phenyl |
| 707 | F | 2-F-phenyl | 4-morpholinocarbonyl |
| 708 | F | 2-F-phenyl | 2-methyl-1-imidazolyl |
| 709 | F | 2-F-phenyl | 5-methyl-1-imidazolyl |
| 710 | F | 2-F-phenyl | 2-methylsulfonyl-1-imidazolyl |
| 711 | F | 2,6-diF-phenyl | 2-(aminosulfonyl)phenyl |
| 712 | F | 2,6-diF-phenyl | 2-(methylaminosulfonyl)phenyl |
| 713 | F | 2,6-diF-phenyl | 1-pyrrolidinocarbonyl |
| 714 | F | 2,6-diF-phenyl | 2-(methylsulfonyl)phenyl |
| 715 | F | 2,6-diF-phenyl | 4-morpholino |
| 716 | F | 2,6-diF-phenyl | 2-(1'-$CF_3$-tetrazol-2-yl)phenyl |
| 717 | F | 2,6-diF-phenyl | 4-morpholinocarbonyl |
| 718 | F | 2,6-diF-phenyl | 2-methyl-1-imidazolyl |
| 719 | F | 2,6-diF-phenyl | 5-methyl-1-imidazolyl |
| 720 | F | 2,6-diF-phenyl | 2-methylsulfonyl-1-imidazolyl |
| 721 | $CO_2CH_3$ | phenyl | 2-(aminosulfonyl)phenyl |
| 722 | $CO_2CH_3$ | phenyl | 2-(methylaminosulfonyl)phenyl |
| 723 | $CO_2CH_3$ | phenyl | 1-pyrrolidinocarbonyl |
| 724 | $CO_2CH_3$ | phenyl | 2-(methylsulfonyl)phenyl |
| 725 | $CO_2CH_3$ | phenyl | 4-morpholino |
| 726 | $CO_2CH_3$ | phenyl | 2-(1'-$CF_3$-tetrazol-2-yl)phenyl |
| 727 | $CO_2CH_3$ | phenyl | 4-morpholinocarbonyl |
| 728 | $CO_2CH_3$ | phenyl | 2-methyl-1-imidazolyl |
| 729 | $CO_2CH_3$ | phenyl | 5-methyl-1-imidazolyl |
| 730 | $CO_2CH_3$ | phenyl | 2-methylsulfonyl-1-imidazolyl |
| 731 | $CO_2CH_3$ | 2-pyridyl | 2-(aminosulfonyl)phenyl |
| 732 | $CO_2CH_3$ | 2-pyridyl | 2-(methylaminosulfonyl)phenyl |
| 733 | $CO_2CH_3$ | 2-pyridyl | 1-pyrrolidinocarbonyl |
| 734 | $CO_2CH_3$ | 2-pyridyl | 2-(methylsulfonyl)phenyl |
| 735 | $CO_2CH_3$ | 2-pyridyl | 4-morpholino |
| 736 | $CO_2CH_3$ | 2-pyridyl | 2-(1'-$CF_3$-tetrazol-2-yl)phenyl |
| 737 | $CO_2CH_3$ | 2-pyridyl | 4-morpholinocarbonyl |
| 738 | $CO_2CH_3$ | 2-pyridyl | 2-methyl-1-imidazolyl |
| 739 | $CO_2CH_3$ | 2-pyridyl | 5-methyl-1-imidazolyl |
| 740 | $CO_2CH_3$ | 2-pyridyl | 2-methylsulfonyl-1-imidazolyl |
| 741 | $CO_2CH_3$ | 3-pyridyl | 2-(aminosulfonyl)phenyl |
| 742 | $CO_2CH_3$ | 3-pyridyl | 2-(methylaminosulfonyl)phenyl |
| 743 | $CO_2CH_3$ | 3-pyridyl | 1-pyrrolidinocarbonyl |
| 744 | $CO_2CH_3$ | 3-pyridyl | 2-(methylsulfonyl)phenyl |
| 745 | $CO_2CH_3$ | 3-pyridyl | 4-morpholino |
| 746 | $CO_2CH_3$ | 3-pyridyl | 2-(1'-$CF_3$-tetrazol-2-yl)phenyl |
| 747 | $CO_2CH_3$ | 3-pyridyl | 4-morpholinocarbonyl |
| 748 | $CO_2CH_3$ | 3-pyridyl | 2-methyl-1-imidazolyl |
| 749 | $CO_2CH_3$ | 3-pyridyl | 5-methyl-1-imidazolyl |
| 750 | $CO_2CH_3$ | 3-pyridyl | 2-methylsulfonyl-1-imidazolyl |
| 751 | $CO_2CH_3$ | 2-pyrimidyl | 2-(aminosulfonyl)phenyl |
| 752 | $CO_2CH_3$ | 2-pyrimidyl | 2-(methylaminosulfonyl)phenyl |
| 753 | $CO_2CH_3$ | 2-pyrimidyl | 1-pyrrolidinocarbonyl |
| 754 | $CO_2CH_3$ | 2-pyrimidyl | 2-(methylsulfonyl)phenyl |
| 755 | $CO_2CH_3$ | 2-pyrimidyl | 4-morpholino |
| 756 | $CO_2CH_3$ | 2-pyrimidyl | 2-(1'-$CF_3$-tetrazol-2-yl)phenyl |
| 757 | $CO_2CH_3$ | 2-pyrimidyl | 4-morpholinocarbonyl |
| 758 | $CO_2CH_3$ | 2-pyrimidyl | 2-methyl-1-imidazolyl |

TABLE 6-continued

| | | | |
|---|---|---|---|
| 759 | $CO_2CH_3$ | 2-pyrimidyl | 5-methyl-1-imidazolyl |
| 760 | $CO_2CH_3$ | 2-pyrimidyl | 2-methylsulfonyl-1-imidazolyl |
| 761 | $CO_2CH_3$ | 5-pyrimidyl | 2-(aminosulfonyl)phenyl |
| 762 | $CO_2CH_3$ | 5-pyrimidyl | 2-(methylaminosulfonyl)phenyl |
| 763 | $CO_2CH_3$ | 5-pyrimidyl | 1-pyrrolidinocarbonyl |
| 764 | $CO_2CH_3$ | 5-pyrimidyl | 2-(methylsulfonyl)phenyl |
| 765 | $CO_2CH_3$ | 5-pyrimidyl | 4-morpholino |
| 766 | $CO_2CH_3$ | 5-pyrimidyl | 2-(1'-$CF_3$-tetrazol-2-yl)phenyl |
| 767 | $CO_2CH_3$ | 5-pyrimidyl | 4-morpholinocarbonyl |
| 768 | $CO_2CH_3$ | 5-pyrimidyl | 2-methyl-1-imidazolyl |
| 769 | $CO_2CH_3$ | 5-pyrimidyl | 5-methyl-1-imidazolyl |
| 770 | $CO_2CH_3$ | 5-pyrimidyl | 2-methylsulfonyl-1-imidazolyl |
| 771 | $CO_2CH_3$ | 2-Cl-phenyl | 2-(aminosulfonyl)phenyl |
| 772 | $CO_2CH_3$ | 2-Cl-phenyl | 2-(methylaminosulfonyl)phenyl |
| 773 | $CO_2CH_3$ | 2-Cl-phenyl | 1-pyrrolidinocarbonyl |
| 774 | $CO_2CH_3$ | 2-Cl-phenyl | 2-(methylsulfonyl)phenyl |
| 775 | $CO_2CH_3$ | 2-Cl-phenyl | 4-morpholino |
| 776 | $CO_2CH_3$ | 2-Cl-phenyl | 2-(1'-$CF_3$-tetrazol-2-yl)phenyl |
| 777 | $CO_2CH_3$ | 2-Cl-phenyl | 4-morpholinocarbonyl |
| 778 | $CO_2CH_3$ | 2-Cl-phenyl | 2-methyl-1-imidazolyl |
| 779 | $CO_2CH_3$ | 2-Cl-phenyl | 5-methyl-1-imidazolyl |
| 780 | $CO_2CH_3$ | 2-Cl-phenyl | 2-methylsulfonyl-1-imidazolyl |
| 781 | $CO_2CH_3$ | 2-F-phenyl | 2-(aminosulfonyl)phenyl |
| 782 | $CO_2CH_3$ | 2-F-phenyl | 2-(methylaminosulfonyl)phenyl |
| 783 | $CO_2CH_3$ | 2-F-phenyl | 1-pyrrolidinocarbonyl |
| 784 | $CO_2CH_3$ | 2-F-phenyl | 2-(methylsulfonyl)phenyl |
| 785 | $CO_2CH_3$ | 2-F-phenyl | 4-morpholino |
| 786 | $CO_2CH_3$ | 2-F-phenyl | 2-(1'-$CF_3$-tetrazol-2-yl)phenyl |
| 787 | $CO_2CH_3$ | 2-F-phenyl | 4-morpholinocarbonyl |
| 788 | $CO_2CH_3$ | 2-F-phenyl | 2-methyl-1-imidazolyl |
| 789 | $CO_2CH_3$ | 2-F-phenyl | 5-methyl-1-imidazolyl |
| 790 | $CO_2CH_3$ | 2-F-phenyl | 2-methylsulfonyl-1-imidazolyl |
| 791 | $CO_2CH_3$ | 2,6-diF-phenyl | 2-(aminosulfonyl)phenyl |
| 792 | $CO_2CH_3$ | 2,6-diF-phenyl | 2-(methylaminosulfonyl)phenyl |
| 793 | $CO_2CH_3$ | 2,6-diF-phenyl | 1-pyrrolidinocarbonyl |
| 794 | $CO_2CH_3$ | 2,6-diF-phenyl | 2-(methylsulfonyl)phenyl |
| 795 | $CO_2CH_3$ | 2,6-diF-phenyl | 4-morpholino |
| 796 | $CO_2CH_3$ | 2,6-diF-phenyl | 2-(1'-$CF_3$-tetrazol-2-yl)phenyl |
| 797 | $CO_2CH_3$ | 2,6-diF-phenyl | 4-morpholinocarbonyl |
| 798 | $CO_2CH_3$ | 2,6-diF-phenyl | 2-methyl-1-imidazolyl |
| 799 | $CO_2CH_3$ | 2,6-diF-phenyl | 5-methyl-1-imidazolyl |
| 800 | $CO_2CH_3$ | 2,6-diF-phenyl | 2-methylsulfonyl-1-imidazolyl |
| 801 | $CH_2OCH_3$ | phenyl | 2-(aminosulfonyl)phenyl |
| 802 | $CH_2OCH_3$ | phenyl | 2-(methylaminosulfonyl)phenyl |
| 803 | $CH_2OCH_3$ | phenyl | 1-pyrrolidinocarbonyl |
| 804 | $CH_2OCH_3$ | phenyl | 2-(methylsulfonyl)phenyl |
| 805 | $CH_2OCH_3$ | phenyl | 4-morpholino |
| 806 | $CH_2OCH_3$ | phenyl | 2-(1'-$CF_3$-tetrazol-2-yl)phenyl |
| 807 | $CH_2OCH_3$ | phenyl | 4-morpholinocarbonyl |
| 808 | $CH_2OCH_3$ | phenyl | 2-methyl-1-imidazolyl |
| 809 | $CH_2OCH_3$ | phenyl | 5-methyl-1-imidazolyl |
| 810 | $CH_2OCH_3$ | phenyl | 2-methylsulfonyl-1-imidazolyl |
| 811 | $CH_2OCH_3$ | 2-pyridyl | 2-(aminosulfonyl)phenyl |
| 812 | $CH_2OCH_3$ | 2-pyridyl | 2-(methylaminosulfonyl)phenyl |
| 813 | $CH_2OCH_3$ | 2-pyridyl | 1-pyrrolidinocarbonyl |
| 814 | $CH_2OCH_3$ | 2-pyridyl | 2-(methylsulfonyl)phenyl |
| 815 | $CH_2OCH_3$ | 2-pyridyl | 4-morpholino |
| 816 | $CH_2OCH_3$ | 2-pyridyl | 2-(1'-$CF_3$-tetrazol-2-yl)phenyl |
| 817 | $CH_2OCH_3$ | 2-pyridyl | 4-morpholinocarbonyl |
| 818 | $CH_2OCH_3$ | 2-pyridyl | 2-methyl-1-imidazolyl |
| 819 | $CH_2OCH_3$ | 2-pyridyl | 5-methyl-1-imidazolyl |
| 820 | $CH_2OCH_3$ | 2-pyridyl | 2-methylsulfonyl-1-imidazolyl |
| 821 | $CH_2OCH_3$ | 3-pyridyl | 2-(aminosulfonyl)phenyl |
| 822 | $CH_2OCH_3$ | 3-pyridyl | 2-(methylaminosulfonyl)phenyl |
| 823 | $CH_2OCH_3$ | 3-pyridyl | 1-pyrrolidinocarbonyl |
| 824 | $CH_2OCH_3$ | 3-pyridyl | 2-(methylsulfonyl)phenyl |
| 825 | $CH_2OCH_3$ | 3-pyridyl | 4-morpholino |
| 826 | $CH_2OCH_3$ | 3-pyridyl | 2-(1'-$CF_3$-tetrazol-2-yl)phenyl |
| 827 | $CH_2OCH_3$ | 3-pyridyl | 4-morpholinocarbonyl |
| 828 | $CH_2OCH_3$ | 3-pyridyl | 2-methyl-1-imidazolyl |
| 829 | $CH_2OCH_3$ | 3-pyridyl | 5-methyl-1-imidazolyl |
| 830 | $CH_2OCH_3$ | 3-pyridyl | 2-methylsulfonyl-1-imidazolyl |
| 831 | $CH_2OCH_3$ | 2-pyrimidyl | 2-(aminosulfonyl)phenyl |
| 832 | $CH_2OCH_3$ | 2-pyrimidyl | 2-(methylaminosulfonyl)phenyl |
| 833 | $CH_2OCH_3$ | 2-pyrimidyl | 1-pyrrolidinocarbonyl |
| 834 | $CH_2OCH_3$ | 2-pyrimidyl | 2-(methylsulfonyl)phenyl |
| 835 | $CH_2OCH_3$ | 2-pyrimidyl | 4-morpholino |
| 836 | $CH_2OCH_3$ | 2-pyrimidyl | 2-(1'-$CF_3$-tetrazol-2-yl)phenyl |
| 837 | $CH_2OCH_3$ | 2-pyrimidyl | 4-morpholinocarbonyl |

TABLE 6-continued

| | | | |
|---|---|---|---|
| 838 | $CH_2OCH_3$ | 2-pyrimidyl | 2-methyl-1-imidazolyl |
| 839 | $CH_2OCH_3$ | 2-pyrimidyl | 5-methyl-1-imidazolyl |
| 840 | $CH_2OCH_3$ | 2-pyrimidyl | 2-methylsulfonyl-1-imidazolyl |
| 841 | $CH_2OCH_3$ | 5-pyrimidyl | 2-(aminosulfonyl)phenyl |
| 842 | $CH_2OCH_3$ | 5-pyrimidyl | 2-(methylaminosulfonyl)phenyl |
| 843 | $CH_2OCH_3$ | 5-pyrimidyl | 1-pyrrolidinocarbonyl |
| 844 | $CH_2OCH_3$ | 5-pyrimidyl | 2-(methylsulfonyl)phenyl |
| 845 | $CH_2OCH_3$ | 5-pyrimidyl | 4-morpholino |
| 846 | $CH_2OCH_3$ | 5-pyrimidyl | 2-(1'-$CF_3$-tetrazol-2-yl)phenyl |
| 847 | $CH_2OCH_3$ | 5-pyrimidyl | 4-morpholinocarbonyl |
| 848 | $CH_2OCH_3$ | 5-pyrimidyl | 2-methyl-1-imidazolyl |
| 849 | $CH_2OCH_3$ | 5-pyrimidyl | 5-methyl-1-imidazolyl |
| 850 | $CH_2OCH_3$ | 5-pyrimidyl | 2-methylsulfonyl-1-imidazolyl |
| 851 | $CH_2OCH_3$ | 2-Cl-phenyl | 2-(aminosulfonyl)phenyl |
| 852 | $CH_2OCH_3$ | 2-Cl-phenyl | 2-(methylaminosulfonyl)phenyl |
| 853 | $CH_2OCH_3$ | 2-Cl-phenyl | 1-pyrrolidinocarbonyl |
| 854 | $CH_2OCH_3$ | 2-Cl-phenyl | 2-(methylsulfonyl)phenyl |
| 855 | $CH_2OCH_3$ | 2-Cl-phenyl | 4-morpholino |
| 856 | $CH_2OCH_3$ | 2-Cl-phenyl | 2-(1'-$CF_3$-tetrazol-2-yl)phenyl |
| 857 | $CH_2OCH_3$ | 2-Cl-phenyl | 4-morpholinocarbonyl |
| 858 | $CH_2OCH_3$ | 2-Cl-phenyl | 2-methyl-1-imidazolyl |
| 859 | $CH_2OCH_3$ | 2-Cl-phenyl | 5-methyl-1-imidazolyl |
| 860 | $CH_2OCH_3$ | 2-Cl-phenyl | 2-methylsulfonyl-1-imidazolyl |
| 861 | $CH_2OCH_3$ | 2-F-phenyl | 2-(aminosulfonyl)phenyl |
| 862 | $CH_2OCH_3$ | 2-F-phenyl | 2-(methylaminosulfonyl)phenyl |
| 863 | $CH_2OCH_3$ | 2-F-phenyl | 1-pyrrolidinocarbonyl |
| 864 | $CH_2OCH_3$ | 2-F-phenyl | 2-(methylsulfonyl)phenyl |
| 865 | $CH_2OCH_3$ | 2-F-phenyl | 4-morpholino |
| 866 | $CH_2OCH_3$ | 2-F-phenyl | 2-(1'-$CF_3$-tetrazol-2-yl)phenyl |
| 867 | $CH_2OCH_3$ | 2-F-phenyl | 4-morpholinocarbonyl |
| 868 | $CH_2OCH_3$ | 2-F-phenyl | 2-methyl-1-imidazolyl |
| 869 | $CH_2OCH_3$ | 2-F-phenyl | 5-methyl-1-imidazolyl |
| 870 | $CH_2OCH_3$ | 2-F-phenyl | 2-methylsulfonyl-1-imidazolyl |
| 871 | $CH_2OCH_3$ | 2,6-diF-phenyl | 2-(aminosulfonyl)phenyl |
| 872 | $CH_2OCH_3$ | 2,6-diF-phenyl | 2-(methylaminosulfonyl)phenyl |
| 873 | $CH_2OCH_3$ | 2,6-diF-phenyl | 1-pyrrolidinocarbonyl |
| 874 | $CH_2OCH_3$ | 2,6-diF-phenyl | 2-(methylsulfonyl)phenyl |
| 875 | $CH_2OCH_3$ | 2,6-diF-phenyl | 4-morpholino |
| 876 | $CH_2OCH_3$ | 2,6-diF-phenyl | 2-(1'-$CF_3$-tetrazol-2-yl)phenyl |
| 877 | $CH_2OCH_3$ | 2,6-diF-phenyl | 4-morpholinocarbonyl |
| 878 | $CH_2OCH_3$ | 2,6-diF-phenyl | 2-methyl-1-imidazolyl |
| 879 | $CH_2OCH_3$ | 2,6-diF-phenyl | 5-methyl-1-imidazolyl |
| 880 | $CH_2OCH_3$ | 2,6-diF-phenyl | 2-methylsulfonyl-1-imidazolyl |
| 881 | $CONH_2$ | phenyl | 2-(aminosulfonyl)phenyl |
| 882 | $CONH_2$ | phenyl | 2-(methylaminosulfonyl)phenyl |
| 883 | $CONH_2$ | phenyl | 1-pyrrolidinocarbonyl |
| 884 | $CONH_2$ | phenyl | 2-(methylsulfonyl)phenyl |
| 885 | $CONH_2$ | phenyl | 4-morpholino |
| 886 | $CONH_2$ | phenyl | 2-(1'-$CF_3$-tetrazol-2-yl)phenyl |
| 887 | $CONH_2$ | phenyl | 4-morpholinocarbonyl |
| 888 | $CONH_2$ | phenyl | 2-methyl-1-imidazolyl |
| 889 | $CONH_2$ | phenyl | 5-methyl-1-imidazolyl |
| 890 | $CONH_2$ | phenyl | 2-methylsulfonyl-1-imidazolyl |
| 891 | $CONH_2$ | 2-pyridyl | 2-(aminosulfonyl)phenyl |
| 892 | $CONH_2$ | 2-pyridyl | 2-(methylaminosulfonyl)phenyl |
| 893 | $CONH_2$ | 2-pyridyl | 1-pyrrolidinocarbonyl |
| 894 | $CONH_2$ | 2-pyridyl | 2-(methylsulfonyl)phenyl |
| 895 | $CONH_2$ | 2-pyridyl | 4-morpholino |
| 896 | $CONH_2$ | 2-pyridyl | 2-(1'-$CF_3$-tetrazol-2-yl)phenyl |
| 897 | $CONH_2$ | 2-pyridyl | 4-morpholinocarbonyl |
| 898 | $CONH_2$ | 2-pyridyl | 2-methyl-1-imidazolyl |
| 899 | $CONH_2$ | 2-pyridyl | 5-methyl-1-imidazolyl |
| 900 | $CONH_2$ | 2-pyridyl | 2-methylsulfonyl-1-imidazolyl |
| 901 | $CONH_2$ | 3-pyridyl | 2-(aminosulfonyl)phenyl |
| 902 | $CONH_2$ | 3-pyridyl | 2-(methylaminosulfonyl)phenyl |
| 903 | $CONH_2$ | 3-pyridyl | 1-pyrrolidinocarbonyl |
| 904 | $CONH_2$ | 3-pyridyl | 2-(methylsulfonyl)phenyl |
| 905 | $CONH_2$ | 3-pyridyl | 4-morpholino |
| 906 | $CONH_2$ | 3-pyridyl | 2-(1'-$CF_3$-tetrazol-2-yl)phenyl |
| 907 | $CONH_2$ | 3-pyridyl | 4-morpholinocarbonyl |
| 908 | $CONH_2$ | 3-pyridyl | 2-methyl-1-imidazolyl |
| 909 | $CONH_2$ | 3-pyridyl | 5-methyl-1-imidazolyl |
| 910 | $CONH_2$ | 3-pyridyl | 2-methylsulfonyl-1-imidazolyl |
| 911 | $CONH_2$ | 2-pyrimidyl | 2-(aminosulfonyl)phenyl |
| 912 | $CONH_2$ | 2-pyrimidyl | 2-(methylaminosulfonyl)phenyl |
| 913 | $CONH_2$ | 2-pyrimidyl | 1-pyrrolidinocarbonyl |
| 914 | $CONH_2$ | 2-pyrimidyl | 2-(methylsulfonyl)phenyl |
| 915 | $CONH_2$ | 2-pyrimidyl | 4-morpholino |
| 916 | $CONH_2$ | 2-pyrimidyl | 2-(1'-$CF_3$-tetrazol-2-yl)phenyl |

TABLE 6-continued

| | | | |
|---|---|---|---|
| 917 | CONH$_2$ | 2-pyrimidyl | 4-morpholinocarbonyl |
| 918 | CONH$_2$ | 2-pyrimidyl | 2-methyl-1-imidazolyl |
| 919 | CONH$_2$ | 2-pyrimidyl | 5-methyl-1-imidazolyl |
| 920 | CONH$_2$ | 2-pyrimidyl | 2-methylsulfonyl-1-imidazolyl |
| 921 | CONH$_2$ | 3-pyrimidyl | 2-(aminosulfonyl)phenyl |
| 922 | CONH$_2$ | 3-pyrimidyl | 2-(methylaminosulfonyl)phenyl |
| 923 | CONH$_2$ | 3-pyrimidyl | 1-pyrrolidinocarbonyl |
| 924 | CONH$_2$ | 3-pyrimidyl | 2-(methylsulfonyl)phenyl |
| 925 | CONH$_2$ | 3-pyrimidyl | 4-morpholino |
| 926 | CONH$_2$ | 3-pyrimidyl | 2-(1'-CF$_3$-tetrazol-2-yl)phenyl |
| 927 | CONH$_2$ | 3-pyrimidyl | 4-morpholinocarbonyl |
| 928 | CONH$_2$ | 3-pyrimidyl | 2-methyl-1-imidazolyl |
| 929 | CONH$_2$ | 3-pyrimidyl | 5-methyl-1-imidazolyl |
| 930 | CONH$_2$ | 3-pyrimidyl | 2-methylsulfonyl-1-imidazolyl |
| 931 | CONH$_2$ | 2-Cl-phenyl | 2-(aminosulfonyl)phenyl |
| 932 | CONH$_2$ | 2-Cl-phenyl | 2-(methylaminosulfonyl)phenyl |
| 933 | CONH$_2$ | 2-Cl-phenyl | 1-pyrrolidinocarbonyl |
| 934 | CONH$_2$ | 2-Cl-phenyl | 2-(methylsulfonyl)phenyl |
| 935 | CONH$_2$ | 2-Cl-phenyl | 4-morpholino |
| 936 | CONH$_2$ | 2-Cl-phenyl | 2-(1'-CF$_3$-tetrazol-2-yl)phenyl |
| 937 | CONH$_2$ | 2-Cl-phenyl | 4-morpholinocarbonyl |
| 938 | CONH$_2$ | 2-Cl-phenyl | 2-methyl-1-imidazolyl |
| 939 | CONH$_2$ | 2-Cl-phenyl | 5-methyl-1-imidazolyl |
| 940 | CONH$_2$ | 2-Cl-phenyl | 2-methylsulfonyl-1-imidazolyl |
| 941 | CONH$_2$ | 2-F-phenyl | 2-(aminosulfonyl)phenyl |
| 942 | CONH$_2$ | 2-F-phenyl | 2-(methylaminosulfonyl)phenyl |
| 943 | CONH$_2$ | 2-F-phenyl | 1-pyrrolidinocarbonyl |
| 944 | CONH$_2$ | 2-F-phenyl | 2-(methylsulfonyl)phenyl |
| 945 | CONH$_2$ | 2-F-phenyl | 4-morpholino |
| 946 | CONH$_2$ | 2-F-phenyl | 2-(1'-CF$_3$-tetrazol-2-yl)phenyl |
| 947 | CONH$_2$ | 2-F-phenyl | 4-morpholinocarbonyl |
| 948 | CONH$_2$ | 2-F-phenyl | 2-methyl-1-imidazolyl |
| 949 | CONH$_2$ | 2-F-phenyl | 5-methyl-1-imidazolyl |
| 950 | CONH$_2$ | 2-F-phenyl | 2-methylsulfonyl-1-imidazolyl |
| 951 | CONH$_2$ | 2,6-diF-phenyl | 2-(aminosulfonyl)phenyl |
| 952 | CONH$_2$ | 2,6-diF-phenyl | 2-(methylaminosulfonyl)phenyl |
| 953 | CONH$_2$ | 2,6-diF-phenyl | 1-pyrrolidinocarbonyl |
| 954 | CONH$_2$ | 2,6-diF-phenyl | 2-(methylsulfonyl)phenyl |
| 955 | CONH$_2$ | 2,6-diF-phenyl | 4-morpholino |
| 956 | CONH$_2$ | 2,6-diF-phenyl | 2-(1'-CF$_3$-tetrazol-2-yl)phenyl |
| 957 | CONH$_2$ | 2,6-diF-phenyl | 4-morpholinocarbonyl |
| 958 | CONH$_2$ | 2,6-diF-phenyl | 2-methyl-1-imidazolyl |
| 959 | CONH$_2$ | 2,6-diF-phenyl | 5-methyl-1-imidazolyl |
| 960 | CONH$_2$ | 2,6-diF-phenyl | 2-methylsulfonyl-1-imidazolyl |

TABLE 7

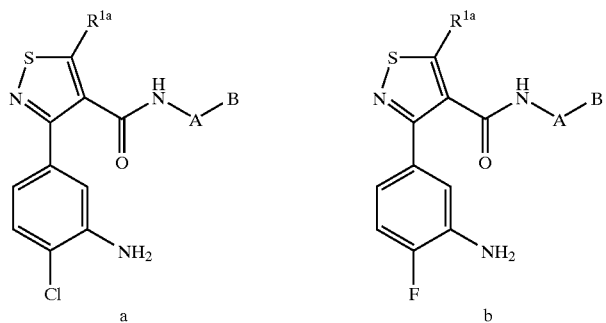

TABLE 7-continued
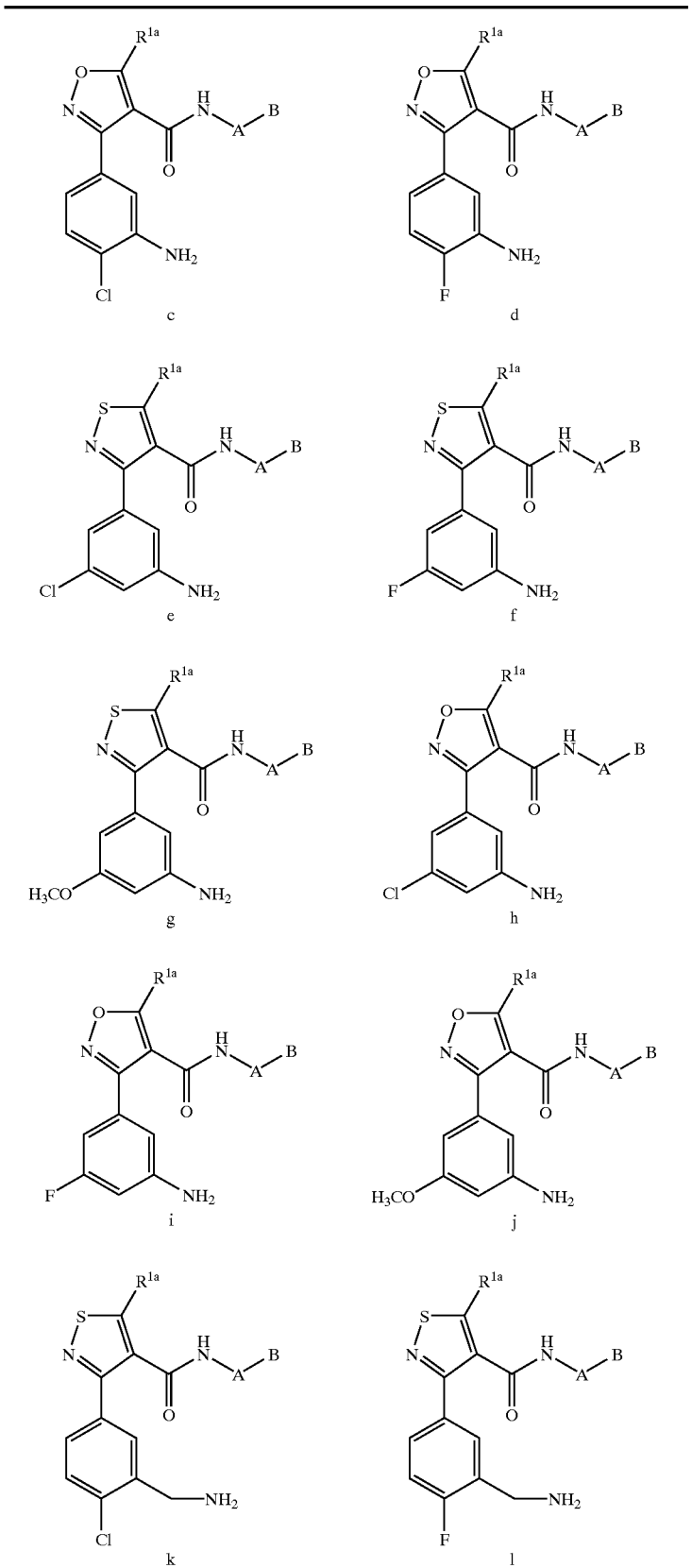

TABLE 7-continued
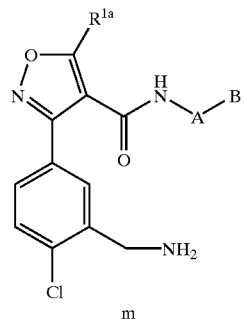
m
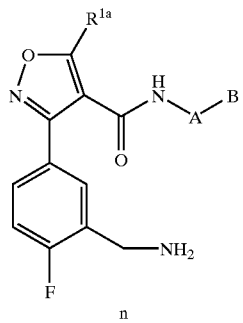
n
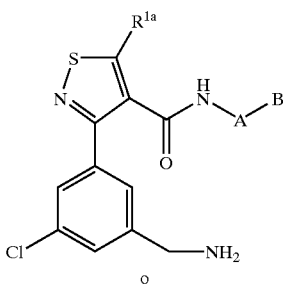
o
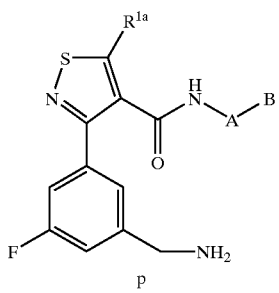
p
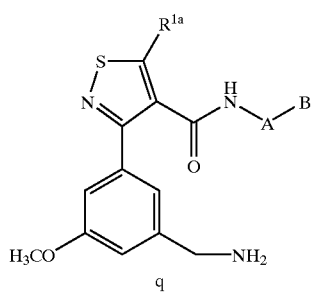
q
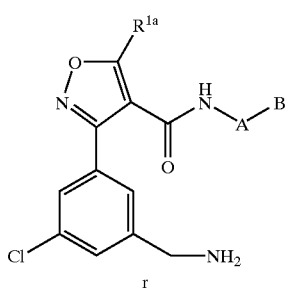
r
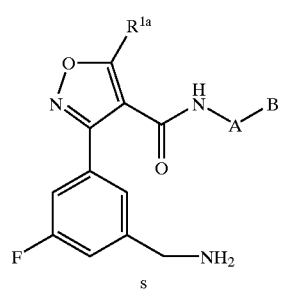
s
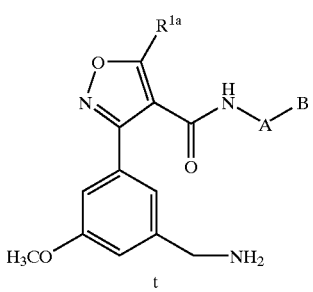
t
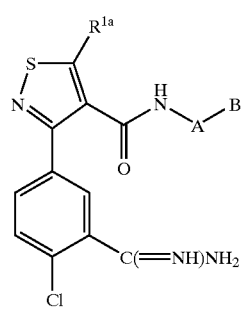
u
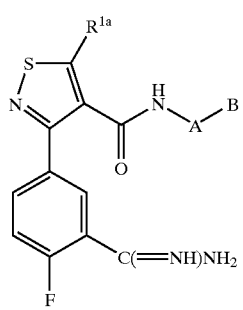
v TABLE 7-continued
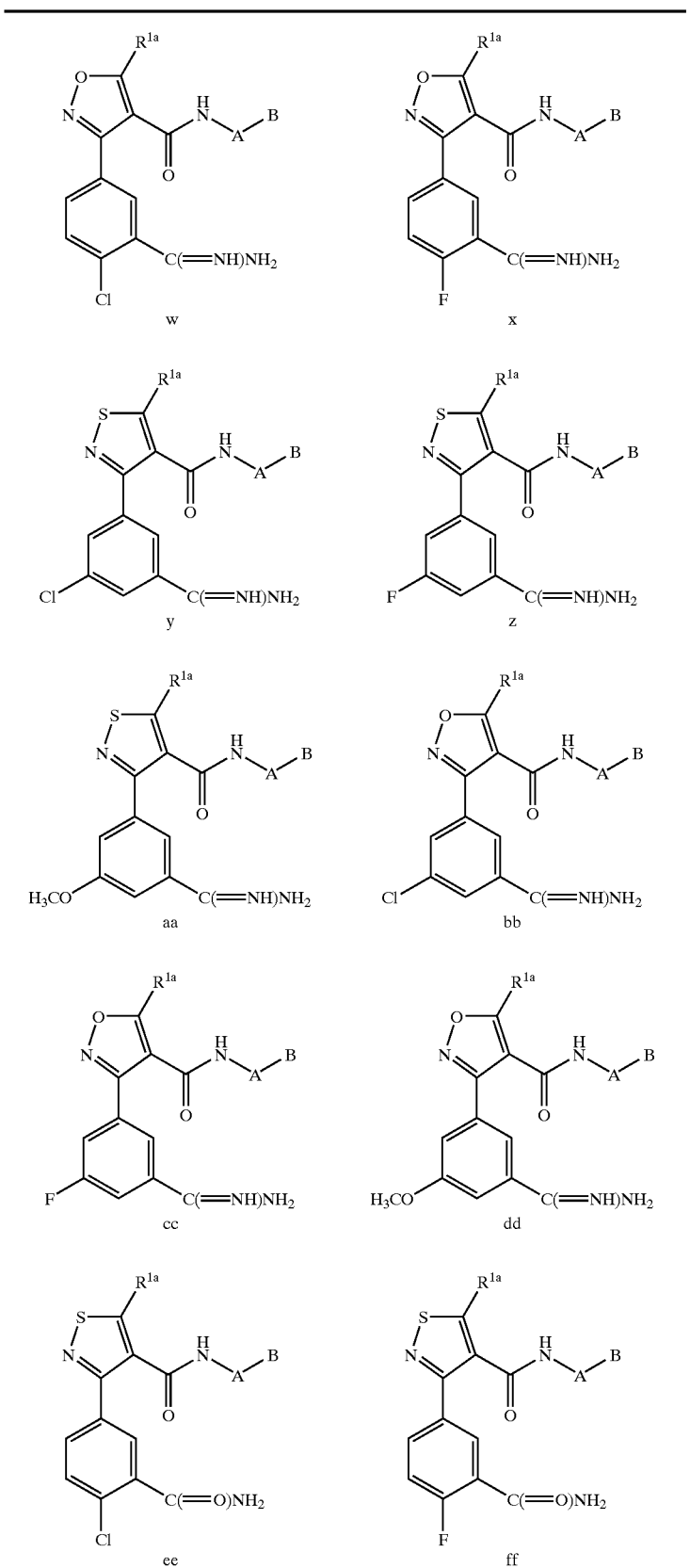

TABLE 7-continued
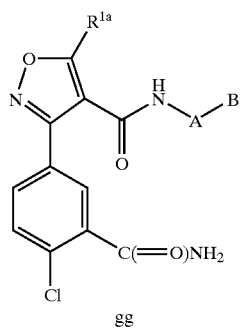
gg
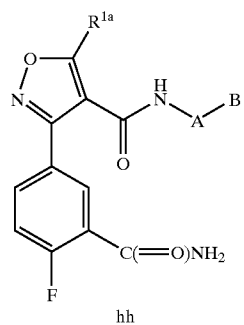
hh
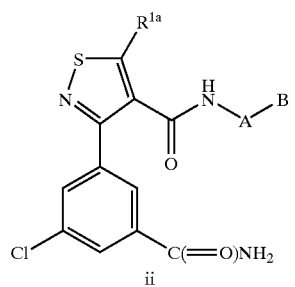
ii
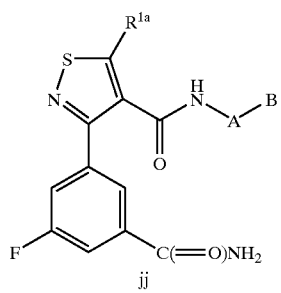
jj
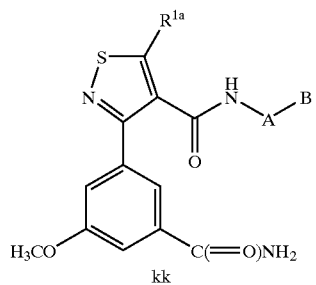
kk
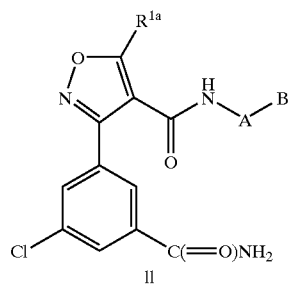
ll
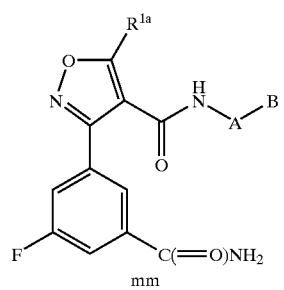
mm
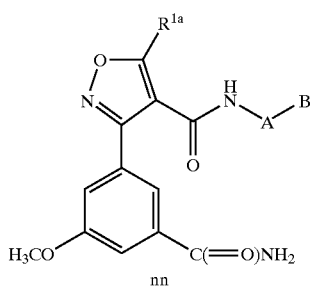
nn
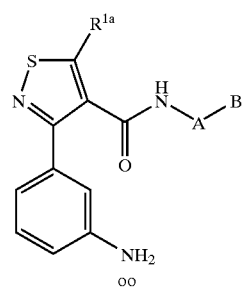
oo
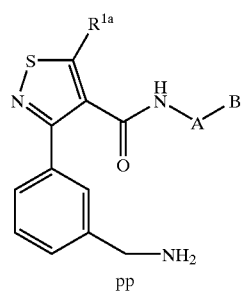
pp TABLE 7-continued

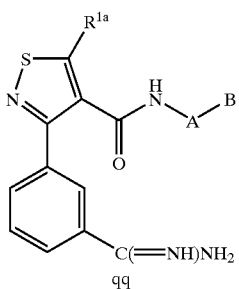
qq

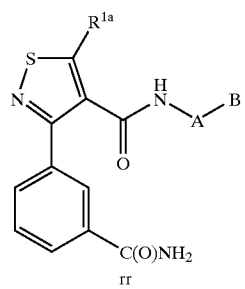
rr

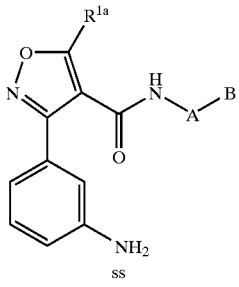
ss

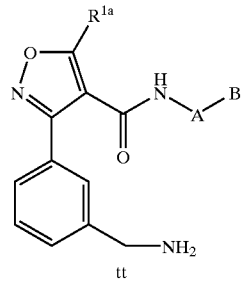
tt

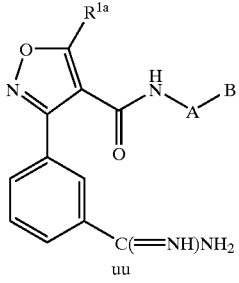
uu

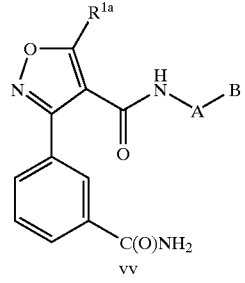
vv

| Ex # | $R^{1a}$ | A | B |
|---|---|---|---|
| 1 | $CH_3$ | phenyl | 2-(aminosulfonyl)phenyl |
| 2 | $CH_3$ | phenyl | 2-(methylaminosulfonyl)phenyl |
| 3 | $CH_3$ | phenyl | 1-pyrrolidinocarbonyl |
| 4 | $CH_3$ | phenyl | 2-(methylsulfonyl)phenyl |
| 5 | $CH_3$ | phenyl | 4-morpholino |
| 6 | $CH_3$ | phenyl | 2-(1'-$CF_3$-tetrazol-2-yl)phenyl |
| 7 | $CH_3$ | phenyl | 4-morpholinocarbonyl |
| 8 | $CH_3$ | phenyl | 2-methyl-1-imidazolyl |
| 9 | $CH_3$ | phenyl | 5-methyl-1-imidazolyl |
| 10 | $CH_3$ | phenyl | 2-methylsulfonyl-1-imidazolyl |
| 11 | $CH_3$ | 2-pyridyl | 2-(aminosulfonyl)phenyl |
| 12 | $CH_3$ | 2-pyridyl | 2-(methylaminosulfonyl)phenyl |
| 13 | $CH_3$ | 2-pyridyl | 1-pyrrolidinocarbonyl |
| 14 | $CH_3$ | 2-pyridyl | 2-(methylsulfonyl)phenyl |
| 15 | $CH_3$ | 2-pyridyl | 4-morpholino |
| 16 | $CH_3$ | 2-pyridyl | 2-(1'-$CF_3$-tetrazol-2-yl)phenyl |
| 17 | $CH_3$ | 2-pyridyl | 4-morpholinocarbonyl |
| 18 | $CH_3$ | 2-pyridyl | 2-methyl-1-imidazolyl |
| 19 | $CH_3$ | 2-pyridyl | 5-methyl-1-imidazolyl |
| 20 | $CH_3$ | 2-pyridyl | 2-methylsulfonyl-1-imidazolyl |
| 21 | $CH_3$ | 3-pyridyl | 2-(aminosulfonyl)phenyl |
| 22 | $CH_3$ | 3-pyridyl | 2-(methylaminosulfonyl)phenyl |
| 23 | $CH_3$ | 3-pyridyl | 1-pyrrolidinocarbonyl |
| 24 | $CH_3$ | 3-pyridyl | 2-(methylsulfonyl)phenyl |
| 25 | $CH_3$ | 3-pyridyl | 4-morpholino |
| 26 | $CH_3$ | 3-pyridyl | 2-(1'-$CF_3$-tetrazol-2-yl)phenyl |
| 27 | $CH_3$ | 3-pyridyl | 4-morpholinocarbonyl |
| 28 | $CH_3$ | 3-pyridyl | 2-methyl-1-imidazolyl |
| 29 | $CH_3$ | 3-pyridyl | 5-methyl-1-imidazolyl |
| 30 | $CH_3$ | 3-pyridyl | 2-methylsulfonyl-1-imidazolyl |

TABLE 7-continued

| | | | |
|---|---|---|---|
| 31 | $CH_3$ | 2-pyrimidyl | 2-(aminosulfonyl)phenyl |
| 32 | $CH_3$ | 2-pyrimidyl | 2-(methylaminosulfonyl)phenyl |
| 33 | $CH_3$ | 2-pyrimidyl | 1-pyrrolidinocarbonyl |
| 34 | $CH_3$ | 2-pyrimidyl | 2-(methylsulfonyl)phenyl |
| 35 | $CH_3$ | 2-pyrimidyl | 4-morpholino |
| 36 | $CH_3$ | 2-pyrimidyl | 2-(1'-$CF_3$-tetrazol-2-yl)phenyl |
| 37 | $CH_3$ | 2-pyrimidyl | 4-morpholinocarbonyl |
| 38 | $CH_3$ | 2-pyrimidyl | 2-methyl-1-imidazolyl |
| 39 | $CH_3$ | 2-pyrimidyl | 5-methyl-1-imidazolyl |
| 40 | $CH_3$ | 2-pyrimidyl | 2-methylsulfonyl-1-imidazolyl |
| 41 | $CH_3$ | 5-pyrimidyl | 2-(aminosulfonyl)phenyl |
| 42 | $CH_3$ | 5-pyrimidyl | 2-(methylaminosulfonyl)phenyl |
| 43 | $CH_3$ | 5-pyrimidyl | 1-pyrrolidinocarbonyl |
| 44 | $CH_3$ | 5-pyrimidyl | 2-(methylsulfonyl)phenyl |
| 45 | $CH_3$ | 5-pyrimidyl | 4-morpholino |
| 46 | $CH_3$ | 5-pyrimidyl | 2-(1'-$CF_3$-tetrazol-2-yl)phenyl |
| 47 | $CH_3$ | 5-pyrimidyl | 4-morpholinocarbonyl |
| 48 | $CH_3$ | 5-pyrimidyl | 2-methyl-1-imidazolyl |
| 49 | $CH_3$ | 5-pyrimidyl | 5-methyl-1-imidazolyl |
| 50 | $CH_3$ | 5-pyrimidyl | 2-methylsulfonyl-1-imidazolyl |
| 51 | $CH_3$ | 2-Cl-phenyl | 2-(aminosulfonyl)phenyl |
| 52 | $CH_3$ | 2-Cl-phenyl | 2-(methylaminosulfonyl)phenyl |
| 53 | $CH_3$ | 2-Cl-phenyl | 1-pyrrolidinocarbonyl |
| 54 | $CH_3$ | 2-Cl-phenyl | 2-(methylsulfonyl)phenyl |
| 55 | $CH_3$ | 2-Cl-phenyl | 4-morpholino |
| 56 | $CH_3$ | 2-Cl-phenyl | 2-(1'-$CF_3$-tetrazol-2-yl)phenyl |
| 57 | $CH_3$ | 2-Cl-phenyl | 4-morpholinocarbonyl |
| 58 | $CH_3$ | 2-Cl-phenyl | 2-methyl-1-imidazolyl |
| 59 | $CH_3$ | 2-Cl-phenyl | 5-methyl-1-imidazolyl |
| 60 | $CH_3$ | 2-Cl-phenyl | 2-methylsulfonyl-1-imidazolyl |
| 61 | $CH_3$ | 2-F-phenyl | 2-(aminosulfonyl)phenyl |
| 62 | $CH_3$ | 2-F-phenyl | 2-(methylaminosulfonyl)phenyl |
| 63 | $CH_3$ | 2-F-phenyl | 1-pyrrolidinocarbonyl |
| 64 | $CH_3$ | 2-F-phenyl | 2-(methylsulfonyl)phenyl |
| 65 | $CH_3$ | 2-F-phenyl | 4-morpholino |
| 66 | $CH_3$ | 2-F-phenyl | 2-(1'-$CF_3$-tetrazol-2-yl)phenyl |
| 67 | $CH_3$ | 2-F-phenyl | 4-morpholinocarbonyl |
| 68 | $CH_3$ | 2-F-phenyl | 2-methyl-1-imidazolyl |
| 69 | $CH_3$ | 2-F-phenyl | 5-methyl-1-imidazolyl |
| 70 | $CH_3$ | 2-F-phenyl | 2-methylsulfonyl-1-imidazolyl |
| 71 | $CH_3$ | 2,6-diF-phenyl | 2-(aminosulfonyl)phenyl |
| 72 | $CH_3$ | 2,6-diF-phenyl | 2-(methylaminosulfonyl)phenyl |
| 73 | $CH_3$ | 2,6-diF-phenyl | 1-pyrrolidinocarbonyl |
| 74 | $CH_3$ | 2,6-diF-phenyl | 2-(methylsulfonyl)phenyl |
| 75 | $CH_3$ | 2,6-diF-phenyl | 4-morpholino |
| 76 | $CH_3$ | 2,6-diF-phenyl | 2-(1'-$CF_3$-tetrazol-2-yl)phenyl |
| 77 | $CH_3$ | 2,6-diF-phenyl | 4-morpholinocarbonyl |
| 78 | $CH_3$ | 2,6-diF-phenyl | 2-methyl-1-imidazolyl |
| 79 | $CH_3$ | 2,6-diF-phenyl | 5-methyl-1-imidazolyl |
| 80 | $CH_3$ | 2,6-diF-phenyl | 2-methylsulfonyl-1-imidazolyl |
| 81 | $CH_2CH_3$ | phenyl | 2-(aminosulfonyl)phenyl |
| 82 | $CH_2CH_3$ | phenyl | 2-(methylaminosulfonyl)phenyl |
| 83 | $CH_2CH_3$ | phenyl | 1-pyrrolidinocarbonyl |
| 84 | $CH_2CH_3$ | phenyl | 2-(methylsulfonyl)phenyl |
| 85 | $CH_2CH_3$ | phenyl | 4-morpholino |
| 86 | $CH_2CH_3$ | phenyl | 2-(1'-$CF_3$-tetrazol-2-yl)phenyl |
| 87 | $CH_2CH_3$ | phenyl | 4-morpholinocarbonyl |
| 88 | $CH_2CH_3$ | phenyl | 2-methyl-1-imidazolyl |
| 89 | $CH_2CH_3$ | phenyl | 5-methyl-1-imidazolyl |
| 90 | $CH_2CH_3$ | phenyl | 2-methylsulfonyl-1-imidazolyl |
| 91 | $CH_2CH_3$ | 2-pyridyl | 2-(aminosulfonyl)phenyl |
| 92 | $CH_2CH_3$ | 2-pyridyl | 2-(methylaminosulfonyl)phenyl |
| 93 | $CH_2CH_3$ | 2-pyridyl | 1-pyrrolidinocarbonyl |
| 94 | $CH_2CH_3$ | 2-pyridyl | 2-(methylsulfonyl)phenyl |
| 95 | $CH_2CH_3$ | 2-pyridyl | 4-morpholino |
| 96 | $CH_2CH_3$ | 2-pyridyl | 2-(1'-$CF_3$-tetrazol-2-yl)phenyl |
| 97 | $CH_2CH_3$ | 2-pyridyl | 4-morpholinocarbonyl |
| 98 | $CH_2CH_3$ | 2-pyridyl | 2-methyl-1-imidazolyl |
| 99 | $CH_2CH_3$ | 2-pyridyl | 5-methyl-1-imidazolyl |
| 100 | $CH_2CH_3$ | 2-pyridyl | 2-methylsulfonyl-1-imidazolyl |
| 101 | $CH_2CH_3$ | 3-pyridyl | 2-(aminosulfonyl)phenyl |
| 102 | $CH_2CH_3$ | 3-pyridyl | 2-(methylaminosulfonyl)phenyl |

TABLE 7-continued

| | | | |
|---|---|---|---|
| 103 | $CH_2CH_3$ | 3-pyridyl | 1-pyrrolidinocarbonyl |
| 104 | $CH_2CH_3$ | 3-pyridyl | 2-(methylsulfonyl)phenyl |
| 105 | $CH_2CH_3$ | 3-pyridyl | 4-morpholino |
| 106 | $CH_2CH_3$ | 3-pyridyl | 2-(1'-$CF_3$-tetrazol-2-yl)phenyl |
| 107 | $CH_2CH_3$ | 3-pyridyl | 4-morpholinocarbonyl |
| 108 | $CH_2CH_3$ | 3-pyridyl | 2-methyl-1-imidazolyl |
| 109 | $CH_2CH_3$ | 3-pyridyl | 5-methyl-1-imidazolyl |
| 110 | $CH_2CH_3$ | 3-pyridyl | 2-methylsulfonyl-1-imidazolyl |
| 111 | $CH_2CH_3$ | 2-pyrimidyl | 2-(aminosulfonyl)phenyl |
| 112 | $CH_2CH_3$ | 2-pyrimidyl | 2-(methylaminosulfonyl)phenyl |
| 113 | $CH_2CH_3$ | 2-pyrimidyl | 1-pyrrolidinocarbonyl |
| 114 | $CH_2CH_3$ | 2-pyrimidyl | 2-(methylsulfonyl)phenyl |
| 115 | $CH_2CH_3$ | 2-pyrimidyl | 4-morpholino |
| 116 | $CH_2CH_3$ | 2-pyrimidyl | 2-(1'-$CF_3$-tetrazol-2-yl)phenyl |
| 117 | $CH_2CH_3$ | 2-pyrimidyl | 4-morpholinocarbonyl |
| 118 | $CH_2CH_3$ | 2-pyrimidyl | 2-methyl-1-imidazolyl |
| 119 | $CH_2CH_3$ | 2-pyrimidyl | 5-methyl-1-imidazolyl |
| 120 | $CH_2CH_3$ | 2-pyrimidyl | 2-methylsulfonyl-1-imidazolyl |
| 121 | $CH_2CH_3$ | 5-pyrimidyl | 2-(aminosulfonyl)phenyl |
| 122 | $CH_2CH_3$ | 5-pyrimidyl | 2-(methylaminosulfonyl)phenyl |
| 123 | $CH_2CH_3$ | 5-pyrimidyl | 1-pyrrolidinocarbonyl |
| 124 | $CH_2CH_3$ | 5-pyrimidyl | 2-(methylsulfonyl)phenyl |
| 125 | $CH_2CH_3$ | 5-pyrimidyl | 4-morpholino |
| 126 | $CH_2CH_3$ | 5-pyrimidyl | 2-(1'-$CF_3$-tetrazol-2-yl)phenyl |
| 127 | $CH_2CH_3$ | 5-pyrimidyl | 4-morpholinocarbonyl |
| 128 | $CH_2CH_3$ | 5-pyrimidyl | 2-methyl-1-imidazolyl |
| 129 | $CH_2CH_3$ | 5-pyrimidyl | 5-methyl-1-imidazolyl |
| 130 | $CH_2CH_3$ | 5-pyrimidyl | 2-methylsulfonyl-1-imidazolyl |
| 131 | $CH_2CH_3$ | 2-Cl-phenyl | 2-(aminosulfonyl)phenyl |
| 132 | $CH_2CH_3$ | 2-Cl-phenyl | 2-(methylaminosulfonyl)phenyl |
| 133 | $CH_2CH_3$ | 2-Cl-phenyl | 1-pyrrolidinocarbonyl |
| 134 | $CH_2CH_3$ | 2-Cl-phenyl | 2-(methylsulfonyl)phenyl |
| 135 | $CH_2CH_3$ | 2-Cl-phenyl | 4-morpholino |
| 136 | $CH_2CH_3$ | 2-Cl-phenyl | 2-(1'-$CF_3$-tetrazol-2-yl)phenyl |
| 137 | $CH_2CH_3$ | 2-Cl-phenyl | 4-morpholinocarbonyl |
| 138 | $CH_2CH_3$ | 2-Cl-phenyl | 2-methyl-1-imidazolyl |
| 139 | $CH_2CH_3$ | 2-Cl-phenyl | 5-methyl-1-imidazolyl |
| 140 | $CH_2CH_3$ | 2-Cl-phenyl | 2-methylsulfonyl-1-imidazolyl |
| 141 | $CH_2CH_3$ | 2-F-phenyl | 2-(aminosulfonyl)phenyl |
| 142 | $CH_2CH_3$ | 2-F-phenyl | 2-(methylaminosulfonyl)phenyl |
| 143 | $CH_2CH_3$ | 2-F-phenyl | 1-pyrrolidinocarbonyl |
| 144 | $CH_2CH_3$ | 2-F-phenyl | 2-(methylsulfonyl)phenyl |
| 145 | $CH_2CH_3$ | 2-F-phenyl | 4-morpholino |
| 146 | $CH_2CH_3$ | 2-F-phenyl | 2-(1'-$CF_3$-tetrazol-2-yl)phenyl |
| 147 | $CH_2CH_3$ | 2-F-phenyl | 4-morpholinocarbonyl |
| 148 | $CH_2CH_3$ | 2-F-phenyl | 2-methyl-1-imidazolyl |
| 149 | $CH_2CH_3$ | 2-F-phenyl | 5-methyl-1-imidazolyl |
| 150 | $CH_2CH_3$ | 2-F-phenyl | 2-methylsulfonyl-1-imidazolyl |
| 151 | $CH_2CH_3$ | 2,6-diF-phenyl | 2-(aminosulfonyl)phenyl |
| 152 | $CH_2CH_3$ | 2,6-diF-phenyl | 2-(methylaminosulfonyl)phenyl |
| 153 | $CH_2CH_3$ | 2,6-diF-phenyl | 1-pyrrolidinocarbonyl |
| 154 | $CH_2CH_3$ | 2,6-diF-phenyl | 2-(methylsulfonyl)phenyl |
| 155 | $CH_2CH_3$ | 2,6-diF-phenyl | 4-morpholino |
| 156 | $CH_2CH_3$ | 2,6-diF-phenyl | 2-(1'-$CF_3$-tetrazol-2-yl)phenyl |
| 157 | $CH_2CH_3$ | 2,6-diF-phenyl | 4-morpholinocarbonyl |
| 158 | $CH_2CH_3$ | 2,6-diF-phenyl | 2-methyl-1-imidazolyl |
| 159 | $CH_2CH_3$ | 2,6-diF-phenyl | 5-methyl-1-imidazolyl |
| 160 | $CH_2CH_3$ | 2,6-diF-phenyl | 2-methylsulfonyl-1-imidazolyl |
| 161 | $CF_3$ | phenyl | 2-(aminosulfonyl)phenyl |
| 162 | $CF_3$ | phenyl | 2-(methylaminosulfonyl)phenyl |
| 163 | $CF_3$ | phenyl | 1-pyrrolidinocarbonyl |
| 164 | $CF_3$ | phenyl | 2-(methylsulfonyl)phenyl |
| 165 | $CF_3$ | phenyl | 4-morpholino |
| 166 | $CF_3$ | phenyl | 2-(1'-$CF_3$-tetrazol-2-yl)phenyl |
| 167 | $CF_3$ | phenyl | 4-morpholinocarbonyl |
| 168 | $CF_3$ | phenyl | 2-methyl-1-imidazolyl |
| 169 | $CF_3$ | phenyl | 5-methyl-1-imidazolyl |
| 170 | $CF_3$ | phenyl | 2-methylsulfonyl-1-imidazolyl |
| 171 | $CF_3$ | 2-pyridyl | 2-(aminosulfonyl)phenyl |
| 172 | $CF_3$ | 2-pyridyl | 2-(methylaminosulfonyl)phenyl |
| 173 | $CF_3$ | 2-pyridyl | 1-pyrrolidinocarbonyl |
| 174 | $CF_3$ | 2-pyridyl | 2-(methylsulfonyl)phenyl |

TABLE 7-continued

| | | | |
|---|---|---|---|
| 175 | $CF_3$ | 2-pyridyl | 4-morpholino |
| 176 | $CF_3$ | 2-pyridyl | 2-(1'-$CF_3$-tetrazol-2-yl)phenyl |
| 177 | $CF_3$ | 2-pyridyl | 4-morpholinocarbonyl |
| 178 | $CF_3$ | 2-pyridyl | 2-methyl-1-imidazolyl |
| 179 | $CF_3$ | 2-pyridyl | 5-methyl-1-imidazolyl |
| 180 | $CF_3$ | 2-pyridyl | 2-methylsulfonyl-1-imidazolyl |
| 181 | $CF_3$ | 3-pyridyl | 2-(aminosulfonyl)phenyl |
| 182 | $CF_3$ | 3-pyridyl | 2-(methylaminosulfonyl)phenyl |
| 183 | $CF_3$ | 3-pyridyl | 1-pyrrolidinocarbonyl |
| 184 | $CF_3$ | 3-pyridyl | 2-(methylsulfonyl)phenyl |
| 185 | $CF_3$ | 3-pyridyl | 4-morpholino |
| 186 | $CF_3$ | 3-pyridyl | 2-(1'-$CF_3$-tetrazol-2-yl)phenyl |
| 187 | $CF_3$ | 3-pyridyl | 4-morpholinocarbonyl |
| 188 | $CF_3$ | 3-pyridyl | 2-methyl-1-imidazolyl |
| 189 | $CF_3$ | 3-pyridyl | 5-methyl-1-imidazolyl |
| 190 | $CF_3$ | 3-pyridyl | 2-methylsulfonyl-1-imidazolyl |
| 191 | $CF_3$ | 2-pyrimidyl | 2-(aminosulfonyl)phenyl |
| 192 | $CF_3$ | 2-pyrimidyl | 2-(methylaminosulfonyl)phenyl |
| 193 | $CF_3$ | 2-pyrimidyl | 1-pyrrolidinocarbonyl |
| 194 | $CF_3$ | 2-pyrimidyl | 2-(methylsulfonyl)phenyl |
| 195 | $CF_3$ | 2-pyrimidyl | 4-morpholino |
| 196 | $CF_3$ | 2-pyrimidyl | 2-(1'-$CF_3$-tetrazol-2-yl)phenyl |
| 197 | $CF_3$ | 2-pyrimidyl | 4-morpholinocarbonyl |
| 198 | $CF_3$ | 2-pyrimidyl | 2-methyl-1-imidazolyl |
| 199 | $CF_3$ | 2-pyrimidyl | 5-methyl-1-imidazolyl |
| 200 | $CF_3$ | 2-pyrimidyl | 2-methylsulfonyl-1-imidazolyl |
| 201 | $CF_3$ | 5-pyrimidyl | 2-(aminosulfonyl)phenyl |
| 202 | $CF_3$ | 5-pyrimidyl | 2-(methylaminosulfonyl)phenyl |
| 203 | $CF_3$ | 5-pyrimidyl | 1-pyrrolidinocarbonyl |
| 204 | $CF_3$ | 5-pyrimidyl | 2-(methylsulfonyl)phenyl |
| 205 | $CF_3$ | 5-pyrimidyl | 4-morpholino |
| 206 | $CF_3$ | 5-pyrimidyl | 2-(1'-$CF_3$-tetrazol-2-yl)phenyl |
| 207 | $CF_3$ | 5-pyrimidyl | 4-morpholinocarbonyl |
| 208 | $CF_3$ | 5-pyrimidyl | 2-methyl-1-imidazolyl |
| 209 | $CF_3$ | 5-pyrimidyl | 5-methyl-1-imidazolyl |
| 210 | $CF_3$ | 5-pyrimidyl | 2-methylsulfonyl-1-imidazolyl |
| 211 | $CF_3$ | 2-Cl-phenyl | 2-(aminosulfonyl)phenyl |
| 212 | $CF_3$ | 2-Cl-phenyl | 2-(methylaminosulfonyl)phenyl |
| 213 | $CF_3$ | 2-Cl-phenyl | 1-pyrrolidinocarbonyl |
| 214 | $CF_3$ | 2-Cl-phenyl | 2-(methylsulfonyl)phenyl |
| 215 | $CF_3$ | 2-Cl-phenyl | 4-morpholino |
| 216 | $CF_3$ | 2-Cl-phenyl | 2-(1'-$CF_3$-tetrazol-2-yl)phenyl |
| 217 | $CF_3$ | 2-Cl-phenyl | 4-morpholinocarbonyl |
| 218 | $CF_3$ | 2-Cl-phenyl | 2-methyl-1-imidazolyl |
| 219 | $CF_3$ | 2-Cl-phenyl | 5-methyl-1-imidazolyl |
| 220 | $CF_3$ | 2-Cl-phenyl | 2-methylsulfonyl-1-imidazolyl |
| 221 | $CF_3$ | 2-F-phenyl | 2-(aminosulfonyl)phenyl |
| 222 | $CF_3$ | 2-F-phenyl | 2-(methylaminosulfonyl)phenyl |
| 223 | $CF_3$ | 2-F-phenyl | 1-pyrrolidinocarbonyl |
| 224 | $CF_3$ | 2-F-phenyl | 2-(methylsulfonyl)phenyl |
| 225 | $CF_3$ | 2-F-phenyl | 4-morpholino |
| 226 | $CF_3$ | 2-F-phenyl | 2-(1'-$CF_3$-tetrazol-2-yl)phenyl |
| 227 | $CF_3$ | 2-F-phenyl | 4-morpholinocarbonyl |
| 228 | $CF_3$ | 2-F-phenyl | 2-methyl-1-imidazolyl |
| 229 | $CF_3$ | 2-F-phenyl | 5-methyl-1-imidazolyl |
| 230 | $CF_3$ | 2-F-phenyl | 2-methylsulfonyl-1-imidazolyl |
| 231 | $CF_3$ | 2,6-diF-phenyl | 2-(aminosulfonyl)phenyl |
| 232 | $CF_3$ | 2,6-diF-phenyl | 2-(methylaminosulfonyl)phenyl |
| 233 | $CF_3$ | 2,6-diF-phenyl | 1-pyrrolidinocarbonyl |
| 234 | $CF_3$ | 2,6-diF-phenyl | 2-(methylsulfonyl)phenyl |
| 235 | $CF_3$ | 2,6-diF-phenyl | 4-morpholino |
| 236 | $CF_3$ | 2,6-diF-phenyl | 2-(1'-$CF_3$-tetrazol-2-yl)phenyl |
| 237 | $CF_3$ | 2,6-diF-phenyl | 4-morpholinocarbonyl |
| 238 | $CF_3$ | 2,6-diF-phenyl | 2-methyl-1-imidazolyl |
| 239 | $CF_3$ | 2,6-diF-phenyl | 5-methyl-1-imidazolyl |
| 240 | $CF_3$ | 2,6-diF-phenyl | 2-methylsulfonyl-1-imidazolyl |
| 241 | $SCH_3$ | phenyl | 2-(aminosulfonyl)phenyl |
| 242 | $SCH_3$ | phenyl | 2-(methylaminosulfonyl)phenyl |
| 243 | $SCH_3$ | phenyl | 1-pyrrolidinocarbonyl |
| 244 | $SCH_3$ | phenyl | 2-(methylsulfonyl)phenyl |
| 245 | $SCH_3$ | phenyl | 4-morpholino |
| 246 | $SCH_3$ | phenyl | 2-(1'-$CF_3$-tetrazol-2- |

TABLE 7-continued

| | | | |
|---|---|---|---|
| 247 | SCH$_3$ | phenyl | yl)phenyl |
| 247 | SCH$_3$ | phenyl | 4-morpholinocarbonyl |
| 248 | SCH$_3$ | phenyl | 2-methyl-1-imidazolyl |
| 249 | SCH$_3$ | phenyl | 5-methyl-1-imidazolyl |
| 250 | SCH$_3$ | phenyl | 2-methylsulfonyl-1-imidazolyl |
| 251 | SCH$_3$ | 2-pyridyl | 2-(aminosulfonyl)phenyl |
| 252 | SCH$_3$ | 2-pyridyl | 2-(methylaminosulfonyl)phenyl |
| 253 | SCH$_3$ | 2-pyridyl | 1-pyrrolidinocarbonyl |
| 254 | SCH$_3$ | 2-pyridyl | 2-(methylsulfonyl)phenyl |
| 255 | SCH$_3$ | 2-pyridyl | 4-morpholino |
| 256 | SCH$_3$ | 2-pyridyl | 2-(1'-CF$_3$-tetrazol-2-yl)phenyl |
| 257 | SCH$_3$ | 2-pyridyl | 4-morpholinocarbonyl |
| 258 | SCH$_3$ | 2-pyridyl | 2-methyl-1-imidazolyl |
| 259 | SCH$_3$ | 2-pyridyl | 5-methyl-1-imidazolyl |
| 260 | SCH$_3$ | 2-pyridyl | 2-methylsulfonyl-1-imidazolyl |
| 261 | SCH$_3$ | 3-pyridyl | 2-(aminosulfonyl)phenyl |
| 262 | SCH$_3$ | 3-pyridyl | 2-(methylaminosulfonyl)phenyl |
| 263 | SCH$_3$ | 3-pyridyl | 1-pyrrolidinocarbonyl |
| 264 | SCH$_3$ | 3-pyridyl | 2-(methylsulfonyl)phenyl |
| 265 | SCH$_3$ | 3-pyridyl | 4-morpholino |
| 266 | SCH$_3$ | 3-pyridyl | 2-(1'-CF$_3$-tetrazol-2-yl)phenyl |
| 267 | SCH$_3$ | 3-pyridyl | 4-morpholinocarbonyl |
| 268 | SCH$_3$ | 3-pyridyl | 2-methyl-1-imidazolyl |
| 269 | SCH$_3$ | 3-pyridyl | 5-methyl-1-imidazolyl |
| 270 | SCH$_3$ | 3-pyridyl | 2-methylsulfonyl-1-imidazolyl |
| 271 | SCH$_3$ | 2-pyrimidyl | 2-(aminosulfonyl)phenyl |
| 272 | SCH$_3$ | 2-pyrimidyl | 2-(methylaminosulfonyl)phenyl |
| 273 | SCH$_3$ | 2-pyrimidyl | 1-pyrrolidinocarbonyl |
| 274 | SCH$_3$ | 2-pyrimidyl | 2-(methylsulfonyl)phenyl |
| 275 | SCH$_3$ | 2-pyrimidyl | 4-morpholino |
| 276 | SCH$_3$ | 2-pyrimidyl | 2-(1'-CF$_3$-tetrazol-2-yl)phenyl |
| 277 | SCH$_3$ | 2-pyrimidyl | 4-morpholinocarbonyl |
| 278 | SCH$_3$ | 2-pyrimidyl | 2-methyl-1-imidazolyl |
| 279 | SCH$_3$ | 2-pyrimidyl | 5-methyl-1-imidazolyl |
| 280 | SCH$_3$ | 2-pyrimidyl | 2-methylsulfonyl-1-imidazolyl |
| 281 | SCH$_3$ | 5-pyrimidyl | 2-(aminosulfonyl)phenyl |
| 282 | SCH$_3$ | 5-pyrimidyl | 2-(methylaminosulfonyl)phenyl |
| 283 | SCH$_3$ | 5-pyrimidyl | 1-pyrrolidinocarbonyl |
| 284 | SCH$_3$ | 5-pyrimidyl | 2-(methylsulfonyl)phenyl |
| 285 | SCH$_3$ | 5-pyrimidyl | 4-morpholino |
| 286 | SCH$_3$ | 5-pyrimidyl | 2-(1'-CF$_3$-tetrazol-2-yl)phenyl |
| 287 | SCH$_3$ | 5-pyrimidyl | 4-morpholinocarbonyl |
| 288 | SCH$_3$ | 5-pyrimidyl | 2-methyl-1-imidazolyl |
| 289 | SCH$_3$ | 5-pyrimidyl | 5-methyl-1-imidazolyl |
| 290 | SCH$_3$ | 5-pyrimidyl | 2-methylsulfonyl-1-imidazolyl |
| 291 | SCH$_3$ | 2-Cl-phenyl | 2-(aminosulfonyl)phenyl |
| 292 | SCH$_3$ | 2-Cl-phenyl | 2-(methylaminosulfonyl)phenyl |
| 293 | SCH$_3$ | 2-Cl-phenyl | 1-pyrrolidinocarbonyl |
| 294 | SCH$_3$ | 2-Cl-phenyl | 2-(methylsulfonyl)phenyl |
| 295 | SCH$_3$ | 2-Cl-phenyl | 4-morpholino |
| 296 | SCH$_3$ | 2-Cl-phenyl | 2-(1'-CF$_3$-tetrazol-2-yl)phenyl |
| 297 | SCH$_3$ | 2-Cl-phenyl | 4-morpholinocarbonyl |
| 298 | SCH$_3$ | 2-Cl-phenyl | 2-methyl-1-imidazolyl |
| 299 | SCH$_3$ | 2-Cl-phenyl | 5-methyl-1-imidazolyl |
| 300 | SCH$_3$ | 2-Cl-phenyl | 2-methylsulfonyl-1-imidazolyl |
| 301 | SCH$_3$ | 2-F-phenyl | 2-(aminosulfonyl)phenyl |
| 302 | SCH$_3$ | 2-F-phenyl | 2-(methylaminosulfonyl)phenyl |
| 303 | SCH$_3$ | 2-F-phenyl | 1-pyrrolidinocarbonyl |
| 304 | SCH$_3$ | 2-F-phenyl | 2-(methylsulfonyl)phenyl |
| 305 | SCH$_3$ | 2-F-phenyl | 4-morpholino |
| 306 | SCH$_3$ | 2-F-phenyl | 2-(1'-CF$_3$-tetrazol-2-yl)phenyl |
| 307 | SCH$_3$ | 2-F-phenyl | 4-morpholinocarbonyl |
| 308 | SCH$_3$ | 2-F-phenyl | 2-methyl-1-imidazolyl |
| 309 | SCH$_3$ | 2-F-phenyl | 5-methyl-1-imidazolyl |
| 310 | SCH$_3$ | 2-F-phenyl | 2-methylsulfonyl-1-imidazolyl |
| 311 | SCH$_3$ | 2,6-diF-phenyl | 2-(aminosulfonyl)phenyl |
| 312 | SCH$_3$ | 2,6-diF-phenyl | 2-(methylaminosulfonyl)phenyl |
| 313 | SCH$_3$ | 2,6-diF-phenyl | 1-pyrrolidinocarbonyl |
| 314 | SCH$_3$ | 2,6-diF-phenyl | 2-(methylsulfonyl)phenyl |
| 315 | SCH$_3$ | 2,6-diF-phenyl | 4-morpholino |
| 316 | SCH$_3$ | 2,6-diF-phenyl | 2-(1'-CF$_3$-tetrazol-2-yl)phenyl |
| 317 | SCH$_3$ | 2,6-diF-phenyl | 4-morpholinocarbonyl |

TABLE 7-continued

| | | | |
|---|---|---|---|
| 318 | SCH$_3$ | 2,6-diF-phenyl | 2-methyl-1-imidazolyl |
| 319 | SCH$_3$ | 2,6-diF-phenyl | 5-methyl-1-imidazolyl |
| 320 | SCH$_3$ | 2,6-diF-phenyl | 2-methylsulfonyl-1-imidazolyl |
| 321 | SOCH$_3$ | phenyl | 2-(aminosulfonyl)phenyl |
| 322 | SOCH$_3$ | phenyl | 2-(methylaminosulfonyl)phenyl |
| 323 | SOCH$_3$ | phenyl | 1-pyrrolidinocarbonyl |
| 324 | SOCH$_3$ | phenyl | 2-(methylsulfonyl)phenyl |
| 325 | SOCH$_3$ | phenyl | 4-morpholino |
| 326 | SOCH$_3$ | phenyl | 2-(1'-CF$_3$-tetrazol-2-yl)phenyl |
| 327 | SOCH$_3$ | phenyl | 4-morpholinocarbonyl |
| 328 | SOCH$_3$ | phenyl | 2-methyl-1-imidazolyl |
| 329 | SOCH$_3$ | phenyl | 5-methyl-1-imidazolyl |
| 330 | SOCH$_3$ | phenyl | 2-methylsulfonyl-1-imidazolyl |
| 331 | SOCH$_3$ | 2-pyridyl | 2-(aminosulfonyl)phenyl |
| 332 | SOCH$_3$ | 2-pyridyl | 2-(methylaminosulfonyl)phenyl |
| 333 | SOCH$_3$ | 2-pyridyl | 1-pyrrolidinocarbonyl |
| 334 | SOCH$_3$ | 2-pyridyl | 2-(methylsulfonyl)phenyl |
| 335 | SOCH$_3$ | 2-pyridyl | 4-morpholino |
| 336 | SOCH$_3$ | 2-pyridyl | 2-(1'-CF$_3$-tetrazol-2-yl)phenyl |
| 337 | SOCH$_3$ | 2-pyridyl | 4-morpholinocarbonyl |
| 338 | SOCH$_3$ | 2-pyridyl | 2-methyl-1-imidazolyl |
| 339 | SOCH$_3$ | 2-pyridyl | 5-methyl-1-imidazolyl |
| 340 | SOCH$_3$ | 2-pyridyl | 2-methylsulfonyl-1-imidazolyl |
| 341 | SOCH$_3$ | 3-pyridyl | 2-(aminosulfonyl)phenyl |
| 342 | SOCH$_3$ | 3-pyridyl | 2-(methylaminosulfonyl)phenyl |
| 343 | SOCH$_3$ | 3-pyridyl | 1-pyrrolidinocarbonyl |
| 344 | SOCH$_3$ | 3-pyridyl | 2-(methylsulfonyl)phenyl |
| 345 | SOCH$_3$ | 3-pyridyl | 4-morpholino |
| 346 | SOCH$_3$ | 3-pyridyl | 2-(1'-CF$_3$-tetrazol-2-yl)phenyl |
| 347 | SOCH$_3$ | 3-pyridyl | 4-morpholinocarbonyl |
| 348 | SOCH$_3$ | 3-pyridyl | 2-methyl-1-imidazolyl |
| 349 | SOCH$_3$ | 3-pyridyl | 5-methyl-1-imidazolyl |
| 350 | SOCH$_3$ | 3-pyridyl | 2-methylsulfonyl-1-imidazolyl |
| 351 | SOCH$_3$ | 2-pyrimidyl | 2-(aminosulfonyl)phenyl |
| 352 | SOCH$_3$ | 2-pyrimidyl | 2-(methylaminosulfonyl)phenyl |
| 353 | SOCH$_3$ | 2-pyrimidyl | 1-pyrrolidinocarbonyl |
| 354 | SOCH$_3$ | 2-pyrimidyl | 2-(methylsulfonyl)phenyl |
| 355 | SOCH$_3$ | 2-pyrimidyl | 4-morpholino |
| 356 | SOCH$_3$ | 2-pyrimidyl | 2-(1'-CF$_3$-tetrazol-2-yl)phenyl |
| 357 | SOCH$_3$ | 2-pyrimidyl | 4-morpholinocarbonyl |
| 358 | SOCH$_3$ | 2-pyrimidyl | 2-methyl-1-imidazolyl |
| 359 | SOCH$_3$ | 2-pyrimidyl | 5-methyl-1-imidazolyl |
| 360 | SOCH$_3$ | 2-pyrimidyl | 2-methylsulfonyl-1-imidazolyl |
| 361 | SOCH$_3$ | 5-pyrimidyl | 2-(aminosulfonyl)phenyl |
| 362 | SOCH$_3$ | 5-pyrimidyl | 2-(methylaminosulfonyl)phenyl |
| 363 | SOCH$_3$ | 5-pyrimidyl | 1-pyrrolidinocarbonyl |
| 364 | SOCH$_3$ | 5-pyrimidyl | 2-(methylsulfonyl)phenyl |
| 365 | SOCH$_3$ | 5-pyrimidyl | 4-morpholino |
| 366 | SOCH$_3$ | 5-pyrimidyl | 2-(1'-CF$_3$-tetrazol-2-yl)phenyl |
| 367 | SOCH$_3$ | 5-pyrimidyl | 4-morpholinocarbonyl |
| 368 | SOCH$_3$ | 5-pyrimidyl | 2-methyl-1-imidazolyl |
| 369 | SOCH$_3$ | 5-pyrimidyl | 5-methyl-1-imidazolyl |
| 370 | SOCH$_3$ | 5-pyrimidyl | 2-methylsulfonyl-1-imidazolyl |
| 371 | SOCH$_3$ | 2-Cl-phenyl | 2-(aminosulfonyl)phenyl |
| 372 | SOCH$_3$ | 2-Cl-phenyl | 2-(methylaminosulfonyl)phenyl |
| 373 | SOCH$_3$ | 2-Cl-phenyl | 1-pyrrolidinocarbonyl |
| 374 | SOCH$_3$ | 2-Cl-phenyl | 2-(methylsulfonyl)phenyl |
| 375 | SOCH$_3$ | 2-Cl-phenyl | 4-morpholino |
| 376 | SOCH$_3$ | 2-Cl-phenyl | 2-(1'-CF$_3$-tetrazol-2-yl)phenyl |
| 377 | SOCH$_3$ | 2-Cl-phenyl | 4-morpholinocarbonyl |
| 378 | SOCH$_3$ | 2-Cl-phenyl | 2-methyl-1-imidazolyl |
| 379 | SOCH$_3$ | 2-Cl-phenyl | 5-methyl-1-imidazolyl |
| 380 | SOCH$_3$ | 2-Cl-phenyl | 2-methylsulfonyl-1-imidazolyl |
| 381 | SOCH$_3$ | 2-F-phenyl | 2-(aminosulfonyl)phenyl |
| 382 | SOCH$_3$ | 2-F-phenyl | 2-(methylaminosulfonyl)phenyl |
| 383 | SOCH$_3$ | 2-F-phenyl | 1-pyrrolidinocarbonyl |
| 384 | SOCH$_3$ | 2-F-phenyl | 2-(methylsulfonyl)phenyl |
| 385 | SOCH$_3$ | 2-F-phenyl | 4-morpholino |
| 386 | SOCH$_3$ | 2-F-phenyl | 2-(1'-CF$_3$-tetrazol-2-yl)phenyl |
| 387 | SOCH$_3$ | 2-F-phenyl | 4-morpholinocarbonyl |
| 388 | SOCH$_3$ | 2-F-phenyl | 2-methyl-1-imidazolyl |
| 389 | SOCH$_3$ | 2-F-phenyl | 5-methyl-1-imidazolyl |

TABLE 7-continued

| | | | |
|---|---|---|---|
| 390 | SOCH$_3$ | 2-F-phenyl | 2-methylsulfonyl-1-imidazolyl |
| 391 | SOCH$_3$ | 2,6-diF-phenyl | 2-(aminosulfonyl)phenyl |
| 392 | SOCH$_3$ | 2,6-diF-phenyl | 2-(methylaminosulfonyl)phenyl |
| 393 | SOCH$_3$ | 2,6-diF-phenyl | 1-pyrrolidinocarbonyl |
| 394 | SOCH$_3$ | 2,6-diF-phenyl | 2-(methylsulfonyl)phenyl |
| 395 | SOCH$_3$ | 2,6-diF-phenyl | 4-morpholino |
| 396 | SOCH$_3$ | 2,6-diF-phenyl | 2-(1'-CF$_3$-tetrazol-2-yl)phenyl |
| 397 | SOCH$_3$ | 2,6-diF-phenyl | 4-morpholinocarbonyl |
| 398 | SOCH$_3$ | 2,6-diF-phenyl | 2-methyl-1-imidazolyl |
| 399 | SOCH$_3$ | 2,6-diF-phenyl | 5-methyl-1-imidazolyl |
| 400 | SOCH$_3$ | 2,6-diF-phenyl | 2-methylsulfonyl-1-imidazolyl |
| 401 | SO$_2$CH$_3$ | phenyl | 2-(aminosulfonyl)phenyl |
| 402 | SO$_2$CH$_3$ | phenyl | 2-(methylaminosulfonyl)phenyl |
| 403 | SO$_2$CH$_3$ | phenyl | 1-pyrrolidinocarbonyl |
| 404 | SO$_2$CH$_3$ | phenyl | 2-(methylsulfonyl)phenyl |
| 405 | SO$_2$CH$_3$ | phenyl | 4-morpholino |
| 406 | SO$_2$CH$_3$ | phenyl | 2-(1'-CF$_3$-tetrazol-2-yl)phenyl |
| 407 | SO$_2$CH$_3$ | phenyl | 4-morpholinocarbonyl |
| 408 | SO$_2$CH$_3$ | phenyl | 2-methyl-1-imidazolyl |
| 409 | SO$_2$CH$_3$ | phenyl | 5-methyl-1-imidazolyl |
| 410 | SO$_2$CH$_3$ | phenyl | 2-methylsulfonyl-1-imidazolyl |
| 411 | SO$_2$CH$_3$ | 2-pyridyl | 2-(aminosulfonyl)phenyl |
| 412 | SO$_2$CH$_3$ | 2-pyridyl | 2-(methylaminosulfonyl)phenyl |
| 413 | SO$_2$CH$_3$ | 2-pyridyl | 1-pyrrolidinocarbonyl |
| 414 | SO$_2$CH$_3$ | 2-pyridyl | 2-(methylsulfonyl)phenyl |
| 415 | SO$_2$CH$_3$ | 2-pyridyl | 4-morpholino |
| 416 | SO$_2$CH$_3$ | 2-pyridyl | 2-(1'-CF$_3$-tetrazol-2-yl)phenyl |
| 417 | SO$_2$CH$_3$ | 2-pyridyl | 4-morpholinocarbonyl |
| 418 | SO$_2$CH$_3$ | 2-pyridyl | 2-methyl-1-imidazolyl |
| 419 | SO$_2$CH$_3$ | 2-pyridyl | 5-methyl-1-imidazolyl |
| 420 | SO$_2$CH$_3$ | 2-pyridyl | 2-methylsulfonyl-1-imidazolyl |
| 421 | SO$_2$CH$_3$ | 3-pyridyl | 2-(aminosulfonyl)phenyl |
| 422 | SO$_2$CH$_3$ | 3-pyridyl | 2-(methylaminosulfonyl)phenyl |
| 423 | SO$_2$CH$_3$ | 3-pyridyl | 1-pyrrolidinocarbonyl |
| 424 | SO$_2$CH$_3$ | 3-pyridyl | 2-(methylsulfonyl)phenyl |
| 425 | SO$_2$CH$_3$ | 3-pyridyl | 4-morpholino |
| 426 | SO$_2$CH$_3$ | 3-pyridyl | 2-(1'-CF$_3$-tetrazol-2-yl)phenyl |
| 427 | SO$_2$CH$_3$ | 3-pyridyl | 4-morpholinocarbonyl |
| 428 | SO$_2$CH$_3$ | 3-pyridyl | 2-methyl-1-imidazolyl |
| 429 | SO$_2$CH$_3$ | 3-pyridyl | 5-methyl-1-imidazolyl |
| 430 | SO$_2$CH$_3$ | 3-pyridyl | 2-methylsulfonyl-1-imidazolyl |
| 431 | SO$_2$CH$_3$ | 2-pyrimidyl | 2-(aminosulfonyl)phenyl |
| 432 | SO$_2$CH$_3$ | 2-pyrimidyl | 2-(methylaminosulfonyl)phenyl |
| 433 | SO$_2$CH$_3$ | 2-pyrimidyl | 1-pyrrolidinocarbonyl |
| 434 | SO$_2$CH$_3$ | 2-pyrimidyl | 2-(methylsulfonyl)phenyl |
| 435 | SO$_2$CH$_3$ | 2-pyrimidyl | 4-morpholino |
| 436 | SO$_2$CH$_3$ | 2-pyrimidyl | 2-(1'-CF$_3$-tetrazol-2-yl)phenyl |
| 437 | SO$_2$CH$_3$ | 2-pyrimidyl | 4-morpholinocarbonyl |
| 438 | SO$_2$CH$_3$ | 2-pyrimidyl | 2-methyl-1-imidazolyl |
| 439 | SO$_2$CH$_3$ | 2-pyrimidyl | 5-methyl-1-imidazolyl |
| 440 | SO$_2$CH$_3$ | 2-pyrimidyl | 2-methylsulfonyl-1-imidazolyl |
| 441 | SO$_2$CH$_3$ | 5-pyrimidyl | 2-(aminosulfonyl)phenyl |
| 442 | SO$_2$CH$_3$ | 5-pyrimidyl | 2-(methylaminosulfonyl)phenyl |
| 443 | SO$_2$CH$_3$ | 5-pyrimidyl | 1-pyrrolidinocarbonyl |
| 444 | SO$_2$CH$_3$ | 5-pyrimidyl | 2-(methylsulfonyl)phenyl |
| 445 | SO$_2$CH$_3$ | 5-pyrimidyl | 4-morpholino |
| 446 | SO$_2$CH$_3$ | 5-pyrimidyl | 2-(1'-CF$_3$-tetrazol-2-yl)phenyl |
| 447 | SO$_2$CH$_3$ | 5-pyrimidyl | 4-morpholinocarbonyl |
| 448 | SO$_2$CH$_3$ | 5-pyrimidyl | 2-methyl-1-imidazolyl |
| 449 | SO$_2$CH$_3$ | 5-pyrimidyl | 5-methyl-1-imidazolyl |
| 450 | SO$_2$CH$_3$ | 5-pyrimidyl | 2-methylsulfonyl-1-imidazolyl |
| 451 | SO$_2$CH$_3$ | 2-Cl-phenyl | 2-(aminosulfonyl)phenyl |
| 452 | SO$_2$CH$_3$ | 2-Cl-phenyl | 2-(methylaminosulfonyl)phenyl |
| 453 | SO$_2$CH$_3$ | 2-Cl-phenyl | 1-pyrrolidinocarbonyl |
| 454 | SO$_2$CH$_3$ | 2-Cl-phenyl | 2-(methylsulfonyl)phenyl |
| 455 | SO$_2$CH$_3$ | 2-Cl-phenyl | 4-morpholino |
| 456 | SO$_2$CH$_3$ | 2-Cl-phenyl | 2-(1'-CF$_3$-tetrazol-2-yl)phenyl |
| 457 | SO$_2$CH$_3$ | 2-Cl-phenyl | 4-morpholinocarbonyl |
| 458 | SO$_2$CH$_3$ | 2-Cl-phenyl | 2-methyl-1-imidazolyl |
| 459 | SO$_2$CH$_3$ | 2-Cl-phenyl | 5-methyl-1-imidazolyl |
| 460 | SO$_2$CH$_3$ | 2-Cl-phenyl | 2-methylsulfonyl-1-imidazolyl |
| 461 | SO$_2$CH$_3$ | 2-F-phenyl | 2-(aminosulfonyl)phenyl |

TABLE 7-continued

| | | | |
|---|---|---|---|
| 462 | $SO_2CH_3$ | 2-F-phenyl | 2-(methylaminosulfonyl)phenyl |
| 463 | $SO_2CH_3$ | 2-F-phenyl | 1-pyrrolidinocarbonyl |
| 464 | $SO_2CH_3$ | 2-F-phenyl | 2-(methylsulfonyl)phenyl |
| 465 | $SO_2CH_3$ | 2-F-phenyl | 4-morpholino |
| 466 | $SO_2CH_3$ | 2-F-phenyl | 2-(1'-$CF_3$-tetrazol-2-yl)phenyl |
| 467 | $SO_2CH_3$ | 2-F-phenyl | 4-morpholinocarbonyl |
| 468 | $SO_2CH_3$ | 2-F-phenyl | 2-methyl-1-imidazolyl |
| 469 | $SO_2CH_3$ | 2-F-phenyl | 5-methyl-1-imidazolyl |
| 470 | $SO_2CH_3$ | 2-F-phenyl | 2-methylsulfonyl-1-imidazolyl |
| 471 | $SO_2CH_3$ | 2,6-diF-phenyl | 2-(aminosulfonyl)phenyl |
| 472 | $SO_2CH_3$ | 2,6-diF-phenyl | 2-(methylaminosulfonyl)phenyl |
| 473 | $SO_2CH_3$ | 2,6-diF-phenyl | 1-pyrrolidinocarbonyl |
| 474 | $SO_2CH_3$ | 2,6-diF-phenyl | 2-(methylsulfonyl)phenyl |
| 475 | $SO_2CH_3$ | 2,6-diF-phenyl | 4-morpholino |
| 476 | $SO_2CH_3$ | 2,6-diF-phenyl | 2-(1'-$CF_3$-tetrazol-2-yl)phenyl |
| 477 | $SO_2CH_3$ | 2,6-diF-phenyl | 4-morpholinocarbonyl |
| 478 | $SO_2CH_3$ | 2,6-diF-phenyl | 2-methyl-1-imidazolyl |
| 479 | $SO_2CH_3$ | 2,6-diF-phenyl | 5-methyl-1-imidazolyl |
| 480 | $SO_2CH_3$ | 2,6-diF-phenyl | 2-methylsulfonyl-1-imidazolyl |
| 481 | $CH_2NH-SO_2CH_3$ | phenyl | 2-(aminosulfonyl)phenyl |
| 482 | $CH_2NH-SO_2CH_3$ | phenyl | 2-(methylaminosulfonyl)phenyl |
| 483 | $CH_2NH-SO_2CH_3$ | phenyl | 1-pyrrolidinocarbonyl |
| 484 | $CH_2NH-SO_2CH_3$ | phenyl | 2-(methylsulfonyl)phenyl |
| 485 | $CH_2NH-SO_2CH_3$ | phenyl | 4-morpholino |
| 486 | $CH_2NH-SO_2CH_3$ | phenyl | 2-(1'-$CF_3$-tetrazol-2-yl)phenyl |
| 487 | $CH_2NH-SO_2CH_3$ | phenyl | 4-morpholinocarbonyl |
| 488 | $CH_2NH-SO_2CH_3$ | phenyl | 2-methyl-1-imidazolyl |
| 489 | $CH_2NH-SO_2CH_3$ | phenyl | 5-methyl-1-imidazolyl |
| 490 | $CH_2NH-SO_2CH_3$ | phenyl | 2-methylsulfonyl-1-imidazolyl |
| 491 | $CH_2NH-SO_2CH_3$ | 2-pyridyl | 2-(aminosulfonyl)phenyl |
| 492 | $CH_2NH-SO_2CH_3$ | 2-pyridyl | 2-(methylaminosulfonyl)phenyl |
| 493 | $CH_2NH-SO_2CH_3$ | 2-pyridyl | 1-pyrrolidinocarbonyl |
| 494 | $CH_2NH-SO_2CH_3$ | 2-pyridyl | 2-(methylsulfonyl)phenyl |
| 495 | $CH_2NH-SO_2CH_3$ | 2-pyridyl | 4-morpholino |
| 496 | $CH_2NH-SO_2CH_3$ | 2-pyridyl | 2-(1'-$CF_3$-tetrazol-2-yl)phenyl |
| 497 | $CH_2NH-SO_2CH_3$ | 2-pyridyl | 4-morpholinocarbonyl |
| 498 | $CH_2NH-SO_2CH_3$ | 2-pyridyl | 2-methyl-1-imidazolyl |
| 499 | $CH_2NH-SO_2CH_3$ | 2-pyridyl | 5-methyl-1-imidazolyl |
| 500 | $CH_2NH-SO_2CH_3$ | 2-pyridyl | 2-methylsulfonyl-1-imidazolyl |
| 501 | $CH_2NH-SO_2CH_3$ | 3-pyridyl | 2-(aminosulfonyl)phenyl |
| 502 | $CH_2NH-SO_2CH_3$ | 3-pyridyl | 2-(methylaminosulfonyl)phenyl |
| 503 | $CH_2NH-SO_2CH_3$ | 3-pyridyl | 1-pyrrolidinocarbonyl |
| 504 | $CH_2NH-SO_2CH_3$ | 3-pyridyl | 2-(methylsulfonyl)phenyl |
| 505 | $CH_2NH-SO_2CH_3$ | 3-pyridyl | 4-morpholino |
| 506 | $CH_2NH-SO_2CH_3$ | 3-pyridyl | 2-(1'-$CF_3$-tetrazol-2-yl)phenyl |
| 507 | $CH_2NH-SO_2CH_3$ | 3-pyridyl | 4-morpholinocarbonyl |
| 508 | $CH_2NH-SO_2CH_3$ | 3-pyridyl | 2-methyl-1-imidazolyl |
| 509 | $CH_2NH-SO_2CH_3$ | 3-pyridyl | 5-methyl-1-imidazolyl |
| 510 | $CH_2NH-SO_2CH_3$ | 3-pyridyl | 2-methylsulfonyl-1-imidazolyl |
| 511 | $CH_2NH-SO_2CH_3$ | 2-pyrimidyl | 2-(aminosulfonyl)phenyl |
| 512 | $CH_2NH-SO_2CH_3$ | 2-pyrimidyl | 2-(methylaminosulfonyl)phenyl |
| 513 | $CH_2NH-SO_2CH_3$ | 2-pyrimidyl | 1-pyrrolidinocarbonyl |
| 514 | $CH_2NH-SO_2CH_3$ | 2-pyrimidyl | 2-(methylsulfonyl)phenyl |
| 515 | $CH_2NH-SO_2CH_3$ | 2-pyrimidyl | 4-morpholino |
| 516 | $CH_2NH-SO_2CH_3$ | 2-pyrimidyl | 2-(1'-$CF_3$-tetrazol-2-yl)phenyl |
| 517 | $CH_2NH-SO_2CH_3$ | 2-pyrimidyl | 4-morpholinocarbonyl |
| 518 | $CH_2NH-SO_2CH_3$ | 2-pyrimidyl | 2-methyl-1-imidazolyl |
| 519 | $CH_2NH-SO_2CH_3$ | 2-pyrimidyl | 5-methyl-1-imidazolyl |
| 520 | $CH_2NH-SO_2CH_3$ | 2-pyrimidyl | 2-methylsulfonyl-1-imidazolyl |
| 521 | $CH_2NH-SO_2CH_3$ | 5-pyrimidyl | 2-(aminosulfonyl)phenyl |
| 522 | $CH_2NH-SO_2CH_3$ | 5-pyrimidyl | 2-(methylaminosulfonyl)phenyl |
| 523 | $CH_2NH-SO_2CH_3$ | 5-pyrimidyl | 1-pyrrolidinocarbonyl |
| 524 | $CH_2NH-SO_2CH_3$ | 5-pyrimidyl | 2-(methylsulfonyl)phenyl |
| 525 | $CH_2NH-SO_2CH_3$ | 5-pyrimidyl | 4-morpholino |
| 526 | $CH_2NH-SO_2CH_3$ | 5-pyrimidyl | 2-(1'-$CF_3$-tetrazol-2-yl)phenyl |
| 527 | $CH_2NH-SO_2CH_3$ | 5-pyrimidyl | 4-morpholinocarbonyl |
| 528 | $CH_2NH-SO_2CH_3$ | 5-pyrimidyl | 2-methyl-1-imidazolyl |
| 529 | $CH_2NH-SO_2CH_3$ | 5-pyrimidyl | 5-methyl-1-imidazolyl |
| 530 | $CH_2NH-SO_2CH_3$ | 5-pyrimidyl | 2-methylsulfonyl-1-imidazolyl |
| 531 | $CH_2NH-SO_2CH_3$ | 2-Cl-phenyl | 2-(aminosulfonyl)phenyl |
| 532 | $CH_2NH-SO_2CH_3$ | 2-Cl-phenyl | 2-(methylaminosulfonyl)phenyl |
| 533 | $CH_2NH-SO_2CH_3$ | 2-Cl-phenyl | 1-pyrrolidinocarbonyl |

TABLE 7-continued

| | | | |
|---|---|---|---|
| 534 | $CH_2NH$—$SO_2CH_3$ | 2-Cl-phenyl | 2-(methylsulfonyl)phenyl |
| 535 | $CH_2NH$—$SO_2CH_3$ | 2-Cl-phenyl | 4-morpholino |
| 536 | $CH_2NH$—$SO_2CH_3$ | 2-Cl-phenyl | 2-(1'-$CF_3$-tetrazol-2-yl)phenyl |
| 537 | $CH_2NH$—$SO_2CH_3$ | 2-Cl-phenyl | 4-morpholinocarbonyl |
| 538 | $CH_2NH$—$SO_2CH_3$ | 2-Cl-phenyl | 2-methyl-1-imidazolyl |
| 539 | $CH_2NH$—$SO_2CH_3$ | 2-Cl-phenyl | 5-methyl-1-imidazolyl |
| 540 | $CH_2NH$—$SO_2CH_3$ | 2-Cl-phenyl | 2-methylsulfonyl-1-imidazolyl |
| 541 | $CH_2NH$—$SO_2CH_3$ | 2-F-phenyl | 2-(aminosulfonyl)phenyl |
| 542 | $CH_2NH$—$SO_2CH_3$ | 2-F-phenyl | 2-(methylaminosulfonyl)phenyl |
| 543 | $CH_2NH$—$SO_2CH_3$ | 2-F-phenyl | 1-pyrrolidinocarbonyl |
| 544 | $CH_2NH$—$SO_2CH_3$ | 2-F-phenyl | 2-(methylsulfonyl)phenyl |
| 545 | $CH_2NH$—$SO_2CH_3$ | 2-F-phenyl | 4-morpholino |
| 546 | $CH_2NH$—$SO_2CH_3$ | 2-F-phenyl | 2-(1'-$CF_3$-tetrazol-2-yl)phenyl |
| 547 | $CH_2NH$—$SO_2CH_3$ | 2-F-phenyl | 4-morpholinocarbonyl |
| 548 | $CH_2NH$—$SO_2CH_3$ | 2-F-phenyl | 2-methyl-1-imidazolyl |
| 549 | $CH_2NH$—$SO_2CH_3$ | 2-F-phenyl | 5-methyl-1-imidazolyl |
| 550 | $CH_2NH$—$SO_2CH_3$ | 2-F-phenyl | 2-methylsulfonyl-1-imidazolyl |
| 551 | $CH_2NH$—$SO_2CH_3$ | 2,6-diF-phenyl | 2-(aminosulfonyl)phenyl |
| 552 | $CH_2NH$—$SO_2CH_3$ | 2,6-diF-phenyl | 2-(methylaminosulfonyl)phenyl |
| 553 | $CH_2NH$—$SO_2CH_3$ | 2,6-diF-phenyl | 1-pyrrolidinocarbonyl |
| 554 | $CH_2NH$—$SO_2CH_3$ | 2,6-diF-phenyl | 2-(methylsulfonyl)phenyl |
| 555 | $CH_2NH$—$SO_2CH_3$ | 2,6-diF-phenyl | 4-morpholino |
| 556 | $CH_2NH$—$SO_2CH_3$ | 2,6-diF-phenyl | 2-(1'-$CF_3$-tetrazol-2-yl)phenyl |
| 557 | $CH_2NH$—$SO_2CH_3$ | 2,6-diF-phenyl | 4-morpholinocarbonyl |
| 558 | $CH_2NH$—$SO_2CH_3$ | 2,6-diF-phenyl | 2-methyl-1-imidazolyl |
| 559 | $CH_2NH$—$SO_2CH_3$ | 2,6-diF-phenyl | 5-methyl-1-imidazolyl |
| 560 | $CH_2NH$—$SO_2CH_3$ | 2,6-diF-phenyl | 2-methylsulfonyl-1-imidazolyl |
| 561 | Cl | phenyl | 2-(aminosulfonyl)phenyl |
| 562 | Cl | phenyl | 2-(methylaminosulfonyl)phenyl |
| 563 | Cl | phenyl | 1-pyrrolidinocarbonyl |
| 564 | Cl | phenyl | 2-(methylsulfonyl)phenyl |
| 565 | Cl | phenyl | 4-morpholino |
| 566 | Cl | phenyl | 2-(1'-$CF_3$-tetrazol-2-yl)phenyl |
| 567 | Cl | phenyl | 4-morpholinocarbonyl |
| 568 | Cl | phenyl | 2-methyl-1-imidazolyl |
| 569 | Cl | phenyl | 5-methyl-1-imidazolyl |
| 570 | Cl | phenyl | 2-methylsulfonyl-1-imidazolyl |
| 571 | Cl | 2-pyridyl | 2-(aminosulfonyl)phenyl |
| 572 | Cl | 2-pyridyl | 2-(methylaminosulfonyl)phenyl |
| 573 | Cl | 2-pyridyl | 1-pyrrolidinocarbonyl |
| 574 | Cl | 2-pyridyl | 2-(methylsulfonyl)phenyl |
| 575 | Cl | 2-pyridyl | 4-morpholino |
| 576 | Cl | 2-pyridyl | 2-(1'-$CF_3$-tetrazol-2-yl)phenyl |
| 577 | Cl | 2-pyridyl | 4-morpholinocarbonyl |
| 578 | Cl | 2-pyridyl | 2-methyl-1-imidazolyl |
| 579 | Cl | 2-pyridyl | 5-methyl-1-imidazolyl |
| 580 | Cl | 2-pyridyl | 2-methylsulfonyl-1-imidazolyl |
| 581 | Cl | 3-pyridyl | 2-(aminosulfonyl)phenyl |
| 582 | Cl | 3-pyridyl | 2-(methylaminosulfonyl)phenyl |
| 583 | Cl | 3-pyridyl | 1-pyrrolidinocarbonyl |
| 584 | Cl | 3-pyridyl | 2-(methylsulfonyl)phenyl |
| 585 | Cl | 3-pyridyl | 4-morpholino |
| 586 | Cl | 3-pyridyl | 2-(1'-$CF_3$-tetrazol-2-yl)phenyl |
| 587 | Cl | 3-pyridyl | 4-morpholinocarbonyl |
| 588 | Cl | 3-pyridyl | 2-methyl-1-imidazolyl |
| 589 | Cl | 3-pyridyl | 5-methyl-1-imidazolyl |
| 590 | Cl | 3-pyridyl | 2-methylsulfonyl-1-imidazolyl |
| 591 | Cl | 2-pyrimidyl | 2-(aminosulfonyl)phenyl |
| 592 | Cl | 2-pyrimidyl | 2-(methylaminosulfonyl)phenyl |
| 593 | Cl | 2-pyrimidyl | 1-pyrrolidinocarbonyl |
| 594 | Cl | 2-pyrimidyl | 2-(methylsulfonyl)phenyl |
| 595 | Cl | 2-pyrimidyl | 4-morpholino |
| 596 | Cl | 2-pyrimidyl | 2-(1'-$CF_3$-tetrazol-2-yl)phenyl |
| 597 | Cl | 2-pyrimidyl | 4-morpholinocarbonyl |
| 598 | Cl | 2-pyrimidyl | 2-methyl-1-imidazolyl |
| 599 | Cl | 2-pyrimidyl | 5-methyl-1-imidazolyl |
| 600 | Cl | 2-pyrimidyl | 2-methylsulfonyl-1-imidazolyl |
| 601 | Cl | 5-pyrimidyl | 2-(aminosulfonyl)phenyl |
| 602 | Cl | 5-pyrimidyl | 2-(methylaminosulfonyl)phenyl |
| 603 | Cl | 5-pyrimidyl | 1-pyrrolidinocarbonyl |
| 604 | Cl | 5-pyrimidyl | 2-(methylsulfonyl)phenyl |
| 605 | Cl | 5-pyrimidyl | 4-morpholino |

TABLE 7-continued

| | | | |
|---|---|---|---|
| 606 | Cl | 5-pyrimidyl | 2-(1'-CF$_3$-tetrazol-2-yl)phenyl |
| 607 | Cl | 5-pyrimidyl | 4-morpholinocarbonyl |
| 608 | Cl | 5-pyrimidyl | 2-methyl-1-imidazolyl |
| 609 | Cl | 5-pyrimidyl | 5-methyl-1-imidazolyl |
| 610 | Cl | 5-pyrimidyl | 2-methylsulfonyl-1-imidazolyl |
| 611 | Cl | 2-Cl-phenyl | 2-(aminosulfonyl)phenyl |
| 612 | Cl | 2-Cl-phenyl | 2-(methylaminosulfonyl)phenyl |
| 613 | Cl | 2-Cl-phenyl | 1-pyrrolidinocarbonyl |
| 614 | Cl | 2-Cl-phenyl | 2-(methylsulfonyl)phenyl |
| 615 | Cl | 2-Cl-phenyl | 4-morpholino |
| 616 | Cl | 2-Cl-phenyl | 2-(1'-CF$_3$-tetrazol-2-yl)phenyl |
| 617 | Cl | 2-Cl-phenyl | 4-morpholinocarbonyl |
| 618 | Cl | 2-Cl-phenyl | 2-methyl-1-imidazolyl |
| 619 | Cl | 2-Cl-phenyl | 5-methyl-1-imidazolyl |
| 620 | Cl | 2-Cl-phenyl | 2-methylsulfonyl-1-imidazolyl |
| 621 | Cl | 2-F-phenyl | 2-(aminosulfonyl)phenyl |
| 622 | Cl | 2-F-phenyl | 2-(methylaminosulfonyl)phenyl |
| 623 | Cl | 2-F-phenyl | 1-pyrrolidinocarbonyl |
| 624 | Cl | 2-F-phenyl | 2-(methylsulfonyl)phenyl |
| 625 | Cl | 2-F-phenyl | 4-morpholino |
| 626 | Cl | 2-F-phenyl | 2-(1'-CF$_3$-tetrazol-2-yl)phenyl |
| 627 | Cl | 2-F-phenyl | 4-morpholinocarbonyl |
| 628 | Cl | 2-F-phenyl | 2-methyl-1-imidazolyl |
| 629 | Cl | 2-F-phenyl | 5-methyl-1-imidazolyl |
| 630 | Cl | 2-F-phenyl | 2-methylsulfonyl-1-imidazolyl |
| 631 | Cl | 2,6-diF-phenyl | 2-(aminosulfonyl)phenyl |
| 632 | Cl | 2,6-diF-phenyl | 2-(methylaminosulfonyl)phenyl |
| 633 | Cl | 2,6-diF-phenyl | 1-pyrrolidinocarbonyl |
| 634 | Cl | 2,6-diF-phenyl | 2-(methylsulfonyl)phenyl |
| 635 | Cl | 2,6-diF-phenyl | 4-morpholino |
| 636 | Cl | 2,6-diF-phenyl | 2-(1'-CF$_3$-tetrazol-2-yl)phenyl |
| 637 | Cl | 2,6-diF-phenyl | 4-morpholinocarbonyl |
| 638 | Cl | 2,6-diF-phenyl | 2-methyl-1-imidazolyl |
| 639 | Cl | 2,6-diF-phenyl | 5-methyl-1-imidazolyl |
| 640 | Cl | 2,6-diF-phenyl | 2-methylsulfonyl-1-imidazolyl |
| 641 | F | phenyl | 2-(aminosulfonyl)phenyl |
| 642 | F | phenyl | 2-(methylaminosulfonyl)phenyl |
| 643 | F | phenyl | 1-pyrrolidinocarbonyl |
| 644 | F | phenyl | 2-(methylsulfonyl)phenyl |
| 645 | F | phenyl | 4-morpholino |
| 646 | F | phenyl | 2-(1'-CF$_3$-tetrazol-2-yl)phenyl |
| 647 | F | phenyl | 4-morpholinocarbonyl |
| 648 | F | phenyl | 2-methyl-1-imidazolyl |
| 649 | F | phenyl | 5-methyl-1-imidazolyl |
| 650 | F | phenyl | 2-methylsulfonyl-1-imidazolyl |
| 651 | F | 2-pyridyl | 2-(aminosulfonyl)phenyl |
| 652 | F | 2-pyridyl | 2-(methylaminosulfonyl)phenyl |
| 653 | F | 2-pyridyl | 1-pyrrolidinocarbonyl |
| 654 | F | 2-pyridyl | 2-(methylsulfonyl)phenyl |
| 655 | F | 2-pyridyl | 4-morpholino |
| 656 | F | 2-pyridyl | 2-(1'-CF$_3$-tetrazol-2-yl)phenyl |
| 657 | F | 2-pyridyl | 4-morpholinocarbonyl |
| 658 | F | 2-pyridyl | 2-methyl-1-imidazolyl |
| 659 | F | 2-pyridyl | 5-methyl-1-imidazolyl |
| 660 | F | 2-pyridyl | 2-methylsulfonyl-1-imidazolyl |
| 661 | F | 3-pyridyl | 2-(aminosulfonyl)phenyl |
| 662 | F | 3-pyridyl | 2-(methylaminosulfonyl)phenyl |
| 663 | F | 3-pyridyl | 1-pyrrolidinocarbonyl |
| 664 | F | 3-pyridyl | 2-(methylsulfonyl)phenyl |
| 665 | F | 3-pyridyl | 4-morpholino |
| 666 | F | 3-pyridyl | 2-(1'-CF$_3$-tetrazol-2-yl)phenyl |
| 667 | F | 3-pyridyl | 4-morpholinocarbonyl |
| 668 | F | 3-pyridyl | 2-methyl-1-imidazolyl |
| 669 | F | 3-pyridyl | 5-methyl-1-imidazolyl |
| 670 | F | 3-pyridyl | 2-methylsulfonyl-1-imidazolyl |
| 671 | F | 2-pyrimidyl | 2-(aminosulfonyl)phenyl |
| 672 | F | 2-pyrimidyl | 2-(methylaminosulfonyl)phenyl |
| 673 | F | 2-pyrimidyl | 1-pyrrolidinocarbonyl |
| 674 | F | 2-pyrimidyl | 2-(methylsulfonyl)phenyl |
| 675 | F | 2-pyrimidyl | 4-morpholino |
| 676 | F | 2-pyrimidyl | 2-(1'-CF$_3$-tetrazol-2-yl)phenyl |

TABLE 7-continued

| | | | |
|---|---|---|---|
| 677 | F | 2-pyrimidyl | 4-morpholinocarbonyl |
| 678 | F | 2-pyrimidyl | 2-methyl-1-imidazolyl |
| 679 | F | 2-pyrimidyl | 5-methyl-1-imidazolyl |
| 680 | F | 2-pyrimidyl | 2-methylsulfonyl-1-imidazolyl |
| 681 | F | 5-pyrimidyl | 2-(aminosulfonyl)phenyl |
| 682 | F | 5-pyrimidyl | 2-(methylaminosulfonyl)phenyl |
| 683 | F | 5-pyrimidyl | 1-pyrrolidinocarbonyl |
| 684 | F | 5-pyrimidyl | 2-(methylsulfonyl)phenyl |
| 685 | F | 5-pyrimidyl | 4-morpholino |
| 686 | F | 5-pyrimidyl | 2-(1'-$CF_3$-tetrazol-2-yl)phenyl |
| 687 | F | 5-pyrimidyl | 4-morpholinocarbonyl |
| 688 | F | 5-pyrimidyl | 2-methyl-1-imidazolyl |
| 689 | F | 5-pyrimidyl | 5-methyl-1-imidazolyl |
| 690 | F | 5-pyrimidyl | 2-methylsulfonyl-1-imidazolyl |
| 691 | F | 2-Cl-phenyl | 2-(aminosulfonyl)phenyl |
| 692 | F | 2-Cl-phenyl | 2-(methylaminosulfonyl)phenyl |
| 693 | F | 2-Cl-phenyl | 1-pyrrolidinocarbonyl |
| 694 | F | 2-Cl-phenyl | 2-(methylsulfonyl)phenyl |
| 695 | F | 2-Cl-phenyl | 4-morpholino |
| 696 | F | 2-Cl-phenyl | 2-(1'-$CF_3$-tetrazol-2-yl)phenyl |
| 697 | F | 2-Cl-phenyl | 4-morpholinocarbonyl |
| 698 | F | 2-Cl-phenyl | 2-methyl-1-imidazolyl |
| 699 | F | 2-Cl-phenyl | 5-methyl-1-imidazolyl |
| 700 | F | 2-Cl-phenyl | 2-methylsulfonyl-1-imidazolyl |
| 701 | F | 2-F-phenyl | 2-(aminosulfonyl)phenyl |
| 702 | F | 2-F-phenyl | 2-(methylaminosulfonyl)phenyl |
| 703 | F | 2-F-phenyl | 1-pyrrolidinocarbonyl |
| 704 | F | 2-F-phenyl | 2-(methylsulfonyl)phenyl |
| 705 | F | 2-F-phenyl | 4-morpholino |
| 706 | F | 2-F-phenyl | 2-(1'-$CF_3$-tetrazol-2-yl)phenyl |
| 707 | F | 2-F-phenyl | 4-morpholinocarbonyl |
| 708 | F | 2-F-phenyl | 2-methyl-1-imidazolyl |
| 709 | F | 2-F-phenyl | 5-methyl-1-imidazolyl |
| 710 | F | 2-F-phenyl | 2-methylsulfonyl-1-imidazolyl |
| 711 | F | 2,6-diF-phenyl | 2-(aminosulfonyl)phenyl |
| 712 | F | 2,6-diF-phenyl | 2-(methylaminosulfonyl)phenyl |
| 713 | F | 2,6-diF-phenyl | 1-pyrrolidinocarbonyl |
| 714 | F | 2,6-diF-phenyl | 2-(methylsulfonyl)phenyl |
| 715 | F | 2,6-diF-phenyl | 4-morpholino |
| 716 | F | 2,6-diF-phenyl | 2-(1'-$CF_3$-tetrazol-2-yl)phenyl |
| 717 | F | 2,6-diF-phenyl | 4-morpholinocarbonyl |
| 718 | F | 2,6-diF-phenyl | 2-methyl-1-imidazolyl |
| 719 | F | 2,6-diF-phenyl | 5-methyl-1-imidazolyl |
| 720 | F | 2,6-diF-phenyl | 2-methylsulfonyl-1-imidazolyl |
| 721 | $CO_2CH_3$ | phenyl | 2-(aminosulfonyl)phenyl |
| 722 | $CO_2CH_3$ | phenyl | 2-(methylaminosulfonyl)phenyl |
| 723 | $CO_2CH_3$ | phenyl | 1-pyrrolidinocarbonyl |
| 724 | $CO_2CH_3$ | phenyl | 2-(methylsulfonyl)phenyl |
| 725 | $CO_2CH_3$ | phenyl | 4-morpholino |
| 726 | $CO_2CH_3$ | phenyl | 2-(1'-$CF_3$-tetrazol-2-yl)phenyl |
| 727 | $CO_2CH_3$ | phenyl | 4-morpholinocarbonyl |
| 728 | $CO_2CH_3$ | phenyl | 2-methyl-1-imidazolyl |
| 729 | $CO_2CH_3$ | phenyl | 5-methyl-1-imidazolyl |
| 730 | $CO_2CH_3$ | phenyl | 2-methylsulfonyl-1-imidazolyl |
| 731 | $CO_2CH_3$ | 2-pyridyl | 2-(aminosulfonyl)phenyl |
| 732 | $CO_2CH_3$ | 2-pyridyl | 2-(methylaminosulfonyl)phenyl |
| 733 | $CO_2CH_3$ | 2-pyridyl | 1-pyrrolidinocarbonyl |
| 734 | $CO_2CH_3$ | 2-pyridyl | 2-(methylsulfonyl)phenyl |
| 735 | $CO_2CH_3$ | 2-pyridyl | 4-morpholino |
| 736 | $CO_2CH_3$ | 2-pyridyl | 2-(1'-$CF_3$-tetrazol-2-yl)phenyl |
| 737 | $CO_2CH_3$ | 2-pyridyl | 4-morpholinocarbonyl |
| 738 | $CO_2CH_3$ | 2-pyridyl | 2-methyl-1-imidazolyl |
| 739 | $CO_2CH_3$ | 2-pyridyl | 5-methyl-1-imidazolyl |
| 740 | $CO_2CH_3$ | 2-pyridyl | 2-methylsulfonyl-1-imidazolyl |
| 741 | $CO_2CH_3$ | 3-pyridyl | 2-(aminosulfonyl)phenyl |
| 742 | $CO_2CH_3$ | 3-pyridyl | 2-(methylaminosulfonyl)phenyl |
| 743 | $CO_2CH_3$ | 3-pyridyl | 1-pyrrolidinocarbonyl |
| 744 | $CO_2CH_3$ | 3-pyridyl | 2-(methylsulfonyl)phenyl |
| 745 | $CO_2CH_3$ | 3-pyridyl | 4-morpholino |
| 746 | $CO_2CH_3$ | 3-pyridyl | 2-(1'-$CF_3$-tetrazol-2-yl)phenyl |
| 747 | $CO_2CH_3$ | 3-pyridyl | 4-morpholinocarbonyl |
| 748 | $CO_2CH_3$ | 3-pyridyl | 2-methyl-1-imidazolyl |

TABLE 7-continued

| | | | |
|---|---|---|---|
| 749 | $CO_2CH_3$ | 3-pyridyl | 5-methyl-1-imidazolyl |
| 750 | $CO_2CH_3$ | 3-pyridyl | 2-methylsulfonyl-1-imidazolyl |
| 751 | $CO_2CH_3$ | 2-pyrimidyl | 2-(aminosulfonyl)phenyl |
| 752 | $CO_2CH_3$ | 2-pyrimidyl | 2-(methylaminosulfonyl)phenyl |
| 753 | $CO_2CH_3$ | 2-pyrimidyl | 1-pyrrolidinocarbonyl |
| 754 | $CO_2CH_3$ | 2-pyrimidyl | 2-(methylsulfonyl)phenyl |
| 755 | $CO_2CH_3$ | 2-pyrimidyl | 4-morpholino |
| 756 | $CO_2CH_3$ | 2-pyrimidyl | 2-(1'-$CF_3$-tetrazol-2-yl)phenyl |
| 757 | $CO_2CH_3$ | 2-pyrimidyl | 4-morpholinocarbonyl |
| 758 | $CO_2CH_3$ | 2-pyrimidyl | 2-methyl-1-imidazolyl |
| 759 | $CO_2CH_3$ | 2-pyrimidyl | 5-methyl-1-imidazolyl |
| 760 | $CO_2CH_3$ | 2-pyrimidyl | 2-methylsulfonyl-1-imidazolyl |
| 761 | $CO_2CH_3$ | 5-pyrimidyl | 2-(aminosulfonyl)phenyl |
| 762 | $CO_2CH_3$ | 5-pyrimidyl | 2-(methylaminosulfonyl)phenyl |
| 763 | $CO_2CH_3$ | 5-pyrimidyl | 1-pyrrolidinocarbonyl |
| 764 | $CO_2CH_3$ | 5-pyrimidyl | 2-(methylsulfonyl)phenyl |
| 765 | $CO_2CH_3$ | 5-pyrimidyl | 4-morpholino |
| 766 | $CO_2CH_3$ | 5-pyrimidyl | 2-(1'-$CF_3$-tetrazol-2-yl)phenyl |
| 767 | $CO_2CH_3$ | 5-pyrimidyl | 4-morpholinocarbonyl |
| 768 | $CO_2CH_3$ | 5-pyrimidyl | 2-methyl-1-imidazolyl |
| 769 | $CO_2CH_3$ | 5-pyrimidyl | 5-methyl-1-imidazolyl |
| 770 | $CO_2CH_3$ | 5-pyrimidyl | 2-methylsulfonyl-1-imidazolyl |
| 771 | $CO_2CH_3$ | 2-Cl-phenyl | 2-(aminosulfonyl)phenyl |
| 772 | $CO_2CH_3$ | 2-Cl-phenyl | 2-(methylaminosulfonyl)phenyl |
| 773 | $CO_2CH_3$ | 2-Cl-phenyl | 1-pyrrolidinocarbonyl |
| 774 | $CO_2CH_3$ | 2-Cl-phenyl | 2-(methylsulfonyl)phenyl |
| 775 | $CO_2CH_3$ | 2-Cl-phenyl | 4-morpholino |
| 776 | $CO_2CH_3$ | 2-Cl-phenyl | 2-(1'-$CF_3$-tetrazol-2-yl)phenyl |
| 777 | $CO_2CH_3$ | 2-Cl-phenyl | 4-morpholinocarbonyl |
| 778 | $CO_2CH_3$ | 2-Cl-phenyl | 2-methyl-1-imidazolyl |
| 779 | $CO_2CH_3$ | 2-Cl-phenyl | 5-methyl-1-imidazolyl |
| 780 | $CO_2CH_3$ | 2-Cl-phenyl | 2-methylsulfonyl-1-imidazolyl |
| 781 | $CO_2CH_3$ | 2-F-phenyl | 2-(aminosulfonyl)phenyl |
| 782 | $CO_2CH_3$ | 2-F-phenyl | 2-(methylaminosulfonyl)phenyl |
| 783 | $CO_2CH_3$ | 2-F-phenyl | 1-pyrrolidinocarbonyl |
| 784 | $CO_2CH_3$ | 2-F-phenyl | 2-(methylsulfonyl)phenyl |
| 785 | $CO_2CH_3$ | 2-F-phenyl | 4-morpholino |
| 786 | $CO_2CH_3$ | 2-F-phenyl | 2-(1'-$CF_3$-tetrazol-2-yl)phenyl |
| 787 | $CO_2CH_3$ | 2-F-phenyl | 4-morpholinocarbonyl |
| 788 | $CO_2CH_3$ | 2-F-phenyl | 2-methyl-1-imidazolyl |
| 789 | $CO_2CH_3$ | 2-F-phenyl | 5-methyl-1-imidazolyl |
| 790 | $CO_2CH_3$ | 2-F-phenyl | 2-methylsulfonyl-1-imidazolyl |
| 791 | $CO_2CH_3$ | 2,6-diF-phenyl | 2-(aminosulfonyl)phenyl |
| 792 | $CO_2CH_3$ | 2,6-diF-phenyl | 2-(methylaminosulfonyl)phenyl |
| 793 | $CO_2CH_3$ | 2,6-diF-phenyl | 1-pyrrolidinocarbonyl |
| 794 | $CO_2CH_3$ | 2,6-diF-phenyl | 2-(methylsulfonyl)phenyl |
| 795 | $CO_2CH_3$ | 2,6-diF-phenyl | 4-morpholino |
| 796 | $CO_2CH_3$ | 2,6-diF-phenyl | 2-(1'-$CF_3$-tetrazol-2-yl)phenyl |
| 797 | $CO_2CH_3$ | 2,6-diF-phenyl | 4-morpholinocarbonyl |
| 798 | $CO_2CH_3$ | 2,6-diF-phenyl | 2-methyl-1-imidazolyl |
| 799 | $CO_2CH_3$ | 2,6-diF-phenyl | 5-methyl-1-imidazolyl |
| 800 | $CO_2CH_3$ | 2,6-diF-phenyl | 2-methylsulfonyl-1-imidazolyl |
| 801 | $CH_2OCH_3$ | phenyl | 2-(aminosulfonyl)phenyl |
| 802 | $CH_2OCH_3$ | phenyl | 2-(methylaminosulfonyl)phenyl |
| 803 | $CH_2OCH_3$ | phenyl | 1-pyrrolidinocarbonyl |
| 804 | $CH_2OCH_3$ | phenyl | 2-(methylsulfonyl)phenyl |
| 805 | $CH_2OCH_3$ | phenyl | 4-morpholino |
| 806 | $CH_2OCH_3$ | phenyl | 2-(1'-$CF_3$-tetrazol-2-yl)phenyl |
| 807 | $CH_2OCH_3$ | phenyl | 4-morpholinocarbonyl |
| 808 | $CH_2OCH_3$ | phenyl | 2-methyl-1-imidazolyl |
| 809 | $CH_2OCH_3$ | phenyl | 5-methyl-1-imidazolyl |
| 810 | $CH_2OCH_3$ | phenyl | 2-methylsulfonyl-1-imidazolyl |
| 811 | $CH_2OCH_3$ | 2-pyridyl | 2-(aminosulfonyl)phenyl |
| 812 | $CH_2OCH_3$ | 2-pyridyl | 2-(methylaminosulfonyl)phenyl |
| 813 | $CH_2OCH_3$ | 2-pyridyl | 1-pyrrolidinocarbonyl |
| 814 | $CH_2OCH_3$ | 2-pyridyl | 2-(methylsulfonyl)phenyl |
| 815 | $CH_2OCH_3$ | 2-pyridyl | 4-morpholino |
| 816 | $CH_2OCH_3$ | 2-pyridyl | 2-(1'-$CF_3$-tetrazol-2-yl)phenyl |
| 817 | $CH_2OCH_3$ | 2-pyridyl | 4-morpholinocarbonyl |
| 818 | $CH_2OCH_3$ | 2-pyridyl | 2-methyl-1-imidazolyl |
| 819 | $CH_2OCH_3$ | 2-pyridyl | 5-methyl-1-imidazolyl |
| 820 | $CH_2OCH_3$ | 2-pyridyl | 2-methylsulfonyl-1-imidazolyl |

TABLE 7-continued

| | | | |
|---|---|---|---|
| 821 | $CH_2OCH_3$ | 3-pyridyl | 2-(aminosulfonyl)phenyl |
| 822 | $CH_2OCH_3$ | 3-pyridyl | 2-(methylaminosulfonyl)phenyl |
| 823 | $CH_2OCH_3$ | 3-pyridyl | 1-pyrrolidinocarbonyl |
| 824 | $CH_2OCH_3$ | 3-pyridyl | 2-(methylsulfonyl)phenyl |
| 825 | $CH_2OCH_3$ | 3-pyridyl | 4-morpholino |
| 826 | $CH_2OCH_3$ | 3-pyridyl | 2-(1'-$CF_3$-tetrazol-2-yl)phenyl |
| 827 | $CH_2OCH_3$ | 3-pyridyl | 4-morpholinocarbonyl |
| 828 | $CH_2OCH_3$ | 3-pyridyl | 2-methyl-1-imidazolyl |
| 829 | $CH_2OCH_3$ | 3-pyridyl | 5-methyl-1-imidazolyl |
| 830 | $CH_2OCH_3$ | 3-pyridyl | 2-methylsulfonyl-1-imidazolyl |
| 831 | $CH_2OCH_3$ | 2-pyrimidyl | 2-(aminosulfonyl)phenyl |
| 832 | $CH_2OCH_3$ | 2-pyrimidyl | 2-(methylaminosulfonyl)phenyl |
| 833 | $CH_2OCH_3$ | 2-pyrimidyl | 1-pyrrolidinocarbonyl |
| 834 | $CH_2OCH_3$ | 2-pyrimidyl | 2-(methylsulfonyl)phenyl |
| 835 | $CH_2OCH_3$ | 2-pyrimidyl | 4-morpholino |
| 836 | $CH_2OCH_3$ | 2-pyrimidyl | 2-(1'-$CF_3$-tetrazol-2-yl)phenyl |
| 837 | $CH_2OCH_3$ | 2-pyrimidyl | 4-morpholinocarbonyl |
| 838 | $CH_2OCH_3$ | 2-pyrimidyl | 2-methyl-1-imidazolyl |
| 839 | $CH_2OCH_3$ | 2-pyrimidyl | 5-methyl-1-imidazolyl |
| 840 | $CH_2OCH_3$ | 2-pyrimidyl | 2-methylsulfonyl-1-imidazolyl |
| 841 | $CH_2OCH_3$ | 5-pyrimidyl | 2-(aminosulfonyl)phenyl |
| 842 | $CH_2OCH_3$ | 5-pyrimidyl | 2-(methylaminosulfonyl)phenyl |
| 843 | $CH_2OCH_3$ | 5-pyrimidyl | 1-pyrrolidinocarbonyl |
| 844 | $CH_2OCH_3$ | 5-pyrimidyl | 2-(methylsulfonyl)phenyl |
| 845 | $CH_2OCH_3$ | 5-pyrimidyl | 4-morpholino |
| 846 | $CH_2OCH_3$ | 5-pyrimidyl | 2-(1'-$CF_3$-tetrazol-2-yl)phenyl |
| 847 | $CH_2OCH_3$ | 5-pyrimidyl | 4-morpholinocarbonyl |
| 848 | $CH_2OCH_3$ | 5-pyrimidyl | 2-methyl-1-imidazolyl |
| 849 | $CH_2OCH_3$ | 5-pyrimidyl | 5-methyl-1-imidazolyl |
| 850 | $CH_2OCH_3$ | 5-pyrimidyl | 2-methylsulfonyl-1-imidazolyl |
| 851 | $CH_2OCH_3$ | 2-Cl-phenyl | 2-(aminosulfonyl)phenyl |
| 852 | $CH_2OCH_3$ | 2-Cl-phenyl | 2-(methylaminosulfonyl)phenyl |
| 853 | $CH_2OCH_3$ | 2-Cl-phenyl | 1-pyrrolidinocarbonyl |
| 854 | $CH_2OCH_3$ | 2-Cl-phenyl | 2-(methylsulfonyl)phenyl |
| 855 | $CH_2OCH_3$ | 2-Cl-phenyl | 4-morpholino |
| 856 | $CH_2OCH_3$ | 2-Cl-phenyl | 2-(1'-$CF_3$-tetrazol-2-yl)phenyl |
| 857 | $CH_2OCH_3$ | 2-Cl-phenyl | 4-morpholinocarbonyl |
| 858 | $CH_2OCH_3$ | 2-Cl-phenyl | 2-methyl-1-imidazolyl |
| 859 | $CH_2OCH_3$ | 2-Cl-phenyl | 5-methyl-1-imidazolyl |
| 860 | $CH_2OCH_3$ | 2-Cl-phenyl | 2-methylsulfonyl-1-imidazolyl |
| 861 | $CH_2OCH_3$ | 2-F-phenyl | 2-(aminosulfonyl)phenyl |
| 862 | $CH_2OCH_3$ | 2-F-phenyl | 2-(methylaminosulfonyl)phenyl |
| 863 | $CH_2OCH_3$ | 2-F-phenyl | 1-pyrrolidinocarbonyl |
| 864 | $CH_2OCH_3$ | 2-F-phenyl | 2-(methylsulfonyl)phenyl |
| 865 | $CH_2OCH_3$ | 2-F-phenyl | 4-morpholino |
| 866 | $CH_2OCH_3$ | 2-F-phenyl | 2-(1'-$CF_3$-tetrazol-2-yl)phenyl |
| 867 | $CH_2OCH_3$ | 2-F-phenyl | 4-morpholinocarbonyl |
| 868 | $CH_2OCH_3$ | 2-F-phenyl | 2-methyl-1-imidazolyl |
| 869 | $CH_2OCH_3$ | 2-F-phenyl | 5-methyl-1-imidazolyl |
| 870 | $CH_2OCH_3$ | 2-F-phenyl | 2-methylsulfonyl-1-imidazolyl |
| 871 | $CH_2OCH_3$ | 2,6-diF-phenyl | 2-(aminosulfonyl)phenyl |
| 872 | $CH_2OCH_3$ | 2,6-diF-phenyl | 2-(methylaminosulfonyl)phenyl |
| 873 | $CH_2OCH_3$ | 2,6-diF-phenyl | 1-pyrrolidinocarbonyl |
| 874 | $CH_2OCH_3$ | 2,6-diF-phenyl | 2-(methylsulfonyl)phenyl |
| 875 | $CH_2OCH_3$ | 2,6-diF-phenyl | 4-morpholino |
| 876 | $CH_2OCH_3$ | 2,6-diF-phenyl | 2-(1'-$CF_3$-tetrazol-2-yl)phenyl |
| 877 | $CH_2OCH_3$ | 2,6-diF-phenyl | 4-morpholinocarbonyl |
| 878 | $CH_2OCH_3$ | 2,6-diF-phenyl | 2-methyl-1-imidazolyl |
| 879 | $CH_2OCH_3$ | 2,6-diF-phenyl | 5-methyl-1-imidazolyl |
| 880 | $CH_2OCH_3$ | 2,6-diF-phenyl | 2-methylsulfonyl-1-imidazolyl |
| 881 | $CONH_2$ | phenyl | 2-(aminosulfonyl)phenyl |
| 882 | $CONH_2$ | phenyl | 2-(methylaminosulfonyl)phenyl |
| 883 | $CONH_2$ | phenyl | 1-pyrrolidinocarbonyl |
| 884 | $CONH_2$ | phenyl | 2-(methylsulfonyl)phenyl |
| 885 | $CONH_2$ | phenyl | 4-morpholino |
| 886 | $CONH_2$ | phenyl | 2-(1'-$CF_3$-tetrazol-2-yl)phenyl |
| 887 | $CONH_2$ | phenyl | 4-morpholinocarbonyl |
| 888 | $CONH_2$ | phenyl | 2-methyl-1-imidazolyl |
| 889 | $CONH_2$ | phenyl | 5-methyl-1-imidazolyl |
| 890 | $CONH_2$ | phenyl | 2-methylsulfonyl-1-imidazolyl |
| 891 | $CONH_2$ | 2-pyridyl | 2-(aminosulfonyl)phenyl |
| 892 | $CONH_2$ | 2-pyridyl | 2-(methylaminosulfonyl)phenyl |

TABLE 7-continued

| | | | |
|---|---|---|---|
| 893 | CONH$_2$ | 2-pyridyl | 1-pyrrolidinocarbonyl |
| 894 | CONH$_2$ | 2-pyridyl | 2-(methylsulfonyl)phenyl |
| 895 | CONH$_2$ | 2-pyridyl | 4-morpholino |
| 896 | CONH$_2$ | 2-pyridyl | 2-(1'-CF$_3$-tetrazol-2-yl)phenyl |
| 897 | CONH$_2$ | 2-pyridyl | 4-morpholinocarbonyl |
| 898 | CONH$_2$ | 2-pyridyl | 2-methyl-1-imidazolyl |
| 899 | CONH$_2$ | 2-pyridyl | 5-methyl-1-imidazolyl |
| 900 | CONH$_2$ | 2-pyridyl | 2-methylsulfonyl-1-imidazolyl |
| 901 | CONH$_2$ | 3-pyridyl | 2-(aminosulfonyl)phenyl |
| 902 | CONH$_2$ | 3-pyridyl | 2-(methylaminosulfonyl)phenyl |
| 903 | CONH$_2$ | 3-pyridyl | 1-pyrrolidinocarbonyl |
| 904 | CONH$_2$ | 3-pyridyl | 2-(methylsulfonyl)phenyl |
| 905 | CONH$_2$ | 3-pyridyl | 4-morpholino |
| 906 | CONH$_2$ | 3-pyridyl | 2-(1'-CF$_3$-tetrazol-2-yl)phenyl |
| 907 | CONH$_2$ | 3-pyridyl | 4-morpholinocarbonyl |
| 908 | CONH$_2$ | 3-pyridyl | 2-methyl-1-imidazolyl |
| 909 | CONH$_2$ | 3-pyridyl | 5-methyl-1-imidazolyl |
| 910 | CONH$_2$ | 3-pyridyl | 2-methylsulfonyl-1-imidazolyl |
| 911 | CONH$_2$ | 2-pyrimidyl | 2-(aminosulfonyl)phenyl |
| 912 | CONH$_2$ | 2-pyrimidyl | 2-(methylaminosulfonyl)phenyl |
| 913 | CONH$_2$ | 2-pyrimidyl | 1-pyrrolidinocarbonyl |
| 914 | CONH$_2$ | 2-pyrimidyl | 2-(methylsulfonyl)phenyl |
| 915 | CONH$_2$ | 2-pyrimidyl | 4-morpholino |
| 916 | CONH$_2$ | 2-pyrimidyl | 2-(1'-CF$_3$-tetrazol-2-yl)phenyl |
| 917 | CONH$_2$ | 2-pyrimidyl | 4-morpholinocarbonyl |
| 918 | CONH$_2$ | 2-pyrimidyl | 2-methyl-1-imidazolyl |
| 919 | CONH$_2$ | 2-pyrimidyl | 5-methyl-1-imidazolyl |
| 920 | CONH$_2$ | 2-pyrimidyl | 2-methylsulfonyl-1-imidazolyl |
| 921 | CONH$_2$ | 5-pyrimidyl | 2-(aminosulfonyl)phenyl |
| 922 | CONH$_2$ | 5-pyrimidyl | 2-(methylaminosulfonyl)phenyl |
| 923 | CONH$_2$ | 5-pyrimidyl | 1-pyrrolidinocarbonyl |
| 924 | CONH$_2$ | 5-pyrimidyl | 2-(methylsulfonyl)phenyl |
| 925 | CONH$_2$ | 5-pyrimidyl | 4-morpholino |
| 926 | CONH$_2$ | 5-pyrimidyl | 2-(1'-CF$_3$-tetrazol-2-yl)phenyl |
| 927 | CONH$_2$ | 5-pyrimidyl | 4-morpholinocarbonyl |
| 928 | CONH$_2$ | 5-pyrimidyl | 2-methyl-1-imidazolyl |
| 929 | CONH$_2$ | 5-pyrimidyl | 5-methyl-1-imidazolyl |
| 930 | CONH$_2$ | 5-pyrimidyl | 2-methylsulfonyl-1-imidazolyl |
| 931 | CONH$_2$ | 2-Cl-phenyl | 2-(aminosulfonyl)phenyl |
| 932 | CONH$_2$ | 2-Cl-phenyl | 2-(methylaminosulfonyl)phenyl |
| 933 | CONH$_2$ | 2-Cl-phenyl | 1-pyrrolidinocarbonyl |
| 934 | CONH$_2$ | 2-Cl-phenyl | 2-(methylsulfonyl)phenyl |
| 935 | CONH$_2$ | 2-Cl-phenyl | 4-morpholino |
| 936 | CONH$_2$ | 2-Cl-phenyl | 2-(1'-CF$_3$-tetrazol-2-yl)phenyl |
| 937 | CONH$_2$ | 2-Cl-phenyl | 4-morpholinocarbonyl |
| 938 | CONH$_2$ | 2-Cl-phenyl | 2-methyl-1-imidazolyl |
| 939 | CONH$_2$ | 2-Cl-phenyl | 5-methyl-1-imidazolyl |
| 940 | CONH$_2$ | 2-Cl-phenyl | 2-methylsulfonyl-1-imidazolyl |
| 941 | CONH$_2$ | 2-F-phenyl | 2-(aminosulfonyl)phenyl |
| 942 | CONH$_2$ | 2-F-phenyl | 2-(methylaminosulfonyl)phenyl |
| 943 | CONH$_2$ | 2-F-phenyl | 1-pyrrolidinocarbonyl |
| 944 | CONH$_2$ | 2-F-phenyl | 2-(methylsulfonyl)phenyl |
| 945 | CONH$_2$ | 2-F-phenyl | 4-morpholino |
| 946 | CONH$_2$ | 2-F-phenyl | 2-(1'-CF$_3$-tetrazol-2-yl)phenyl |
| 947 | CONH$_2$ | 2-F-phenyl | 4-morpholinocarbonyl |
| 948 | CONH$_2$ | 2-F-phenyl | 2-methyl-1-imidazolyl |
| 949 | CONH$_2$ | 2-F-phenyl | 5-methyl-1-imidazolyl |
| 950 | CONH$_2$ | 2-F-phenyl | 2-methylsulfonyl-1-imidazolyl |
| 951 | CONH$_2$ | 2,6-diF-phenyl | 2-(aminosulfonyl)phenyl |
| 952 | CONH$_2$ | 2,6-diF-phenyl | 2-(methylaminosulfonyl)phenyl |
| 953 | CONH$_2$ | 2,6-diF-phenyl | 1-pyrrolidinocarbonyl |
| 954 | CONH$_2$ | 2,6-diF-phenyl | 2-(methylsulfonyl)phenyl |
| 955 | CONH$_2$ | 2,6-diF-phenyl | 4-morpholino |
| 956 | CONH$_2$ | 2,6-diF-phenyl | 2-(1'-CF$_3$-tetrazol-2-yl)phenyl |
| 957 | CONH$_2$ | 2,6-diF-phenyl | 4-morpholinocarbonyl |
| 958 | CONH$_2$ | 2,6-diF-phenyl | 2-methyl-1-imidazolyl |
| 959 | CONH$_2$ | 2,6-diF-phenyl | 5-methyl-1-imidazolyl |
| 960 | CONH$_2$ | 2,6-diF-phenyl | 2-methylsulfonyl-1-imidazolyl |

Utility

The compounds of this invention are useful as anticoagulants for the treatment or prevention of thromboembolic disorders in mammals. The term "thromboembolic disorders" as used herein includes arterial or venous cardiovascular or cerebrovascular thromboembolic disorders, including, for example, unstable angina, first or recurrent myocardial infarction, ischemic sudden death, transient ischemic attack, stroke, atherosclerosis, venous thrombosis, deep vein thrombosis, thrombophlebitis, arterial embolism, coronary and cerebral arterial thrombosis, cerebral embolism, kidney embolisms, and pulmonary embolisms. The anticoagulant effect of compounds of the present invention is believed to be due to inhibition of factor Xa or thrombin.

The effectiveness of compounds of the present invention as inhibitors of factor Xa was determined using purified human factor Xa and synthetic substrate. The rate of factor Xa hydrolysis of chromogenic substrate S2222 (Kabi Pharmacia, Franklin, Ohio) was measured both in the absence and presence of compounds of the present invention. Hydrolysis of the substrate resulted in the release of pNA, which was monitored spectrophotometrically by measuring the increase in absorbance at 405 nM. A decrease in the rate of absorbance change at 405 nm in the presence of inhibitor is indicative of enzyme inhibition. The results of this assay are expressed as inhibitory constant, $K_i$.

Factor Xa determinations were made in 0.10 M sodium phosphate buffer, pH 7.5, containing 0.20 M NaCl, and 0.5% PEG 8000. The Michaelis constant, $K_m$, for substrate hydrolysis was determined at 25° C. using the method of Lineweaver and Burk. Values of $K_i$ were determined by allowing 0.2–0.5 nM human factor Xa (Enzyme Research Laboratories, South Bend, Ind.) to react with the substrate (0.20 mM–1 mM) in the presence of inhibitor. Reactions were allowed to go for 30 minutes and the velocities (rate of absorbance change vs time) were measured in the time frame of 25–30 minutes. The following relationship was used to calculate $K_i$ values:

$$(v_o-v_s)/v_s = I/(K_i(1+S/K_m))$$

where:

$v_o$ is the velocity of the control in the absence of inhibitor;

$v_s$ is the velocity in the presence of inhibitor;

I is the concentration of inhibitor;

$K_i$ is the dissociation constant of the enzyme:inhibitor complex;

S is the concentration of substrate;

$K_m$ is the Michaelis constant.

Using the methodology described above, a number of compounds of the present invention were found to exhibit a $K_i$ of $\leq 10 \mu M$, thereby confirming the utility of the compounds of the present invention as effective Xa inhibitors.

The antithrombotic effect of compounds of the present invention can be demonstrated in a rabbit arterio-venous (AV) shunt thrombosis model. In this model, rabbits weighing 2–3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing which contains a piece of silk thread. Blood will flow from the femoral artery via the AV-shunt into the femoral vein. The exposure of flowing blood to a silk thread will induce the formation of a significant thrombus. After forty minutes, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The ID50 values (dose which produces 50% inhibition of thrombus formation) are estimated by linear regression.

The compounds of formula (I) may also be useful as inhibitors of serine proteases, notably human thrombin, plasma kallikrein and plasmin. Because of their inhibitory action, these compounds are indicated for use in the prevention or treatment of physiological reactions, blood coagulation and inflammation, catalyzed by the aforesaid class of enzymes. Specifically, the compounds have utility as drugs for the treatment of diseases arising from elevated thrombin activity such as myocardial infarction, and as reagents used as anticoagulants in the processing of blood to plasma for diagnostic and other commercial purposes.

Some compounds of the present invention were shown to be direct acting inhibitors of the serine protease thrombin by their ability to inhibit the cleavage of small molecule substrates by thrombin in a purified system. In vitro inhibition constants were determined by the method described by Kettner et al. in J. Biol. Chem. 265, 18289–18297 (1990), herein incorporated by reference. In these assays, thrombin-mediated hydrolysis of the chromogenic substrate S2238 (Helena Laboratories, Beaumont, Tex.) was monitored spectrophotometrically. Addition of an inhibitor to the assay mixture results in decreased absorbance and is indicative of thrombin inhibition. Human thrombin (Enzyme Research Laboratories, Inc., South Bend, Ind.) at a concentration of 0.2 nM in 0.10 M sodium phosphate buffer, pH 7.5, 0.20 M NaCl, and 0.5% PEG 6000, was incubated with various substrate concentrations ranging from 0.20 to 0.02 mM. After 25 to 30 minutes of incubation, thrombin activity was assayed by monitoring the rate of increase in absorbance at 405 nm which arises owing to substrate hydrolysis. Inhibition constants were derived from reciprocal plots of the reaction velocity as a function of substrate concentration using the standard method of Lineweaver and Burk. Using the methodology described above, some compounds of this invention were evaluated and found to exhibit a $K_i$ of less than $10 \mu m$, thereby confirming the utility of the compounds of the present invention as effective Xa inhibitors.

The compounds of the present invention can be administered alone or in combination with one or more additional therapeutic agents. These include other anti-coagulant or coagulation inhibitory agents, anti-platelet or platelet inhibitory agents, thrombin inhibitors, or thrombolytic or fibrinolytic agents.

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the thromboembolic disease condition or the progression of the disease.

By "administered in combination" or "combination therapy" it is meant that the compound of Formula I and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect. Other anticoagulant agents (or coagulation inhibitory agents) that may be used in combination with the compounds of this invention include warfarin and heparin, as well as other factor Xa inhibitors such as those described in the publications identified above under Background of the Invention.

The term anti-platelet agents (or platelet inhibitory agents), as used herein, denotes agents that inhibit platelet function such as by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicyclic acid or ASA), and piroxicam are preferred. Other suitable anti-platelet agents include ticlopidine, including pharmaceutically acceptable salts or prodrugs thereof. Ticlopidine is also a preferred compound since it is known to be gentle on the gastro-intestinal tract in use. Still other suitable platelet inhibitory agents include IIb/IIIa antagonists, thromboxane-A2-receptor antagonists and thromboxane-A2-synthetase inhibitors, as well as pharmaceutically acceptable salts or prodrugs thereof.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin and argatroban, including pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. Boropeptide thrombin inhibitors include compounds described in Kettner et al., U.S. Pat. No. 5,187,157 and European Patent Application Publication Number 293 881 A2, the disclosures of which are hereby incorporated herein by reference. Other suitable boroarginine derivatives and boropeptide thrombin inhibitors include those disclosed in PCT Application Publication Number 92/07869 and European Patent Application Publication Number 471,651 A2, the disclosures of which are hereby incorporated herein by reference.

The term thrombolytics (or fibrinolytic) agents (or thrombolytics or fibrinolytics), as used herein, denotes agents that lyse blood clots (thrombi). Such agents include tissue plasminogen activator, anistreplase, urokinase or streptokinase, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Administration of the compounds of Formula I of the invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

The compounds of the present invention are also useful as standard or reference compounds, for example as a quality standard or control, in tests or assays involving the inhibition of factor Xa. Such compounds may be provided in a commercial kit, for example, for use in pharmaceutical research involving factor Xa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving factor Xa. For example, the presence of factor Xa in an unknown sample could be determined by addition of chromogenic substrate S2222 to a series of solutions containing test sample and optionally one of the compounds of the present invention. If production of pNA is observed in the solutions containing test sample, but no compound of the present invention, then one would conclude factor Xa was present.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient,and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of Formula I are administered in combination with an anti-platelet agent, by way of general guidance, typically a daily dosage may be about 0.01 to 25 milligrams of the compound of Formula I and about 50 to 150 milligrams of the anti-platelet agent, preferably about 0.1 to 1 milligrams of the compound of Formula I and about 1 to 3 milligrams of antiplatelet agents, per kilogram of patient body weight.

Where the compounds of Formula I are adminstered in combination with thrombolytic agent, typically a daily dosage may be about 0.1 to 1 milligrams of the compound of Formula I, per kilogram of patient body weight and, in the case of the thrombolytic agents, the usual dosage of the thrombolyic agent when administered alone may be reduced by about 70–80% when administered with a compound of Formula I.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Obviously, numerous modifications and variations of the present invention are possible in light of the above teachings. It is therefore to be understood that within the scope of the appended claims, the invention may be practiced otherwise that as specifically described herein.

What is claimed as new and desired to be secured by Letter Patent of United States is:

1. A compound of formula Ic:

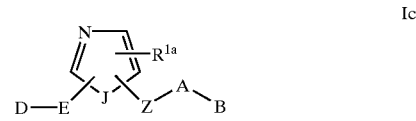

or a stereoisomer or pharmaceutically acceptable salt thereof, wherein;

J is S;

D is selected from CN, C(=NR$^8$)NR$^7$R$^9$, NHC(=NR$^8$)NR$^7$R$^9$, NR$^8$CH(=NR$^7$), C(O)NR$^7$R$^8$, and (CR$^8$R$^9$)$_t$NR$^7$R$^8$;

E is selected from phenyl, pyridyl, pyrimidyl, pyrazinyl, pyridazinyl, and piperidinyl substituted with 1 R;

alternatively, D—E together represent pyridyl substituted with 1 R;

R is selected from H, halogen, (CH$_2$)$_t$OR$^3$, C$_{1-4}$ alkyl, OCF$_3$, and CF$_3$;

Z is (CH$_2$)$_r$C(O)NR$^3$(CH$_2$)$_r$;

R$^{1a}$ is independently absent or selected from —(CH$_2$)$_r$—R$^{1'}$, NHCH$_2$R$^{1''}$, OCH$_2$R$^{1''}$, SCH$_2$R$^{1''}$, NH(CH$_2$)$_2$(CH$_2$)$_t$R$^{1'}$, O(CH$_2$)$_2$(CH$_2$)$_t$R$^{1'}$, and S(CH$_2$)$_2$(CH$_2$)$_t$R$^{1''}$, or combined to form a 5–8 membered saturated, partially saturated or unsaturated ring substituted with 0–2 R$^4$ and which contains from 0–2 heteroatoms selected from the group consisting of N, O, and S;

R$^{1'}$ is selected from H, C$_{1-3}$ alkyl, halo, (CF$_2$)$_r$CF$_3$, OR$^2$, NR$^2$R$^{2a}$, C(O)R$^{2c}$, OC(O)R$^2$, (CF$_2$)$_r$C$_2$R$^{2c}$, S(O)R$^{2b}$, NR$^2$(CH$_2$)$_r$OR$^2$, NR$^2$C(O)R$^{2b}$, NR$^2$C(O)NHR$^{2b}$, NR$^2$C(O)$_2$R$^{2a}$, OC(O)NR$^{2b}$, C(O)NR$^2$R$^{2a}$, SO$_2$NR$^2$R$^{2a}$, NR$^2$SO$_2$R$^{2b}$, C$_{3-6}$ carbocycle substituted with 0–2 R$^4$, and 5–10 membered heterocycle containing from 1–4 heteroatoms selected from the group consisting of N, O, and S substituted with 0–2 R$^4$, provided that when R$^{1'}$ is substituted by R$^4$, R$^4$ is other than NH(CH$_2$)$_2$(CH$_2$)$_t$R$^{1'}$, O(CH$_2$)$_2$(CH$_2$)$_t$R$^{1'}$, and S(CH$_2$)$_2$(CH$_2$)$_t$R$^{1'}$;

R$^{1''}$ is selected from H, C(O)R$^{2b}$, C(O)NR$^2$R$^{2a}$, S(O)R$^{2b}$, S(O)$_2$R$^{2b}$, and SO$_2$NR$^2$R$^{2a}$;

R$^2$, at each occurrence, is selected from H, CF$_3$, C$_{1-6}$ alkyl, benzyl, C$_{3-6}$ carbocycle substituted with 0–2 R$^{4b}$, and 5–6 membered heterocycle containing from 1–4 heteroatoms selected from the group consisting of N, O, and S substituted with 0–2 R$^{4b}$;

R$^{2a}$, at each occurrence, is selected from H, CF$_3$, C$_{1-6}$ alkyl, benzyl, C$_{3-6}$ carbocycle substituted with 0–2 R$^{4b}$, and 5–6 membered heterocycle containing from 1–4 heteroatoms selected from the group consisting of N, O, and S substituted with 0–2 R$^{4b}$;

R$^{2b}$, at each occurrence, is selected from CF$_3$, C$_{1-4}$ alkoxy, C$_{1-6}$ alkyl, benzyl, C$_{3-6}$ carbocycle substituted with 0–2 R$^{4b}$, and 5–6 membered heterocycle containing from 1–4 heteroatoms selected from the group consisting of N, O, and S substituted with 0–2 R$^{4b}$;

R$^{2c}$, at each occurrence, is selected from CF$_3$, OH, C$_{1-4}$ alkoxy, C$_{1-6}$ alkyl, benzyl, C$_{3-6}$ carbocycle substituted with 0–2 $R^{4b}$, and 5–6 membered heterocycle containing from 1–4 heteroatoms selected from the group consisting of N, O, and S substituted with 0–2 $R^{4b}$;

alternatively, $R^2$ and $R^{2a}$ combine to form a 5 or 6 membered saturated, partially saturated or unsaturated ring substituted with 0–2 $R^{4b}$ which contains from 0–1 additional heteroatoms selected from the group consisting of N, O, and S;

$R^3$, at each occurrence, is selected from H, $C_{1-4}$ alkyl, and phenyl $R^{3a}$, at each occurrence, is selected from H, $C_{1-4}$ alkyl, and phenyl;

A is a $C_{3-10}$ carbocycle substituted with 0–2 $R^4$;

B is $C_{3-10}$ carbocycle substituted with 0–2 $R^{4a}$;

$R^4$, at each occurrence, is selected from =O, $(CH_2)_rOR^2$, halo, $C_{1-4}$ alkyl, —CN, $NO_2$, $(CH_2)_rNR^2R^{2a}$, $(CH_2)_rC(O)R^{2b}$, $NR^2C(O)R^{2b}$, $C(O)NR^2R^{2a}$, $NR^2C(O)NR^2R^{2a}$, $C(=NR^2)NR^2R^{2a}$, $NHC(=NR^2)NR^2R^{2a}$, $SO_2NR^2R^{2a}$, $NR^2SO_2NR^2R^{2a}$, $NR^2SO_2$—$C_{1-4}$ alkyl, $NR^2SO_2R^5$, $S(O)_pR^5$, $(CF_2)_rCF_3$, $NHCH_2R^{1'}$, $OCH_2R^{1'}$, $SCH_2R^{1'}$, $NH(CH_2)_2(CH_2)_rR^{1'}$, $O(CH_2)_2(CH_2)_rR^{1'}$, and $S(CH_2)_2(CH_2)_rR^{1'}$;

alternatively, one $R^4$ is a 5–6 membered aromatic heterocycle containing from 1–4 heteroatoms selected from the group consisting of N, O, and S;

$R^{4a}$, at each occurrence, is selected from =O, $(CH_2)_rOR^2$, halo, $C_{1-4}$ alkyl, —CN, $NO_2$, $(CH_2)_rNR^2R^{2a}$, $(CH_2)_rC(O)R^{2b}$, $NR^2C(O)R^{2b}$, $C(O)NR^2R^{2a}$, $NR^2C(O)NR^2R^{2a}$, $C(=NR^2)NR^2R^{2a}$, $NHC(=NR^2)NR^2R^{2a}$, $SO_2NR^2R^{2a}$, $NR^2SO_2NR^2R^{2a}$, $NR^2SO_2$—$C_{1-4}$ alkyl, $NR^2SO_2R^5$, $S(O)_pR^5$, and $(CF_2)_rCF_3$;

alternatively, one $R^{4a}$ is a 5–6 membered aromatic heterocycle containing from 1–4 heteroatoms selected from the group consisting of N, O, and S substituted with 0–1 $R^5$;

$R^{4b}$, at each occurrence, is selected from =O, $(CH_2)_rOR^3$, halo, $C_{1-4}$ alkyl, —CN, $NO_2$, $(CH_2)_rNR^3R^{3a}$, $(CH_2)_rC(O)R^3$, $NR^3C(O)R^{3a}$, $C(O)NR^3R^{3a}$, $NR^3C(O)NR^3R^{3a}$, $C(=NR^3)NR^3R^{3a}$, $NH^3C(=NR^3)NR^3R^{3a}$, $SO_2NR^3R^{3a}$, $NR^3SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, and $(CF_2)_rCF_3$;

$R^5$, at each occurrence, is selected from $CF_3$, $C_{1-6}$ alkyl, phenyl substituted with 0–2 $R^6$, and benzyl substituted with 0–2 $R^6$;

$R^6$, at each occurrence, is selected from H, OH, $(CH_2)_rOR^2$, halo, $C_{1-4}$ alkyl, CN, $NO_2$, $(CH_2)_rNR^2R^{2a}$, $(CH_2)_rC(O)R^{2b}$, $NR^2C(O)R^{2b}$, $NR^2C(O)NR^2R^{2a}$, $C(=NH)NH_2$, $NHC(=NH)NH_2$, $SO_2NR^2R^{2a}$, $NR^2SO_2NR^2R^{2a}$, and $NR^2SO_2C_{1-4}$ alkyl;

$R^7$, at each occurrence, is selected from H, OH, $C_{1-6}$ alkyl, $C_{1-6}$ alkylcarbonyl, $C_{1-6}$ alkoxy, $C_{1-4}$ alkoxycarbonyl, $(CH_2)_n$-phenyl, $C_{6-10}$ aryloxy, $C_{6-10}$ aryloxycarbonyl, $C_{6-10}$ arylmethylcarbonyl, $C_{1-4}$ alkylcarbonyloxy $C_{1-4}$ alkoxycarbonyl, $C_{6-10}$ arylcarbonyloxy $C_{1-4}$ alkoxycarbonyl, $C_{1-6}$ alkylaminocarbonyl, phenylaminocarbonyl, and phenyl $C_{1-4}$ alkoxycarbonyl;

$R^8$, at each occurrence, is selected from H, $C_{1-6}$ alkyl and $(CH_2)_n$-phenyl;

alternatively, $R^7$ and $R^8$ combine to form a 5 or 6 membered saturated, ring which contains from 0–1 additional heteroatoms selected from the group consisting of N, O, and S;

$R^9$, at each occurrence, is selected from H, $C_{1-6}$ alkyl and $(CH_2)_n$-phenyl;

n, at each occurrence, is selected from 0, 1, 2, and 3;

p, at each occurrence, is selected from 0, 1, and 2;

r, at each occurrence, is selected from 0, 1, 2, and 3;

s, at each occurrence, is selected from 0, 1, and 2; and, t, at each occurrence, is selected from 0 and 1.

2. A compound according to claim 1, wherein, groups D—E— and —Z—A—B are attached to adjacent atoms on the ring;

Z is C(O)NH;

A is phenyl substituted with 0–2 $R^4$; and,

B is selected from one of the following rings which are substituted with 0–2 $R^{4a}$;

cyclopropyl, cyclopentyl, cyclohexyl, and phenyl.

3. A compound according to claim 2, wherein the compound is of formulae $Ic_1$ or $Ic_2$:

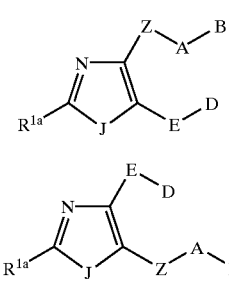

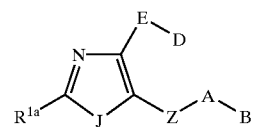

wherein;

J is S; and,

Z is selected from $C(O)CH_2$, NHC(O), and C(O)NH, provided that Z does not form a N—N or $NCH_2N$ bond with ring M or group A.

4. A compound according to claim 3, wherein the compound is of formulae $Ic_1$ or $Ic_2$:

E is phenyl substituted with R or 2-pyridyl substituted with R;

D is selected from $NH_2$, $C(O)NH_2$, $C(=NH)NH_2$, $CH_2NH_2$, $CH_2NHCH_3$, $CH(CH_3)NH_2$, and $C(CH_3)_2NH_2$, provided that D is substituted meta or para to ring M on E; and, R is selected from H, $OCH_3$, Cl, and F.

5. A compound according to claim 4, wherein the compound is of formulae $Ic_1$ or $Ic_2$:

D—E is selected from 3-aminophenyl, 3-amidinophenyl, 3-aminomethylphenyl, 3-aminocarbonylphenyl, 3-(methylaminomethyl)phenyl, 3-(1-aminoethyl) phenyl, 3-(2-amino-2-propyl)phenyl, 4-chloro-3-aminophenyl, 4-chloro-3-amidinophenyl, 4-chloro-3-aminomethylphenyl, 4-chloro-3-(methylaminomethyl) phenyl, 4-fluoro-3-aminophenyl, 4-fluoro-3-amidinophenyl, 4-fluoro-3-aminomethylphenyl, 4-fluoro-3-(methylaminomethyl)phenyl, 6-aminopyrid-2-yl, 6-amidinopyrid-2-yl, 6-aminomethylpyrid-2-yl, 6-aminocarbonylpyrid-2-yl, 6-(methylaminomethyl)pyrid-2-yl, 6-(1-aminoethyl) pyrid-2-yl, and 6-(2-amino-2-propyl)pyrid-2-yl.

6. A compound according to claim 3, wherein the compound is of formulae $Ic_1$ or $Ic_2$:

B is phenyl substituted with 0–1 $R^{4a}$;

$R^4$, at each occurrence, is selected from OH, $(CH_2)_rOR^2$, halo, $C_{1-4}$ alkyl, $(CH_2)_rNR^2R^{2a}$, and $(CF_2)_rCF_3$;

$R^{4a}$ is selected from $C_{1-4}$ alkyl, $CF_3$, $S(O)_pR^5$, $SO_2NR^2R^{2a}$, and 1-$CF_3$-tetrazol-2-yl; and, $R^5$, at each occurrence, is selected from $CF_3$, $C_{1-6}$ alkyl, phenyl, and benzyl.

7. A compound according to claim 6, wherein the compound is of formulae $Ic_1$ or $Ic_2$:

A is selected from the group: phenyl, 2-Cl-phenyl, 3-Cl-phenyl, 2-F-phenyl, 3-F-phenyl, 2-methylphenyl, 2-aminophenyl, and 2-methoxyphenyl; and, B is selected from the group: 2-$CF_3$-phenyl, 2-(aminosulfonyl)phenyl, 2-(methylaminosulfonyl)phenyl, 2-(dimethylaminosulfonyl)phenyl, 2-(methylsulfonyl)phenyl, and 2-(1'-$CF_3$-tetrazol-2-yl) phenyl.

8. A compound according to claim 3, wherein the compound is of formulae $Ic_1$ or $Ic_2$:

E is phenyl substituted with R or 2-pyridyl substituted with R;

D is selected from $NH_2$, $C(O)NH_2$, $C(=NH)NH_2$, $CH_2NH_2$, $CH_2NHCH_3$, $CH(CH_3)NH_2$, and $C(CH_3)_2NH_2$;

R is selected from H, $OCH_3$, Cl, and F;

$R^4$, at each occurrence, is selected from OH, $(CH_2)_rOR^2$, halo, $C_{1-4}$ alkyl, $(CH_2)_rNR^2R^{2a}$, and $(CF_2)_rCF_3$;

$R^{4a}$ is selected from $C_{1-4}$ alkyl, $CF_3$, $S(O)_pR^5$, $SO_2NR^2R^{2a}$, and 1-$CF_3$-tetrazol-2-yl; and, $R^5$, at each occurrence, is selected from $CF_3$, $C_{1-6}$ alkyl, phenyl, and benzyl.

9. A compound according to claim 8, wherein the compound is of formulae $Ic_1$ or $Ic_2$:

D—E is selected from 3-aminophenyl, 3-amidinophenyl, 3-aminomethylphenyl, 3-aminocarbonylphenyl, 3-(methylaminomethyl)phenyl, 3-(1-aminoethyl)phenyl, 3-(2-amino-2-propyl)phenyl, 4-chloro-3-aminophenyl, 4-chloro-3-amidinophenyl, 4-chloro-3-aminomethylphenyl, 4-chloro-3-(methylaminomethyl)phenyl, 4-fluoro-3-aminophenyl, 4-fluoro-3-amidinophenyl, 4-fluoro-3-aminomethylphenyl, 4-fluoro-3-(methylaminomethyl)phenyl, 6-aminopyrid-2-yl, 6-amidinopyrid-2-yl, 6-aminomethylpyrid-2-yl, 6-aminocarbonylpyrid-2-yl, 6-(methylaminomethyl)pyrid-2-yl, 6-(1-aminoethyl)pyrid-2-yl, 6-(2-amino-2-propyl)pyrid-2-yl;

A is selected from the group: phenyl, 2-Cl-phenyl, 3-Cl-phenyl, 2-F-phenyl, 3-F-phenyl, 2-methylphenyl, 2-aminophenyl, and 2-methoxyphenyl; and, B is selected from the group: 2-$CF_3$-phenyl, 2-(aminosulfonyl)phenyl, 2-(methylaminosulfonyl)phenyl, 2-(dimethylaminosulfonyl)phenyl, 1-pyrrolidinocarbonyl, 2-(methylsulfonyl)phenyl, 4-morpholino, and 2-(1'-$CF_3$-tetrazol-2-yl)phenyl.

10. A compound according to claim 9, wherein the compound is of formula $Ic_1$.

11. A compound according to claim 9, wherein the compound is of formula $Ic_2$.

12. A compound according to claim 3, wherein the compound is of formulae $Ic_1$ or $Ic_2$:

D is selected from $C(=NR^8)NR^7R^9$, $C(O)NR^7R^8$, $NR^7R^8$, and $CH_2NR^7R^8$;

E is phenyl substituted with R or pyridyl substituted with R;

R is selected from H, Cl, F, $OR^3$, $CH_3$, $CH_2CH_3$, $OCF_3$, and $CF_3$;

$R^{1a}$ is absent or selected from —$(CH_2)_r$—$R^{1'}$, $NHCH_2R^{1''}$, $OCH_2R^{1''}$, $SCH_2R^{1''}$, $NH(CH_2)_2(CH_2)_rR^{1'}$, $O(CH_2)_2(CH_2)_rR^{1'}$, and $S(CH_2)_2(CH_2)_rR^{1'}$, or combined to form a 5–8 membered saturated, partially saturated or unsaturated ring substituted with 0–2 $R^4$ and which contains from 0–2 heteroatoms selected from the group consisting of N, O, and S;

$R^{1'}$, at each occurrence, is selected from H, $C_{1-3}$ alkyl, halo, $(CF_2)_rCF_3$, $OR^2$, $NR^2R^{2a}$, $C(O)R^{2c}$, $(CF_2)_rCO_2R^{2c}$, $S(O)_pR^{2b}$, $NR^2(CH_2)_rOR^2$, $NR^2C(O)R^{2b}$, $NR^2C(O)_2R^{2a}$, $C(O)NR^2R^{2a}$, $SO_2NR^2R^{2a}$, and $NR^2SO_2R^{2b}$;

B is phenyl substituted with 0–2 $R^{4a}$;

$R^4$, at each occurrence, is selected from =O, OH, Cl, F, $C_{1-4}$ alkyl, $(CH_2)_rNR^2R^{2a}$, $(CH_2)_rC(O)R^{2b}$, $NR^2C(O)R^{2b}$, $C(O)NR^2R^{2a}$, $C(=NH)NH_2$, $NHC(=NH)NH_2$, $SO_2NR^2R^{2a}$, $NR^2SO_2$—$C_{1-4}$ alkyl, $NR^2SO^2R^5$, $S(O)_pR^5$, and $(CF_2)_rCF_3$;

$R^{4a}$, at each occurrence, is selected from =O, OH, Cl, F, $C_{1-4}$ alkyl, $(CH_2)_rNR^2R^{2a}$, $(CH_2)_rC(O)R^{2b}$, $NR^2C(O)R^{2b}$, $C(O)NR^2R^{2a}$, $C(=NH)NH_2$, $NHC(=NH)NH_2$, $SO_2NR^2R^{2a}$, $NR^2SO_2$—$C_{1-4}$ alkyl, $NR^2SO_2R^5$, $S(O)_pR^5$, $(CF_2)_rCF_3$, and 1-$CF_3$-tetrazol-2-yl;

$R^5$, at each occurrence, is selected from $CF_3$, $C_{1-6}$ alkyl, phenyl substituted with 0–2 $R^6$, and benzyl substituted with 0–2 $R^6$;

$R^6$, at each occurrence, is selected from H, OH, $OR^2$, Cl, F, $CH_3$, CN, $NO_2$, $(CH_2)_rNR^2R^{2a}$, $(CH_2)_rC(O)R^{2b}$, $NR^2C(O)R^{2b}$, $C(=NH)NH_2$, $NHC(=NH)NH_2$, and $SO_2NR^2R^{2a}$;

$R^7$, at each occurrence, is selected from H, OH, $C_{1-6}$ alkyl, $C_{1-6}$ alkylcarbonyl, $C_{1-6}$ alkoxy, $C_{1-4}$ alkoxycarbonyl, benzyl, $C_{6-10}$ aryloxy, $C_{6-10}$ aryloxycarbonyl, $C_{6-10}$ arylmethylcarbonyl, $C_{1-4}$ alkylcarbonyloxy $C_{1-4}$ alkoxycarbonyl, $C_{6-10}$ arylcarbonyloxy $C_{1-4}$ alkoxycarbonyl, $C_{1-6}$ alkylaminocarbonyl, phenylaminocarbonyl, and phenyl $C_{1-4}$ alkoxycarbonyl;

$R^8$, at each occurrence, is selected from H, $C_{1-6}$ alkyl and benzyl;

alternatively, $R^7$ and $R^8$ combine to form a morpholino group; and, $R^9$, at each occurrence, is selected from H, $C_{1-6}$ alkyl and benzyl.

13. A compound according to claim 12, wherein the compound is of formulae $Ic_1$ or $Ic_2$:

E is phenyl substituted with R or 2-pyridyl substituted with R;

R is selected from H, Cl, F, $OCH_3$, $CH_3$, $OCF_3$, and $CF_3$;

Z is selected from a $C(O)CH_2$ and $C(O)NH$;

$R^{1a}$ is selected from H, $CH_3$, $CH_2CH_3$, Cl, F, $CF_3$, $OCH_3$, $NR^2R^{2a}$, $S(O)_pR^{2b}$, $CH_2S(O)_2R^2b$, $CH_2NR^2S(O)_pR^{2b}$, $C(O)R^{2c}$, $CH_2C(O)R^{2c}$, $C(O)NR^2R^{2a}$, and $SO_2NR^2R^{2a}$;

$R^2$, at each occurrence, is selected from H, $CF_3$, $CH_3$, benzyl, and phenyl;

$R^{2a}$, at each occurrence, is selected from H, $CF_3$, $CH_3$, benzyl, and phenyl;

$R^{2b}$, at each occurrence, is selected from $CF_3$, $OCH_3$, $CH_3$, benzyl, and phenyl;

$R^{2c}$, at each occurrence, is selected from $CF_3$, OH, $OCH_3$, $CH_3$, benzyl, and phenyl;

alternatively, $R^2$ and $R^{2a}$ combine to form a 5 or 6 membered saturated, partially unsaturated, or unsaturated ring which contains from 0–1 additional heteroatoms selected from the group consisting of N, O, and S;

R³, at each occurrence, is selected from H, CH₃, CH₂CH₃, and phenyl;

R³ᵃ, at each occurrence, is selected from H, CH₃, CH₂CH₃, and phenyl;

R⁴, at each occurrence, is selected from OH, Cl, F, CH₃, CH₂CH₃, NR²R²ᵃ, CH₂NR²R²ᵃ, C(O)R²ᵇ, NR²C(O)R²ᵇ, C(O)NR²R²ᵃ, and CF₃;

R⁴ᵃ, at each occurrence, is selected from OH, Cl, F, CH₃, CH₂CH₃, NR²R²ᵃ, CH₂NR²R²ᵃ, C(O)R²ᵇ, C(O)NR²R²ᵃ, SO₂NR²R²ᵃ, S(O)ₚR⁵, CF₃, and 1-CF₃-tetrazol-2-yl;

R⁵, at each occurrence, is selected from CF₃, C₁₋₆ alkyl, phenyl substituted with 0–2 R⁶, and benzyl substituted with 1 R⁶;

R⁶, at each occurrence, is selected from H, OH, OCH₃, Cl, F, CH₃, CN, NO₂, NR²R²ᵃ, CH₂NR²R²ᵃ, and SO₂NR²R²ᵃ;

R⁷, at each occurrence, is selected from H, OH, C₁₋₃ alkyl, C₁₋₃ alkylcarbonyl, C₁₋₃ alkoxy, C₁₋₄ alkoxycarbonyl, benzyl, phenoxy, phenoxycarbonyl, benzylcarbonyl, C₁₋₄ alkylcarbonyloxy C₁₋₄ alkoxycarbonyl, phenylcarbonyloxy C₁₋₄ alkoxycarbonyl, C₁₋₆ alkylaminocarbonyl, phenylaminocarbonyl, and phenyl C₁₋₄ alkoxycarbonyl;

R⁸, at each occurrence, is selected from H, CH₃, and benzyl;

alternatively, R⁷ and R⁸ combine to form a morpholino group; and,

R⁹, at each occurrence, is selected from H, CH₃, and benzyl.

14. A compound according to claim 13 wherein the compound is of formulae Ic₁ or Ic₂:

R¹ᵃ is selected from H, CH₃, CH₂CH₃, Cl, F, CF₃, OCH₃, NR²R²ᵃ, S(O)ₚR²ᵇ, C(O)NR²R²ᵃ, CH₂S(O)ₚR²ᵇ, C(O)R²ᶜ, CH₂C(O)R²ᶜ, and SO₂NR²R²ᵃ;

B is phenyl substituted with 0–2 R⁴ᵃ;

R², at each occurrence, is selected from H, CF₃, CH₃, benzyl, and phenyl;

R²ᵃ, at each occurrence, is selected from H, CF₃, CH₃, benzyl, and phenyl;

R²ᵇ, at each occurrence, is selected from CF₃, OCH₃, CH₃, benzyl, and phenyl;

R²ᶜ, at each occurrence, is selected from CF₃, OH, OCH₃, CH₃, benzyl, and phenyl;

alternatively, R² and R²ᵃ combine to form a ring system selected from pyrrolidinyl, piperazinyl and morpholino;

R⁴, at each occurrence, is selected from Cl, F, CH₃, NR²R²ᵃ, and CF₃;

R⁴ᵃ, at each occurrence, is selected from Cl, F, CH₃, SO₂NR²R²ᵃ, S(O)ₚR⁵, and CF₃; and, R⁵, at each occurrence, is selected from CF₃ and CH₃.

15. A compound according to claim 1, wherein the compound is selected from the group:

2-acetylamino-4-(3-amidinophenyl)-5-[(2'-aminosulfonyl-[1,1']-biphen-4-yl)aminocarbonyl]thiazole;

2-amino-4-(3-amidinophenyl)-5-[(2'-aminosulfonyl-[1,1']-biphen-4-yl)aminocarbonyl]thiazole;

2-methyl-4-(3-amidinophenyl)-5-[(2'-aminosulfonyl-[1,1']-biphen-4-yl)aminocarbonyl]thiazole;

2-methyl-4-(3-amidinophenyl)-5-[(2'-trifluoromethyl-[1,1']-biphen-4-yl)aminocarbonyl]thiazole;

2-phenyl-4-(3-amidinophenyl)-5-[(2'-aminosulfonyl-[1,1']-biphen-4-yl)aminocarbonyl]thiazole;

2-(phenylamino)-4-(3-amidinophenyl)-5-[(2'-aminosulfonyl-[1,1']-biphen-4-yl)aminocarbonyl]thiazole;

2-(benzylamino)-4-(3-amidinophenyl)-5-[(2'-aminosulfonyl-[1,1']-biphen-4-yl)aminocarbonyl]thiazole;

2-(methylamino)-4-(3-amidinophenyl)-5-[(2'-aminosulfonyl-[1,1']-biphen-4-yl)aminocarbonyl]thiazole;

2-(methylamino)-4-(3-carboxamidophenyl)-5-[(2'-aminosulfonyl-[1,1']-biphen-4-yl)aminocarbonyl]thiazole;

2-(3-pyridyl)-4-(3-amidinophenyl)-5-[(2'-aminosulfonyl-[1,1']-biphen-4-yl)aminocarbonyl]thiazole;

2-(3-pyridyl)-4-(3-carboxamidophenyl)-5-[(2'-aminosulfonyl-[1,1']-biphen-4-yl)aminocarbonyl]thiazole;

2-chloro-4-(3-amidinophenyl)-5-[(2'-aminosulfonyl-[1,1']-biphen-4-yl)aminocarbonyl]thiazole;

2-chloro-4-(3-carboxamidophenyl)-5-[(2'-aminosulfonyl-[1,1']-biphen-4-yl)aminocarbonyl]thiazole;

2-chloro-4-(3-aminophenyl)-5-[(2'-aminosulfonyl-[1,1']-biphen-4-yl)aminocarbonyl]thiazole;

2-amino-4-[(3-amino-4-chloro)phenyl]-5-[(2'-aminosulfonyl-[1,1']-biphen-4-yl)aminocarbonyl]thiazole;

2-chloro-4-[(3-amino-4-chloro)phenyl]-5-[(2'-aminosulfonyl-[1,1']-biphen-4-yl)aminocarbonyl]thiazole; and, 2-amino-4-[(3-aminomethyl)phenyl]-5-[(2'-aminosulfonyl-[1,1']-biphen-4-yl)aminocarbonyl]thiazole;

or a pharmaceutically acceptable salt thereof.

16. A pharmaceutical composition, comprising: a pharmaceutically acceptable carrier and a therapeutically effective amount of a compound according to claim 1 or a pharmaceutically acceptable salt thereof.

17. A pharmaceutical composition, comprising: a pharmaceutically acceptable carrier and a therapeutically effective amount of a compound according to claim 2 or a pharmaceutically acceptable salt thereof.

18. A pharmaceutical composition, comprising: a pharmaceutically acceptable carrier and a therapeutically effective amount of a compound according to claim 3 or a pharmaceutically acceptable salt thereof.

19. A pharmaceutical composition, comprising: a pharmaceutically acceptable carrier and a therapeutically effective amount of a compound according to claim 4 or a pharmaceutically acceptable salt thereof.

20. A pharmaceutical composition, comprising: a pharmaceutically acceptable carrier and a therapeutically effective amount of a compound according to claim 5 or a pharmaceutically acceptable salt thereof.

21. A pharmaceutical composition, comprising: a pharmaceutically acceptable carrier and a therapeutically effective amount of a compound according to claim 6 or a pharmaceutically acceptable salt thereof.

22. A pharmaceutical composition, comprising: a pharmaceutically acceptable carrier and a therapeutically effective amount of a compound according to claim 7 or a pharmaceutically acceptable salt thereof.

23. A pharmaceutical composition, comprising: a pharmaceutically acceptable carrier and a therapeutically effective amount of a compound according to claim 8 or a pharmaceutically acceptable salt thereof.

24. A pharmaceutical composition, comprising: a pharmaceutically acceptable carrier and a therapeutically effective amount of a compound according to claim 9 or a pharmaceutically acceptable salt thereof.

25. A pharmaceutical composition, comprising: a pharmaceutically acceptable carrier and a therapeutically effective amount of a compound according to claim 10 or a pharmaceutically acceptable salt thereof.

26. A pharmaceutical composition, comprising: a pharmaceutically acceptable carrier and a therapeutically effective amount of a compound according to claim 11 or a pharmaceutically acceptable salt thereof.

27. A pharmaceutical composition, comprising: a pharmaceutically acceptable carrier and a therapeutically effective amount of a compound according to claim 12 or a pharmaceutically acceptable salt thereof.

28. A pharmaceutical composition, comprising: a pharmaceutically acceptable carrier and a therapeutically effective amount of a compound according to claim 13 or a pharmaceutically acceptable salt thereof.

29. A pharmaceutical composition, comprising: a pharmaceutically acceptable carrier and a therapeutically effective amount of a compound according to claim 14 or a pharmaceutically acceptable salt thereof.

30. A pharmaceutical composition, comprising: a pharmaceutically acceptable carrier and a therapeutically effective amount of a compound according to claim 15 or a pharmaceutically acceptable salt thereof.

31. A method for treating or preventing a thromboembolic disorder, comprising: administering to a patient in need thereof a therapeutically effective amount of a compound according to claim 1 or a pharmaceutically acceptable salt thereof.

32. A method for treating a thromboembolic disorder, comprising: administering to a patient in need thereof a therapeutically effective amount of a compound according to claim 2 or a pharmaceutically acceptable salt thereof.

33. A method for treating a thromboembolic disorder, comprising: administering to a patient in need thereof a therapeutically effective amount of a compound according to claim 3 or a pharmaceutically acceptable salt thereof.

34. A method for treating a thromboembolic disorder, comprising: administering to a patient in need thereof a therapeutically effective amount of a compound according to claim 4 or a pharmaceutically acceptable salt thereof.

35. A method for treating a thromboembolic disorder, comprising: administering to a patient in need thereof a therapeutically effective amount of a compound according to claim 5 or a pharmaceutically acceptable salt thereof.

36. A method for treating a thromboembolic disorder, comprising: administering to a patient in need thereof a therapeutically effective amount of a compound according to claim 6 or a pharmaceutically acceptable salt thereof.

37. A method for treating a thromboembolic disorder, comprising: administering to a patient in need thereof a therapeutically effective amount of a compound according to claim 7 or a pharmaceutically acceptable salt thereof.

38. A method for treating a thromboembolic disorder, comprising: administering to a patient in need thereof a therapeutically effective amount of a compound according to claim 8 or a pharmaceutically acceptable salt thereof.

39. A method for treating a thromboembolic disorder, comprising: administering to a patient in need thereof a therapeutically effective amount of a compound according to claim 9 or a pharmaceutically acceptable salt thereof.

40. A method for treating a thromboembolic disorder, comprising: administering to a patient in need thereof a therapeutically effective amount of a compound according to claim 10 or a pharmaceutically acceptable salt thereof.

41. A method for treating a thromboembolic disorder, comprising: administering to a patient in need thereof a therapeutically effective amount of a compound according to claim 11 or a pharmaceutically acceptable salt thereof.

42. A method for treating a thromboembolic disorder, comprising: administering to a patient in need thereof a therapeutically effective amount of a compound according to claim 12 or a pharmaceutically acceptable salt thereof.

43. A method for treating a thromboembolic disorder, comprising: administering to a patient in need thereof a therapeutically effective amount of a compound according to claim 13 or a pharmaceutically acceptable salt thereof.

44. A method for treating a thromboembolic disorder, comprising: administering to a patient in need thereof a therapeutically effective amount of a compound according to claim 14 or a pharmaceutically acceptable salt thereof.

45. A method for treating a thromboembolic disorder, comprising: administering to a patient in need thereof a therapeutically effective amount of a compound according to claim 15 or a pharmaceutically acceptable salt thereof.

* * * * *